United States Patent
Collins et al.

(10) Patent No.: US 10,570,121 B2
(45) Date of Patent: *Feb. 25, 2020

(54) SUBSTITUTED DIHYDROISOQUINOLINONE COMPOUNDS

(71) Applicant: Pfizer Inc., New York, NY (US)

(72) Inventors: Michael Raymond Collins, San Diego, CA (US); Robert Steven Kania, San Diego, CA (US); Robert Arnold Kumpf, Carlsbad, CA (US); Pei-Pei Kung, San Diego, CA (US); Daniel Tyler Richter, San Diego, CA (US); Scott Channing Sutton, San Diego, CA (US); Martin James Wythes, Solana Beach, CA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/156,304

(22) Filed: Oct. 10, 2018

(65) Prior Publication Data

US 2019/0040047 A1  Feb. 7, 2019

Related U.S. Application Data

(63) Continuation of application No. 15/635,648, filed on Jun. 28, 2017, now abandoned, which is a continuation of application No. 15/262,230, filed on Sep. 12, 2016, now abandoned, which is a continuation of application No. 14/740,439, filed on Jun. 16, 2015, now Pat. No. 9,481,666.

(60) Provisional application No. 62/156,533, filed on May 4, 2015, provisional application No. 62/013,410, filed on Jun. 17, 2014.

(51) Int. Cl.

| C07D 401/06 | (2006.01) |
| C07B 59/00 | (2006.01) |
| A61K 31/4725 | (2006.01) |
| C07D 405/14 | (2006.01) |
| C07D 401/14 | (2006.01) |
| C07D 413/14 | (2006.01) |
| C07D 409/14 | (2006.01) |

(52) U.S. Cl.
CPC .......... C07D 405/14 (2013.01); C07B 59/002 (2013.01); C07D 401/06 (2013.01); C07D 401/14 (2013.01); C07D 409/14 (2013.01); C07D 413/14 (2013.01); C07B 2200/05 (2013.01)

(58) Field of Classification Search
None
See application file for complete search history.

(56) References Cited

U.S. PATENT DOCUMENTS

| 3,846,412 A | 11/1974 | Nathansohn et al. |
| 8,410,088 B2 | 4/2013 | Kuntz et al. |
| 9,040,515 B2 | 5/2015 | Edwards et al. |
| 9,481,666 B2 | 11/2016 | Kania et al. |
| 2007/0093515 A1 | 4/2007 | Arrington et al. |
| 2008/0182844 A1 | 7/2008 | Bjergarde et al. |
| 2010/0113415 A1 | 5/2010 | Rajapakse et al. |
| 2015/0175572 A1 | 6/2015 | Edwards et al. |
| 2015/0239842 A1 | 8/2015 | Edwards et al. |
| 2015/0307397 A1 | 10/2015 | Bouteiller et al. |
| 2015/0307471 A1 | 10/2015 | Willand et al. |
| 2015/0361067 A1 | 12/2015 | Collins et al. |
| 2016/0376254 A1 | 12/2016 | Collins et al. |
| 2017/0152239 A1 | 6/2017 | Edwards et al. |
| 2017/0233368 A1 | 8/2017 | Edwards et al. |

FOREIGN PATENT DOCUMENTS

| WO | 2011103016 | 8/2011 |
| WO | 2011140324 | 11/2011 |
| WO | 2011140325 | 11/2011 |
| WO | 2012005805 | 1/2012 |
| WO | 2012034132 | 3/2012 |
| WO | 2012035078 | 3/2012 |
| WO | 2012068589 | 5/2012 |
| WO | 2012118812 | 9/2012 |

(Continued)

OTHER PUBLICATIONS

Bachmann et al., "EZH2 Expression Is Associated With High Proliferation Rate and Aggressive Tumor Subgroups in Cutaneous Melanoma and Cancers of the Endometrium, Prostate, and Breast." J. Clin. Oncol. (2006), 24:268-273.

(Continued)

*Primary Examiner* — Zinna Northington Davis
(74) *Attorney, Agent, or Firm* — Mary J. Hosley

(57) ABSTRACT

This invention relates to compounds of general formula (I)

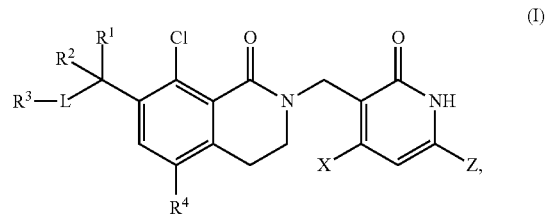

in which $R^1$, $R^2$, $R^3$, $R^4$, L, X and Z are as defined herein, and the pharmaceutically acceptable salts thereof, to pharmaceutical compositions comprising such compounds and salts, and to methods of using such compounds, salts and compositions for the treatment of abnormal cell growth, including cancer.

4 Claims, No Drawings

(56) References Cited

FOREIGN PATENT DOCUMENTS

| WO | 2012142504 | 10/2012 |
| --- | --- | --- |
| WO | 2012142513 | 10/2012 |
| WO | 2013049770 | 4/2013 |
| WO | 2013173441 | 11/2013 |
| WO | 2014049488 | 4/2014 |
| WO | 2014095773 | 6/2014 |
| WO | 2014096145 | 6/2014 |
| WO | 2014096148 | 6/2014 |
| WO | 2014096149 | 6/2014 |
| WO | 2014096150 | 6/2014 |
| WO | 2014096378 | 6/2014 |
| WO | 2014096698 | 6/2014 |
| WO | 2014097041 | 6/2014 |
| WO | 2014100323 | 6/2014 |
| WO | 2014100500 | 6/2014 |
| WO | 2014100505 | 6/2014 |
| WO | 2014100620 | 6/2014 |
| WO | 2014100719 | 6/2014 |
| WO | 2015193765 | 12/2015 |

OTHER PUBLICATIONS

Breuer et al., "Increased expression of the EZH2 polycomb group gene in BMI-1-positive neoplastic cells during bronchial carcinogenesis." Neoplasia (2004), 6:736-43.
Cardoso et al., "The human EZH2 gene: genomic organisation and revised mapping in 7q35 within the critical region for malignant myeloid disorders." Eur. J. Hum. Genet. (2000), 8:174-180.
Crea et al., "Polycomb genes and cancer: Time for clinical application?" Crit. Rev. Oncol. Hematol. (2012), 83:184-193.
Kleer et al., "EZH2 is a marker of aggressive breast cancer and promotes neoplastic transformation of breast epithelial cells." Proc. Natl. Acad. Sci. USA (2003), 100:11606-11.
Lu et al., "Gene alterations identified by expression profiling in tumor-associated endothelial cells from invasive ovarian carcinoma." Cancer Res. (2007), 67:1757-1768.
Majer et al., "A687V EZH2 is a gain-of-function mutation found in lymphoma patients." FEBS Letters (2012), 586:3448-3451.
Matsukawa et al., "Expression of the enhancer of zeste homolog 2 is correlated with poor prognosis in human gastric cancer." Cancer Sci. (2006), 97:484-491.
McCabe et al., Mutation of A677 in histonemethyltransferase EZH2 in human B-cell lymphonoma promotes hypertrimethylation of histone H3 on lysine 27 (H3K27). Proc. Natl. Acad. Sci. USA (2012), 109:2989-2994).
Mimori et al., "Clinical significance of enhancer of zeste homolog 2 expression in colorectal cancer cases." Eur. J. Surg. Oncol. (2005), 31:376-80.
Morin et al., "Somatic mutation of EZH2 (Y641) in Follicular and Diffuse Large B-cell Lymphomas of Germinal Center Origin." Nat. Genetics (2010) Feb.; 42(2):181-185.
Ougolkov et al., "Regulation of pancreatic tumor cell proliferation and chemoresistance by the histone methyltransferase enhancer of zeste homologue 2." Clin. Cancer Res. (2008), 14:6790-6796.
Sasaki et al., "The overexpression of polycomb group proteins Bmi1 and EZH2 is associated with the progression and aggressive biological behaviour of hepatocellular carcinoma." Lab. Invest. (2008), 88:873-882.
Sudo et al., "Clinicopathological significance of EZH2 mRNA expression in patients with hepatocellular carcinoma." Br. J. Cancer (2005), 92(9):1754-1758.
Varambally et al., "The polycomb group protein EZH2 is involved in progression of prostate cancer" Nature (2002), 419:624-629.
Wagener et al., "The enhancer of zeste homolog 2 gene contributes to cell proliferation and apoptosis resistance in renal cell carcinoma cells." Int. J. Cancer (2008), 123:1545-1550.
Weikert et al., "Expression levels of the EZH2 polycomb transcriptional repressor correlate with aggressiveness and invasive potential of bladder carcinomas." Int. J. Mol. Med. (2005), 16:349-353.
International Search Report dated Mar. 21, 2014 for International application No. PCT/IB2013/060682, filed Dec. 5, 2013.
Written Opinion of the International Searching Authority for International application No. PCT/IB2013/060682, filed Dec. 5, 2013.
International Search Report dated Jul. 14, 2015 for International application No. PCT/IB2015/054272, filed Jun. 5, 2015.
International Preliminary Report on Patentability dated Dec. 20, 2016 for International application No. PCT/IB2015/054272, filed Jun. 5, 2015.
Written Opinion dated Dec. 23, 2015, for International Application No. PCT/IB2015/054272 filed Jun. 5, 2015 and published as WO2015193765.
Request for Certificate of Correction, for U.S. Pat. No. 9,040,515 (U.S. Appl. No. 14/132,567), filed with the USPTO on Sep. 27, 2018.

SUBSTITUTED DIHYDROISOQUINOLINONE COMPOUNDS

CROSS-REFERENCE TO RELATED APPLICATIONS

This application is a continuation of U.S. patent application Ser. No. 15/635,648 filed Jun. 28, 2017, which is in turn is a continuation of U.S. patent application Ser. No. 15/262,230, filed Sep. 12, 2016, now abandoned, which in turn is a continuation of U.S. patent application Ser. No. 14/740,439, filed on Jun. 16, 2015, issued as U.S. Pat. No. 9,481,666 Nov. 1, 2016, which in turn claims the benefit of priority to U.S. Provisional Application Ser. No. 62/013,410, filed on Jun. 17, 2014, and to U.S. Provisional Application Ser. No. 62/156,533, filed on May 4, 2015, the disclosure of each of which is hereby incorporated by reference in its entirety.

BACKGROUND OF THE INVENTION

Field of the Invention

The present invention relates to compounds of Formulae I, I', II, II' and III, and their pharmaceutically acceptable salts, to pharmaceutical compositions comprising such compounds and salts, and to the uses thereof. The compounds, salts and compositions of the present invention may be useful for treating or ameliorating abnormal cell proliferative disorders, such as cancer.

Description of Related Art

Epigenetic alterations play an important role in the regulation of cellular processes, including cell proliferation, cell differentiation and cell survival. The epigenetic silencing of tumor suppressor genes and activation of oncogenes may occur through alteration of CpG island methylation patterns, histone modification, and dysregulation of DNA binding protein. Polycomb genes are a set of epigenetic effectors. EZH2 (enhancer of zeste homolog 2) is the catalytic component of the Polycomb Repressor Complex 2 (PRC2), a conserved multi-subunit complex that represses gene transcription by methylating lysine 27 on Histone H3 (H3K27). EZH2 plans a key role in regulating gene expression patterns that regulate cell fate decisions, such as differentiation and self-renewal. EZH2 is overexpressed in certain cancer cells, where it has been linked to cell proliferation, cell invasion, chemoresistance and metastasis.

High EZH2 expression has been correlated with poor prognosis, high grade, and high stage in several cancer types, including breast, colorectal, endometrial, gastric, liver, kidney, lung, melanoma, ovarian, pancreatic, prostate, and bladder cancers. See Crea et al., *Crit. Rev. Oncol. Hematol.* 2012, 83:184-193, and references cited therein; see also Kleer et al., *Proc. Natl. Acad. Sci. USA* 2003, 100:11606-11; Mimori et al., *Eur. J. Surg. Oncol.* 2005, 31:376-80; Bachmann et al., *J. Clin. Oncol.* 2006, 24:268-273; Matsukawa et al., *Cancer Sci.* 2006, 97:484-491; Sasaki et al. *Lab. Invest.* 2008, 88:873-882; Sudo et al., *Br. J. Cancer* 2005, 92(9):1754-1758; Breuer et al., *Neoplasia* 2004, 6:736-43; Lu et al., *Cancer Res.* 2007, 67:1757-1768; Ougolkov et al., *Clin. Cancer Res.* 2008, 14:6790-6796; Varambally et al., *Nature* 2002, 419:624-629; Wagener et al., *Int. J. Cancer* 2008, 123:1545-1550; and Weikert et al., *Int. J. Mol. Med.* 2005, 16:349-353.

Recurring somatic mutations in EZH2 have been identified in diffuse large B-cell lymphoma (DLBCL) and follicular lymphomas (FL). Mutations altering EZH2 tyrosine 641 (e.g., Y641C, Y641F, Y641N, Y641S, and Y641H) were reportedly observed in up to 22% of germinal center B-cell DLBCL and 7% of FL. Morin et al. *Nat. Genetics* 2010 February; 42(2):181-185. Mutations of alanine 677 (A677) and alanine 687 (A687) have also been reported. McCabe et al., *Proc. Natl. Acad. Sci. USA* 2012, 109:2989-2994; Majer et al. *FEBS Letters* 2012, 586:3448-3451. EZH2 activating mutations have been suggested to alter substrate specificity resulting in elevated levels of trimethylated H3K27 (H3K27me3).

Accordingly, compounds that inhibit the activity of wild type and/or mutant forms of EZH2 may be of interest for the treatment of cancer.

BRIEF SUMMARY OF THE INVENTION

The present invention provides, in part, novel compounds and pharmaceutically acceptable salts. Such compounds may modulate the activity of EZH2, thereby effecting biological functions, for example by inhibiting cell proliferation and cell invasiveness, inhibiting metastasis, inducing apoptosis or inhibiting angiogenesis. Also provided are pharmaceutical compositions and medicaments, comprising the compounds or salts of the invention, alone or in combination with other therapeutic agents or palliative agents. The present invention also provides, in part, methods for preparing the novel compounds, salts and compositions thereof, and methods of using the foregoing.

In one aspect, the invention provides a compound of formula (I):

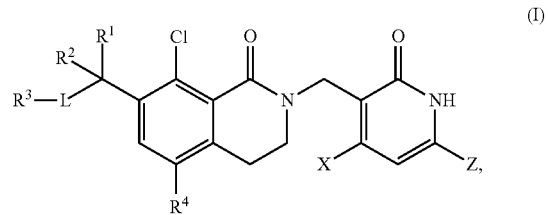

or a pharmaceutically acceptable salt thereof,
wherein:
$R^1$ is selected from the group consisting of H, F, $C_1$-$C_4$ alkyl, $C_1$-$C_4$ alkoxy, $C(O)R^5$, $C_3$-$C_8$ cycloalkyl, 3-12 membered heterocyclyl and 5-12 membered heteroaryl, where each said $C_1$-$C_4$ alkyl or $C_1$-$C_4$ alkoxy is optionally substituted by one or more $R^6$, and each said $C_3$-$C_8$ cycloalkyl, 3-12 membered heterocyclyl or 5-12 membered heteroaryl is optionally substituted by one or more $R^7$;
$R^2$ is H, F or $C_1$-$C_4$ alkyl;
L is a bond or a $C_1$-$C_4$ alkylene;
$R^3$ is selected from the group consisting of $C_1$-$C_4$ alkyl, $C_1$-$C_4$ alkoxy, OH, CN, $C(O)R^8$, $COOR^9$, $NR^{10}R^{11}$, $OR^{12}$, $C_3$-$C_8$ cycloalkyl, 3-12 membered heterocyclyl and 5-12 membered heteroaryl, where each said $C_1$-$C_4$ alkyl or $C_1$-$C_4$ alkoxy is optionally substituted by one or more $R^6$, and each said $C_3$-$C_8$ cycloalkyl, 3-12 membered heterocyclyl or 5-12 membered heteroaryl is optionally substituted by one or more $R^7$;
$R^4$ is H, halo or $C_1$-$C_4$ alkyl, where each said $C_1$-$C_4$ alkyl is optionally substituted by one or more $R^6$;
$R^5$ is $C_1$-$C_4$ alkyl, where each said $C_1$-$C_4$ alkyl is optionally substituted by one or more $R^{14}$;

each $R^6$ is independently OH, F, CN or $C_1$-$C_4$ alkoxy;

each $R^7$ is independently $C_1$-$C_4$ alkyl, OH, F, CN, $C_1$-$C_4$ alkoxy, =O, CHO, $C(O)R^{13}$, $SO_2R^{13}$ or 3-6 membered heterocyclyl;

$R^8$ is $C_1$-$C_4$ alkyl, where each said $C_1$-$C_4$ alkyl is optionally substituted by one or more $R^{14}$;

$R^9$ is H or $C_1$-$C_4$ alkyl, where each said $C_1$-$C_4$ alkyl is optionally substituted by one or more $R^{14}$;

$R^{10}$ and $R^{11}$ are independently H or $C_1$-$C_4$ alkyl, where each said $C_1$-$C_4$ alkyl is optionally substituted by one or more $R^{14}$;

$R^{12}$ is selected from the group consisting of $C_3$-$C_8$ cycloalkyl, 3-12 membered heterocyclyl and 5-12 membered heteroaryl, where each said $C_3$-$C_8$ cycloalkyl, 3-12 membered heterocyclyl or 5-12 membered heteroaryl is optionally substituted by one or more $R^7$;

each $R^{13}$ is independently $C_1$-$C_4$ alkyl, where each said $C_1$-$C_4$ alkyl is optionally substituted by one or more $R^{15}$;

each $R^{14}$ and $R^{15}$ is independently OH, F, CN or $C_1$-$C_4$ alkoxy; and X and Z are independently $C_1$-$C_4$ alkyl, $C_1$-$C_4$ fluoroalkyl, $C_1$-$C_4$ alkoxy or $C_1$-$C_4$ fluoroalkoxy.

In some embodiments, the compound of Formula (I) has the absolute stereochemistry at the carbon atom bearing the $R^1$ and $R^2$ substituents as shown in Formula (I-A) or (I-B):

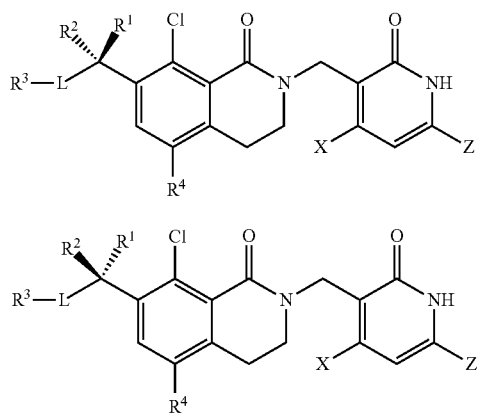

(I-A)

or (I-B)

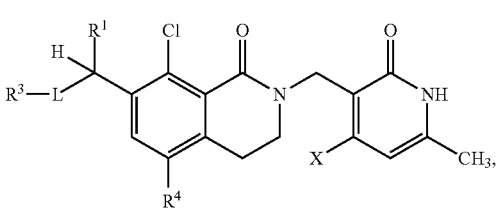

or a pharmaceutically acceptable salt thereof,
wherein:
$R^1$, $R^2$, L, $R^3$, $R^4$, X and Z are defined as for Formula (I).

In another aspect, the invention provides a compound of Formula (II), (II-A) or (II-B):

(II)

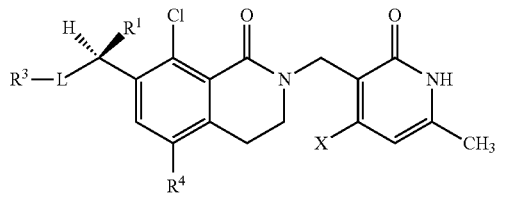

(II-A)

(II-B)

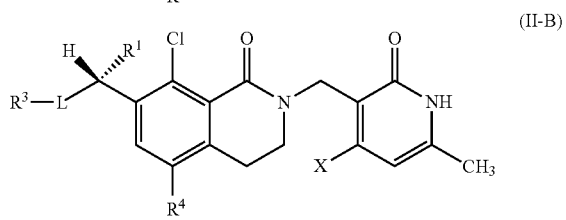

or a pharmaceutically acceptable salt thereof,
wherein:
$R^1$, L, $R^3$ and X are defined as for Formula (I); and
$R^4$ is H, Cl, Br, F or $CH_3$.

In another aspect, the invention provides a compound of formula (III):

(III)

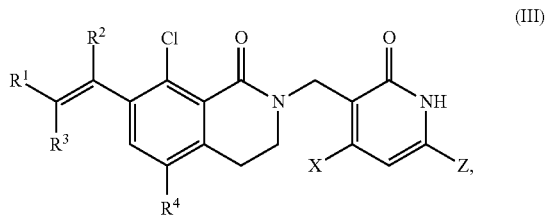

or a pharmaceutically acceptable salt thereof,
wherein:
$R^1$ and $R^3$ are taken together to form a 3-12 membered heterocyclyl optionally substituted by one or more $R^7$;

$R^2$ is H, F or $C_1$-$C_4$ alkyl;

$R^4$ is H, halo or $C_1$-$C_4$ alkyl, where each said $C_1$-$C_4$ alkyl is optionally substituted by one or more $R^6$;

each $R^6$ is independently OH, F, CN or $C_1$-$C_4$ alkoxy;

each $R^7$ is independently $C_1$-$C_4$ alkyl, OH, F, CN, $C_1$-$C_4$ alkoxy, =O, CHO, $C(O)R^{13}$, $SO_2R^{13}$ or 3-6 membered heterocyclyl;

each $R^{13}$ is independently $C_1$-$C_4$ alkyl, where each said $C_1$-$C_4$ alkyl is optionally substituted by one or more $R^{15}$;

each $R^{15}$ is independently OH, F, CN or $C_1$-$C_4$ alkoxy; and

X and Z are independently $C_1$-$C_4$ alkyl, $C_1$-$C_4$ fluoroalkyl, $C_1$-$C_4$ alkoxy or $C_1$-$C_4$ fluoroalkoxy.

In another aspect, the invention provides a pharmaceutical composition comprising a compound of one of the formulae described herein, or a pharmaceutically acceptable salt thereof, and a pharmaceutically acceptable carrier or excipient. In some embodiments, the pharmaceutical composition comprises two or more pharmaceutically acceptable carriers and/or excipients.

The invention also provides therapeutic methods and uses comprising administering a compound of the invention, or a pharmaceutically acceptable salt thereof.

In one aspect, the invention provides a method for the treatment of abnormal cell growth in a subject comprising administering to the subject a therapeutically effective amount of a compound of the invention, or a pharmaceutically acceptable salt thereof.

In frequent embodiments of the methods provided herein, the abnormal cell growth is cancer. In some embodiments, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

In another aspect, the invention provides a method for the treatment of a disorder mediated by EZH2 in a subject comprising administering to the subject a compound of the invention, or a pharmaceutically acceptable salt thereof, in an amount that is effective for treating said disorder. The compounds and salts of the present invention may inhibit wild-type and certain mutant forms of human histone methyltransferase EZH2.

In another aspect, the invention provides a compound of one of the formulae described herein, or pharmaceutically acceptable salt thereof, for use in the treatment of abnormal cell growth in a subject.

In a further aspect, the invention provides the use of a compound of one of the formulae described herein, or pharmaceutically acceptable salt thereof, for the treatment of abnormal cell growth in a subject.

In yet another aspect, the invention provides the use of a compound of one of the formulae described herein, or a pharmaceutically acceptable salt thereof, for the preparation of a medicament for the treatment of abnormal cell growth.

In frequent embodiments, the abnormal cell growth is cancer and the subject is a human.

In some embodiments, the methods described herein further comprise administering to the subject an amount of an anti-cancer therapeutic agent or a palliative agent, which amounts may be together effective in treating said abnormal cell growth. In some embodiments, the one or more anti-cancer therapeutic agent is selected from anti-tumor agents, anti-angiogenesis agents, signal transduction inhibitors and antiproliferative agents, which amounts are together effective in treating said abnormal cell growth. In some such embodiments, the anti-tumor agent is selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

In other embodiments, the uses described herein comprise the use of a compound of one of the formulae described herein or pharmaceutically acceptable salt thereof, in combination with one or more substances selected from anti-tumor agents, anti-angiogenesis agents, signal transduction inhibitors and antiproliferative agents.

In some embodiments, the medicaments described herein may be adapted for use in combination with one or more substances selected from anti-tumor agents, anti-angiogenesis agents, signal transduction inhibitors and antiproliferative agents.

Each of the embodiments of the compounds of the present invention described below may be combined with one or more other embodiments of the compounds of the present invention described herein not inconsistent with the embodiment(s) with which it is combined.

In addition, each of the embodiments below describing the invention envisions within its scope the pharmaceutically acceptable salts of the compounds of the invention. Accordingly, the phrase "or a pharmaceutically acceptable salt thereof" is implicit in the description of all compounds described herein.

DETAILED DESCRIPTION OF THE INVENTION

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

"Alkyl" refers to a saturated, monovalent aliphatic hydrocarbon radical including straight chain and branched chain groups having the specified number of carbon atoms. Alkyl substituents typically contain 1 to 20 carbon atoms ("$C_1$-$C_{20}$ alkyl"), preferably 1 to 12 carbon atoms ("$C_1$-$C_{12}$ alkyl"), more preferably 1 to 8 carbon atoms ("$C_1$-$C_8$ alkyl"), or 1 to 6 carbon atoms ("$C_1$-$C_6$ alkyl"), or 1 to 4 carbon atoms ("$C_1$-$C_4$ alkyl"). Examples of alkyl groups include methyl, ethyl, n-propyl, isopropyl, n-butyl, iso-butyl, tert-butyl, n-pentyl, isopentyl, neopentyl, n-hexyl, n-heptyl, n-octyl and the like. Alkyl groups may be substituted or unsubstituted. In particular, unless otherwise specified, alkyl groups may be substituted by one or more halo groups, up to the total number of hydrogen atoms present on the alkyl moiety. Thus, $C_1$-$C_4$ alkyl includes halogenated alkyl groups, and in particular fluorinated alkyl groups, having 1 to 4 carbon atoms, e.g., trifluoromethyl or difluoroethyl (i.e., $CF_3$ and —$CH_2CHF_2$).

Alkyl groups described herein as optionally substituted by may be substituted by one or more substituent groups, which are selected independently unless otherwise indicated. The total number of substituent groups may equal the total number of hydrogen atoms on the alkyl moiety, to the extent such substitution makes chemical sense. Optionally substituted alkyl groups typically contain from 1 to 6 optional substituents, sometimes 1 to 5 optional substituents, preferably from 1 to 4 optional substituents, or more preferably from 1 to 3 optional substituents.

Optional substituent groups suitable for alkyl include, but are not limited to $C_3$-$C_8$ cycloalkyl, 3-12 membered heterocyclyl, $C_6$-$C_{12}$ aryl and 5-12 membered heteroaryl, halo, =O (oxo), =S (thiono), =N—CN, =N—OR$^x$, =NR$^x$, —CN, —C(O)R$^x$, —CO$_2$R$^x$, —C(O)NR$^x$R$^y$, —SR$^x$, —SOR$^x$, —SO$_2$R$^x$, —SO$_2$NR$^x$R$^y$, —NO$_2$, —NR$^x$R$^y$, —NR$^x$C(O)R$^y$, —NR$^x$C(O)NR$^x$R$^y$, —NR$^x$C(O)OR$^x$, —NR$^x$SO$_2$R$^y$, —NR$^x$SO$_2$NR$^x$R$^y$, —OR$^x$, —OC(O)R$^x$ and —OC(O)NR$^x$R$^y$; wherein each R$^x$ and R$^y$ is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl, or R$^x$ and R$^y$ may be taken together with the N atom to which they are attached to form a 3-12 membered heterocyclyl or 5-12 membered heteroaryl, each optionally containing 1, 2 or 3 additional heteroatoms selected from O, N and S; each R$^x$ and R$^y$ is optionally substituted with 1 to 3 substituents independently selected from the group consisting of halo, =O, =S, =N—CN, =N—OR', =NR', —CN, —C(O)R', —CO$_2$R', —C(O)NR'$_2$, —SR', —SOR', —SO$_2$R', —SO$_2$NR'$_2$, —NO$_2$, —NR'$_2$, —NR'C(O)R', —NR'C(O)NR'$_2$, —NR'C(O)OR', —NR'SO$_2$R', —NR'SO$_2$NR'$_2$, —OR', —OC(O)R' and —OC(O)NR'$_2$, wherein each R' is independently H, C$_1$-C$_8$ alkyl, C$_1$-C$_8$ acyl, C$_2$-C$_8$ alkenyl, C$_2$-C$_8$ alkynyl, C$_3$-C$_8$ cycloalkyl, 3-12 membered heterocyclyl, C$_6$-C$_{12}$ aryl, or C$_5$-C$_{12}$ heteroaryl; and wherein each said C$_3$-C$_8$ cycloalkyl, 3-12 membered heterocyclyl, C$_6$-C$_{12}$ aryl and 5-12 membered heteroaryl is optionally substituted as further defined herein.

Typical substituent groups on alkyl include halo, —OH, C$_1$-C$_4$ alkoxy, —O—C$_6$-C$_{12}$ aryl, —CN, =O, —COOR$^x$, —OC(O)R$^x$, —C(O)NR$^x$R$^y$, —NR$^x$C(O)R$^y$, —NR$^x$R$^y$, C$_3$-C$_8$ cycloalkyl, C$_6$-C$_{12}$ aryl, 5-12 membered heteroaryl and 3-12 membered heterocyclyl; where each R$^x$ and R$^y$ is independently H or C$_1$-C$_4$ alkyl, or R$^x$ and R$^y$ may be taken together with the N to which they are attached form a 3-12 membered heterocyclyl or 5-12 membered heteroaryl ring, each optionally containing 1, 2 or 3 additional heteroatoms selected from O, N and S; wherein each said C$_3$-C$_8$ cycloalkyl, C$_6$-C$_{12}$ aryl, 5-12 membered heteroaryl and 3-12 membered heterocyclyl is optionally substituted by 1 to 3 substituents independently selected from the group consisting of halo, —OH, =O, C$_1$-C$_4$ alkyl, C$_1$-C$_4$ alkoxy, C$_1$-C$_6$ haloalkyl, C$_1$-C$_6$ hydroxyalkyl, C$_1$-C$_4$ alkoxy-C$_1$-C$_6$ alkyl, —CN, —NH$_2$, —NH(C$_1$-C$_4$ alkyl), and —N(C$_1$-C$_4$ alkyl)$_2$.

In some embodiments, alkyl is optionally substituted by one or more substituents, and preferably by 1 to 3 substituents, which are independently selected from the group consisting of halo, —OH, C$_1$-C$_4$ alkoxy, —O—C$_6$-C$_{12}$ aryl, —CN, =O, —COOR$^x$, —OC(O)R$^x$, —C(O)NR$^x$R$^y$, —NR$^x$C(O)R$^y$, —NR$^x$R$^y$, C$_3$-C$_8$ cycloalkyl, C$_6$-C$_{12}$ aryl, 5-12 membered heteroaryl and 3-12 membered heterocyclyl; where each R$^x$ and R$^y$ is independently H or C$_1$-C$_4$ alkyl, or R$^x$ and R$^y$ may be taken together with the N to which they are attached form a 3-12 membered heterocyclyl or 5-12 membered heteroaryl ring, each optionally containing 1, 2 or 3 additional heteroatoms selected from O, N and S; and each said C$_3$-C$_8$ cycloalkyl, C$_6$-C$_{12}$ aryl, 5-12 membered heteroaryl and 3-12 membered heterocyclyl is optionally substituted by 1 to 3 substituents independently selected from the group consisting of halo, —OH, =O, C$_1$-C$_4$ alkyl, C$_1$-C$_4$ alkoxy, C$_1$-C$_6$ haloalkyl, C$_1$-C$_6$ hydroxyalkyl, C$_1$-C$_4$ alkoxy-C$_1$-C$_6$ alkyl, —CN, —NH$_2$, —NH(C$_1$-C$_4$ alkyl) and —N(C$_1$-C$_4$ alkyl)$_2$.

In other embodiments, alkyl is optionally substituted by one or more substituent, and preferably by 1 to 3 substituents, independently selected from the group consisting of halo, —OH, C$_1$-C$_4$ alkoxy, —CN, —NR$^x$R$^y$, C$_3$-C$_8$ cycloalkyl, 3-12 membered heterocyclyl, C$_6$-C$_{12}$ aryl and 5-12 membered heteroaryl; where each R$^x$ and R$^y$ is independently H or C$_1$-C$_4$ alkyl, or R$^x$ and R$^y$ may be taken together with the N to which they are attached form a 3-12 membered heterocyclyl or 5-12 membered heteroaryl ring, each optionally containing 1, 2 or 3 additional heteroatoms selected from O, N and S; and where each said cycloalkyl, heterocyclyl, aryl or heteroaryl is optionally substituted by 1 to 3 substituents independently selected from the group consisting of halo, —OH, =O, C$_1$-C$_4$ alkyl, C$_1$-C$_4$ alkoxy, C$_1$-C$_6$ haloalkyl, C$_1$-C$_6$ hydroxyalkyl, C$_1$-C$_4$ alkoxy-C$_1$-C$_6$ alkyl, —CN, —NH$_2$, —NH(C$_1$-C$_4$ alkyl) and —N(C$_1$-C$_4$ alkyl)$_2$.

In some instances, substituted alkyl groups may be specifically named with reference to the substituent group. For example, "haloalkyl" refers to an alkyl group having the specified number of carbon atoms that is substituted by one or more halo substituents, and typically contain 1-6 carbon atoms and 1, 2 or 3 halo atoms (i.e., "C$_1$-C$_6$ haloalkyl") or sometimes 1-4 carbon atoms and 1, 2 or 3 halo atoms (i.e., "C$_1$-C$_4$ haloalkyl"). Thus, a C$_1$-C$_4$ haloalkyl group includes trifluoromethyl (—CF$_3$) and difluoromethyl (—CF$_2$H). More specifically, fluorinated alkyl groups may be specifically referred to as fluoroalkyl groups, e.g., C$_1$-C$_6$ or C$_1$-C$_4$ fluoroalkyl groups.

Similarly, "hydroxyalkyl" refers to an alkyl group having the specified number of carbon atoms that is substituted by one or more hydroxy substituents, and typically contain 1-6 carbon atoms and 1, 2 or 3 hydroxy (i.e., "C$_1$-C$_6$ hydroxyalkyl"). Thus, C$_1$-C$_6$ hydroxyalkyl includes hydroxymethyl (—CH$_2$OH) and 2-hydroxyethyl (—CH$_2$CH$_2$OH).

"Alkoxyalkyl" refers to an alkyl group having the specified number of carbon atoms that is substituted by one or more alkoxy substituents. Alkoxyalkyl groups typically contain 1-6 carbon atoms in the alkyl portion and are substituted by 1, 2 or 3 C$_1$-C$_4$ alkoxy substituents. Such groups are sometimes described herein as C$_1$-C$_4$ alkyoxy-C$_1$-C$_6$ alkyl.

"Aminoalkyl" refers to alkyl group having the specified number of carbon atoms that is substituted by one or more substituted or unsubstituted amino groups, as such groups are further defined herein. Aminoalkyl groups typically contain 1-6 carbon atoms in the alkyl portion and are substituted by 1, 2 or 3 amino substituents. Thus, a C$_1$-C$_6$ aminoalkyl group includes, for example, aminomethyl (—CH$_2$NH$_2$), N,N-dimethylamino-ethyl (—CH$_2$CH$_2$N(CH$_3$)$_2$), 3-(N-cyclopropylamino)propyl (—CH$_2$CH$_2$CH$_2$NH-$^c$Pr) and N-pyrrolidinylethyl (—CH$_2$CH$_2$N-pyrrolidinyl).

"Alkenyl" refers to an alkyl group, as defined herein, consisting of at least two carbon atoms and at least one carbon-carbon double bond. Typically, alkenyl groups have 2 to 20 carbon atoms ("C$_2$-C$_{20}$ alkenyl"), preferably 2 to 12 carbon atoms ("C$_2$-C$_{12}$ alkenyl"), more preferably 2 to 8 carbon atoms ("C$_2$-C$_8$ alkenyl"), or 2 to 6 carbon atoms ("C$_2$-C$_6$ alkenyl"), or 2 to 4 carbon atoms ("C$_2$-C$_4$ alkenyl"). Representative examples include, but are not limited to, ethenyl, 1-propenyl, 2-propenyl, 1-, 2-, or 3-butenyl, and the like. Alkenyl groups may be unsubstituted or substituted by the same groups that are described herein as suitable for alkyl.

"Alkynyl" refers to an alkyl group, as defined herein, consisting of at least two carbon atoms and at least one carbon-carbon triple bond. Alkynyl groups have 2 to 20 carbon atoms ("C$_2$-C$_{20}$ alkynyl"), preferably 2 to 12 carbon atoms ("C$_2$-C$_{12}$ alkynyl"), more preferably 2 to 8 carbon atoms ("C$_2$-C$_8$ alkynyl"), or 2 to 6 carbon atoms ("C$_2$-C$_6$ alkynyl"), or 2 to 4 carbon atoms ("C$_2$-C$_4$ alkynyl"). Representative examples include, but are not limited to, ethynyl, 1-propynyl, 2-propynyl, 1-, 2-, or 3-butynyl, and the like. Alkynyl groups may be unsubstituted or substituted by the same groups that are described herein as suitable for alkyl.

"Alkylene" as used herein refers to a divalent hydrocarbyl group having the specified number of carbon atoms which can link two other groups together. Sometimes it refers to a group —(CH$_2$)$_n$— where n is 1-8, and preferably n is 1-4. Where specified, an alkylene may also be substituted by other groups and may include one or more degrees of unsaturation (i.e., an alkenylene or alkynlene moiety) or rings. The open valences of an alkylene need not be at opposite ends of the chain. Thus branched alkylene groups such as —CH(Me)- and —C(Me)$_2$- are also included within the scope of the term 'alkylenes', as are cyclic groups such as cyclopropan-1,1-diyl and unsaturated groups such as ethylene (—CH=CH—) or propylene (—CH$_2$—CH=CH—). Where an alkylene group is described as optionally substituted, the substituents include those typically present on alkyl groups as described herein.

"Heteroalkylene" refers to an alkylene group as described above, wherein one or more non-contiguous carbon atoms of the alkylene chain are replaced by —N(R)—, —O— or —S(O)$^q$—, where R is H or $C_1$-$C_4$ alkyl and q is 0-2. For example, the group —O—$(CH_2)_{1-4}$— is a '$C_2$-$C_5$'-heteroalkylene group, where one of the carbon atoms of the corresponding alkylene is replaced by O.

"Alkoxy" refers to a monovalent —O-alkyl group, wherein the alkyl portion has the specified number of carbon atoms. Alkoxy groups typically contain 1 to 8 carbon atoms ("$C_1$-$C_8$ alkoxy"), or 1 to 6 carbon atoms ("$C_1$-$C_6$ alkoxy"), or 1 to 4 carbon atoms ("$C_1$-$C_4$ alkoxy"). For example, $C_1$-$C_4$ alkoxy includes —$OCH_3$, —$OCH_2CH_3$, —$OCH(CH_3)_2$, —$OC(CH_3)_3$, and the like. Such groups may also be referred to herein as methoxy, ethoxy, isopropoxy, tert-butyloxy, etc. Alkoxy groups may be unsubstituted or substituted on the alkyl portion by the same groups that are described herein as suitable for alkyl. In particular, alkoxy groups may be substituted by one or more halo groups, up to the total number of hydrogen atoms present on the alkyl portion. Thus, $C_1$-$C_4$ alkoxy includes halogenated alkoxy groups, e.g., trifluoromethoxy and 2,2-difluoroethoxy (i.e., —$OCF_3$ and —$OCH_2CHF_2$). In some instances, such groups may be referred to as "haloalkoxy" (or, where fluorinated, more specifically as "fluoroalkoxy") groups having the specified number of carbon atoms and substituted by one or more halo substituents, and typically contain 1-6 carbon atoms and 1, 2 or 3 halo atoms (i.e., "$C_1$-$C_6$ haloalkoxy") or sometimes 1-4 carbon atoms and 1, 2 or 3 halo atoms (i.e., "$C_1$-$C_4$ haloalkoxy"). Thus, a $C_1$-$C_4$ haloalkoxy group includes trifluoromethoxy (—$OCF_3$) and difluoromethoxy (—$OCF_2H$). More specifically, fluorinated alkyl groups may be specifically referred to as fluoroalkoxy groups, e.g., $C_1$-$C_6$ or $C_1$-$C_4$ fluoroalkoxy groups.

Similarly, "thioalkoxy" refers to a monovalent —S-alkyl group, wherein the alkyl portion has the specified number of carbon atoms, and may be optionally substituted on the alkyl portion by the same groups that are described herein as suitable for alkyl. For example, a $C_1$-$C_4$ thioalkoxy includes —$SCH_3$ and —$SCH_2CH_3$.

"Cycloalkyl" refers to a non-aromatic, saturated or partially unsaturated carbocyclic ring system containing the specified number of carbon atoms, which may be a monocyclic, bridged or fused bicyclic or polycyclic ring system that is connected to the base molecule through a carbon atom of the cycloalkyl ring. Typically, the cycloalkyl groups of the invention contain 3 to 12 carbon atoms ("$C_3$-$C_{12}$ cycloalkyl"), preferably 3 to 8 carbon atoms ("$C_3$-$C_8$ cycloalkyl"). Representative examples include, e.g., cyclopropane, cyclobutane, cyclopentane, cyclopentene, cyclohexane, cyclohexene, cyclohexadiene, cycloheptane, cycloheptatriene, adamantane, and the like. Cycloalkyl groups may be unsubstituted or substituted by the same groups that are described herein as suitable for alkyl.

Illustrative examples of cycloalkyl rings include, but are not limited to, the following:

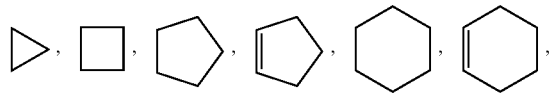

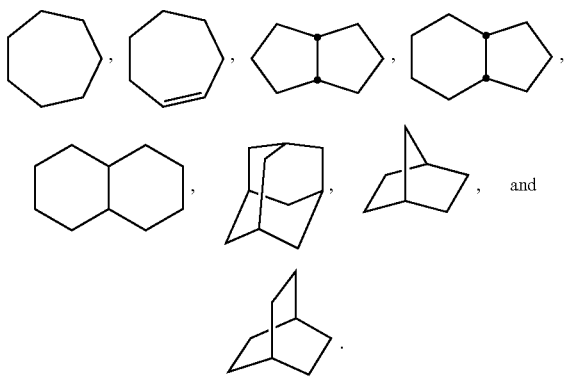

"Cycloalkylalkyl" may be used to describe a cycloalkyl ring, typically a $C_3$-$C_8$ cycloalkyl, which is connected to the base molecule through an alkylene linker, typically a $C_1$-$C_4$ alkylene. Cycloalkylalkyl groups are described by the total number of carbon atoms in the carbocyclic ring and linker, and typically contain from 4-12 carbon atoms ("$C_4$-$C_{12}$ cycloalkylalkyl"). Thus a cyclopropylmethyl group is a $C_4$-cycloalkylalkyl group and a cyclohexylethyl is a $C_8$-cycloalkylalkyl. Cycloalkylalkyl groups may be unsubstituted or substituted on the cycloalkyl and/or alkylene portions by the same groups that are described herein as suitable for alkyl groups.

The terms "heterocyclyl", "heterocyclic" or "heteroalicyclic" may be used interchangeably herein to refer to a non-aromatic, saturated or partially unsaturated ring system containing the specified number of ring atoms, including at least one heteroatom selected from N, O and S as a ring member, wherein the heterocyclic ring is connected to the base molecule via a ring atom, which may be C or N. Heterocyclic rings may be fused to one or more other heterocyclic or carbocyclic rings, which fused rings may be saturated, partially unsaturated or aromatic. Preferably, heterocyclic rings contain 1 to 4 heteroatoms selected from N, O, and S as ring members, and more preferably 1 to 2 ring heteroatoms, provided that such heterocyclic rings do not contain two contiguous oxygen atoms. Heterocyclyl groups may be unsubstituted or substituted by the same groups that are described herein as suitable for alkyl, aryl or heteroaryl. In addition, ring N atoms may be optionally substituted by groups suitable for an amine, e.g., alkyl, acyl, carbamoyl, sulfonyl substituents, etc., and ring S atoms may be optionally substituted by one or two oxo groups (i.e., $S(O)_q$, where q is 0, 1 or 2).

Preferred heterocycles include 3-12 membered heterocyclyl groups in accordance with the definition herein.

Illustrative examples of partially unsaturated heterocyclic groups include, but are not limited to:

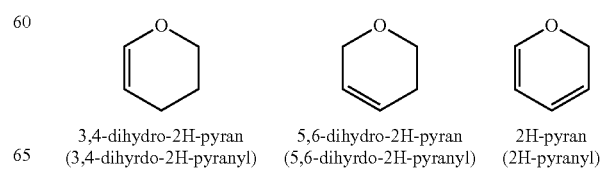

3,4-dihydro-2H-pyran (3,4-dihyrdo-2H-pyranyl)    5,6-dihydro-2H-pyran (5,6-dihyrdo-2H-pyranyl)    2H-pyran (2H-pyranyl)

-continued

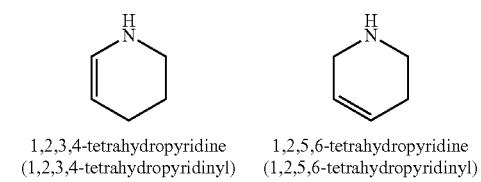

Illustrative examples of bridged and fused heterocyclic groups include, but are not limited to:

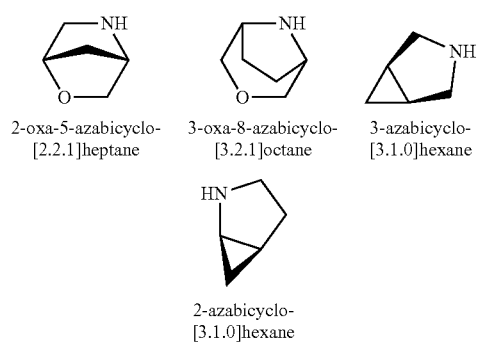

Illustrative examples of saturated heterocyclic groups include, but are not limited to:

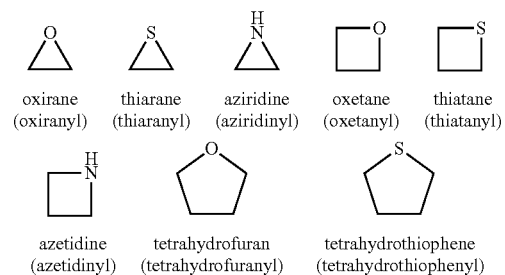

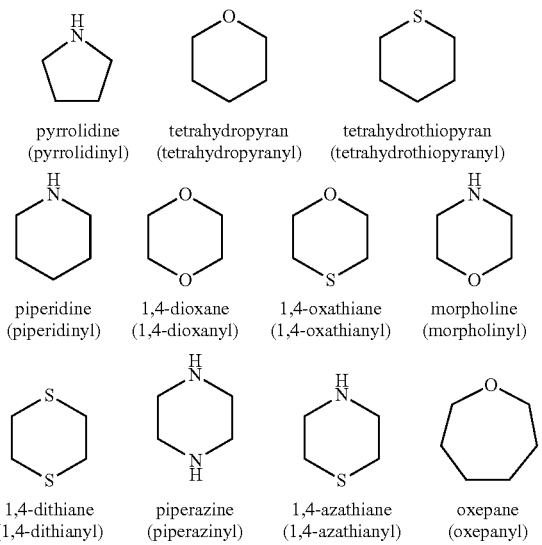

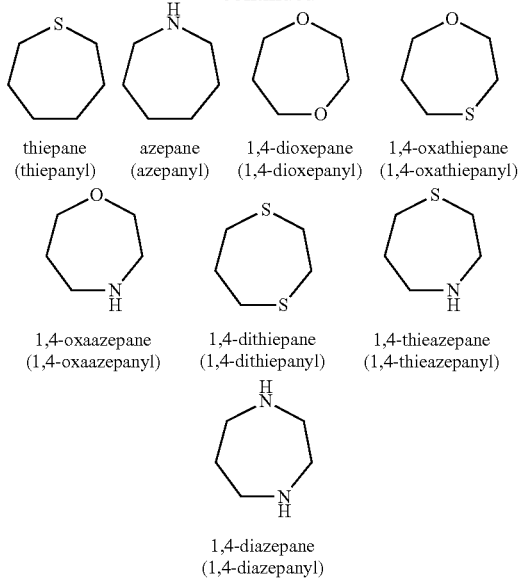

In frequent embodiments, heterocyclic groups contain 3-12 ring members, including both carbon and non-carbon heteroatoms, and preferably 4-6 ring members. In certain embodiments, substituent groups comprising 3-12 membered heterocycles are selected from the group consisting of azetidinyl, pyrrolidinyl, piperidinyl, piperazinyl, morpholinyl and thiomorpholinyl, each of which may be optionally substituted to the extent such substitution makes chemical sense. In other embodiments, substituent groups comprising 3-12 membered heterocycles are selected from the group consisting of oxetanyl, tetrahydrofuranyl and tetrahydropyranyl, each of which may be optionally substituted to the extent such substitution makes chemical sense. In particular embodiments, said 3-12 membered heterocycle is oxetanyl, optionally substituted to the extent such substitution makes chemical sense.

It is understood that no more than two N, O or S atoms are ordinarily connected sequentially except where an oxo group is attached to N or S to form a nitro or sulfonyl group, or in the case of certain heteroaromatic rings, such as triazine, triazole, tetrazole, oxadiazole, thiadiazole, and the like.

The term "heterocyclylalkyl" may be used to describe a heterocyclic group of the specified size that is connected to the base molecule through an alkylene linker of the specified length. Typically, such groups contain an optionally substituted 3-12 membered heterocycle attached to the base molecule through a $C_1$-$C_4$ alkylene linker. Where so indicated, such groups may be optionally substituted on the alkylene portion by the same groups that are described herein as suitable for alkyl groups and on the heterocyclic portion by groups described as suitable for heterocyclic rings.

"Aryl" or "aromatic" refer to an optionally substituted monocyclic, biaryl or fused bicyclic or polycyclic ring systems, having the well-known characteristics of aromaticity, wherein at least one ring contains a completely conjugated pi-electron system. Typically, aryl groups contain 6 to 20 carbon atoms ("$C_6$-$C_{20}$ aryl") as ring members, preferably 6 to 14 carbon atoms ("$C_6$-$C_{14}$ aryl") or more preferably, 6 to 12 carbon atoms ("$C_6$-$C_{12}$ aryl"). Fused aryl groups may include an aryl ring (e.g., a phenyl ring) fused to another aryl ring, or fused to a saturated or partially unsaturated carbocyclic or heterocyclic ring. The point of attachment to the base molecule on such fused aryl ring systems may be a C atom the aromatic portion or a C or N atom of the non-aromatic portion of the ring system. Examples, without limitation, of aryl groups include phenyl, biphenyl, naphthyl, anthracenyl, phenanthrenyl, indanyl, indenyl, and tetrahydronaphthyl. The aryl group may be unsubstituted or substituted as further described herein.

Similarly, "heteroaryl" or "heteroaromatic" refer to monocyclic, heterobiaryl or fused bicyclic or polycyclic ring systems having the well-known characteristics of aromaticity that contain the specified number of ring atoms and include at least one heteroatom selected from N, O and S as a ring member in an aromatic ring. The inclusion of a heteroatom permits aromaticity in 5-membered rings as well as 6-membered rings. Typically, heteroaryl groups contain 5 to 20 ring atoms ("5-20 membered heteroaryl"), preferably 5 to 14 ring atoms ("5-14 membered heteroaryl"), and more preferably 5 to 12 ring atoms ("5-12 membered heteroaryl"). Heteroaryl rings are attached to the base molecule via a ring atom of the heteroaromatic ring, such that aromaticity is maintained. Thus, 6-membered heteroaryl rings may be attached to the base molecule via a ring C atom, while 5-membered heteroaryl rings may be attached to the base molecule via a ring C or N atom. Examples of unsubstituted heteroaryl groups often include, but are not limited to, pyrrole, furan, thiophene, pyrazole, imidazole, isoxazole, oxazole, isothiazole, thiazole, triazole, oxadiazole, thiadiazole, tetrazole, pyridine, pyridazine, pyrimidine, pyrazine, benzofuran, benzothiophene, indole, benzimidazole, indazole, quinoline, isoquinoline, purine, triazine, naphthyridine and carbazole. In frequent preferred embodiments, 5- or 6-membered heteroaryl groups are selected from the group consisting of pyrrolyl, furanyl, thiophenyl, pyrazolyl, imidazolyl, isoxazolyl, oxazolyl, isothiazolyl, thiazolyl, triazolyl, pyridinyl, pyrimidinyl, pyrazinyl and pyridazinyl rings. The heteroaryl group may be unsubstituted or substituted as further described herein.

Aryl, heteroaryl and heterocyclyl moieties described herein as optionally substituted by may be substituted by one or more substituent groups, which are selected independently unless otherwise indicated. The total number of substituent groups may equal the total number of hydrogen atoms on the aryl, heteroaryl or heterocyclyl moiety, to the extent such substitution makes chemical sense and aromaticity is maintained in the case of aryl and heteroaryl rings. Optionally substituted aryl, heteroaryl or heterocyclyl groups typically contain from 1 to 5 optional substituents, sometimes 1 to 4 optional substituents, preferably 1 to 3 optional substituents, or more preferably 1-2 optional substituents.

Optional substituent groups suitable for aryl, heteroaryl and heterocyclyl rings include, but are not limited to: $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl and 5-12 membered heteroaryl; and halo, =O, —CN, —C(O)$R^x$, —CO$_2R^x$, —C(O)N$R^xR^y$, —$SR^x$, —$SOR^x$, —$SO_2R^x$, —$SO_2NR^xR^y$, —NO$_2$, —$NR^xR^y$, —$NR^xC(O)R^y$, —$NR^xC(O)NR^xR^y$, —$NR^xC(O)OR^x$, —$NR^xSO_2R^y$, —$NR^xSO_2NR^xR^y$, —$OR^x$, —$OC(O)R^x$ and —$OC(O)NR^xR^y$; where each $R^x$ and $R^y$ is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl, or $R^x$ and $R^y$ may be taken together with the N atom to which they are attached to form a 3-12 membered heterocyclyl or 5-12 membered heteroaryl, each optionally containing 1, 2 or 3 additional heteroatoms selected from O, N and S; each $R^x$ and $R^y$ is optionally substituted with 1 to 3 substituents independently selected from the group consisting of halo, =O, =S, =N—CN, =N—OR', =NR', —CN, —C(O)R', —CO$_2$R', —C(O)NR'$_2$, —SR', —SOR', —SO$_2$R', —SO$_2$NR'$_2$, —NO$_2$, —NR'$_2$, —NR'C(O)R', —NR'C(O)NR'$_2$, —NR'C(O)OR', —NR'SO$_2$R', —NR'SO$_2$NR'$_2$, —OR', —OC(O)R' and —OC(O)NR'$_2$, wherein each R' is independently H, $C_1$-$C_8$ alkyl, $C_1$-$C_8$ acyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl, or 5-12 membered heteroaryl; and each said $C_1$-$C_8$ alkyl, $C_2$-$C_8$ alkenyl, $C_2$-$C_8$ alkynyl, $C_3$-$C_8$ cycloalkyl, 3-12 membered heterocyclyl, $C_6$-$C_{12}$ aryl and 5-12 membered heteroaryl is optionally substituted as further defined herein.

In typical embodiments, optional substitution on aryl, heteroaryl and heterocyclyl rings includes one or more substituents, and preferably 1 to 3 substituents, independently selected from the group consisting of halo, $C_1$-$C_8$ alkyl, —OH, $C_1$-$C_8$ alkoxy, CN, =O, —C(O)$R^x$, —COOR$^x$, —OC(O)$R^x$, —C(O)N$R^xR^y$, —$NR^xC(O)R^y$, —$SR^x$, —$SOR^x$, —$SO_2R^x$, —$SO_2NR^xR^y$, —NO$_2$, —$NR^xR^y$, —$NR^xC(O)R^y$, —$NR^xC(O)NR^xR^y$, —$NR^xC(O)OR^y$—$NR^xSO_2R^y$, —$NR^xSO_2NR^xR^y$, —$OC(O)R^x$, —$OC(O)NR^xR^y$, $C_3$-$C_8$ cycloalkyl, 3-12 membered heterocyclyl, $C_6$-$C_{12}$ aryl, 5-12 membered heteroaryl, —O—($C_3$-$C_8$ cycloalkyl), —O-(3-12 membered heterocyclyl), —O—($C_6$-$C_{12}$ aryl) and —O-(5-12 membered heteroaryl); where each $R^x$ and $R^y$ is independently H or $C_1$-$C_4$ alkyl, or $R^x$ and $R^y$ may be taken together with the N to which they are attached form a 3-12 membered heterocyclyl or 5-12 membered heteroaryl ring, each optionally containing 1, 2 or 3 additional heteroatoms selected from O, N and S; and wherein each said $C_1$-$C_8$ alkyl, $C_1$-$C_8$ alkoxy, $C_3$-$C_8$ cycloalkyl, 3-12 membered heterocyclyl, $C_6$-$C_{12}$ aryl, 5-12 membered heteroaryl, —O—($C_3$-$C_8$ cycloalkyl), —O-(3-12 membered heterocyclyl), —O—($C_6$-$C_{12}$ aryl) and —O-(5-12 membered heteroaryl) that is described as an optional substituent or is part of $R^x$ or $R^y$ is optionally substituted by 1 to 3 substituents independently selected from the group consisting of halo, —OH, =O, $C_1$-$C_4$ alkyl, $C_1$-$C_4$ alkoxy, $C_1$-$C_6$ haloalkyl, $C_1$-$C_6$ hydroxyalkyl, $C_1$-$C_4$ alkoxy-$C_1$-$C_6$ alkyl, —CN, —NH$_2$, —NH($C_1$-$C_4$ alkyl), —N($C_1$-$C_4$ alkyl)$_2$ and N-pyrrolidinyl.

Illustrative examples of monocyclic heteroaryl groups include, but are not limited to:

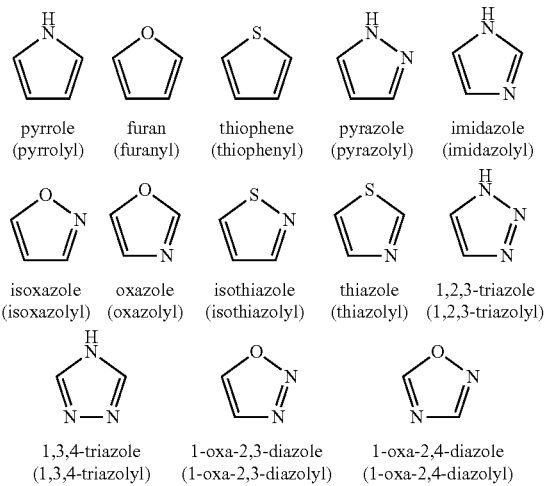

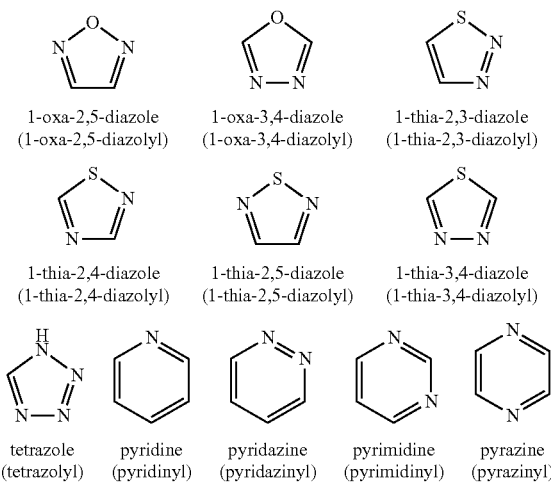

1-oxa-2,5-diazole (1-oxa-2,5-diazolyl)   1-oxa-3,4-diazole (1-oxa-3,4-diazolyl)   1-thia-2,3-diazole (1-thia-2,3-diazolyl)

1-thia-2,4-diazole (1-thia-2,4-diazolyl)   1-thia-2,5-diazole (1-thia-2,5-diazolyl)   1-thia-3,4-diazole (1-thia-3,4-diazolyl)

tetrazole (tetrazolyl)   pyridine (pyridinyl)   pyridazine (pyridazinyl)   pyrimidine (pyrimidinyl)   pyrazine (pyrazinyl)

Illustrative examples of fused ring heteroaryl groups include, but are not limited to:

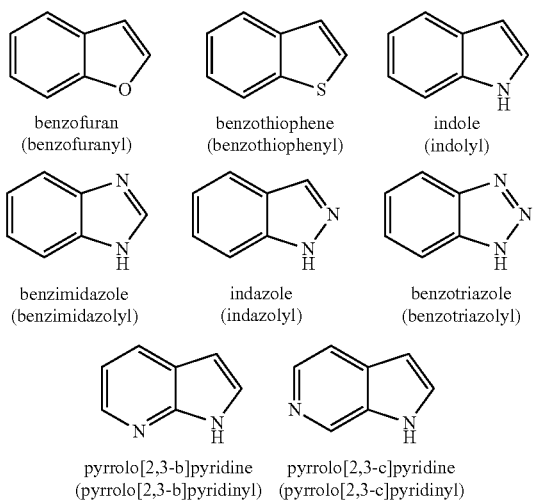

benzofuran (benzofuranyl)   benzothiophene (benzothiophenyl)   indole (indolyl)

benzimidazole (benzimidazolyl)   indazole (indazolyl)   benzotriazole (benzotriazolyl)

pyrrolo[2,3-b]pyridine (pyrrolo[2,3-b]pyridinyl)   pyrrolo[2,3-c]pyridine (pyrrolo[2,3-c]pyridinyl)

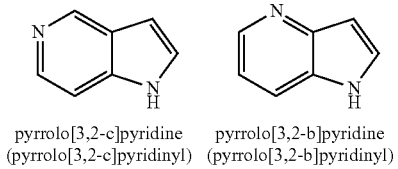

pyrrolo[3,2-c]pyridine (pyrrolo[3,2-c]pyridinyl)   pyrrolo[3,2-b]pyridine (pyrrolo[3,2-b]pyridinyl)

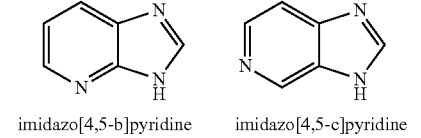

imidazo[4,5-b]pyridine (imidazo[4,5-b]pyridinyl)   imidazo[4,5-c]pyridine (imidazo[4,5-c]pyridinyl)

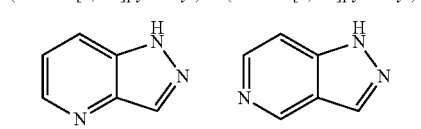

pyrazolo[4,3-d]pyridine (pyrazolo[4,3-d]pyridinyl)   pyrazolo[4,3-c]pyridine (pyrazolo[4,3-c]pyridinyl)

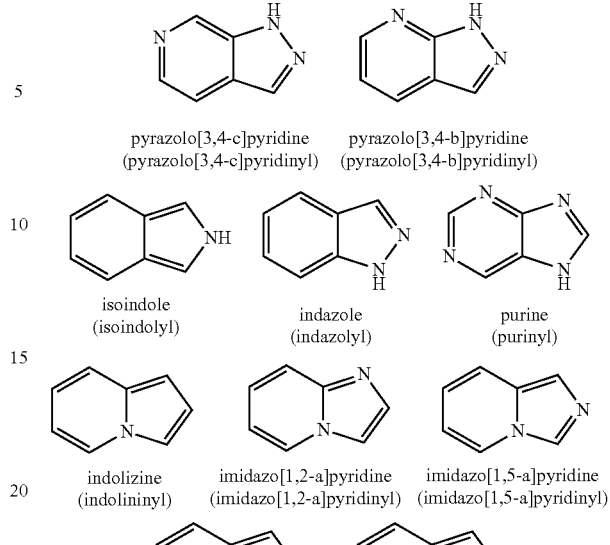

pyrazolo[3,4-c]pyridine (pyrazolo[3,4-c]pyridinyl)   pyrazolo[3,4-b]pyridine (pyrazolo[3,4-b]pyridinyl)

isoindole (isoindolyl)   indazole (indazolyl)   purine (purinyl)

indolizine (indolininyl)   imidazo[1,2-a]pyridine (imidazo[1,2-a]pyridinyl)   imidazo[1,5-a]pyridine (imidazo[1,5-a]pyridinyl)

pyrazolo[1,5-a]pyridine (pyrazolo[1,5-a]pyridinyl)   pyrrolo[1,2-b]pyridazine (imidazo[1,2-b]pyridazinyl)

imidazo[1,2-c]pyrimidine (imidazo[1,2-c]pyrimidinyl)   quinoline (quinolinyl)

isoquinoline (isoquinolinyl)   cinnoline (cinnolinyl)   quinazoline (azaquinazoline)

quinoxaline (quinoxalinyl)   phthalazine (phthalazinyl)   1,6-naphthyridine (1,6-naphthyridinyl)

1,7-naphthyridine (1,7-naphthyridinyl)   1,8-naphthyridine (1,8-naphthyridinyl)   1,5-naphthyridine (1,5-naphthyridinyl)

2,6-naphthyridine (2,6-naphthyridinyl)   2,7-naphthyridine (2,7-naphthyridinyl)

pyrido[3,2-d]pyrimidine (pyrido[3,2-d]pyrimidinyl)   pyrido[4,3-d]pyrimidine (pyrido[4,3-d]pyrimidinyl)

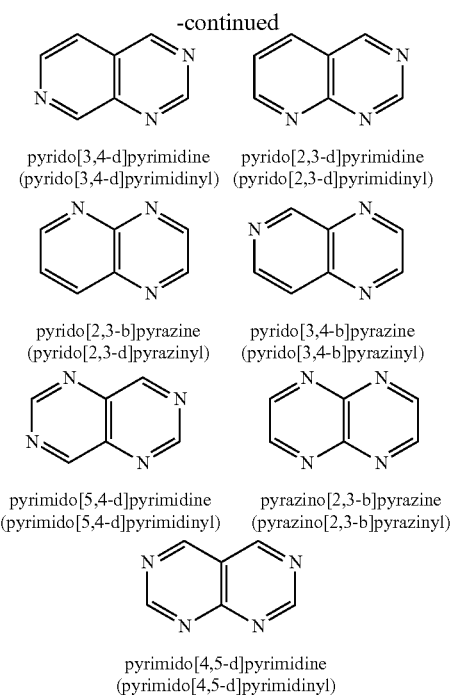

pyrido[3,4-d]pyrimidine (pyrido[3,4-d]pyrimidinyl)    pyrido[2,3-d]pyrimidine (pyrido[2,3-d]pyrimidinyl)

pyrido[2,3-b]pyrazine (pyrido[2,3-d]pyrazinyl)    pyrido[3,4-b]pyrazine (pyrido[3,4-b]pyrazinyl)

pyrimido[5,4-d]pyrimidine (pyrimido[5,4-d]pyrimidinyl)    pyrazino[2,3-b]pyrazine (pyrazino[2,3-b]pyrazinyl)

pyrimido[4,5-d]pyrimidine (pyrimido[4,5-d]pyrimidinyl)

An "arylalkyl" group refers to an aryl group as described herein which is linked to the base molecule through an alkylene or similar linker. Arylalkyl groups are described by the total number of carbon atoms in the ring and linker. Thus a benzyl group is a $C_7$-arylalkyl group and a phenylethyl is a $C_8$-arylalkyl. Typically, arylalkyl groups contain 7-16 carbon atoms ("$C_7$-$C_{16}$ arylalkyl"), wherein the aryl portion contains 6-12 carbon atoms and the alkylene portion contains 1-4 carbon atoms. Such groups may also be represented as —$C_1$-$C_4$ alkylene-$C_6$-$C_{12}$ aryl.

"Heteroarylalkyl" refers to a heteroaryl group as described above that is attached to the base molecule through an alkylene linker, and differs from "arylalkyl" in that at least one ring atom of the aromatic moiety is a heteroatom selected from N, O and S. Heteroarylalkyl groups are sometimes described herein according to the total number of non-hydrogen atoms (i.e., C, N, S and O atoms) in the ring and linker combined, excluding substituent groups. Thus, for example, pyridinylmethyl may be referred to as a "$C_7$"-heteroarylalkyl. Typically, unsubstituted heteroarylalkyl groups contain 6-20 non-hydrogen atoms (including C, N, S and O atoms), wherein the heteroaryl portion typically contains 5-12 atoms and the alkylene portion typically contains 1-4 carbon atoms. Such groups may also be represented as —$C_1$-$C_4$ alkylene-5-12 membered heteroaryl.

Similarly, "arylalkoxy" and "heteroarylalkoxy" refer to aryl and heteroaryl groups, attached to the base molecule through a heteroalkylene linker (i.e., —O-alkylene-), wherein the groups are described according to the total number of non-hydrogen atoms (i.e., C, N, S and O atoms) in the ring and linker combined. Thus, —O—$CH_2$-phenyl and —O—$CH_2$-pyridinyl groups would be referred to as $C_8$-arylalkoxy and $C_8$-heteroarylalkoxy groups, respectively.

Where an arylalkyl, arylalkoxy, heteroarylalkyl or heteroarylalkoxy group is described as optionally substituted, the substituents may be on either the divalent linker portion or on the aryl or heteroaryl portion of the group. The substituents optionally present on the alkylene or heteroalkylene portion are the same as those described above for alkyl or alkoxy groups generally, while the substituents optionally present on the aryl or heteroaryl portion are the same as those described above for aryl or heteroaryl groups generally.

"Hydroxy" refers to an —OH group.

"Acyloxy" refers to a monovalent group —OC(O)alkyl, wherein the alkyl portion has the specified number of carbon atoms (typically $C_1$-$C_8$, preferably $C_1$-$C_6$ or $C_1$-$C_4$) and may be optionally substituted by groups suitable for alkyl. Thus, $C_1$-$C_4$ acyloxy includes an —OC(O)$C_1$-$C_4$ alkyl substituent, e.g., —OC(O)$CH_3$.

"Acylamino" refers to a monovalent group, —NHC(O)alkyl or —NRC(O)alkyl, wherein the alkyl portion has the specified number of carbon atoms (typically $C_1$-$C_8$, preferably $C_1$-$C_6$ or $C_1$-$C_4$) and may be optionally substituted by groups suitable for alkyl. Thus, $C_1$-$C_4$ acylamino includes an —NHC(O)$C_1$-$C_4$ alkyl substituent, e.g., —NHC(O)$CH_3$.

"Aryloxy" or "heteroaryloxy" refer to optionally substituted —O-aryl or —O-heteroaryl, in each case where aryl and heteroaryl are as further defined herein.

"Arylamino" or "heteroarylamino" refer to optionally substituted —NH-aryl, —NR-aryl, —NH— heteroaryl or —NR-heteroaryl, in each case where aryl and heteroaryl are as further defined herein and R represents a substituent suitable for an amine, e.g., an alkyl, acyl, carbamoyl or sulfonyl group, or the like.

"Cyano" refers to a —C≡N group.

"Unsubstituted amino" refers to a group —$NH_2$. Where the amino is described as substituted or optionally substituted, the term includes groups of the form —$NR^xR^y$, where each or $R^x$ and $R^y$ is independently H, alkyl, alkenyl, alkynyl, cycloalkyl, heterocyclyl, acyl, thioacyl, aryl, heteroaryl, cycloalkylalkyl, arylalkyl or heteroarylalkyl, in each case having the specified number of atoms and optionally substituted as described herein. For example, "alkylamino" refers to a group —$NR^xR^y$, wherein one of $R^x$ and $R^y$ is an alkyl moiety and the other is H, and "dialkylamino" refers to —$NR^xR^y$ wherein both of $R^x$ and $R^y$ are alkyl moieties, where the alkyl moieties having the specified number of carbon atoms (e.g., —NH—$C_1$-$C_4$ alkyl or —N($C_1$-$C_4$ alkyl)$_2$). Typically, alkyl substituents on amines contain 1 to 8 carbon atoms, preferably 1 to 6 carbon atoms, or more preferably 1 to 4 carbon atoms. The term also includes forms wherein $R^x$ and $R^y$ are taken together with the N atom to which they are attached to form a 3-12 membered heterocyclyl or 5-12 membered heteroaryl ring, each of which may itself be optionally substituted as described herein for heterocyclyl or heteroaryl rings, and which may contain 1 to 3 additional heteroatoms selected from N, O and S as ring members, provided that such rings do not contain two contiguous oxygen atoms.

"Halogen" or "halo" refers to fluoro, chloro, bromo and iodo (F, Cl, Br, I). Preferably, halo refers to fluoro or chloro (F or Cl).

"Heteroform" is sometimes used herein to refer to a derivative of a group such as, e.g., an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Optional" or "optionally" means that the subsequently described event or circumstance may but need not occur, and the description includes instances where the event or circumstance occurs and instances in which it does not.

The terms "optionally substituted" and "substituted or unsubstituted" may be used interchangeably to indicate that the particular group being described may have no non-hydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described, to the extent that such substitution makes chemical sense. Where an optional substituent is attached via a double bond, such as an oxo (=O) substituent, the group occupies two available valences, so the total number of other substituents that may be included is reduced by two. In the case where optional substituents are selected independently from a list of alternatives, the selected groups may be the same or different.

In one aspect, the invention provides a compound of formula (I):

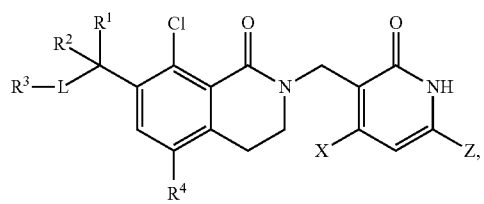

or a pharmaceutically acceptable salt thereof,
wherein:
$R^1$ is selected from the group consisting of H, F, $C_1$-$C_4$ alkyl, $C_1$-$C_4$ alkoxy, $C(O)R^5$, $C_3$-$C_8$ cycloalkyl, 3-12 membered heterocyclyl and 5-12 membered heteroaryl, where each said $C_1$-$C_4$ alkyl or $C_1$-$C_4$ alkoxy is optionally substituted by one or more $R^6$, and each said $C_3$-$C_8$ cycloalkyl, 3-12 membered heterocyclyl or 5-12 membered heteroaryl is optionally substituted by one or more $R^7$;
$R^2$ is H, F or $C_1$-$C_4$ alkyl;
L is a bond or a $C_1$-$C_4$ alkylene;
$R^3$ is selected from the group consisting of $C_1$-$C_4$ alkyl, $C_1$-$C_4$ alkoxy, OH, CN, $C(O)R^8$, $COOR^9$, $NR^{10}R^{11}$, $OR^{12}$, $C_3$-$C_8$ cycloalkyl, 3-12 membered heterocyclyl and 5-12 membered heteroaryl, where each said $C_1$-$C_4$ alkyl or $C_1$-$C_4$ alkoxy is optionally substituted by one or more $R^6$, and each said $C_3$-$C_8$ cycloalkyl, 3-12 membered heterocyclyl or 5-12 membered heteroaryl is optionally substituted by one or more $R^7$;
$R^4$ is H, halo or $C_1$-$C_4$ alkyl, where each said $C_1$-$C_4$ alkyl is optionally substituted by one or more $R^6$;
$R^5$ is $C_1$-$C_4$ alkyl, where each said $C_1$-$C_4$ alkyl is optionally substituted by one or more $R^{14}$;
each $R^6$ is independently OH, F, CN or $C_1$-$C_4$ alkoxy;
each $R^7$ is independently $C_1$-$C_4$ alkyl, OH, F, CN, $C_1$-$C_4$ alkoxy, =O, CHO, $C(O)R^{13}$, $SO_2R^{13}$ or 3-6 membered heterocyclyl;
$R^8$ is $C_1$-$C_4$ alkyl, where each said $C_1$-$C_4$ alkyl is optionally substituted by one or more $R^{14}$;
$R^9$ is H or $C_1$-$C_4$ alkyl, where each said $C_1$-$C_4$ alkyl is optionally substituted by one or more $R^{14}$;

$R^{10}$ and $R^{11}$ are independently H or $C_1$-$C_4$ alkyl, where each said $C_1$-$C_4$ alkyl is optionally substituted by one or more $R^{14}$;
$R^{12}$ is selected from the group consisting of $C_3$-$C_8$ cycloalkyl, 3-12 membered heterocyclyl and 5-12 membered heteroaryl, where each said $C_3$-$C_8$ cycloalkyl, 3-12 membered heterocyclyl or 5-12 membered heteroaryl is optionally substituted by one or more $R^7$;
each $R^{13}$ is independently $C_1$-$C_4$ alkyl, where each said $C_1$-$C_4$ alkyl is optionally substituted by one or more $R^{15}$;
each $R^{14}$ and $R^{15}$ is independently OH, F, CN or $C_1$-$C_4$ alkoxy; and
X and Z are independently $C_1$-$C_4$ alkyl, $C_1$-$C_4$ fluoroalkyl, $C_1$-$C_4$ alkoxy or $C_1$-$C_4$ fluoroalkoxy.

In some embodiments, the compound of Formula (I) has the absolute stereochemistry at the carbon atom bearing the $R^1$ and $R^2$ substituents as shown in Formula (I-A) or (I-B):

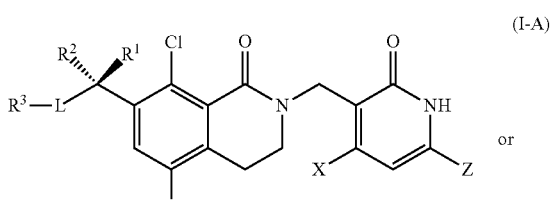

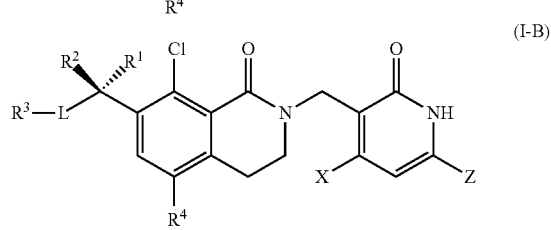

or a pharmaceutically acceptable salt thereof,
wherein:
$R^1$, $R^2$, L, $R^3$, $R^4$, X and Z are defined as for Formula (I).
Each of the aspects and embodiments described herein with respect to Formula (I) is also applicable to compounds of Formula (I-A) or (I-B).
In frequent embodiments of Formula (I), $R^2$ is H.
In frequent embodiments of Formula (I), $R^4$ is H, Cl, Br, F or $CH_3$. In some such embodiments, $R^4$ is H or Cl. In some embodiments, $R^4$ is H. In other embodiments, $R^4$ is Cl. In further embodiments, $R^4$ is Cl or Br.
In compounds of Formula (I), X and Z are independently $C_1$-$C_4$ alkyl, $C_1$-$C_4$ fluoroalkyl, $C_1$-$C_4$ alkoxy or $C_1$-$C_4$ fluoroalkoxy. In some embodiments, Z is $C_1$-$C_4$ alkyl, for example $CH_3$ or $C_2H_5$ (i.e., methyl or ethyl). In some embodiments, X is $C_1$-$C_4$ alkyl, $C_1$-$C_4$ fluoroalkyl, $C_1$-$C_4$ alkoxy. In specific embodiments, X is $CH_3$, $OCH_3$ or $OCHF_2$ (i.e., methyl, methoxy or difluoromethoxy). In further embodiments, X is $CH_3$, $OCH_3$ or $OCHF_2$, and Z is $CH_3$.
In some embodiments of Formula (I), $R^1$ is H or F.
In other embodiments of Formula (I), $R^1$ is $C_1$-$C_4$ alkyl or $C_1$-$C_4$ alkoxy, each optionally substituted by one or more $R^6$. In some such embodiments, said alkyl or alkoxy is substituted by at least one OH or CN. In specific embodiments, $R^1$ is $CH_3$, $C_2H_5$, $CH_2OH$, $CH_2CH_2OH$, $CH(OH)CH_3$ or $CH_2CN$ (i.e., methyl, ethyl, hydroxymethyl, 2-hydroxyethyl, 1-hydroxyethyl or cyanomethyl). In other specific embodiments, $R^1$ is $OCH_3$ (i.e., methoxy).
In other embodiments of Formula (I), $R^1$ is $C(O)R^5$, where $R^5$ is $C_1$-$C_4$ alkyl optionally substituted by one or more $R^{14}$. In some such embodiments, $R^5$ is $C_1$-$C_4$ alkyl optionally substituted by OH. In specific embodiments, $R^5$ is $CH_3$, $CH_2OH$, $CH_2CH_2OH$ or $CH(CH_3)OH$ such that $R^1$ is $C(O)CH_3$, $C(O)CH_2OH$, $C(O)CH_2CH_2OH$ or $C(O)CH(CH_3)OH$ (i.e., acetyl, α-hydroxyacetyl, 3-hydroxypropionyl or 2-hydroxypropionyl).

In still other embodiments of Formula (I), $R^1$ is $O3$-$C_8$ cycloalkyl, 3-12 membered heterocyclyl or 5-12 membered heteroaryl, where each said $C_3$-$C_8$ cycloalkyl, 3-12 membered heterocyclyl or 5-12 membered heteroaryl is optionally substituted by one or more $R^7$.

In some such embodiments, $R^1$ is $C_3$-$C_8$ cycloalkyl optionally substituted by one or more $R^7$. In some such embodiments, $R^1$ is cyclopropyl, cyclobutyl, cyclopentyl or cyclohexyl, each optionally substituted by one or more $R^7$.

In other embodiments, $R^1$ is 3-12 membered heterocyclyl optionally substituted by one or more $R^7$. In some such embodiments, said 3-12 membered heterocyclyl is selected from the group consisting of tetrahydrofuranyl, tetrahydropyranyl, tetrahydrothiophenyl, tetrahydrothiopyranyl, pyrrolidinyl, piperidinyl and morpholinyl, each optionally substituted by one or more $R^7$. In other such embodiments, said 3-12 membered heterocyclyl is selected from the group consisting of oxetanyl, tetrahydrofuranyl and tetrahydropyranyl, each optionally substituted by one or more $R^7$. In specific embodiments, said 3-12 membered heterocyclyl is oxetanyl optionally substituted by one or more $R^7$. In some such embodiments, said oxetanyl is unsubstituted.

In still other such embodiments, $R^1$ is 5-12 membered heteroaryl, where each said 5-12 membered heteroaryl is optionally substituted by one or more $R^7$. In some such embodiments, $R^1$ is a 5- or 6-membered heteroaryl. In specific embodiments, said 5- or 6-membered heteroaryl is selected from the group consisting of pyrazolyl, imidazolyl, isoxazolyl, oxazolyl, isothiazolyl, thiazolyl, and triazolyl groups, each optionally substituted by one or more $R^7$.

In certain embodiments, when $R^1$ is $C_3$-$C_8$ cycloalkyl, 3-12 membered heterocyclyl or 5-12 membered heteroaryl, each $R^7$ is independently $CH_3$, OH, F, CN, $OCH_3$, =O, CHO, $C(O)R^{13}$, $SO_2R^{13}$ or 3-6 membered heterocyclyl, where $R^{13}$ is $CH_3$ or $C_2H_5$ each optionally substituted by OH (e.g., $R^{13}$ is $CH_3$, $CH_2OH$, $CH_2CH_2OH$ or $CH(CH_3)OH$.

In compounds of Formula (I), L is a bond or a $C_1$-$C_4$ alkylene. In some embodiments of Formula (I), L is a bond. In other embodiments of Formula (I), L is a $C_1$-$C_4$ alkylene. In specific embodiments, L is a methylene or ethylene.

In compounds of Formula (I), $R^3$ is selected from the group consisting of $C_1$-$C_4$ alkyl, $C_1$-$C_4$ alkoxy, OH, CN, $C(O)R^8$, $COOR^9$, $NR^{10}R^{11}$, $OR^{12}$, $C_3$-$C_8$ cycloalkyl, 3-12 membered heterocyclyl and 5-12 membered heteroaryl, where each said $C_1$-$C_4$ alkyl or $C_1$-$C_4$ alkoxy is optionally substituted by one or more $R^6$, and each said $C_3$-$C_8$ cycloalkyl, 3-12 membered heterocyclyl or 5-12 membered heteroaryl is optionally substituted by one or more $R^7$.

In some embodiments, $R^3$ is $C_1$-$C_4$ alkyl, $C_1$-$C_4$ alkoxy or 3-12 membered heterocyclyl, each optionally substituted as described above. In some embodiments, $R^3$ is $C_1$-$C_4$ alkyl or $C_1$-$C_4$ alkoxy, in particular $CH_3$ or $OCH_3$ (i.e., methyl or methoxy).

In further embodiments, $R^3$ is 3-12 membered heterocyclyl optionally substituted by one or more $R^7$. In some such embodiments, said 3-12 membered heterocyclyl is selected from the group consisting of tetrahydrofuranyl, tetrahydropyranyl, tetrahydrothiophenyl, tetrahydrothiopyranyl, pyrrolidinyl, piperidinyl and morpholinyl, each optionally substituted by one or more $R^7$. In other such embodiments, said 3-12 membered heterocyclyl is selected from the group consisting of oxetanyl, tetrahydrofuranyl and tetrahydropyranyl, each optionally substituted by one or more $R^7$. In specific embodiments, said 3-12 membered heterocyclyl is oxetanyl, optionally substituted by one or more $R^7$. In some such embodiments, said oxetanyl is unsubstituted.

In further embodiments, L is a bond and $R^3$ is $C_1$-$C_4$ alkyl, $C_1$-$C_4$ alkoxy or 3-12 membered heterocyclyl, each optionally substituted as described above. In specific embodiments, L is a bond and $R^3$ is $C_1$-$C_4$ alkyl or $C_1$-$C_4$ alkoxy, in particular $CH_3$ or $OCH_3$ (i.e., methyl or methoxy).

In still further embodiments, L is a bond and $R^3$ is 3-12 membered heterocyclyl optionally substituted by one or more $R^7$. In some such embodiments, L is a bond and said 3-12 membered heterocyclyl is selected from the group consisting of tetrahydrofuranyl, tetrahydropyranyl, tetrahydrothiophenyl, tetrahydrothiopyranyl, pyrrolidinyl, piperidinyl and morpholinyl, each optionally substituted by one or more $R^7$. In other such embodiments, L is a bond and said 3-12 membered heterocyclyl is selected from the group consisting of oxetanyl, tetrahydrofuranyl and tetrahydropyranyl, each optionally substituted by one or more $R^7$. In specific embodiments, L is a bond and said 3-12 membered heterocyclyl is oxetanyl, optionally substituted by one or more $R^7$. In some such embodiments, said oxetanyl is unsubstituted.

In other such embodiments, L is a $C_1$-$C_4$ alkylene and $R^3$ is $C_1$-$C_4$ alkyl, $C_1$-$C_4$ alkoxy or 3-12 membered heterocyclyl, each optionally substituted as described above.

In still other embodiments, $R^3$ is OH, CN, $C(O)R^8$ or $COOR^9$, where $R^8$ is $C_1$-$C_4$ alkyl optionally substituted by one or more $R^{14}$, and $R^9$ is H or $C_1$-$C_4$ alkyl optionally substituted by one or more $R^{14}$.

In some such embodiments, L is a bond and $R^3$ is OH, CN, $C(O)R^8$ or $COOR^9$, where $R^8$ and $R^9$ are described as above.

In other embodiments, L is a $C_1$-$C_4$ alkylene and $R^3$ is OH, CN, $C(O)R^8$ or $COOR^9$ where $R^8$ and $R^9$ are described as above. In specific embodiments, L is a $C_1$-$C_4$ alkylene, for example methylene or ethylene, and $R^3$ is OH or CN.

In further embodiments, $R^3$ is $OR^{12}$, $C_3$-$C_8$ cycloalkyl, 3-12 membered heterocyclyl or 5-12 membered heteroaryl, where each said $C_3$-$C_8$ cycloalkyl, 3-12 membered heterocyclyl or 5-12 membered heteroaryl is optionally substituted by one or more $R^7$, and where $R^{12}$ is $C_3$-$C_8$ cycloalkyl, 3-12 membered heterocyclyl or 5-12 membered heteroaryl, each optionally substituted by one or more $R^7$.

In some such embodiments, L is a bond and $R^3$ is $OR^{12}$, $C_3$-$C_8$ cycloalkyl, 3-12 membered heterocyclyl or 5-12 membered heteroaryl, as described above. In other such embodiments, L is a $C_1$-$C_4$ alkylene and $R^3$ is $OR^{12}$, $C_3$-$C_8$ cycloalkyl, 3-12 membered heterocyclyl or 5-12 membered heteroaryl, as described above.

In compounds of Formula (I), each $R^6$ is independently OH, F, CN or $C_1$-$C_4$ alkoxy. In frequent embodiments, at least one $R^6$ is OH or F.

In compounds of Formula (I), each $R^7$ is independently $C_1$-$C_4$ alkyl, OH, F, CN, $C_1$-$C_4$ alkoxy, =O, CHO, $C(O)R^{13}$, $SO_2R^{13}$ or 3-6 membered heterocyclyl. In some embodiments, at least one $R^7$ is $C(O)R^{13}$, where $R^{13}$ is $C_1$-$C_4$ alkyl and said $C_1$-$C_4$ alkyl is optionally further substituted by one or more $R^{15}$. In some embodiments, at least one $R^7$ is $SO_2R^{13}$, where $R^{13}$ is $C_1$-$C_4$ alkyl and said $C_1$-$C_4$ alkyl is optionally further substituted by one or more $R^{15}$. In other specific embodiments, at least one $R^7$ is OH, F or $C_1$-$C_4$ alkyl, e.g., $CH_3$.

In specific embodiments, $R^1$ and/or $R^3$ is a 3-12 membered heterocyclyl substituted by one or more $R^7$, where at least one $R^7$ is CHO or $C(O)R^{13}$, and where $R^{13}$ is $CH_3$, $CH_2OH$ or $CH_2CN$, such that $R^7$ is CHO, $C(O)CH_3$, $C(O)CH_2OH$ or $C(O)CH_2CN$ (i.e., formyl, acetyl, hydroxyacetyl or cyanoacetyl, respectively).

In specific embodiments, $R^1$ and/or $R^3$ is a 3-12 membered heterocyclyl substituted by one or more $R^7$, where at least one $R^7$ is $SO_2R^{13}$, and where $R^{13}$ is $CH_3$, $CH_2OH$ or $CH_2CN$, such that $R^7$ is $SO_2CH_3$, $SO_2CH_2OH$ or $SO_2CH_2CN$.

In further specific embodiments, $R^1$ and/or $R^3$ is a 3-12 membered heterocyclyl substituted by one or more $R^7$, where at least one $R^7$ is OH.

In compounds of Formula (I), $R^8$ is $C_1$-$C_4$ alkyl, where each said $C_1$-$C_4$ alkyl is optionally substituted by one or more $R^{14}$.

In compounds of Formula (I), $R^9$ is H or $C_1$-$C_4$ alkyl, where each said $C_1$-$C_4$ alkyl is optionally substituted by one or more $R^{14}$. In some such embodiments, $R^9$ is H. In other such embodiments, $R^9$ is $C_1$-$C_4$ alkyl, optionally substituted as described above.

In compounds of Formula (I), $R^{10}$ and $R^{11}$ are independently H or $C_1$-$C_4$ alkyl, where each said $C_1$-$C_4$ alkyl is optionally substituted by one or more $R^{14}$.

Each $R^{14}$ and $R^{15}$ is independently OH, F, CN or $C_1$-$C_4$ alkoxy.

In one preferred embodiment, the invention provides a compound of Formula (I), (I-A) or (I-B), or a pharmaceutically acceptable salt thereof, wherein:
$R^1$ is 3-12 membered heterocyclyl or 5-12 membered heteroaryl, where each said 3-12 membered heterocyclyl or 5-12 membered heteroaryl is optionally substituted by one or more $R^7$;
$R^2$ is H;
L is $C_1$-$C_4$ alkylene;
$R^3$ is OH or CN;
$R^4$ is H or Cl;
each $R^7$ is independently $C_1$-$C_4$ alkyl, OH, F, CN, $C_1$-$C_4$ alkoxy, =O, CHO, $C(O)R^{13}$, $SO_2R^{13}$ or 3-6 membered heterocyclyl;
each $R^{13}$ is independently $C_1$-$C_4$ alkyl, where each said $C_1$-$C_4$ alkyl is optionally substituted by one or more $R^{15}$;
each $R^{15}$ is independently OH, F, CN or $C_1$-$C_4$ alkoxy; and
X and Z are independently $C_1$-$C_4$ alkyl, $C_1$-$C_4$ fluoroalkyl, $C_1$-$C_4$ alkoxy or $C_1$-$C_4$ fluoroalkoxy.

In another preferred embodiment, the invention provides a compound of Formula (I), (I-A) or (I-B), or a pharmaceutically acceptable salt thereof, wherein:
$R^1$ is H or $C_1$-$C_4$ alkyl, where said $C_1$-$C_4$ alkyl is optionally substituted by one or more $R^6$;
$R^2$ is H;
L is a bond or $C_1$-$C_4$ alkylene;
$R^3$ is selected from the group consisting of $C_1$-$C_4$ alkyl, OH, CN, $C(O)R^8$, $COOR^9$, $NR^{10}R^{11}$, $C_3$-$C_8$ cycloalkyl, 3-12 membered heterocyclyl and 5-12 membered heteroaryl, where each said $C_1$-$C_4$ alkyl is optionally substituted by one or more $R^6$, and each said $C_3$-$C_8$ cycloalkyl, 3-12 membered heterocyclyl or 5-12 membered heteroaryl is optionally substituted by one or more $R^7$;
$R^4$ is H or Cl;
each $R^6$ is independently OH, F, CN or $C_1$-$C_4$ alkoxy;
each $R^7$ is independently $C_1$-$C_4$ alkyl, OH, F, CN, $C_1$-$C_4$ alkoxy, =O, CHO, $C(O)R^{13}$, $SO_2R^{13}$ or 3-6 membered heterocyclyl;
$R^8$ is $C_1$-$C_4$ alkyl, where each said $C_1$-$C_4$ alkyl is optionally substituted by one or more $R^{14}$;
$R^9$ is H or $C_1$-$C_4$ alkyl, where each said $C_1$-$C_4$ alkyl is optionally substituted by one or more $R^{14}$;
$R^{10}$ and $R^{11}$ are independently H or $C_1$-$C_4$ alkyl, where each said $C_1$-$C_4$ alkyl is optionally substituted by one or more $R^{14}$;
each $R^{13}$ is independently $C_1$-$C_4$ alkyl, where each said $C_1$-$C_4$ alkyl is optionally substituted by one or more $R^{15}$;
each $R^{14}$ and $R^{15}$ is independently OH, F, CN or $C_1$-$C_4$ alkoxy; and
X and Z are independently $C_1$-$C_4$ alkyl, $C_1$-$C_4$ fluoroalkyl, $C_1$-$C_4$ alkoxy or $C_1$-$C_4$ fluoroalkoxy.

In another preferred embodiment, the invention provides a compound of Formula (I), (I-A) or (I-B), or a pharmaceutically acceptable salt thereof, wherein:
$R^1$ is $C_1$-$C_4$ alkoxy, where said $C_1$-$C_4$ alkoxy is optionally substituted by one or more $R^6$;
$R^2$ is H;
L is a bond or a $C_1$-$C_4$ alkylene;
$R^3$ is selected from the group consisting of $C_1$-$C_4$ alkyl, OH, $C(O)R^8$ and 3-12 membered heterocyclyl, where each said $C_1$-$C_4$ alkyl is optionally substituted by one or more $R^6$, and each said 3-12 membered heterocyclyl is optionally substituted by one or more $R^7$;
$R^4$ is H or Cl;
each $R^6$ is independently OH, F, CN or $C_1$-$C_4$ alkoxy;
each $R^7$ is independently $C_1$-$C_4$ alkyl, OH, F, CN, $C_1$-$C_4$ alkoxy, =O, CHO, $C(O)R^{13}$, $SO_2R^{13}$ or 3-6 membered heterocyclyl;
$R^8$ is $C_1$-$C_4$ alkyl, where each said $C_1$-$C_4$ alkyl is optionally substituted by one or more $R^{14}$;
each $R^{13}$ is independently $C_1$-$C_4$ alkyl, where each said $C_1$-$C_4$ alkyl is optionally substituted by one or more $R^{15}$;
each $R^{14}$ and $R^{15}$ is independently OH, F, CN or $C_1$-$C_4$ alkoxy; and
X and Z are independently $C_1$-$C_4$ alkyl, $C_1$-$C_4$ fluoroalkyl, $C_1$-$C_4$ alkoxy or $C_1$-$C_4$ fluoroalkoxy.

In another preferred embodiment, the invention provides a compound of Formula (I), (I-A) or (I-B), or a pharmaceutically acceptable salt thereof, wherein:
$R^1$ is $C_1$-$C_4$ alkyl, where said $C_1$-$C_4$ alkyl is optionally substituted by one or more $R^6$;
$R^2$ is H;
L is a bond or a $C_1$-$C_4$ alkylene;
$R^3$ is $OR^{12}$;
$R^4$ is H or Cl;
each $R^6$ is independently OH, F, CN or $C_1$-$C_4$ alkoxy;
each $R^7$ is independently $C_1$-$C_4$ alkyl, OH, F, CN, $C_1$-$C_4$ alkoxy, =O, CHO, $C(O)R^{13}$, $SO_2R^{13}$ or 3-6 membered heterocyclyl;
$R^{12}$ is selected from the group consisting of $C_3$-$C_8$ cycloalkyl, 3-12 membered heterocyclyl and 5-12 membered heteroaryl, where each said $C_3$-$C_8$ cycloalkyl, 3-12 membered heterocyclyl or 5-12 membered heteroaryl is optionally substituted by one or more $R^7$;
each $R^{13}$ is independently $C_1$-$C_4$ alkyl, where each said $C_1$-$C_4$ alkyl is optionally substituted by one or more $R^{15}$;
each $R^{15}$ is independently OH, F, CN or $C_1$-$C_4$ alkoxy; and
X and Z are independently $C_1$-$C_4$ alkyl, $C_1$-$C_4$ fluoroalkyl, $C_1$-$C_4$ alkoxy or $C_1$-$C_4$ fluoroalkoxy.

In another preferred embodiment, the invention provides a compound of Formula (I), (I-A) or (I-B), or a pharmaceutically acceptable salt thereof, wherein:
$R^1$ is $C_1$-$C_4$ alkoxy;
$R^2$ is H;
L is a bond;

$R^3$ is 3-12 membered heterocyclyl, preferably selected from the group consisting of oxetanyl, tetrahydrofuranyl and tetrahydropyranyl, each optionally substituted by one or more $R^7$;

$R^4$ is H or Cl;

each $R^7$ is independently $C_1$-$C_4$ alkyl, OH, F, CN, $C_1$-$C_4$ alkoxy, =O, CHO, C(O)$R^{13}$, SO$_2$$R^{13}$ or 3-6 membered heterocyclyl;

each $R^{13}$ is independently $C_1$-$C_4$ alkyl, where each said $C_1$-$C_4$ alkyl is optionally substituted by one or more $R^{15}$;

each $R^{15}$ is independently OH, F, CN or $C_1$-$C_4$ alkoxy; and

X and Z are independently $C_1$-$C_4$ alkyl, $C_1$-$C_4$ fluoroalkyl, $C_1$-$C_4$ alkoxy or $C_1$-$C_4$ fluoroalkoxy.

In another preferred embodiment, the invention provides a compound of Formula (I), (I-A) or (I-B), or a pharmaceutically acceptable salt thereof, wherein:

$R^1$ is 3-12 membered heterocyclyl, preferably selected from the group consisting of oxetanyl, tetrahydrofuranyl and tetrahydropyranyl, each optionally substituted by one or more $R^7$;

$R^2$ is H;

L is a bond;

$R^3$ is $C_1$-$C_4$ alkoxy, optionally substituted by one or more $R^6$, $R^4$ is H or Cl;

each $R^6$ is independently OH, F, CN or $C_1$-$C_4$ alkoxy;

each $R^7$ is independently $C_1$-$C_4$ alkyl, OH, F, CN, $C_1$-$C_4$ alkoxy, =O, CHO, C(O)$R^{13}$, SO$_2$$R^{13}$ or 3-6 membered heterocyclyl;

each $R^{13}$ is independently $C_1$-$C_4$ alkyl, where each said $C_1$-$C_4$ alkyl is optionally substituted by one or more $R^{15}$;

each $R^{15}$ is independently OH, F, CN or $C_1$-$C_4$ alkoxy; and

X and Z are independently $C_1$-$C_4$ alkyl, $C_1$-$C_4$ fluoroalkyl, $C_1$-$C_4$ alkoxy or $C_1$-$C_4$ fluoroalkoxy.

In another aspect, the invention provides a compound of formula (II), (II-A) or (II-B):

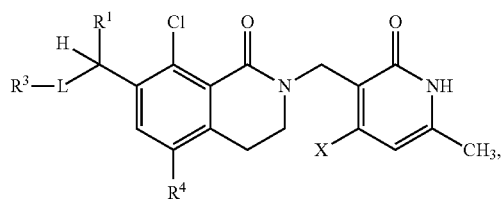

(II)

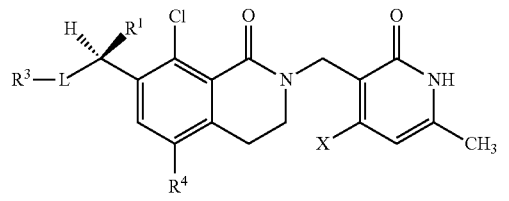

(II-A)

or

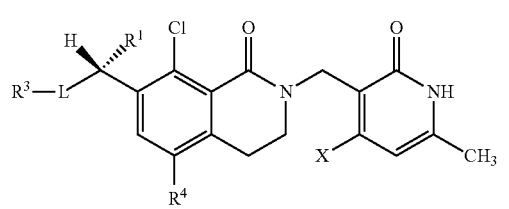

(II-B)

or a pharmaceutically acceptable salt thereof, wherein:

$R^1$, L, $R^3$ and X are defined as for Formula (I); and $R^4$ is H, Cl, Br, F or CH$_3$.

The embodiments described herein for Formula (I), (I-A) and (I-B) are also applicable to compounds of Formulae (II), (II-A) and (II-B) to the extent they are not inconsistent.

In a further aspect, the invention provides a compound of formula (III):

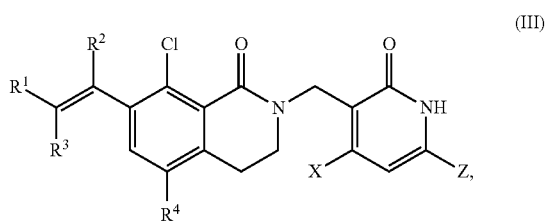

(III)

or a pharmaceutically acceptable salt thereof, wherein:

$R^1$ and $R^3$ are taken together to form a 3-12 membered heterocyclyl optionally substituted by one or more $R^7$;

$R^2$ is H, F or $C_1$-$C_4$ alkyl;

$R^4$ is H, halo or $C_1$-$C_4$ alkyl, where each said $C_1$-$C_4$ alkyl is optionally substituted by one or more $R^6$;

each $R^6$ is independently OH, F, CN or $C_1$-$C_4$ alkoxy;

each $R^7$ is independently $C_1$-$C_4$ alkyl, OH, F, CN, $C_1$-$C_4$ alkoxy, =O, CHO, C(O)$R^{13}$, SO$_2$$R^{13}$ or 3-6 membered heterocyclyl;

each $R^{13}$ is independently $C_1$-$C_4$ alkyl, where each said $C_1$-$C_4$ alkyl is optionally substituted by one or more $R^{15}$;

each $R^{15}$ is independently OH, F, CN or $C_1$-$C_4$ alkoxy; and

X and Z are independently $C_1$-$C_4$ alkyl, $C_1$-$C_4$ fluoroalkyl, $C_1$-$C_4$ alkoxy or $C_1$-$C_4$ fluoroalkoxy.

In some embodiments of Formula (III), $R^2$ is F or CH$_3$.

In compounds of Formula (III), $R^1$ and $R^3$ are taken together to form a 3-12 membered heterocyclyl optionally substituted by one or more $R^7$. In some such embodiments, said 3-12 membered heterocyclyl is selected from the group consisting of azetidinyl, pyrrolidinyl, piperidinyl and homopiperidinyl, each optionally substituted by one or more $R^7$. In other such embodiments, said 3-12 membered heterocyclyl is selected from the group consisting of oxetanyl, tetrahydrofuranyl and tetrahydropyranyl, each optionally substituted by one or more $R^7$.

In compounds of Formula (III), each $R^7$ is independently $C_1$-$C_4$ alkyl, OH, F, CN, $C_1$-$C_4$ alkoxy, =O, CHO, C(O)$R^{13}$, SO$_2$$R^{13}$ or 3-6 membered heterocyclyl. In some embodiments, $R^7$ is CHO, C(O)$R^{13}$ or SO$_2$$R^{13}$, where each $R^{13}$ is independently $C_1$-$C_4$ alkyl optionally substituted by one or more $R^{15}$. In some such embodiments, $R^{13}$ is $C_1$-$C_4$ alkyl optionally substituted by one or more $R^{15}$ and each $R^{15}$ is independently OH, F, CN or $C_1$-$C_4$ alkoxy. In particular embodiments, $R^{13}$ is $C_1$-$C_4$ alkyl optionally substituted by OH. In specific embodiments, $R^{13}$ is CH$_3$ or CH$_2$OH, such that $R^7$ is C(O)CH$_3$, C(O)CH$_2$OH, SO$_2$CH$_3$ or SO$_2$CH$_2$OH (i.e., acetyl, α-hydroxyacetyl, methylsulfonyl or α-hydroxymethylsulfonyl).

In some embodiments, $R^4$ is H, CH$_3$ or Cl.

In some embodiments, Z is CH$_3$.

In some embodiments, X is CH$_3$ or OCH$_3$.

In a preferred embodiment, the invention provides a compound of Formula (III), or a pharmaceutically acceptable salt thereof, wherein:

$R^2$ is F or $CH_3$;
$R^1$ and $R^3$ are taken together to form a 3-12 membered heterocyclyl, each optionally substituted by one or more $R^7$;
$R^4$ is H, $CH_3$ or Cl;
Z is $CH_3$; and
X is $CH_3$ or $OCH_3$.

In another preferred embodiment, the invention provides a compound of Formula (III), or a pharmaceutically acceptable salt thereof, wherein:

$R^2$ is F or $CH_3$;
$R^1$ and $R^3$ are taken together to form a 3-12 membered heterocyclyl selected from the group consisting of azetidinyl, pyrrolidinyl, piperidinyl and homopiperidinyl, each optionally substituted by one or more $R^7$;
$R^4$ is H, $CH_3$ or Cl;
$R^7$ is $C(O)R^{13}$ or $SO_2R^{13}$;
each $R^{13}$ is independently $C_1$-$C_4$ alkyl optionally substituted by one or more $R^{15}$;
each $R^{15}$ is independently OH, F, CN or $C_1$-$C_4$ alkoxy;
Z is $CH_3$; and
X is $CH_3$ or $OCH_3$.

In another aspect, the invention provides a compound of formula (I'):

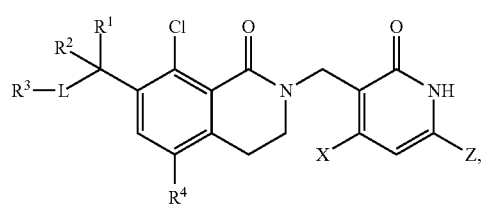

(I')

or a pharmaceutically acceptable salt thereof,
wherein:
$R^1$ is selected from the group consisting of H, F, $C_1$-$C_4$ alkyl, $C_1$-$C_4$ alkoxy, $C(O)R^5$, $C_3$-$C_8$ cycloalkyl, 3-12 membered heterocyclyl and 5-12 membered heteroaryl, where each said $C_1$-$C_4$ alkyl or $C_1$-$C_4$ alkoxy is optionally substituted by one or more $R^6$, and each said $C_3$-$C_8$ cycloalkyl, 3-12 membered heterocyclyl or 5-12 membered heteroaryl is optionally substituted by one or more $R^7$;
$R^2$ is H, F or $C_1$-$C_4$ alkyl;
L is a bond or a $C_1$-$C_4$ alkylene;
$R^3$ is selected from the group consisting of $C_1$-$C_4$ alkyl, $C_1$-$C_4$ alkoxy, OH, CN, $C(O)R^8$, $COOR^9$, $NR^{10}R^{11}$, $OR^{12}$, $C_3$-$C_8$ cycloalkyl, 3-12 membered heterocyclyl and 5-12 membered heteroaryl, where each said $C_1$-$C_4$ alkyl or $C_1$-$C_4$ alkoxy is optionally substituted by one or more $R^6$, and each said $C_3$-$C_8$ cycloalkyl, 3-12 membered heterocyclyl or 5-12 membered heteroaryl is optionally substituted by one or more $R^7$;
$R^4$ is H, halo or $C_1$-$C_4$ alkyl, where each said $C_1$-$C_4$ alkyl is optionally substituted by one or more $R^6$;
$R^5$ is $C_1$-$C_4$ alkyl, where each said $C_1$-$C_4$ alkyl is optionally substituted by one or more $R^{14}$;
each $R^6$ is independently OH, F, CN or $C_1$-$C_4$ alkoxy;
each $R^7$ is independently $C_1$-$C_4$ alkyl, OH, F, CN, $C_1$-$C_4$ alkoxy, =O or $C(O)R^{13}$;
$R^8$ is $C_1$-$C_4$ alkyl, where each said $C_1$-$C_4$ alkyl is optionally substituted by one or more $R^{14}$;

$R^9$ is H or $C_1$-$C_4$ alkyl, where each said $C_1$-$C_4$ alkyl is optionally substituted by one or more $R^{14}$;
$R^{10}$ and $R^{11}$ are independently H or $C_1$-$C_4$ alkyl, where each said $C_1$-$C_4$ alkyl is optionally substituted by one or more $R^{14}$;
$R^{12}$ is selected from the group consisting of $C_3$-$C_8$ cycloalkyl, 3-12 membered heterocyclyl and 5-12 membered heteroaryl, where each said $C_3$-$C_8$ cycloalkyl, 3-12 membered heterocyclyl or 5-12 membered heteroaryl is optionally substituted by one or more $R^7$;
each $R^{13}$ is independently H or $C_1$-$C_4$ alkyl, where each said $C_1$-$C_4$ alkyl is optionally substituted by one or more $R^{15}$;
each $R^{14}$ and $R^{15}$ is independently OH, F, CN or $C_1$-$C_4$ alkoxy; and
X and Z are independently $C_1$-$C_4$ alkyl, $C_1$-$C_4$ fluoroalkyl, $C_1$-$C_4$ alkoxy or $C_1$-$C_4$ fluoroalkoxy.

In some embodiments, the compound of Formula (I') has the absolute stereochemistry at the carbon atom bearing the $R^1$ and $R^2$ substituents as shown in Formula (I-A') or (I-B'):

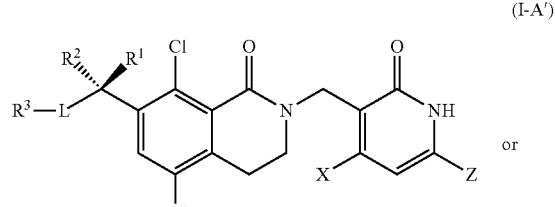

(I-A')

or

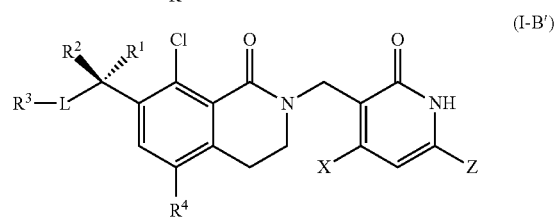

(I-B')

or a pharmaceutically acceptable salt thereof,
wherein:
$R^1$, $R^2$, L, $R^3$, $R^4$, X and Z are defined as for Formula (I).

The embodiments described herein for Formula (I), (I-A) and (I-B) are also applicable to compounds of Formulae (I'), (I-A') and (I-B') to the extent they are not inconsistent.

In another aspect, the invention provides a compound of Formula (II'), (II-A') or (II-B'):

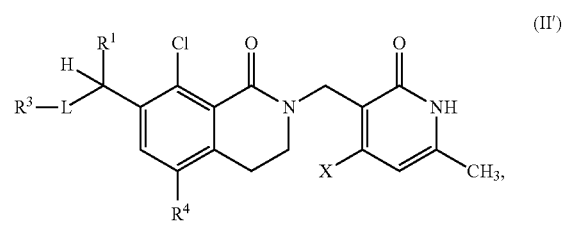

(II')

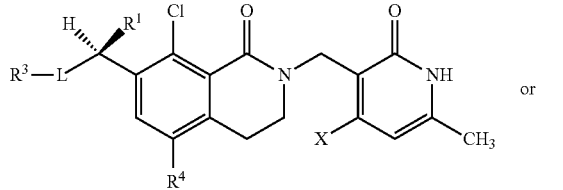

(II-A')

or (II-B')

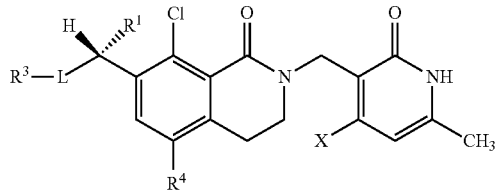

or a pharmaceutically acceptable salt thereof,
wherein:
$R^1$, L, $R^3$ and X are defined as for Formula (I'); and
$R^4$ is H, Cl, Br, F or $CH_3$.

The embodiments described herein for Formula (I), (I-A) and (I-B) are also applicable to compounds of Formulae (II'), (II-A') and (II-B') to the extent they are not inconsistent.

A "pharmaceutical composition" refers to a mixture of one or more of the compounds described herein, or a pharmaceutically acceptable salt, solvate, hydrate or prodrug thereof as an active ingredient, and at least one pharmaceutically acceptable carrier or excipient.

In another aspect the invention provides a pharmaceutical composition comprising a compound of one of the formulae described herein, or a pharmaceutically acceptable salt thereof, and a pharmaceutically acceptable carrier or excipient. In some embodiments, the pharmaceutical composition comprises two or more pharmaceutically acceptable carriers and/or excipients.

In some embodiments, the pharmaceutical composition may further comprise at least one additional an anti-cancer therapeutic agent or a palliative agent. In some such embodiments, the at least one additional medicinal or pharmaceutical agent is an anti-cancer agent as described below. In some such embodiments, the combination provides an additive, greater than additive, or synergistic anti-cancer effect. In some such embodiments, the one or more anti-cancer therapeutic agent is selected from the group consisting of anti-tumor agents, anti-angiogenesis agents, signal transduction inhibitors and antiproliferative agents.

In one aspect, the invention provides a method for the treatment of abnormal cell growth in a subject comprising administering to the subject a therapeutically effective amount of a compound of the invention, or a pharmaceutically acceptable salt thereof.

In some embodiments, the methods described herein further comprise administering to the subject an amount of an anti-cancer therapeutic agent or a palliative agent, which amounts are together effective in treating said abnormal cell growth. In some embodiments, the one or more anti-cancer therapeutic agent are selected from anti-tumor agents, anti-angiogenesis agents, signal transduction inhibitors and anti-proliferative agents, which amounts are together effective in treating said abnormal cell growth. In some such embodiments, the anti-tumor agent is selected from the group consisting of mitotic inhibitors, alkylating agents, antimetabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

In frequent embodiments of the methods provided herein, the abnormal cell growth is cancer. In some embodiments, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

In another aspect, the invention provides a method for the treatment of a disorder mediated by EZH2 in a subject comprising administering to the subject a compound of the invention, or a pharmaceutically acceptable salt thereof, in an amount that is effective for treating said disorder.

Unless indicated otherwise, all references herein to the inventive compounds include references to salts, solvates, hydrates and complexes thereof, and to solvates, hydrates and complexes of salts thereof, including polymorphs, stereoisomers, and isotopically labeled versions thereof.

Compounds of the invention may exist in the form of pharmaceutically acceptable salts such as, e.g., acid addition salts and base addition salts of the compounds of one of the formulae provided herein. As used herein, the term "pharmaceutically acceptable salt" refers to those salts which retain the biological effectiveness and properties of the parent compound. The phrase "pharmaceutically acceptable salt(s)", as used herein, unless otherwise indicated, includes salts of acidic or basic groups which may be present in the compounds of the formulae disclosed herein.

For example, the compounds of the invention that are basic in nature may be capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention may be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt may also be precipitated from a solution of the free base in an organic solvent by adding an appropriate mineral or organic acid to the solution.

The acids that may be used to prepare pharmaceutically acceptable acid addition salts of such basic compounds of those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate and pamoate [i.e., 1,1'-methylene-bis-(2-hydroxy-3-naphthoate)] salts.

Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methane-sulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The compounds of the invention that include a basic moiety, such as an amino group, may form pharmaceutically acceptable salts with various amino acids, in addition to the acids mentioned above.

Those compounds of the invention that are acidic in nature may be capable of forming base salts with various pharmacologically acceptable cations. Examples of such salts include the alkali metal or alkaline-earth metal salts and particularly, the sodium and potassium salts. These salts may be prepared by conventional techniques. The chemical bases which may be used as reagents to prepare the pharmaceutically acceptable base salts of this invention include those which form non-toxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts may also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents may be employed in order to ensure completeness of reaction and maximum yields of the desired final product.

The chemical bases that may be used as reagents to prepare pharmaceutically acceptable base salts of the compounds of the invention that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts are known to those of skill in the art.

Salts of the present invention may be prepared according to methods known to those of skill in the art. A pharmaceutically acceptable salt of the inventive compounds may be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

It will be understood by those of skill in the art that the compounds of the invention in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at a temperature of between about 0° C. and 100° C. The free base form may be isolated by conventional means, such as extraction with an organic solvent. In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt. This conversion is typically carried out at a temperature between about 0° C. and the boiling point of the solvent being used as the medium for the procedure. Similar exchanges are possible with base addition salts, typically via the intermediacy of the free base form.

The compounds of the invention may exist in both unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone and $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

The invention also relates to prodrugs of the compounds of the formulae provided herein. Thus, certain derivatives of compounds of the invention which may have little or no pharmacological activity themselves may, when administered to a subject, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties. As used herein, "subject" may refer to a human or animal subject.

Prodrugs in accordance with the invention may, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some non-limiting examples of potential prodrugs in accordance with the invention include:

(i) where the compound contains a carboxylic acid functionality (—COOH), an ester thereof, for example, replacement of the hydrogen with ($C_1$-$C_8$)alkyl;

(ii) where the compound contains an alcohol functionality (—OH), an ether thereof, for example, replacement of the hydrogen with ($C_1$-$C_6$)alkanoyloxymethyl; and (iii) where the compound contains a primary or secondary amino functionality (—$NH_2$ or —NHR where R≠H), an amide thereof, for example, replacement of one or both hydrogens with a suitably metabolically labile group, such as an amide, carbamate, urea, phosphonate, sulfonate, etc.

Further examples of replacement groups in accordance with the foregoing examples and examples of other potential prodrug types may be found in the aforementioned references.

Finally, certain inventive compounds may themselves act as potential prodrugs of other of the inventive compounds.

Also included within the scope of the invention are metabolites of compounds of the formulae described herein, i.e., compounds formed in vivo upon administration of a drug.

The compounds of the formulae provided herein may have asymmetric carbon atoms.

The carbon-carbon bonds of the compounds of the invention may be depicted herein using a solid line ( —— ), a solid wedge ( ▬ ), or a dotted wedge ( ▬▬ ). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the invention may exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Compounds of the invention that have chiral centers may exist as stereoisomers, such as racemates, enantiomers, or diastereomers.

Stereoisomers of the compounds of the formulae herein may include cis and trans isomers, optical isomers such as (R) and (S) enantiomers, diastereomers, geometric isomers, rotational isomers, atropisomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, d-lactate or l-lysine, or racemic, for example, dl-tartrate or dl-arginine.

When a racemate crystallizes, crystals of two different types may be possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of the formulae provided.

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Where a compound of the invention contains an alkenyl or alkenylene group, geometric cis/trans (or Z/E) isomers may be possible. Cis/trans isomers may be separated by conventional techniques well known to those skilled in the art, for example, chromatography or fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

"Enantiomerically pure" as used herein, describes a compound that is present as a single enantiomer and which is described in terms of enantiomeric excess (e.e.). Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, "diastereomerically pure" as used herein, describes a compound that is present as a diastereomer and which is described in terms of diasteriomeric excess (d.e.). Preferably, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

The present invention also includes isotopically-labeled compounds, which are identical to those recited in one of the formulae provided, but for the fact that one or more atoms are replaced by an atom having an atomic mass or mass number different from the atomic mass or mass number usually found in nature.

Isotopically-labeled compounds of the invention may generally be prepared by conventional techniques known to those skilled in the art or by processes analogous to those described herein, using an appropriate isotopically-labeled reagent in place of the non-labeled reagent otherwise employed.

Examples of isotopes that may be incorporated into compounds of the invention include isotopes of hydrogen, carbon, nitrogen, oxygen, phosphorus, fluorine and chlorine, such as, but not limited to, $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$. Certain isotopically-labeled compounds of the invention, for example those into which radioactive isotopes such as $^3H$ and $^{14}C$ are incorporated, may be useful in drug and/or substrate tissue distribution assays. Tritiated, i.e., $^3H$, and carbon-14, i.e., $^{14}C$, isotopes may be particularly preferred for their ease of preparation and detectability. Further, substitution with heavier isotopes such as deuterium, i.e., $^2H$, may afford certain potential therapeutic advantages resulting from potentially greater metabolic stability, for example potentially increased in vivo half-life or potentially reduced dosage requirements and, hence, may be preferred in some circumstances. Isotopically-labeled compounds of the invention may generally be prepared by carrying out the procedures disclosed in the Schemes and/or in the Examples and Preparations below, by substituting an isotopically-labeled reagent for a non-isotopically-labeled reagent.

Compounds of the invention may be used as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

Therapeutic Methods and Uses

The invention further provides therapeutic methods and uses comprising administering a compound of the invention, or pharmaceutically acceptable salt thereof, alone or in combination with one or more other therapeutic agents or palliative agents.

In one aspect, the invention provides a method for the treatment of abnormal cell growth in a subject comprising administering to the subject a therapeutically effective amount of a compound of the invention, or a pharmaceutically acceptable salt thereof.

In another aspect, the invention provides a method for the treatment of abnormal cell growth in a subject comprising administering to the subject an amount of a compound of the invention, or a pharmaceutically acceptable salt thereof, in combination with an amount of an anti-tumor agent, which amounts are together effective in treating said abnormal cell growth. In some such embodiments, the anti-tumor agent is selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

Compounds of the invention include compounds of any of the formulae described herein, namely compounds of formulae I, I', II, II', I-A, I-A', I-B, I-B', II-A, II-A', II-B, II-B' and III as provided and defined herein, or a pharmaceutically acceptable salt thereof.

In another aspect, the invention provides a method for the treatment of abnormal cell growth in a subject comprising administering to the subject an amount of a compound of the invention, or a pharmaceutically acceptable salt thereof, that is effective in treating abnormal cell growth.

In still another aspect, the invention provides a method of inhibiting cancer cell proliferation in a subject, comprising administering to the subject a compound of the invention, or pharmaceutically acceptable salt thereof, in an amount effective to inhibit cell proliferation.

In another aspect, the invention provides a method of inhibiting cancer cell invasiveness in a subject, comprising administering to the subject a compound of the invention, or pharmaceutically acceptable salt thereof, in an amount effective to inhibit cell invasiveness.

In another aspect, the invention provides a method of inducing apoptosis in cancer cells in a subject, comprising administering to the subject a compound of the invention, or pharmaceutically acceptable salt thereof, in an amount effective to induce apoptosis.

In a further aspect, the invention provides a method of inducing apoptosis in a subject, comprising administering to the subject a therapeutically effective amount of a compound of one of the formulae described herein, or pharmaceutically acceptable salt thereof.

In frequent embodiments of the methods provided herein, the abnormal cell growth is cancer, wherein said cancer is selected from the group consisting of basal cell cancer, medulloblastoma cancer, liver cancer, rhabdomyosarcoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

In some embodiments, a compound of the invention is selective for the mutant form of the EZH2, such that trimethylation of H3K27, which is associated with certain cancers, is inhibited. The methods and uses provided herein may be used to treat cancers including follicular lymphoma and diffuse large B-cell lymphoma (DLBCL).

Compounds of the invention may be useful for the treatment of cancers, such as tumors such as brain, breast, cervical, colorectal, endometrial, esophageal, gastric/stomach, head and neck, hepatocellular, laryngeal, lung, oral, ovarian, prostate, testicular and thyroid carcinomas and sarcomas.

The term "therapeutically effective amount" as used herein refers to that amount of a compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, and/or (4) relieving to some extent (or, preferably, eliminating) one or more signs or symptoms associated with the cancer.

As used herein, "subject" refers to a human or animal subject. In certain preferred embodiments, the subject is a human.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

The terms "abnormal cell growth" and "hyperproliferative disorder" are used interchangeably in this application.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous). This includes the abnormal growth of: (1) tumor cells (tumors) that show increased expression of EZH2; (2) benign and malignant cells of other proliferative diseases in which EZH2 is over-expressed; (3) tumors that proliferate by aberrant EZH2 activation; and (4) benign and malignant cells of other proliferative diseases in which aberrant EZH2 activation occurs.

As used herein "cancer" refers to any malignant and/or invasive growth or tumor caused by abnormal cell growth. As used herein "cancer" refers to solid tumors named for the type of cells that form them, cancer of blood, bone marrow, or the lymphatic system. Examples of solid tumors include but not limited to sarcomas and carcinomas. Examples of cancers of the blood include but not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one. The compounds of the invention may inhibit EZH2, and thus may be useful as antiproliferative agents (e.g., cancer) or antitumor agent (e.g., effect against solid tumors) in mammals, particularly in humans. In particular, the compounds of the invention may be useful in the prevention and treatment of a variety of human hyperproliferative disorders, such as malignant or benign abnormal cell growth.

The compounds, compositions and methods provided herein may be useful for the treatment of cancers including but not limited to cancers of the:

circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue;

respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma);

bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

reproductive system, for example, gynecological, uterus (endometrial carcinoma), cervix (cervical carcinoma, pretumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs;

hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx;

skin, for example, malignant melanoma, cutaneous melanoma, basal cell carcinoma, squamous cell carcinoma, Karposi's sarcoma, moles dysplastic nevi, lipoma, angioma, dermatofibroma, and keloids;

adrenal glands: neuroblastoma; and other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

More specifically, examples of "cancer" when used herein in connection with the present invention include cancer selected from lung cancer (NSCLC and SCLC), cancer of the head or neck, ovarian cancer, colon cancer, rectal cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non-Hodgkin's lymphoma, spinal axis tumors, or a combination of one or more of the foregoing cancers.

Still more specifically, examples of "cancer" when used herein in connection with the present invention include cancer selected from lung cancer (NSCLC and SCLC), breast cancer, ovarian cancer, colon cancer, rectal cancer, cancer of the anal region, or a combination of one or more of the foregoing cancers.

In one embodiment of the present invention the non-cancerous conditions include such hyperplastic conditions such as benign hyperplasia of the skin (e.g., psoriasis) and benign hyperplasia of the prostate (e.g., BPH).

In another aspect, the invention provides a method for inhibiting cell proliferation, comprising contacting cells with a compound of the invention or a pharmaceutically acceptable salt thereof in an amount effective to inhibit proliferation of the cells.

In another aspect, the invention provides methods for inducing cell apoptosis, comprising contacting cells with a compound described herein in an amount effective to induce apoptosis of the cells.

"Contacting" refers to bringing a compound or pharmaceutically acceptable salt of the invention and a cell expressing EZH2 together in such a manner that the compound may affect the activity of EZH2, either directly or indirectly. Contacting may be accomplished in vitro (i.e., in an artificial environment such as, e.g., without limitation, in a test tube or culture medium) or in vivo (i.e., within a living organism such as, without limitation, a mouse, rat or rabbit.)

In some embodiments, the cells are in a cell line, such as a cancer cell line. In other embodiments, the cells are in a tissue or tumor, and the tissue or tumor may be in a subject, including a human.

Dosage Forms and Regimens Administration of compounds of the invention may be effected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention may be dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose may be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of the invention administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Formulations and Routes of Administration

As used herein, a "pharmaceutically acceptable carrier" refers to a carrier or diluent that does not cause significant irritation to an organism and does not abrogate the biological activity and properties of the active compound.

The pharmaceutical acceptable carrier may comprise any conventional pharmaceutical carrier or excipient. The choice of carrier and/or excipient will to a large extent depend on factors such as the particular mode of administration, the effect of the excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream, or for rectal administration as a suppository.

Exemplary parenteral administration forms include solutions or suspensions of an active compound in a sterile aqueous solution, for example, aqueous propylene glycol or dextrose solutions. Such dosage forms may be suitably buffered, if desired.

The pharmaceutical composition may be in unit dosage forms suitable for single administration of precise amounts.

Pharmaceutical compositions suitable for the delivery of active agents and methods for their preparation will be readily apparent to those skilled in the art. Such compositions and methods for their preparation may be found, for example, in 'Remington's Pharmaceutical Sciences', 19th Edition (Mack Publishing Company, 1995), the disclosure of which is incorporated herein by reference in its entirety.

Compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, the active agent may make up from 1 wt % to 80 wt % of the dosage form, more typically from 5 wt % to 60 wt % of the dosage form. In addition to the active agent, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant may comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets may contain up to about 80 wt % active agent, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles may be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

Compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may potentially be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may potentially be formulated as a solid, semi-solid, or thixotropic liquid for administration as an implanted depot providing modified release of the active compound. Examples of such formulations include drug-coated stents and PGLA microspheres.

The compounds of the invention may also potentially be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

Compounds of the invention may also potentially be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer may contain a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the compound may be micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Compounds of the invention may potentially be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Compounds of the invention may also potentially be administered directly to the eye or ear, typically in the form of drops of a micronized suspension or solution in isotonic, pH-adjusted, sterile saline. Other formulations suitable for ocular and aural administration may include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, may be useful for different dosage forms and administration routes. Both inclusion and non-inclusion complexes may potentially be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention may be particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

Combination Therapy

As used herein, the term "combination therapy" refers to the administration of a compound of the invention together with an at least one additional pharmaceutical or medicinal agent (e.g., an anti-cancer agent), either sequentially or simultaneously.

As noted above, the compounds of the invention may potentially be used in combination with one or more additional anti-cancer agents which are described below. When a combination therapy is used, the one or more additional anti-cancer agents may be administered sequentially or simultaneously with the compound of the invention. In one embodiment, the additional anti-cancer agent is administered to a mammal (e.g., a human) prior to administration of the compound of the invention. In another embodiment, the additional anti-cancer agent is administered to the mammal after administration of the compound of the invention. In another embodiment, the additional anti-cancer agent is administered to the mammal (e.g., a human) simultaneously with the administration of the compound of the invention.

The invention also relates to a pharmaceutical composition for the treatment of abnormal cell growth in a mammal, including a human, which comprises an amount of a compound of the invention, as defined above (including hydrates, solvates and polymorphs of said compound or pharmaceutically acceptable salts thereof), in combination with one or more (preferably one to three) anti-cancer agents selected from the group consisting of anti-angiogenesis agents and signal transduction inhibitors and a pharmaceutically acceptable carrier, wherein the amounts of the active agent and the combination anti-cancer agents when taken as a whole is therapeutically effective for treating said abnormal cell growth.

In one embodiment of the present invention the anti-cancer agent used in conjunction with a compound of the invention and pharmaceutical compositions described herein is an anti-angiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKCβ inhibitors, COX-2 (cyclooxygenase II) inhibitors, integrins (alpha-v/beta-3), MMP-2 (matrix-metalloprotienase 2) inhibitors, and MMP-9 (matrix-metalloprotienase 9) inhibitors.

Preferred anti-angiogenesis agents include sunitinib (Sutent™), bevacizumab (Avastin™), axitinib (AG 13736), SU 14813 (Pfizer), and AG 13958 (Pfizer).

Additional anti-angiogenesis agents include vatalanib (CGP 79787), Sorafenib (Nexavar™), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex™) and UCN 01 (Kyowa Hakko).

Other examples of anti-angiogenesis agents which may be used in conjunction with a compound of the invention and pharmaceutical compositions described herein include celecoxib (Celebrex™), parecoxib (Dynastat™), deracoxib (SC 59046), lumiracoxib (Preige™), valdecoxib (Bextra™), rofecoxib (Vioxx™), iguratimod (Careram™), IP 751 (Invedus), SC-58125 (Pharmacia) and etoricoxib (Arcoxia™).

Other anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™), diclofenac (Voltaren™), indomethacin (Indocin™), sulindac (Clinoril™), tolmetin (Tolectin™), etodolac (Lodine™), ketorolac (Toradol™), and oxaprozin (Daypro™).

Other anti-angiogenesis agents include ABT 510 (Abbott), apratastat (TMI 005), AZD 8955 (AstraZeneca), incyclinide (Metastat™), and PCK 3145 (Procyon).

Other anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™), thalidomide (Thalomid™), Ukrain™ (NSC 631570), Vitaxin™ (MEDI 522), and zoledronic acid (Zometa™).

In another embodiment the anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EGF inhibitor, ErbB-1 (EGFR), ErbB-2, pan erb, IGF1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi-targeted kinase inhibitors.

Preferred signal transduction inhibitors include gefitinib (Iressa™), cetuximab (Erbitux™), erlotinib (Tarceva™), trastuzumab (Herceptin™), sunitinib (Sutent™), imatinib (Gleevec™), and PD325901 (Pfizer).

Additional examples of signal transduction inhibitors which may be used in conjunction with a compound of the invention and pharmaceutical compositions described herein include BMS 214662 (Bristol-Myers Squibb), lonafarnib (Sarasar™), pelitrexol (AG 2037), matuzumab (EMD 7200), nimotuzumab (TheraCIM h-R3™), panitumumab (Vectibix™), Vandetanib (Zactima™), pazopanib (SB 786034), ALT 110 (Alteris Therapeutics), BIBW 2992 (Boehringer Ingelheim), and Cervene™ (TP 38).

Other examples of signal transduction inhibitor include PF-2341066 (Pfizer), PF-299804 (Pfizer), canertinib (CI 1033), pertuzumab (Omnitarg™), Lapatinib (Tycerb™), pelitinib (EKB 569), miltefosine (Miltefosin™), BMS 599626 (Bristol-Myers Squibb), Lapuleucel-T (Neuvenge™), NeuVax™ (E75 cancer vaccine), Osidem™ (IDM 1), mubritinib (TAK-165), CP-724,714 (Pfizer), panitumumab (Vectibix™), lapatinib (Tycerb™), PF-299804 (Pfizer), pelitinib (EKB 569), and pertuzumab (Omnitarg™).

Other examples of signal transduction inhibitors include ARRY 142886 (Array Biopharm), everolimus (Certican™), zotarolimus (Endeavor™), temsirolimus (Torisel™), AP 23573 (ARIAD), and VX 680 (Vertex).

Additionally, other signal transduction inhibitors include XL 647 (Exelixis), sorafenib (Nexavar™), LE-AON (Georgetown University), and GI-4000 (Globelmmune).

Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (Onc Bio), BMS 387032 (Bristol-Myers Squibb), PD 0332991 (Pfizer), and AG 024322 (Pfizer).

This invention contemplates the use of a compound of the invention together with classical antineoplastic agents. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor, microtubulin inhibitors, antibiotics, plant derived spindle inhibitors, platinum-coordinated compounds, gene therapeutic agents, antisense oligonucleotides, vascular targeting agents (VTAs), and statins Examples of classical antineoplastic agents used in combination therapy with a compound of the invention, optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi), Selective Estrogen-Receptor Downregulators (SERD's; such as fulvestrant), exemestane (Aromasin), anastrozole (Arimidex), atamestane, fadrozole, letrozole (Femara), gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), bicalutamide (Casodex), cyproterone, flutamide (Eulexin), megestrol, nilutamide (Nilandron), and osaterone, dutasteride, epristeride, finasteride, Serenoa repens, PHL 00801, abarelix, goserelin, leuprorelin, triptorelin, bicalutamide, tamoxifen, exemestane, anastrozole, fadrozole, formestane, letrozole, and combinations thereof.

Other examples of classical antineoplastic agents used in combination with a compound of the invention include but are not limited to suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

The invention also contemplates the use of the a compound of the invention together with dihydrofolate reductase inhibitors (such as methotrexate and NeuTrexin (trimetresate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda™), cytosine arabinoside, Gemzar™ (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents used in combination therapy with a compound of the invention, optionally with one or more other agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paclitaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta™), DMXAA (Antisoma), ibandronic acid, L-asparaginase, pegaspargase (Oncaspar™), Efaproxiral (Efaproxyn™—radiation therapy), bexarotene (Targretin™), Tesmilifene (DPPE—enhances efficacy of cytotoxics), Theratope™ (Biomira), Tretinoin (Vesanoid™), tirapazamine (Trizaone™), motexafin gadolinium (Xcytrin™) Cotara™ (mAb), and NBI-3001 (Protox Therapeutics), polyglutamate-paclitaxel (Xyotax™) and combinations thereof.

Further examples of classical antineoplastic agents used in combination therapy with a compound of the invention, optionally with one or more other agents include, but are not limited to, as Advexin (ING 201), TNFerade (GeneVec, a compound which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

Another embodiment of the present invention of particular interest relates to a method for the treatment of breast cancer in a human in need of such treatment, comprising administering to said human an amount of a compound of the invention, in combination with one or more (preferably one to three) anti-cancer agents selected from the group consisting of trastuzumab, tamoxifen, docetaxel, paclitaxel, capecitabine, gemcitabine, vinorelbine, exemestane, letrozole and anastrozole.

In one embodiment the invention provides a method of treating colorectal cancer in a mammal, such as a human, in need of such treatment, by administering an amount of a compound of the invention, in combination with one or more (preferably one to three) anti-cancer agents. Examples of particular anti-cancer agents include those typically used in adjuvant chemotherapy, such as FOLFOX, a combination of 5-fluorouracil (5-FU) or capecitabine (Xeloda), leucovorin and oxaliplatin (Eloxatin). Further examples of particular anti-cancer agents include those typically used in chemotherapy for metastatic disease, such as FOLFOX or FOLFOX in combination with bevacizumab (Avastin); and FOLFIRI, a combination of 5-FU or capecitabine, leucovorin and irinotecan (Camptosar). Further examples include 17-DMAG, ABX-EFR, AMG-706, AMT-2003, ANX-510 (CoFactor), aplidine (plitidepsin, Aplidin), Aroplatin, axitinib (AG-13736), AZD-0530, AZD-2171, bacillus Calmette-Guerin (BCG), bevacizumab (Avastin), BIO-117, BIO-145, BMS-184476, BMS-275183, BMS-528664, bortezomib (Velcade), C-1311 (Symadex), cantuzumab mertansine, capecitabine (Xeloda), cetuximab (Erbitux), clofarabine (Clofarex), CMD-193, combretastatin, Cotara, CT-2106, CV-247, decitabine (Dacogen), E-7070, E-7820, edotecarin, EMD-273066, enzastaurin (LY-317615)epothilone B (EPO-906), erlotinib (Tarceva), flavopyridol, GCAN-101, gefitinib (Iressa), huA33, huC242-DM4, imatinib (Gleevec), indisulam, ING-1, irinotecan (CPT-11, Camptosar) ISIS 2503, ixabepilone, lapatinib (Tykerb), mapatumumab (HGS-ETR1), MBT-0206, MEDI-522 (Abregrin), Mitomycin, MK-0457 (VX-680), MLN-8054, NB-1011, NGR-TNF, NV-1020, oblimersen (Genasense, G3139), OncoVex, ONYX 015 (CI-1042), oxaliplatin (Eloxatin), panitumumab (ABX-EGF, Vectibix), pelitinib (EKB-569), pemetrexed (Alimta), PD-325901, PF-0337210, PF-2341066, RAD-001 (Everolimus), RAV-12, Resveratrol, Rexin-G, S-1 (TS-1), seliciclib, SN-38 liposome, Sodium stibogluconate (SSG), sorafenib (Nexavar), SU-14813, sunitinib (Sutent), temsirolimus (CCI 779), tetrathiomolybdate, thalomide, TLK-286 (Telcyta), topotecan (Hycamtin), trabectedin (Yondelis), vatalanib (PTK-787), vorinostat (SAHA, Zolinza), WX-UK1, and ZYC300, wherein the amounts of the active agent together with the amounts of the combination anticancer agents are effective in treating colorectal cancer.

Another embodiment of the present invention of particular interest relates to a method for the treatment of renal cell carcinoma in a human in need of such treatment, comprising administering to said human an amount of a compound of the invention, in combination with one or more (preferably one to three) anti-cancer agents selected from the group consisting of axitinib (AG 13736), capecitabine (Xeloda), interferon alpha, interleukin-2, bevacizumab (Avastin), gemcitabine (Gemzar), thalidomide, cetuximab (Erbitux), vatalanib (PTK-787), sunitinib (Sutent™), AG-13736, SU-11248, Tarceva, Iressa, Lapatinib and Gleevec, wherein the amounts of the active agent together with the amounts of the combination anticancer agents is effective in treating renal cell carcinoma.

Another embodiment of the present invention of particular interest relates to a method for the treatment of melanoma in a human in need of such treatment, comprising administering to said human an amount of a compound of the invention, in combination with one or more (preferably one to three) anti-cancer agents selected from the group consisting of interferon alpha, interleukin-2, temozolomide (Temodar), docetaxel (Taxotere), paclitaxel, Dacarbazine (DTIC), carmustine (also known as BCNU), Cisplatin, vinblastine, tamoxifen, PD-325,901, axitinib (AG 13736), bevacizumab (Avastin), thalidomide, sorafanib, vatalanib (PTK-787), sunitinib (Sutent™), CpG-7909, AG-13736, Iressa, Lapatinib and Gleevec, wherein the amounts of the active agent together with the amounts of the combination anticancer agents is effective in treating melanoma.

Another embodiment of the present invention of particular interest relates to a method for the treatment of lung cancer in a human in need of such treatment, comprising administering to said human an amount of a compound of the invention, in combination with one or more (preferably one to three) anti-cancer agents selected from the group consisting of capecitabine (Xeloda), axitinib (AG 13736), bevacizumab (Avastin), gemcitabine (Gemzar), docetaxel (Taxotere), paclitaxel, premetrexed disodium (Alimta), Tarceva, Iressa, Vinorelbine, Irinotecan, Etoposide, Vinblastine, sunitinib (Sutent™), and Paraplatin (carboplatin), wherein the amounts of the active agent together with the amounts of the combination anticancer agents is effective in treating lung cancer.

Synthetic Methods

Compounds of the invention may be prepared according to the exemplary procedures provided herein and modifications thereof known to those of skill in the art. In addition, synthetic routes for the formation of various compounds useful as staring materials for the preparation of the compounds claimed herein are described in International Application No. PCT/IB2013/060682, the content of which is incorporated by reference herein in its entirely.

These and other methods are exemplified in the preparation of the examples provided herein. It will be understood by those of skill in the art that the selection of starting materials and the particular order of the steps, including, e.g., formation of the lactam ring, installation or manipulation of various substituent groups on the fused lactam or its precursors, and installation of the pyridinone moiety, may be varied by selection of a suitable synthetic strategy.

Synthetic examples are provided throughout the Examples and in Table 1 below. EZH2 $IC_{50}$ values (µM) for WT EZH2 and Mutant Y641N EZH2 are provided in Table 2 for exemplary compounds of the invention.

The following abbreviations are used throughout the Examples: "Ac" means acetyl, "AcO" or "OAc" means acetoxy, "Ac$_2$O" means acetic anhydride, "ACN" or "MeCN" means acetonitrile, "AIBN" means azobisisobutyronitrile, "BOC", "Boc" or "boc" means N-tert-butoxycarbonyl, "Bn" means benzyl, "BPO" means dibenzoyl peroxide, "Bu" means butyl, "iBu" means isobutyl, "sBu" means sec-butyl, "tBu" means tert-butyl, "tBuOK" or "KOtBu" means potassium tert-butoxide, "CDI" means carbonyldiimidazole, "DCE" means 1,2-dichloroethane, "DCM" ($CH_2Cl_2$) means methylene chloride, "DEAD" means diethyl azodicarboxylate, "DIAD" means diisopropyl azodicarboxylate, "DIPEA" or "DIEA" means diisopropyl ethyl amine, "DBU" means 1,8-diazabicyclo[5.4.0]undec-7-ene, "DIBAL-H" means diisobutylaluminum hydride, "DMA" means N,N-dimethylacetamide, "DMAP" means 4-dimethylaminopyridine, "DME" means dimethoxyethane, "DMF" means N—N-dimethyl formamide, "DMS" means dimethylsulfide, "DMSO" means dimethylsulfoxide, "dppf" means (diphenylphosphino)ferrocene, "DPPP" means 1,3-bis(diphenylphosphino)propane, "Et" means ethyl, "EtOAc" means ethyl acetate, "EtOH" means ethanol, "HATU" means 2-(7-Aza-1H-benzotriazole-1-yl)-1,1,3,3-tetramethyluronium hexafluorophosphate, "HOAc" or "AcOH" means acetic acid, "i-Pr" or "'Pr" means isopropyl, "IPA" means isopropyl alcohol, "KHMDS" means potassium hexamethyldisilazide (potassium bis(trimethylsilyl)amide), "LiHMDS" means lithium hexamethyldisilazide (lithium bis(t-rimethylsilyl)amide), "mCPBA" means meta-chloroperoxybenzoic acid, "Me" means methyl, "MeOH" means methanol, "Ms" means methanesulfonate (commonly called 'mesylate'), "MTBE" means methyl t-butyl ether, "NBS" means N-bromosuccinimide, "NCS" means N-chlorosuccinimide, "NIS" means N-iodosuccinimide, "NMM" means N-methylmorpholine, "NMP" means 1-methyl 2-pyrrolidinone, "Ph" means phenyl, "RuPhos" means 2-Dicyclohexylphosphino-2',6'-diisopropoxybiphenyl, "Selectfluor" means Chloromethyl-4-fluoro-1,4-diazoniabicyclo[2.2.2] octane bis(tetrafluoroborate), "TEA" means triethylamine, "TFA" means trifluoroacetic acid, "Tf" means trifluoromethanesulfonate (commonly called 'triflate'), "THF" means tetrahydrofuran, "TMS" means trimethylsilyl, "TMSA" means trimethylsilylazide, "TsCl" means toluenesulfonyl chloride (commonly called 'tosylate'), "SFC" means supercritical fluid chromatography, "TLC" means thin layer chromatography, "Rf" means retention fraction, "~" means approximately, "rt" means room temperature, "h" means hours, "min" means minutes, "eq." means equivalents.

Preparation of Synthetic Intermediates

Compound D: 2-(benzyloxy)-3-(chloromethyl)-4,6-dimethylpyridine

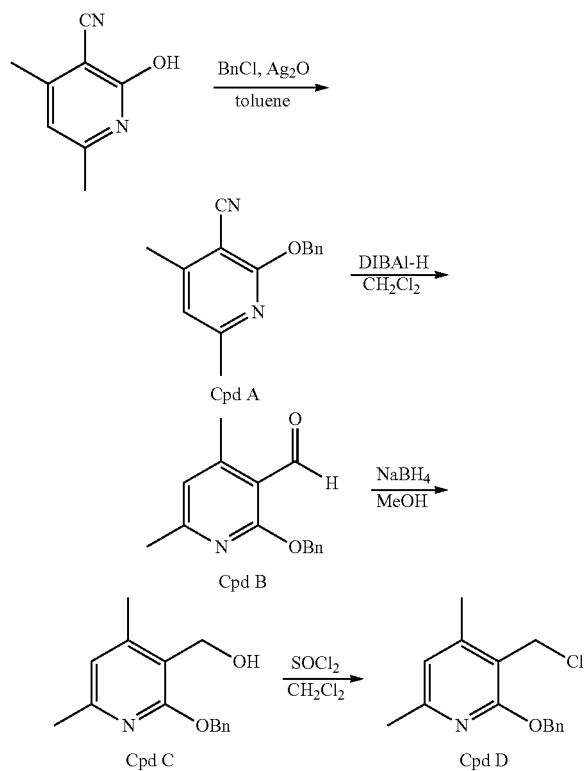

To a solution of 2-hydroxy-4,6-dimethylpyridine-3-carbonitrile (85.0 g, 0.574 mol) and benzyl chloride (87.0 g, 0.688 mol) in toluene (800 mL) was added Ag$_2$O (146 g, 0.631 mol). The reaction mixture was stirred at 110° C. overnight. The reaction mixture was filtered through CELITE® and the solids washed with dichloromethane. The filtrate was concentrated under vacuum and purified by column chromatography (petroleum ether/ethyl acetate) to give 2-(benzyloxy)-4,6-dimethylpyridine-3-carbonitrile (Cpd A, 89 g, 65%) as a white solid.

44.5 g×2 batches: To a stirred solution of 2-(benzyloxy)-4,6-dimethylpyridine-3-carbonitrile (Cpd A, 44.5 g, 187 mmol) in dichloromethane (500 mL) was added drop wise DIBAL-H (224 mL, 224 mmol, 1M in toluene) at 0~5° C. The reaction mixture was allowed to warm to room temperature and stirred for an additional 3 hours. The mixture was quenched with 1N HCl (200 mL) and was stirred vigorously for 30 minutes. The reaction mixture was neutralized with 4N NaOH (20 mL) and the biphasic mixture was filtered and washed with dichloromethane (500 mL). The aqueous layer was extracted with dichloromethane (200 mL), the combined organic layers were dried over sodium sulfate, and concentrated under vacuum. The residue was purified by column chromatography (petroleum ether/EtOAc) to give 2-(benzyloxy)-4,6-dimethylpyridine-3-carbaldehyde (Cpd B, 70 g, 78%) as a yellow solid.

35 g×2 batches: To a 0° C. solution of 2-(benzyloxy)-4,6-dimethylpyridine-3-carbaldehyde (Cpd B, 35.0 g, 145 mmol) in methanol (1000 mL) was added sodium borohydride (6.60 g, 174 mmol) in portions. The reaction mixture was stirred at room temperature for 2 hours. The reaction mixture was concentrated under vacuum and the residue was diluted with NaHCO$_3$ (sat., aq.). After the bubbling had stopped, the aqueous solution was extracted with ethyl acetate (2×500 mL). The combined organic layers were dried over sodium sulfate, concentrated under vacuum, and purified by column chromatography (petroleum ether/ethyl acetate) to give [2-(benzyloxy)-4,6-dimethylpyridin-3-yl]methanol (Cpd C, 43 g, 61%) as a colorless oil.

21.5 g×2 batches: To a solution of [2-(benzyloxy)-4,6-dimethylpyridin-3-yl]methanol (Cpd C, 21.5 g, 88.5 mmol) in anhydrous dichloromethane (400 mL) was added thionyl chloride (16.0 g, 133 mmol) at −40° C. under N$_2$. The mixture was stirred at −40° C. for 30 minutes. The reaction mixture was poured into ice-water (300 mL) and adjusted to pH 7~8 with NaHCO$_3$ (solid). The mixture was separated and the aqueous layer was extracted with dichloromethane (300 mL). The combined organic layers were washed with brine (300 mL), dried over sodium sulfate, and concentrated under vacuum. The residue was purified by column chromatography (petroleum ether/ethyl acetate, 100:1) to give 2-(benzyloxy)-3-(chloromethyl)-4,6-dimethylpyridine (Cpd D, 27.5 g, 60%) as a white solid. $^1$H NMR (400 MHz, CDCl3) δ 7.51-7.49 (d, 2H), 7.41-7.37 (t, 2H), 7.34-7.30 (t, 1H), 6.62 (s, 1H), 5.45 (s, 2H), 4.73 (s, 2H), 2.42 (s, 3H), 2.37 (s, 3H). MS: 261.9 [M+H]$^+$.

Compound L: 2-(benzyloxy)-3-(chloromethyl)-4-(difluoromethoxy)-6-methylpyridine

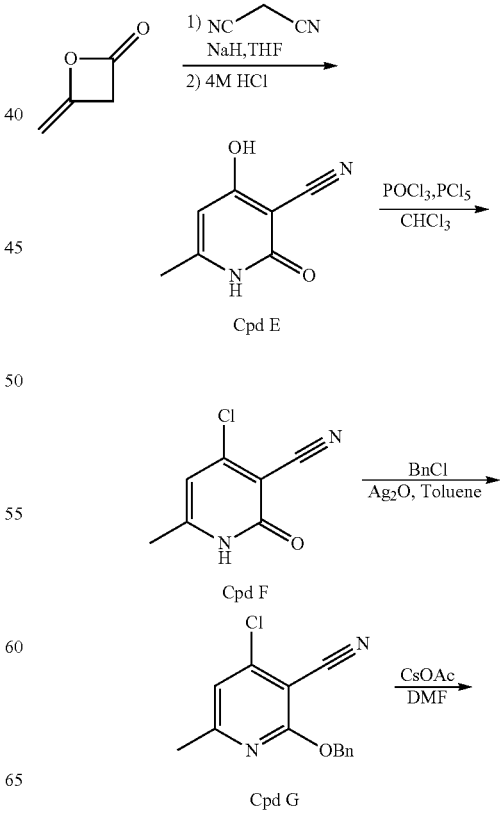

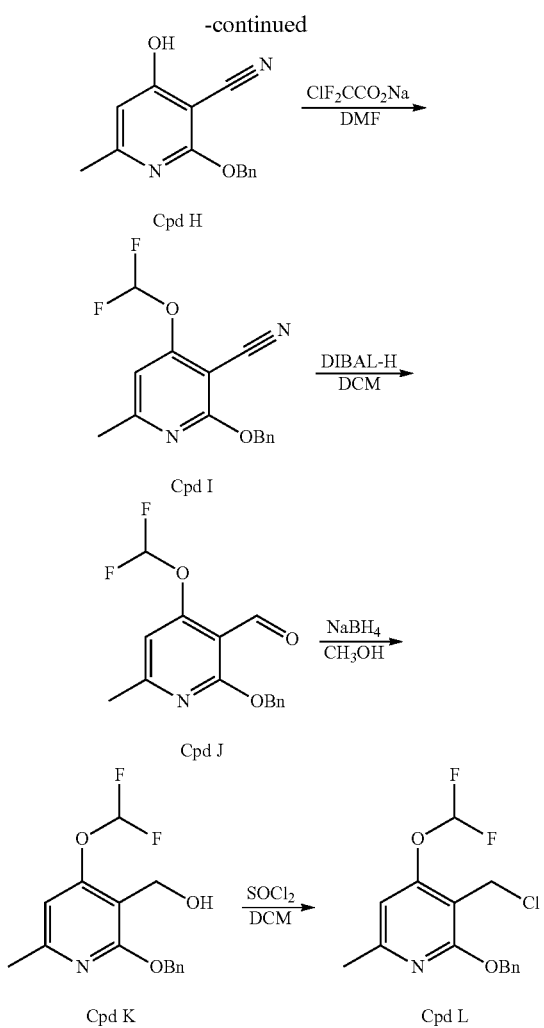

Cpd H

Cpd I

Cpd J

Cpd K                    Cpd L

To a cooled (−10° C.) suspension of sodium hydride (60 wt % dispersion in mineral oil, 59.9 g, 1500 mmol) in dry tetrahydrofuran (1200 mL) was added solution of malononitrile (100 g, 1190 mmol) in dry tetrahydrofuran (30 mL) dropwise, slowly enough to maintain the internal temperature below 5° C. After the addition was complete, the mixture was stirred at 0° C. for 1.5 hours, then diketene (80.1 g, 1190 mmol) was added dropwise, slowly enough to maintain the internal temperature below 0° C. The mixture was stirred at −10° C. for 1.5 hours, then neutralized with 4N aq. HCl, and concentrated to remove volatiles. The remaining suspension in 4N aq. HCl (2000 mL) was stirred at reflux for 5 hours, then stirred at room temperature overnight. The resulting white precipitate was collected by suction filtration. The filter cake was washed sequentially with water (500 mL), ethanol (500 mL) and MTBE (300 mL). The solid was dried to obtain 4-hydroxy-6-methyl-2-oxo-1,2-dihydropyridine-3-carbonitrile (Cpd E, 108 g, 60.3%) as a yellow powder. $^1$H NMR (400 MHz, DMSO-d6) δ 12.40 (br. s., 1H), 11.72 (br. s., 1H), 5.82 (s, 1H), 2.17 (s, 3H).

A suspension of 4-hydroxy-6-methyl-2-oxo-1,2-dihydropyridine-3-carbonitrile (Cpd E, 91 g, 610 mmol), phosphorus oxychloride (195 g, 1270 mmol) and phosphorus pentachloride (265 g, 1270 mmol) in chloroform (1200 mL) was heated at reflux for 5 hours, resulting in a red homogeneous mixture. The mixture was poured into water (2000 mL) carefully with stirring, then neutralized by ammonium hydroxide (28% aqueous). The resulting solid precipitate was filtered off, washed sequential with dichloromethane (400 mL) and ethanol (500 mL), and dried to give 4-chloro-6-methyl-2-oxo-1,2-dihydropyridine-3-carbonitrile (Cpd F, 78 g, 76%) as a yellow solid. $^1$H NMR (400 MHz, DMSO-d6) δ 12.43 (br. s., 1H), 6.53 (s, 1H), 2.28 (s, 3H).

A suspension of 4-chloro-6-methyl-2-oxo-1,2-dihydropyridine-3-carbonitrile (Cpd F, 90 g, 530 mmol), silver(I) oxide (136 g, 587 mmol) and benzyl chloride (81.1 g, 641 mmol) in anhydrous toluene (1500 mL) was heated at reflux for 12 hours. The mixture was filtered through a CELITE® pad and the filter cake washed with dichloromethane (500 mL). The filtrate was concentrated to give a residue (~100 g), which was purified by column chromatography (silica gel, petroleum ether/EtOAc=50:130:1), affording 2-(benzyloxy)-4-chloro-6-methylnicotinonitrile (Cpd G, 70 g, 51%) as a light yellow solid. $^1$H NMR (400 MHz, CDCl3) δ 7.49-7.47 (m, 2H), 7.40-7.33 (m, 3H), 6.91 (s, 1H), 5.05 (s, 2H), 2.50 (s, 3H).

To a stirred solution of 2-(benzyloxy)-4-chloro-6-methylnicotinonitrile (Cpd G, 70 g, 270.58 mmol) in N,N-dimethylformamide (300 mL) was added cesium acetate (156.0 g, 812 mmol) at room temperature. The resulting mixture was stirred at 80° C. for 40 hours. The mixture was diluted with ethyl acetate (500 mL) and washed with brine (3×400 mL). The organic phase was dried over sodium sulfate, filtered, and concentrated to give a residue (~50 g), which was purified by column chromatography (silica gel, petroleum ether/EtOAc=10:1-3:1) to give 2-(benzyloxy)-4-hydroxy-6-methylnicotinonitrile (Cpd H, 31 g, 48%) as a light yellow solid. $^1$H NMR (400 MHz, DMSO-d6) δ 12.28 (br. s., 1H), 7.51-6.98 (m, 5H), 6.50 (s, 1H), 5.41 (s, 2H), 2.34 (s, 3H). MS 226.8 [M+Na]$^+$.

To a suspension of 2-(benzyloxy)-4-hydroxy-6-methylnicotinonitrile (Cpd H, 20.0 g, 83 mmol) and sodium chlorodifluoroacetate (25.4 g, 166 mmol) in N,N-dimethylformamide (200 mL) was added potassium carbonate (34.5 g, 250 mmol) at room temperature. The resulting mixture was heated to 100° C. for 10 minutes. The reaction mixture was diluted with ethyl acetate (300 mL) and washed with sat. aq. NH4Cl (3×400 mL), and brine (3×400 mL). The aqueous layer was back-extracted with ethyl acetate (400 mL). The combined organic layers were dried over sodium sulfate, filtered, and concentrated to give a residue (18 g), which was purified by column chromatography (silica gel, petroleum ether/EtOAc=50:1-20:1) to give 2-(benzyloxy)-4-(difluoromethoxy)-6-methylnicotinonitrile (Cpd I, 16.3 g, 67%) as light yellow solid. $^1$H NMR (400 MHz, CDCl3) δ 7.49-7.46 (m, 2H), 7.40-7.33 (m, 3H), 6.69 (t, J=71 Hz, 1H), 6.67 (s, 1H), 5.51 (s, 2H), 2.52 (s, 3H).

To a solution of 2-(benzyloxy)-4-(difluoromethoxy)-6-methylnicotinonitrile (Cpd I, 11 g, 38 mmol) in dry dichloromethane (250 mL) under nitrogen was added diisobutyl-aluminium hydride (1.0 M in toluene, 72 mL, 72 mmol) dropwise at 0° C. After the addition was complete, the mixture was stirred at room temperature for 2.5 hours. The mixture was acidified to pH~5 with 1M aq. HCl. After stirring at room temperature for 2 hours, the mixture was neutralized with 4.0 M aq. NaOH. The mixture was filtered off through a CELITE® pad and the filter cake was washed with dichloromethane (300 mL). The filtrate was extracted with dichloromethane (2×500 mL). The combined organic layers were washed with brine (800 mL), dried over sodium sulfate, and concentrated to give a residue (13.4 g), which was purified by column chromatography (silica gel, petroleum ether/EtOAc=30:1-10:1) to give 2-(benzyloxy)-4-(difluoromethoxy)-6-methylnicotinaldehyde (Cpd J, 6 g, 50%) as a light yellow solid. $^{1}$H NMR (400 MHz, CDCl3) δ 10.40 (s, 1H), 7.49~7.48 (m, 2H), 7.40-7.31 (m, 3H), 6.68 (t, J=72 Hz, 1H), 6.62 (s, 1H), 5.53 (s, 2H), 2.50 (s, 3H).

To a solution of 2-(benzyloxy)-4-(difluoromethoxy)-6-methylnicotinaldehyde (Cpd J, 12 g, 41 mmol) in methanol (120 mL) was added sodium borohydride (1.86 g, 49.16 mmol) portion-wise at 0° C. After the addition was complete, the mixture was stirred at room temperature for 2 hours. The reaction was quenched with sat. aq. NH4Cl (50 mL), then diluted with ethyl acetate (500 mL) and water (100 mL) and extracted with ethyl acetate (2×100 mL). The combined organic layers were washed with brine (300 mL), dried over sodium sulfate and concentrated to give a residue (~13.1 g), which was purified by column chromatography (silica gel, petroleum ether: EtOAc=6:1) to give (2-(benzyloxy)-4-(difluoromethoxy)-6-methylpyridin-3-yl)methanol (Cpd K, 11.7 g, 97%) as a white solid. $^{1}$H NMR (400 MHz, CDCl3) δ 7.52-7.46 (m, 2H), 7.44-7.33 (m, 3H), 6.60 (t, J=73 Hz, 1H), 6.55 (s, 1H), 5.46 (s, 2H), 2.46 (s, 3H).

To a solution of (2-(benzyloxy)-4-(difluoromethoxy)-6-methylpyridin-3-yl)methanol (Cpd K, 7.6 g, 26 mmol) in anhydrous dichloromethane (120 mL) was added thionyl chloride (3.67 g, 30.9 mmol) dropwise at −20° C. The mixture was stirred at −20° C. for 1 hour, then poured into water (50 mL), and neutralized with saturated aq. NaHCO$_3$. The aqueous phase was extracted with dichloromethane (2×90 mL). The combined organic phases were dried over sodium sulfate, filtered and concentrated to give a residue (~6.1 g), which was purified by silica gel chromatography (petroleum ether/EtOAc=6:1) to give the title compound, 2-(benzyloxy)-3-(chloromethyl)-4-(difluoromethoxy)-6-methylpyridine (Cpd L, 5.7 g, 71%) as a white solid. $^{1}$H NMR (400 MHz, CDCl3) δ 7.50 (d, J=7.2, 2H), 7.41-7.33 (m, 3H), 6.64 (t, J=73 Hz, 1H), 6.56 (s, 1H), 5.48 (s, 2H), 4.69 (s, 2H), 2.47 (s, 3H). MS: 314 [M+H]$^+$.

Compound S: 2-{[2-(benzyloxy)-4,6-dimethylpyridin-3-yl]methyl}-7-bromo-5,8-dichloro-3,4-dihydroisoquinolin-1(2H)-one

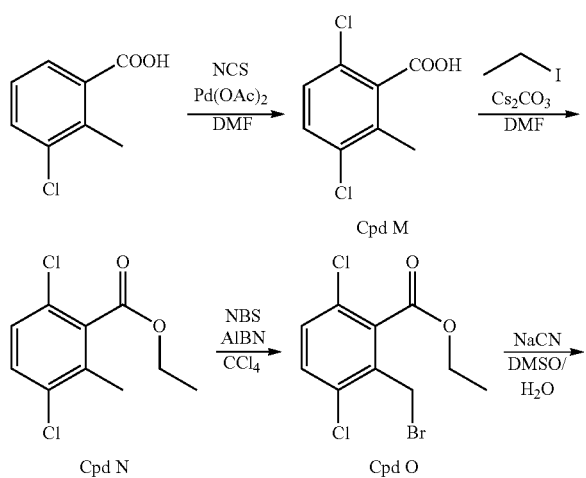

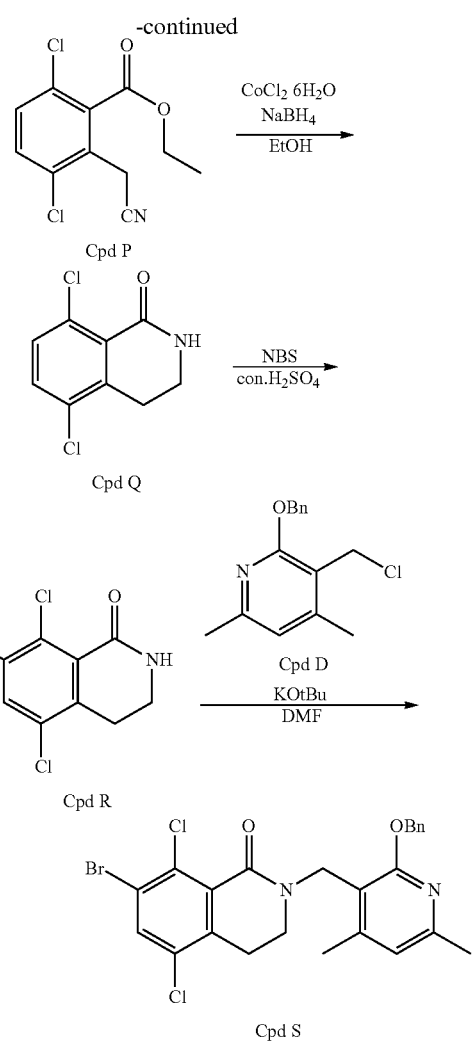

A mixture of 3-chloro-2-methylbenzoic acid (100 g, 0.58 mol), N-chlorosuccinimide (90 g, 0.67 mol) and palladium (II) acetate (14.7 g, 65.7 mmol) in N,N-dimethylformamide (1 L) was stirred at 110° C. under a nitrogen atmosphere overnight. After cooling to room temperature, cesium carbonate (378 g, 1.16 mol) and iodoethane (317 g, 2.03 mol) were added and stirring continued at room temperature for 1.5 hours. The reaction mixture was poured into a mixture of water (1 L) and methyl tert-butyl ether (800 mL). Solids were removed by filtration, and the filtrate layers separated. The aqueous layer was extracted with more methyl tert-butyl ether (600 mL). The combined organic extracts were washed with saturated aqueous sodium chloride solution (1.2 L), dried over sodium sulfate, and concentrated in vacuo. The residue was purified by silica gel chromatography (eluting with 50:1 petroleum ether/ethyl acetate), affording ethyl 3,6-dichloro-2-methylbenzoate (Cpd N, 110 g, ~80% pure, 80% yield) as a yellow oil.

A solution of ethyl 3,6-dichloro-2-methylbenzoate (Cpd N, 120 g, 0.52 mol) and N-bromosuccinimide (147 g, 0.82 mol) in chloroform (1 L) was treated with azobisisobutyronitrile (25.3 g, 0.15 mol) and the mixture refluxed overnight. After cooling to room temperature, the mixture was diluted with dichloromethane (800 mL) and washed with water (1.2 L). The aqueous layer was extracted with dichloromethane (800 mL). The combined organic extracts were washed with saturated aqueous sodium chloride solution (1.5 L), dried over sodium sulfate, and concentrated in vacuo to give ethyl 2-(bromomethyl)-3,6-dichlorobenzoate (Cpd O, 160 g, 100% yield) which was used without further purification.

A solution of sodium cyanide (75.12 g, 1.53 mol) in water (300 mL) was added dropwise to a solution of ethyl 2-(bromomethyl)-3,6-dichlorobenzoate (Cpd O, 320 g, 1.03 mol) in dimethysulfoxide (2.4 L) at room temperature. The mixture was stirred at room temperature for 1.5 hours. The reaction mixture was poured into a mixture of water (4 L) and methyl tert-butyl ether (2 L), and the layers separated. The organic layer was washed with water (2 L) and with saturated aqueous sodium chloride solution (2 L), dried over sodium sulfate, and concentrated in vacuo. The residue was purified by silica gel chromatography (eluting with 30:1 petroleum ether/ethyl acetate), affording ethyl 3,6-dichloro-2-(cyanomethyl)benzoate (Cpd P, 150 g, ~75% pure, 47% yield) as a yellow oil.

Cobalt (II) chloride hexahydrate (166 g, 0.70 mol) was added to a room temperature solution of ethyl 3,6-dichloro-2-(cyanomethyl)benzoate (Cpd P, 90 g, 0.35 mol) in ethanol (1.5 L), and the resulting mixture cooled to 0° C. Sodium borohydride (66.3 g, 1.74 mol) was added in portions. The mixture was stirred at room temperature for 1 hour, and then refluxed overnight. The resulting suspension was filtered and the filtrate concentrated in vacuo. The solids in the filter cake were stirred in ethyl acetate (600 mL), and then filtered again. This procedure was repeated a second time. The combined filtrates were added to the original filtrate residue, and this organic solution washed with water (800 mL) and saturated aqueous sodium chloride solution (800 mL), dried over sodium sulfate, and concentrated in vacuo to give 5,8-dichloro-3,4-dihydroisoquinolin-1(2H)-one (Cpd Q, 29.3 g, 39% yield) as an off-white solid.

To a solution of 5,8-dichloro-3,4-dihydroisoquinolin-1(2H)-one (Cpd Q, 40 g, 0.186 mol) in concentrated sulfuric acid (200 mL) at 60° C. was added N-bromosuccinimide (49.7 g, 0.279 mol) in portions. Stirring was continued at 60° C. for 2 hours, then more N-bromosuccinimide (5 g. 28 mmol) was added. After stirring at 60° C. for 1 hour more, the mixture was poured onto ice water (500 mL), then extracted with dichloromethane (3×500 mL). The combined organic extracts were washed with saturated aqueous sodium chloride solution (800 mL), dried over sodium sulfate, and concentrated in vacuo. The residue was stirred in ethyl acetate (40 mL) and petroleum ether (20 mL), and the resulting solids collected by filtration and dried under vacuum to give 7-bromo-5,8-dichloro-3,4-dihydroisoquinolin-1(2H)-one (Cpd R, 41 g, 75% yield) as an off-white solid.

Potassium tert-butoxide solution in tetrahydrofuran (1.0 M, 190 mL, 0.19 mol) was added dropwise to a cooled (0° C.) solution of 7-bromo-5,8-dichloro-3,4-dihydroisoquinolin-1(2H)-one (Cpd R, 47 g, 0.16 mol) in anhydrous N,N-dimethylformamide (500 mL) under a nitrogen atmosphere. Stirring was continued at 0° C. for 5 minutes, then 2-(benzyloxy)-3-(chloromethyl)-4,6-dimethylpyridine (Cpd D, 40.2 g, 0.15 mol) was added in one portion. After stirring for 10 minutes at 0° C., the mixture was treated with concentrated acetic acid (2 mL) and poured into methyl tert-butyl ether (600 mL). The organic solution was washed with water (800 mL) and saturated aqueous sodium chloride solution (800 mL), dried over sodium sulfate, and concentrated in vacuo. The residue was purified by silica gel chromatography (eluting with 30:1 to 20:1 petroleum ether/ethyl acetate), affording 2-{[2-(benzyloxy)-4,6-dimethylpyridin-3-yl]methyl}-7-bromo-5,8-dichloro-3,4-dihydroisoquinolin-1(2H)-one (Cpd S, 50 g, 64% yield) as an off-white solid. $^1$H NMR (400 MHz, DMSO-d6) δ 8.08 (s, 1H), 7.45-7.43 (m, 2H), 7.32-7.29 (m, 3H), 6.76 (s, 1H), 5.38 (s, 2H), 4.71 (s, 2H), 3.24 (t, J=6 Hz, 2H), 2.72 (t, J=6 Hz, 2H), 2.36 (s, 3H), 2.31 (s, 3H). MS: 521 [M+H]$^+$.

Compound T: Methyl 2-(2-((2-(benzyloxy)-4,6-dimethylpyridin-3-yl)methyl)-5,8-dichloro-1-oxo-1,2,3,4-tetrahydroisoquinolin-7-yl)acetate

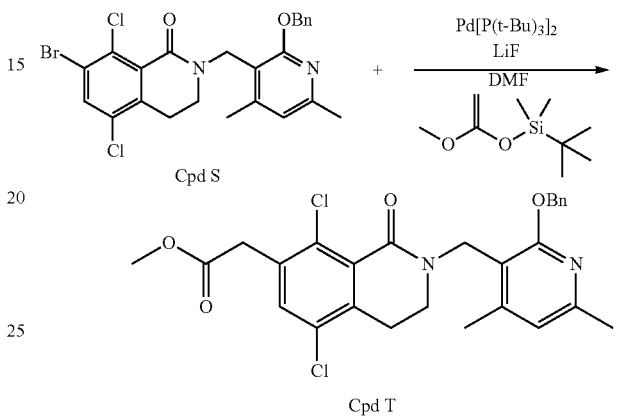

A mixture of 2-{[2-(benzyloxy)-4,6-dimethylpyridin-3-yl]methyl}-7-bromo-5,8-dichloro-3,4-dihydroisoquinolin-1(2H)-one (Cpd S, 1.0 g, 1.9222 mmol), 1-(tert-butyldimethylsilyloxy)-1-methoxyethene (1.09 g, 5.77 mmol), bis(tri-tert-butylphosphine)palladium(0) (98.2 mg, 0.192 mmol) and lithium fluoride (299 mg, 11.5 mmol) in dry N,N-dimethylformamide (18 mL) was degassed with nitrogen for 10 minutes. Then the mixture was heated in a microwave reactor at 100° C. for 3 hours. Water (20 mL) was added to the reaction mixture, which was then extracted with ethyl acetate (2×40 mL). The combined organic layers were washed with brine (4×50 mL), dried over sodium sulfate, and concentrated under vacuum. The crude product was purified by silica gel chromatography (petroleum ether/EtOAc=3:1, Rf 0.45) to give methyl 2-(2-((2-(benzyloxy)-4,6-dimethylpyridin-3-yl)methyl)-5,8-dichloro-1-oxo-1,2,3,4-tetrahydroisoquinolin-7-yl)acetate (Cpd T, 600 mg, 60.8%) as a light yellow solid. $^1$H NMR (400 MHz, CDCl3) δ 7.45 (d, J=6.8 Hz, 2H), 7.37-7.30 (m, 4H), 6.62 (s, 1H), 5.42 (s, 2H), 4.87 (s, 2H), 3.80 (s, 2H), 3.72 (s, 3H), 3.28 (t, J=6.4 Hz, 2H), 2.73 (t, J=6.4 Hz, 2H), 2.42 (s, 3H), 2.32 (s, 3H). MS: 535.0 [M+Na]$^+$ Compound U: Methyl 2-(2-((2-(benzyloxy)-4,6-dimethylpyridin-3-yl)methyl)-5,8-dichloro-1-oxo-1,2,3,4-tetrahydroisoquinolin-7-yl)-2-diazoacetate

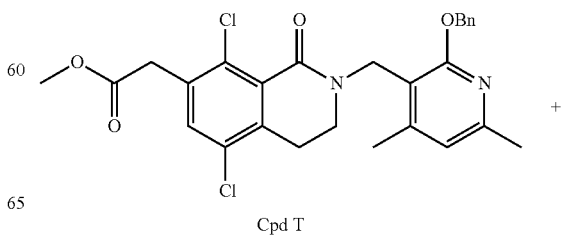

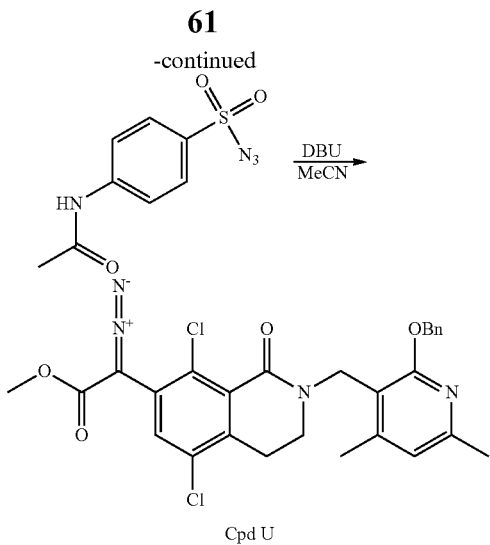

Cpd U

To a solution of methyl 2-(2-((2-(benzyloxy)-4,6-dimethylpyridin-3-yl)methyl)-5,8-dichloro-1-oxo-1,2,3,4-tetrahydroisoquinolin-7-yl)acetate (500 mg, 0.974 mmol) and 4-acetyl aminobenzenesulfonyl azide (281 mg, 1.17 mmol) in anhydrous acetonitrile (8 mL) was added 1,8-diazabicyclo [5.4.0]undec-7-ene (0.22 mL, 1.47 mmol). The resulting reaction mixture was stirred at room temperature for 3 h. After removing solvent, the resulting residue was purified by a silica gel column with a gradient elution of 0→40% EtOAc/heptane to afford methyl 2-(2-((2-(benzyloxy)-4,6-dimethylpyridin-3-yl)methyl)-5,8-dichloro-1-oxo-1,2,3,4-tetrahydroisoquinolin-7-yl)-2-diazoacetate as a foam like solid (Cpd U, 454 mg, 86% yield). LCMS: 511.10/512.10 (M−N$_2$). $^1$H NMR (400 MHz, CDCl3) δ 7.64 (s, 1H), 7.44 (d, J=6.60 Hz, 2H), 7.29-7.39 (m, 3H), 6.63 (s, 1H), 5.47 (s, 2H), 4.89 (s, 2H), 3.86 (s, 3H), 3.30 (t, J=5.99 Hz, 2H), 2.74-2.86 (m, 2H), 2.43 (s, 3H), 2.36 (s, 3H).

Compound W: Methyl 2-(2-((2-(benzyloxy)-4-(difluoromethoxy)-6-methylpyridin-3-yl)methyl)-5,8-dichloro-1-oxo-1,2,3,4-tetrahydroisoquinolin-7-yl) acetate

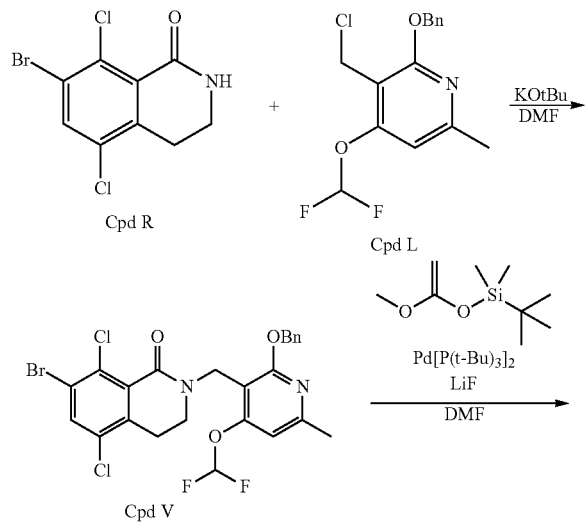

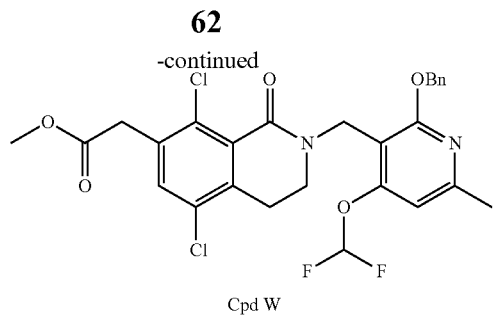

Cpd W

Potassium tert-butoxide solution in tetrahydrofuran (1.0 M, 3.2 mL, 3.2 mmol) was added dropwise to a cooled (0° C.) solution of 7-bromo-5,8-dichloro-3,4-dihydroisoquinolin-1(2H)-one (Cpd R, 750 mg, 2.54 mmol) in dry N,N-dimethylformamide (15 mL). The mixture was stirred at 0° C. for 15 minutes, and then a solution of 2-(benzyloxy)-3-(chloromethyl)-4-(difluoromethoxy)-6-methylpyridine (Cpd L, 798 mg, 2.54 mmol) in dry N,N-dimethylformamide (5 mL) was added dropwise. After stirring at 0° C. for 30 minutes, the solution was quenched with water (30 mL) and extracted with ethyl acetate (3×15 mL). The combined organic layers were washed sequentially with water (2×20 mL) and brine (20 mL), dried over sodium sulfate, filtered, concentrated, and was purified by column chromatography (silica gel, petroleum ether/EtOAc=7:1) to give 2-((2-(benzyloxy)-4-(difluoromethoxy)-6-methylpyridin-3-yl) methyl)-7-bromo-5,8-dichloro-3,4-dihydroisoquinolin-1 (2H)-one (Cpd V, 0.97 g, 67%) as a light-yellow solid.

A mixture of 2-((2-(benzyloxy)-4-(difluoromethoxy)-6-methylpyridin-3-yl)methyl)-7-bromo-5,8-dichloro-3,4-dihydroisoquinolin-1(2H)-one (Cpd V, 500 mg, 0.874 mmol), 1-(tert-butyldimethylsilyloxy)-1-methoxyethene (494 mg, 2.62 mmol), bis(tri-tert-butylphosphine)palladium(0) (67 mg, 0.313 mmol) and lithium fluoride (136 mg, 5.24 mmol) in dry N,N-dimethylformamide (15 mL) was degassed with nitrogen for 10 minutes, then heated to 100° C. in a microwave reactor for 3 hours. After cooling, the mixture was diluted with water (30 mL) and extracted with ethyl acetate (4×20 mL). The combined organic layers were washed with water (3×15 mL) and brine (15 mL), dried and concentrated. The residue was purified by prep. TLC (silica gel, petroleum ether/EtOAc=2:1, Rf-0.35) to give methyl 2-(2-((2-(benzyloxy)-4-(difluoromethoxy)-6-methylpyridin-3-yl)methyl)-5,8-dichloro-1-oxo-1,2,3,4-tetrahydroisoquinolin-7-yl)acetate (Cpd W, 175 mg, 35.4%) as a white solid. $^1$H NMR (400 MHz, CDCl3) δ 7.42-7.41 (m, 2H), 7.37 (s, 1H), 7.29-7.27 (m, 3H), 6.66 (t, J=72 Hz, 1H), 6.62 (s, 1H), 5.45 (s, 2H), 4.82 (s, 2H), 3.80 (s, 2H), 3.72 (s, 3H), 3.26 (t, J=6.0 Hz, 2H), 2.73 (t, J=6.4 Hz, 2H), 2.46 (s, 3H).

Compound Z: 2-((2-(benzyloxy)-4,6-dimethylpyridin-3-yl)methyl)-7-bromo-8-chloro-3,4-dihydroisoquinolin-1(2H)-one

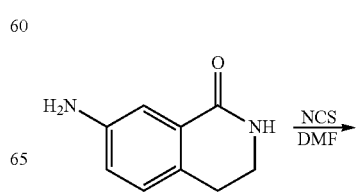

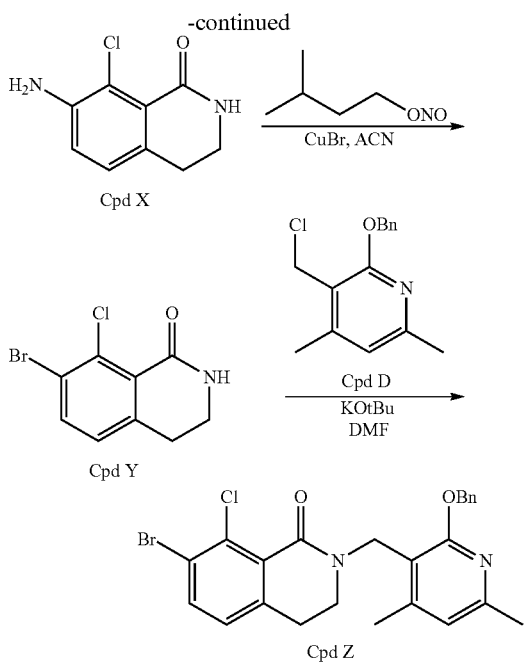

A solution of 7-amino-3,4-dihydroisoquinolin-1(2H)-one (1.01 g, 6.23 mmol) and N-chlorosuccinimide (832 mg, 6.23 mmol) in N,N-dimethylformamide (10 mL) was and heated to 55° C. for 5 hours. The mixture was poured into water and extracted with ethyl acetate (3×). The combined ethyl acetate layers were concentrated, and residual DMF was removed on high vacuum overnight. The resulting dark oil was purified on silica gel (Biotage SNAP, 50 g, gradient of 50-100% ethyl acetate in heptanes) to give 7-amino-8-chloro-3,4-dihydroisoquinolin-1(2H)-one (Cpd X, 0.539 g, 44%) as a white solid. $^1$H NMR (400 MHz, DMSO-d$_6$) δ 7.87 (br. s., 1H), 6.96 (d, J=8.19 Hz, 1H), 6.87 (d, J=8.19 Hz, 1H), 5.32 (s, 2H), 3.20 (dt, J=3.79, 6.17 Hz, 2H), 2.69 (t, J=6.24 Hz, 2H); MS 197 [M+H]$^+$.

A suspension of copper(I)bromide (1.04 g, 7.28 mmol) in acetonitrile (20 mL) was stirred at 60° C. for 10 minutes. Isoamyl nitrite (0.348 mL, 2.91 mmol) was added, followed by 7-amino-8-chloro-3,4-dihydroisoquinolin-1(2H)-one (Cpd X, 0.477 g, 2.43 mmol) in one portion. The reaction mixture was stirred at 60° C. for 1 hour. After cooling to room temperature, saturated aq. NH$_4$Cl and EtOAc were added to the solution, and the biphasic mixture stirred vigorously for 20 minutes. The layers were separated, the organic layer concentrated, and the residue was purified on silica gel (Biotage SNAP, 10 g, HP-Sil, gradient of 40-100% ethyl acetate in heptane) to give 7-bromo-8-chloro-3,4-dihydroisoquinolin-1(2H)-one (Cpd Y, 0.287 g, 45%) as a yellow solid. $^1$H NMR (400 MHz, CDCl3) δ 7.70 (d, J=8.07 Hz, 1H), 7.03 (d, J=8.07 Hz, 1H), 6.14 (br. s., 1H), 3.43-3.57 (m, 2H), 2.95 (t, J=6.36 Hz, 2H); MS 260, 262 [M+H]$^+$.

Potassium t-butoxide (1.3 mL, 1.3 mmol, 1.0 M in THF) was added to a cooled (0° C.) solution of 7-bromo-8-chloro-3,4-dihydroisoquinolin-1(2H)-one (Cpd Y, 0.287 g, 1.10 mmol) in N,N-dimethylformamide (10 mL). After 5 minutes, 2-(benzyloxy)-3-(chloromethyl)-4,6-dimethylpyridine (Cpd D 0.311 g, 1.19 mmol) was added in one portion. The mixture was stirred for 30 minutes, then quenched with acetic acid (3 drops), diluted with MTBE, and washed with water (2×). The organic layer was concentrated, and the resulting oil purified on silica gel (Biotage SNAP, 10 g, gradient of 0-25% ethyl acetate in heptane) to 2-((2-(benzyloxy)-4,6-dimethylpyridin-3-yl)methyl)-7-bromo-8-chloro-3,4-dihydroisoquinolin-1(2H)-one (Cpd Z, 0.387 g, 72%) as a clear gum. $^1$H NMR (400 MHz, CDCl3) δ 7.61 (d, J=8.07 Hz, 1H), 7.42-7.47 (m, 2H), 7.28-7.38 (m, 3H), 6.89 (d, J=8.07 Hz, 1H), 6.63 (s, 1H), 5.43 (s, 2H), 4.90 (s, 2H), 3.22-3.29 (m, 2H), 2.60-2.66 (m, 2H), 2.42 (s, 3H), 2.34 (s, 3H); MS 485, 487 [M+H]$^+$.

Compound FF: 2-((2-(benzyloxy)-4,6-dimethylpyridin-3-yl)methyl)-5-bromo-8-chloro-7-iodo-3,4-dihydroisoquinolin-1(2H)-one

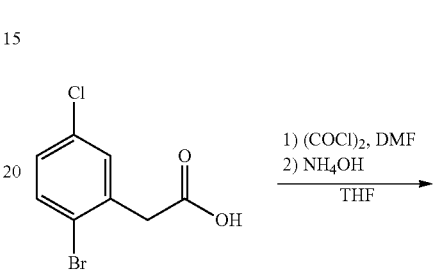

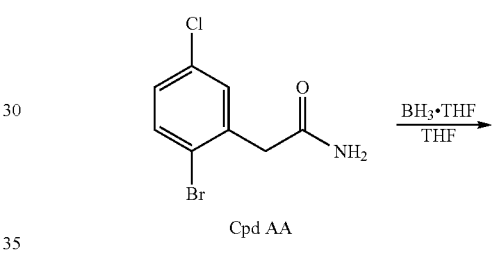

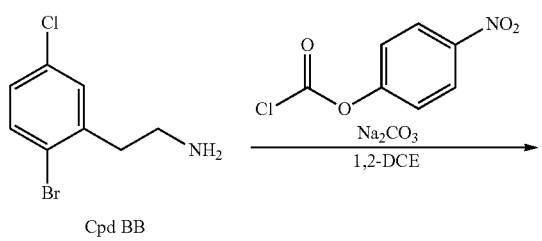

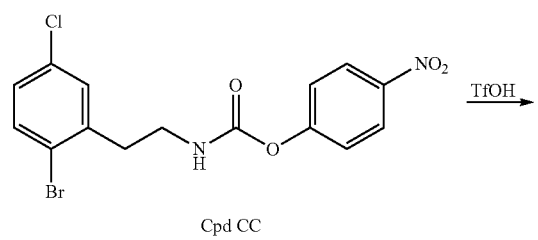

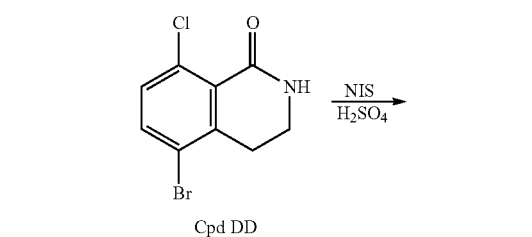

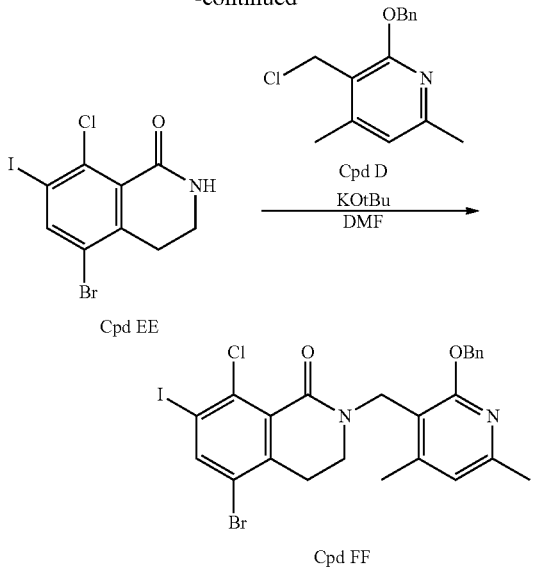

Two batches were run in parallel under the following conditions, then combined for workup and purification: To a room temperature (15-20° C.) solution of 2-(2-bromo-5-chlorophenyl)acetic acid (25.0 g, 100.2 mmol) in anhydrous THF (300 mL) was added oxalyl chloride (14.5 g, 9.97 mL, 114 mmol) and DMF (150 mg, 2.05 mmol), initiating gas evolution. The mixture was stirred at room temperature for two hours, until TLC showed the starting acid was completely consumed. The mixture was cooled to 0° C., and ammonium hydroxide (28 wt % in water, 154 mL) was added in one portion, causing the internal temperature to rise to 40° C. The cooling bath was removed, and the solution stirred vigorously at room temperature for one hour. The two batches were combined, diluted with water (500 mL), and extracted with ethyl acetate (2×1000 mL). The combined organic extracts were washed with water (2×500 mL), 1N aqueous HCl (500 mL), and brine (500 mL), then dried over anhydrous sodium sulfate and concentrated to give crude product (~50 g) as a yellow solid. The crude product was crystallized from 5/1 petroleum ether/ethyl acetate (200 mL×2) and dried to give 2-(2-bromo-5-chlorophenyl)acetamide (Cpd AA, 44.0 g, 88% combined yield for the two batches) as a white solid. $^1$H NMR (400 MHz, CDCl3) δ 7.52 (d, J=8.8 Hz, 1H), 7.37 (d, J=2.8 Hz, 1H), 7.16 (dd, J=2.8, 8.8 Hz, 1H), 5.67 (br s, 1H), 5.50 (br s, 1H), 3.70 (s, 2H).

Two batches were run in parallel under the following conditions, then combined for purification: Borane-THF complex (1.0 M in THF, 400 mL, 400 mmol) was added dropwise to a cooled (0° C.) suspension of 2-(2-bromo-5-chlorophenyl)acetamide (Cpd AA, 22.0 g, 88.5 mmol) in anhydrous THF (300 mL). The resulting clear solution was heated to 80° C. for two hours, then cooled again to 0° C. The mixture was quenched by sequential addition of water (45 mL) and conc. HCl (120 mL), causing significant gas evolution. Stirring was continued at 10-15° C. for 16 hours, after which the mixture was concentrated to remove THF. The aqueous residue was cooled to 0° C., then 12 N aqueous sodium hydroxide was added to bring the pH to 11. The basified solution was extracted with ethyl acetate (3×500 mL). The combined organic extracts were washed with brine (500 mL), dried over anhydrous sodium sulfate, filtered, and concentrated to give crude product (~25 g) as a yellow oil. Two ~25 g batches of this crude product were combined, treated with 4N HCl/MeOH (500 mL), and stirred at 10-15° C. for 16 hours. The mixture was concentrated, and the residue stirred in ethyl acetate (500 mL) for 30 minutes. The resulting white solid was collected by filtration, and the filter cake washed with ethyl acetate (3×100 mL). The solids were dissolved in water (500 mL), filtered to remove insolubles, and the filtrate extracted with ethyl acetate (2×500 mL). The aqueous layer was basified with solid NaOH to pH 10, then extracted with ethyl acetate (2×500 mL). The combined organic extracts were washed with brine (500 mL), dried over anhydrous sodium sulfate, filtered, and concentrated to give 2-(2-bromo-5-chlorophenyl)ethan-1-amine (Cpd BB, 30.0 g, 72% combined yield for the two batches) as a colorless oil. $^1$H NMR (400 MHz, CDCl3) δ 7.47 (d, J=8.4 Hz, 1H), 7.23 (d, J=2.4 Hz, 1H), 7.07 (dd, J=2.4, 8.4 Hz, 1H), 2.98 (t, J=6.8 Hz, 2H), 2.86 (t, J=6.8 Hz, 2H), 1.28 (m, 2H).

To a cooled (0° C.) suspension of 2-(2-bromo-5-chlorophenyl)ethan-1-amine (Cpd BB, 28.0 g, 119 mmol) and sodium carbonate (32.3 g, 304 mmol) in anhydrous 1,2-dichloroethane (600 mL) was added 4-nitrophenyl chloroformate (25.5 g, 127 mmol). The mixture was stirred at 0° C. for 30 minutes, then at 10-15° C. for 16 hours. The solution was diluted with water (1000 mL) and extracted with dichloromethane (3×1000 mL). The combined organic extracts were washed with water (1000 mL) and brine (1000 mL), dried over anhydrous sodium sulfate, and concentrated. The crude product (~55 g, yellow solid) was crystallized from 5/1 petroleum ether/EtOAc (100 mL×2) to give 4-nitrophenyl (2-bromo-5-chlorophenethyl)carbamate (Cpd CC, 40.0 g, 84% yield) as a white solid. $^1$H NMR (400 MHz, CDCl3) δ 8.25 (d, J=9.2 Hz, 2H), 7.51 (d, J=8.4 Hz, 1H), 7.31 (m, 3H), 7.13 (dd, J=2.0, 8.4 Hz, 1H), 5.22 (br s, 1H), 3.57 (t, J=6.8 Hz, 2H), 3.05 (t, J=6.8 Hz, 2H).

Trifluoromethanesulfonic acid (150 g, 1000 mmol) was added dropwise to a cooled (0° C.) suspension of 4-nitrophenyl (2-bromo-5-chlorophenethyl)carbamate (Cpd CC, 40.0 g, 100 mmol) in anhydrous 1,2-dichloroethane (300 mL). Solids gradually dissolve over the course of the addition, resulting in a clear yellow solution. The mixture was stirred at 0° C. for 10 minutes, then heated at 60-70° C. for 3 hours. The resulting brown solution was poured into ice-water (1000 mL) and stirred until all the ice had melted. The layers were separated, and the aqueous layer extracted with dichloromethane (2×1000 mL). The combined organic layers were washed with 2N aqueous sodium hydroxide (3×500 mL), water (500 mL), and brine (500 mL), then dried over anhydrous sodium sulfate and concentrated. The crude product (~30 g brown solid) was crystalized from 2/1 petroleum ether/ethyl acetate (150 mL×2), to give 5-bromo-8-chloro-3,4-dihydroisoquinolin-1(2H)-one (Cpd DD, 20.7 g, 80% yield) as a brown solid. $^1$H NMR (400 MHz, DMSO-d6) δ 8.25 (br s, 1H), 7.72 (d, J=8.4 Hz, 1H), 7.35 (d, J=8.4 Hz, 1H), 3.12 (t, J=4.4 Hz, 2H), 2.95 (t, J=6.2 Hz, 2H).

N-iodosuccinimide (53.7 g, 239 mmol) was added to a cooled (0° C.) solution of 5-bromo-8-chloro-3,4-dihydroisoquinolin-1(2H)-one (Cpd DD, 20.7 g, 79.6 mmol) in conc. sulfuric acid (98% w/w, 300 mL). The resulting brown suspension was stirred at 10-15° C. for 16 hours, then poured into ice-water (1000 mL) and stirred until all the ice had melted. The resulting aqueous suspension was extracted with ethyl acetate (3×1000 mL). The combined organic extracts were washed with saturated aqueous NaHSO3 (2×500 mL), 2N aqueous sodium hydroxide (2×500 mL), and brine (500 mL), then dried over anhydrous sodium sulfate and concentrated. The crude product (~30 g yellow solid) was crystalized with 1/1 petroleum ether/ethyl acetate (100 mL×2) to give 5-bromo-8-chloro-7-iodo-3,4-dihydroisoquinolin-1(2H)-one (Cpd EE, 23.0 g, 75% yield) as an off-white solid. $^1$H NMR (400 MHz, DMSO-d6) δ ppm 8.35 (br. s, 1H), 8.33 (s, 1H), 3.30-3.25 (2H, m), 2.89 (t, J=6.0 Hz, 2H). MS: 386 [M+H]$^+$.

Potassium tert-butoxide (1.0M solution in THF, 7.30 mL, 7.30 mmol) was added dropwise to a cooled (0° C.) suspension of 5-bromo-8-chloro-7-iodo-3,4-dihydroisoquinolin-1(2H)-one (Cpd EE, 2.35 g, 6.08 mmol) in anhydrous DMF (30 mL). The mixture was stirred at 0° C. for 30 minutes, then a solution of 2-(benzyloxy)-3-(chloromethyl)-4,6-dimethylpyridine (Cpd D, 1.75 g, 6.69 mmol) in anhydrous DMF (10 mL) was added, and stirring continued at 0° C. for 30 minutes. The reaction mixture was partitioned between ethyl acetate (100 mL) and water (100 mL). The organic phase was washed with water (1×100 mL) and brine (1×100 mL), dried over sodium sulfate, concentrated to dryness, and purified by silica gel chromatography, eluting with a gradient of 0-40% ethyl acetate in heptane to afford 2-((2-(benzyloxy)-4,6-dimethylpyridin-3-yl)methyl)-5-bromo-8-chloro-7-iodo-3,4-dihydroisoquinolin-1 (2H)-one (Cpd FF, 2.95 g, 79% yield) as a gum. $^1$H NMR (400 MHz, CDCl3) δ ppm 8.11 (s, 1H), 7.40-7.47 (m, 2H), 7.27-7.37 (m, 3H), 6.62 (s, 1H), 5.42 (s, 2H), 4.85 (s, 2H), 3.25 (t, J=6.24 Hz, 2H), 2.68 (t, J=6.24 Hz, 2H), 2.41 (s, 3H), 2.32 (s, 3H). MS: 611, 613 [M+H]$^+$.

Compound KK: 2-(benzyloxy)-3-(chloromethyl)-4-methoxy-6-methylpyridine

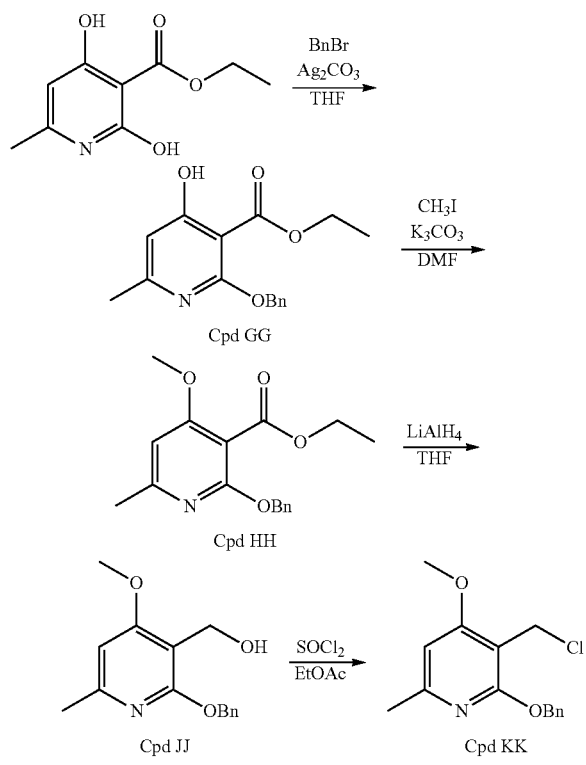

Benzyl bromide (19.1 g, 112 mmol) was added to a room temperature solution of ethyl 2,4-dihydroxy-6-methylnicotinate (20.0 g, 101.4 mmol) and silver carbonate (15.4 g, 55.8 mmol) in THF (100 mL), then the mixture was heated to 60° C. for 18 hours. After cooling to room temperature, the suspension was filtered through a CELITE® pad, the filtrate concentrated and purified by silica gel chromatography (eluting with 5% ethyl acetate in heptane) to give ethyl 2-(benzyloxy)-4-hydroxy-6-methylnicotinate (Cpd GG, 18 g, 62% yield) as a white solid. $^1$H NMR (400 MHz, DMSO-d6) δ 11.14 (s, 1H), 7.40-7.44 (m, 2H), 7.36 (t, J=7.34 Hz, 2H), 7.27-7.33 (m, 1H), 6.44 (s, 1H), 5.35 (s, 2H), 4.23 (q, J=7.13 Hz, 2H), 2.30 (s, 3H), 1.22 (t, J=7.09 Hz, 3H). MS: 288 [M+H]$^+$.

A solution of ethyl 2-(benzyloxy)-4-hydroxy-6-methylnicotinate (Cpd GG, 18.0 g, 62.6 mmol) and potassium carbonate (9.52 g, 68.9 mmol) in DMF (50 mL) was stirred at room temperature for 10 minutes, then iodomethane (9.98 g, 68.9 mmol) was added and stirring continued at room temperature for 18 hours. The mixture was partitioned between water and ethyl acetate. The organic extracts were washed with sat. aq. NaCl, dried over sodium sulfate, and concentrated. The residue was purified by silica gel chromatography (eluting with 0-35% ethyl acetate in heptane), affording ethyl 2-(benzyloxy)-4-methoxy-6-methylnicotinate (Cpd HH, 16.7 g, 89% yield) as a colorless oil. $^1$H NMR (400 MHz, DMSO-d6) δ 7.33-7.42 (m, 4H), 7.26-7.33 (m, 1H), 6.75 (s, 1H), 5.36 (s, 2H), 4.22 (q, J=7.13 Hz, 2H), 3.83 (s, 3H), 2.39 (s, 3H), 1.20 (t, J=7.09 Hz, 3H).). MS: 302 [M+H]$^+$.

Lithium aluminium hydride solution (2.0M in THF) was added dropwise to a cooled (0° C.) solution of ethyl 2-(benzyloxy)-4-methoxy-6-methylnicotinate (Cpd HH, 16.7 g, 55.4 mmol) in THF (100 mL). After addition was complete, the solution was allowed to gradually warm to room temperature with stirring for 18 hours. The mixture was diluted with THF (200 mL), cooled to 0° C., and quenched by sequential dropwise addition of water (3.4 mL), 15% aq. sodium hydroxide, and water (10.2 mL). The resulting slurry was stirred at room temperature for 2 hours, then filtered through a pad of CELITE®. Concentration of the filtrate yielded (2-(benzyloxy)-4-methoxy-6-methylpyridin-3-yl)methanol (Cpd JJ, 14 g, 97% yield) as colorless oil. $^1$H NMR (400 MHz, DMSO-d6) δ 7.46 (d, J=7.09 Hz, 2H), 7.36 (t, J=7.40 Hz, 2H), 7.25-7.33 (m, 1H), 6.63 (s, 1H), 5.35 (s, 2H), 4.37-4.46 (m, 3H), 3.82 (s, 3H), 2.35 (s, 3H). MS: 260 [M+H]$^+$.

Thionyl chloride (6.57 g, 54.7 mmol) was added dropwise to a cooled (0° C.) solution of (2-(benzyloxy)-4-methoxy-6-methylpyridin-3-yl)methanol (Cpd JJ, 13.5 g, 52.1 mmol) in ethyl acetate (300 mL), causing formation of a solid precipitate. The slurry was stirred in the cooling bath for 30 minutes, then water was added to dissolve the solids. After separation of the phases, the organic layer was washed with sat. aq. NaCl, dried over sodium sulfate, and concentrated to dryness. The residue was dissolved in heptane and again concentrated to dryness, affording 2-(benzyloxy)-3-(chloromethyl)-4-methoxy-6-methylpyridine (Cpd KK, 13.9 g, 95% yield) as white solid. $^1$H NMR (400 MHz, DMSO-d6) δ 7.47 (d, J=7.34 Hz, 2H), 7.38 (t, J=7.40 Hz, 2H), 7.27-7.34 (m, 1H), 6.71 (s, 1H), 5.40 (s, 2H), 4.66 (s, 2H), 3.89 (s, 3H), 2.38 (s, 3H). MS: 260 [M+H]$^+$.

69

Compound RR: 8-chloro-7-iodo-5-methyl-3,4-dihydroisoquinolin-1(2H)-one

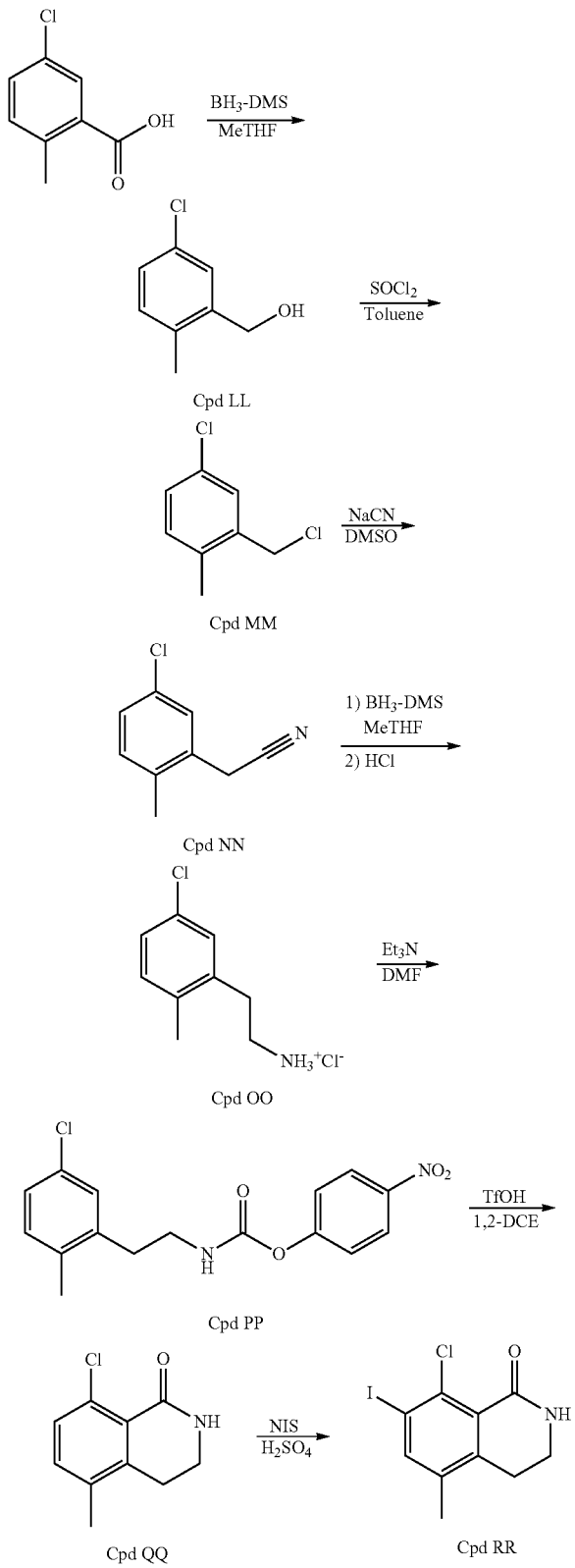

70

To a cooled (0° C.) solution of 5-chloro-2-methylbenzoic acid (20.0 g, 117 mmol) in anhydrous 2-methyltetrahydrofuran (200 mL), borane-dimethylsulfide complex (28.0 g, 35.0 mL, 369 mmol) was added dropwise over 1 hour, slowly enough to maintain the internal temperature below 10° C. Gas evolution was observed, and some precipitate formed. After the addition was complete, the cooling bath was removed and stirring continued at room temperature overnight. Methanol (50 mL) was carefully added to quench the mixture. The solution was concentrated to dryness, and the residue partitioned between ether (200 mL) and saturated aqueous sodium bicarbonate. The organic layer was washed with brine (200 mL), dried over sodium sulfate, filtered, and concentrated to give ethyl 2-(benzyloxy)-4-hydroxy-6-methylnicotinate (Cpd LL, 18.4 g, 100% yield) as an oil. 1H NMR (400 MHz, CDCl3) δ 7.36 (d, J=2.08 Hz, 1H), 7.13-7.19 (m, 1H), 7.04-7.11 (m, 1H), 4.63 (s, 2H), 2.27 (s, 3H), 2.12 (s, 1H).

A solution of 2-(benzyloxy)-4-hydroxy-6-methylnicotinate (Cpd LL, 18.0 g, 115 mmol) in anhydrous toluene (300 mL) was cooled to below 10° C. internal. Thionyl chloride (21.3 g, 179 mmol) was added dropwise, slowly enough to maintain the internal temperature below 10° C. The mixture was stirred at this temperature for 30 minutes, then the cooling bath was removed and stirring continued at room temperature for 5 hours. The solution was concentrated to remove volatiles, and the residue partitioned between ethyl acetate (200 mL) and sodium bicarbonate (200 mL). The organic phase was washed with brine (200 mL), dried over sodium sulfate, and concentrated to give 4-chloro-2-(chloromethyl)-1-methylbenzene (Cpd MM, 17.5 g, 87% yield) as an oil. $^1$H NMR (400 MHz, CDCl3) δ 7.33 (d, J=2.20 Hz, 1H), 7.20-7.25 (m, 1H), 7.14 (d, J=8.07 Hz, 1H), 4.55 (s, 2H), 2.39 (s, 3H).

To a solution of 4-chloro-2-(chloromethyl)-1-methylbenzene ((Cpd MM, 17.5 g, 100 mmol) in DMSO (200.0 mL) and water (50.0 mL) was added solid sodium cyanide (5.88 g, 120 mmol) in one portion. The reaction was slightly exothermic, and the internal temperature of the reaction mixture rose to 43° C. Stirring was continued for one hour. The reaction mixture was partitioned between ethyl acetate (300 mL) and water (300 mL). The organic phase was washed with sodium bicarbonate (300 mL) and brine (300 mL), dried over sodium sulfate, and concentrated to give 2-(5-chloro-2-methylphenyl)acetonitrile (Cpd NN, 16.1 g, 97% yield) as an oil. $^1$H NMR (400 MHz, CDCl3) δ 7.37 (d, J=1.96 Hz, 1H), 7.21-7.26 (m, 1H), 7.13-7.17 (m, 1H), 3.64 (s, 2H), 2.32 (s, 3H).

Borane dimethylsulfide complex (22.3 g, 293 mmol, 26.0 mL) was added dropwise to a solution of 2-(5-chloro-2-methylphenyl)acetonitrile (Cpd NN, 16.0 g, 96.6 mmol) in 2-methyl tetrahydrofuran (150 mL), causing gas evolution. After the addition was complete, the mixture was heated to reflux for 5 hours. After cooling to room temperature, methanol was added to quench the mixture until no more bubbles were generated. The solution was concentrated to dryness. The residue was dissolved in methanol and treated with 4M HCl/dioxane solution (100 mL) to break up the boron complex. The solution was concentrated to dryness. The white solid residue was dissolved in minimal methanol (~20 mL), ethyl acetate (~200 mL) was added, and the mixture stirred vigorously until a thick paste formed. The solids were collected by filtration, washed with ethyl acetate, and dried to give 2-(5-chloro-2-methylphenyl)ethan-1-amine hydrochloride (Cpd OO, 9.5 g, 48% yield) as a white solid. $^1$H NMR (400 MHz, DMSO-d6) δ 8.24 (br. s., 3H), 7.26 (s, 1H), 7.20 (d, J=1.34 Hz, 2H), 2.84-3.02 (m, 4H), 2.27 (s, 3H). MS: 170 [M+H]⁺.

A cooled (0° C.) solution of 2-(5-chloro-2-methylphenyl)ethanamine hydrochloride (Cpd OO, 8.41 g, 40.8 mmol) in DMF (200 mL) was stirred with triethylamine (10.3 g, 102 mmol) for 10 minutes, then solid 4-nitrophenyl chloroformate (8.14 g, 38.8 mmol) was added in one portion. A thick paste formed, and the reaction mixture became slightly yellow. Stirring was continued at 0° C. for 1 hour. The reaction mixture was partitioned between ethyl acetate (300 mL) and water (300 mL). The organic phase was washed with water (200 mL), 10% sodium carbonate (200 mL), and brine (200 mL), then dried over sodium sulfate, and concentrated to give 4-nitrophenyl (5-chloro-2-methylphenethyl)carbamate (Cpd PP, 9.94 g, 73% yield) as a solid. ¹H NMR (400 MHz, CDCl3) δ 8.18-8.29 (m, 2H), 7.24-7.32 (m, 2H), 7.11-7.17 (m, 3H), 5.28 (br. s., 1H), 3.45-3.53 (m, 2H), 2.85-2.92 (m, 2H), 2.32 (s, 3H).

A cooled (0° C.) suspension of 4-nitrophenyl (5-chloro-2-methylphenethyl)carbamate (Cpd PP, 9.94 g, 29.7 mmol) in anhydrous 1,2-dichloroethane (120 mL) was treated with freshly opened trifluoromethylsulfonic acid (45.8 g, 305 mmol, 27.0 mL), and stirring continued at 0° C. for 30 minutes. The reaction mixture was then heated to 70° C. for 3 hours. After cooling to room temperature, the reaction mixture was carefully poured into ice water (200 mL), and stirred until all the ice had melted. The biphasic mixture was extracted with dichloromethane (2×200 mL). The combined organic extracts were washed with 2M sodium carbonate (200 mL). The aqueous phase was back-extracted with dichloromethane (200 mL). The dichloromethane extracts were combined, dried over sodium sulfate, and concentrated to give 8-chloro-5-methyl-3,4-dihydroisoquinolin-1(2H)-one (Cpd QQ, 4.17 g, 72% yield) as a solid. ¹H NMR (400 MHz, CDCl3) δ: 7.15-7.22 (m, 1H), 7.08 (d, J=13.69 Hz, 1H), 6.46 (br. s., 1H), 3.43-3.51 (m, 2H), 2.88 (t, J=6.17 Hz, 2H), 2.28 (s, 3H). MS: 196 [M+H]⁺.

A flask containing 8-chloro-5-methyl-3,4-dihydroisoquinolin-1(2H)-one (Cpd QQ, 6.0 g, 30.7 mmol) was cooled in an ice bath. Concentrated sulfuric acid (125.0 mL) was added, and the mixture stirred at 0° C. for 30 min. N-iodosuccinimide (20.7 g, 92.0 mmol) was added as a solid in one portion, and the mixture stirred at 0° C. for 3 hours. The solution was carefully poured into ice water (300 mL), causing a precipitate to form. The suspension was extracted with ethyl acetate (300 mL). Both organic and aqueous phases contained precipitates. The organic phase was washed with 10% Na₂S₂O₃ (300 mL) to remove excess iodine, and the aqueous layer was extracted with ethyl acetate (200 mL). The combined organic phases were dried over sodium sulfate and concentrated to dryness. The solid residue was stirred in methanol (100 mL). Insolubles were collected by filtration, and the precipitate (~14 g white solid) was slurried in carbon disulfide (100 mL). Solids were collected by filtration, washed with carbon disulfide, and dried under vacuum to yield 8-chloro-7-iodo-5-methyl-3,4-dihydroisoquinolin-1(2H)-one (Cpd RR, 8.57 g, 87% yield) as a solid. ¹H NMR (400 MHz, DMSO-d6) δ 8.15 (br. s., 1H), 7.94 (s, 1H), 3.26 (td, J=6.17, 4.03 Hz, 2H), 2.75 (t, J=6.24 Hz, 2H), 2.22 (s, 3H). MS: 321 [M=H]⁺.

Compound SS: 2-((2-(benzyloxy)-4-methoxy-6-methylpyridin-3-yl)methyl)-7-bromo-5,8-dichloro-3,4-dihydroisoquinolin-1(2H)-one

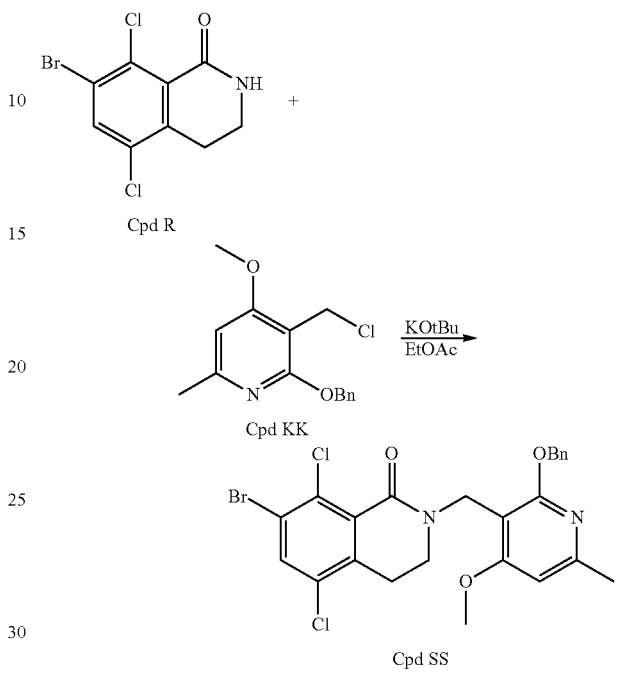

A room-temperature suspension of 7-bromo-5,8-dichloro-3,4-dihydroisoquinolin-1(2H)-one (Cpd R, 14.9 g, 50.4 mmol) in ethyl acetate (300 mL) was treated with potassium tert-butoxide (1.0 M solution in THF, 65.5 mL, 65.5 mmol), causing the solids to dissolve. After a few minutes, a precipitate begins to form. To this was added 2-(benzyloxy)-3-(chloromethyl)-4-methoxy-6-methylpyridine (Cpd KK, 14.0 g, 50.4 mmol), and the resulting suspension heated at 75° C. for 4 hours. After cooling to room temperature, the mixture was washed with water (2×) and sat. aq. NaCl, concentrated, and the residue crystalized from ethyl acetate, affording 2-((2-(benzyloxy)-4-methoxy-6-methylpyridin-3-yl)methyl)-7-bromo-5,8-dichloro-3,4-dihydroisoquinolin-1(2H)-one (Cpd SS, 21.96 g, 81% yield) as a white solid. ¹H NMR (400 MHz, DMSO-d6) δ 8.05 (s, 1H), 7.34-7.40 (m, 2H), 7.18-7.25 (m, 3H), 6.70 (s, 1H), 5.36 (s, 2H), 4.68 (s, 2H), 3.83 (s, 3H), 3.16 (t, J=6.17 Hz, 2H), 2.71 (t, J=6.17 Hz, 2H), 2.38 (s, 3H). MS: 535, 537 [M+H]⁺.

Compound TT: 2-((2-(benzyloxy)-4,6-dimethylpyridin-3-yl)methyl)-8-chloro-7-iodo-5-methyl-3,4-dihydroisoquinolin-1 (2H)-one

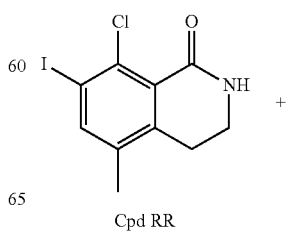

-continued

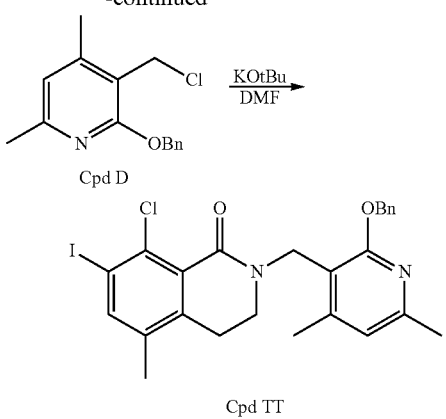

To a cooled (0° C.) solution of 8-chloro-7-iodo-5-methyl-3,4-dihydroisoquinolin-1(2H)-one (Cpd RR, 1.52 g, 4.73 mmol) in anhydrous DMF (20 mL) was added solid potassium tert-butoxide (796 mg, 7.09 mmol) in portions. Stirring was continued at 0° C. for 30 minutes, then a solution of 2-(benzyloxy)-3-(chloromethyl)-4,6-dimethylpyridine (Cpd D, 1.18 g, 4.49 mmol) in anhydrous DMF (5 mL) was added dropwise. After stirring for 20 more minutes at 0° C., the mixture was poured into ice-water (50 mL) and extracted with ethyl acetate (4×50 mL). The combined organic layers were washed with brine (4×50 mL), dried over sodium sulfate, filtered, and concentrated. The crude product (~2.4 g yellow solid) was purified by silica gel chromatography, eluting with 5/1 petroleum ether/ethyl acetate, affording 2-((2-(benzyloxy)-4,6-dimethylpyridin-3-yl)methyl)-8-chloro-7-iodo-5-methyl-3,4-dihydroisoquinolin-1(2H)-one (Cpd TT, 1.7 g, 66% yield) as an off-white solid. $^1$H NMR (400 MHz, CDCl3) δ 7.76 (s, 1H), 7.45 (d, J=7.2 Hz, 2H), 7.36-7.30 (m, 3H), 6.62 (s, 1H), 5.42 (s, 2H), 4.88 (s, 2H), 3.24 (t, J=6.2 Hz, 2H), 2.50 (t, J=6 Hz, 2H), 2.42 (s, 3H), 2.32 (s, 3H), 2.13 (s, 3H). MS: 547 [M+H]$^+$.

Compound UU: 2-((2-(benzyloxy)-4-methoxy-6-methylpyridin-3-yl)methyl)-8-chloro-7-iodo-5-methyl-3,4-dihydroisoquinolin-1(2H)-one

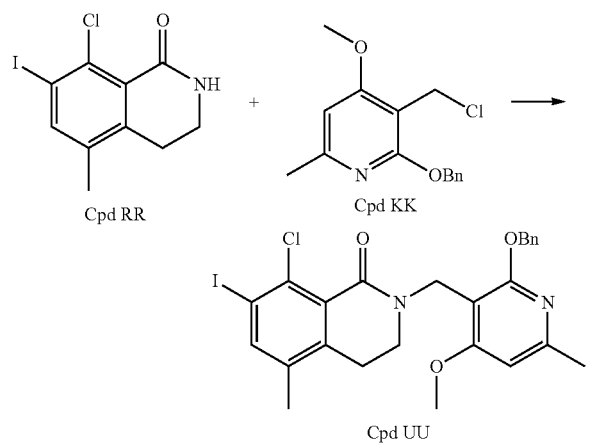

To a cooled (0° C.) solution of 8-chloro-7-iodo-5-methyl-3,4-dihydroisoquinolin-1(2H)-one (Cpd RR, 3.2 g, 9.95 mmol) in anhydrous DMF (50 mL) was added solid potassium tert-butoxide (1.68 g, 14.9 mmol) in portions. Stirring was continued at 0° C. for 30 minutes, then a solution of 2-(benzyloxy)-3-(chloromethyl)-4-methoxy-6-methylpyridine (Cpd KK, 2.63 g, 14.9 mmol) in anhydrous DMF (50 mL) was added dropwise. After stirring for 30 more minutes at 0° C., the mixture was poured into ice-water (100 mL) and extracted with ethyl acetate (3×100 mL). The combined organic layers were washed with brine (4×100 mL), dried over sodium sulfate, filtered, and concentrated. The crude product (~5 g yellow solid) was purified by silica gel chromatography, eluting with 20-50% ethyl acetate in petroleum ether. The resulting product was dissolved in dichloromethane (10 mL), added to petroleum ether (30 mL) and stirred at room temperature until a precipitate forms (30 minutes). The precipitate was collected by filtration and dried to a white solid. TLC of the precipitate still showed impurities, so it was repurified by silica gel chromatography, eluting with 0-10% methanol in dichloromethane, yielding 2-((2-(benzyloxy)-4-methoxy-6-methylpyridin-3-yl) methyl)-8-chloro-7-iodo-5-methyl-3,4-dihydroisoquinolin-1(2H)-one (Cpd UU, 2.8 g, 50% yield) as a white solid. $^1$H NMR (400 MHz, CDCl3) δ 7.75 (s, 1H), 7.42-7.40 (m, 2H), 7.29-7.27 (m, 1H), 7.25-7.22 (m, 2H), 6.38 (s, 1H), 5.42 (s, 2H), 4.87 (s, 2H), 3.83 (s, 3H), 3.14 (t, J=6.2 Hz, 2H), 2.50 (t, J=6.2 Hz, 2H), 2.44 (s, 3H), 2.13 (s, 3H). MS: 563 [M+H]$^+$.

EXAMPLES

General Methods and Representative Examples

Method A

Example 1: 5,8-dichloro-2-[(4,6-dimethyl-2-oxo-1,2-dihydropyridin-3-yl)methyl]-7-{(1R)-2-hydroxy-1-[(3R)-tetrahydrofuran-3-yl]ethyl}-3,4-dihydroisoquinolin-1(2H)-one Example 2: 5,8-dichloro-2-[(4,6-dimethyl-2-oxo-1,2-dihydropyridin-3-yl)methyl]-7-{(1R*)-2-hydroxy-1-[(3S*)-tetrahydrofuran-3-yl]ethyl}-3,4-dihydroisoquinolin-1(2H)-one Example 3: 5,8-dichloro-2-[(4,6-dimethyl-2-oxo-1,2-dihydropyridin-3-yl)methyl]-7-{(1S*)-2-hydroxy-1-[(3R*)-tetrahydrofuran-3-yl]ethyl}-3,4-dihydroisoquinolin-1(2H)-one Example 4: 5,8-dichloro-2-[(4,6-dimethyl-2-oxo-1,2-dihydropyridin-3-yl)methyl]-7-{(1S)-2-hydroxy-1-[(3S)-tetrahydrofuran-3-yl]ethyl}-3,4-dihydroisoquinolin-1(2H)-one

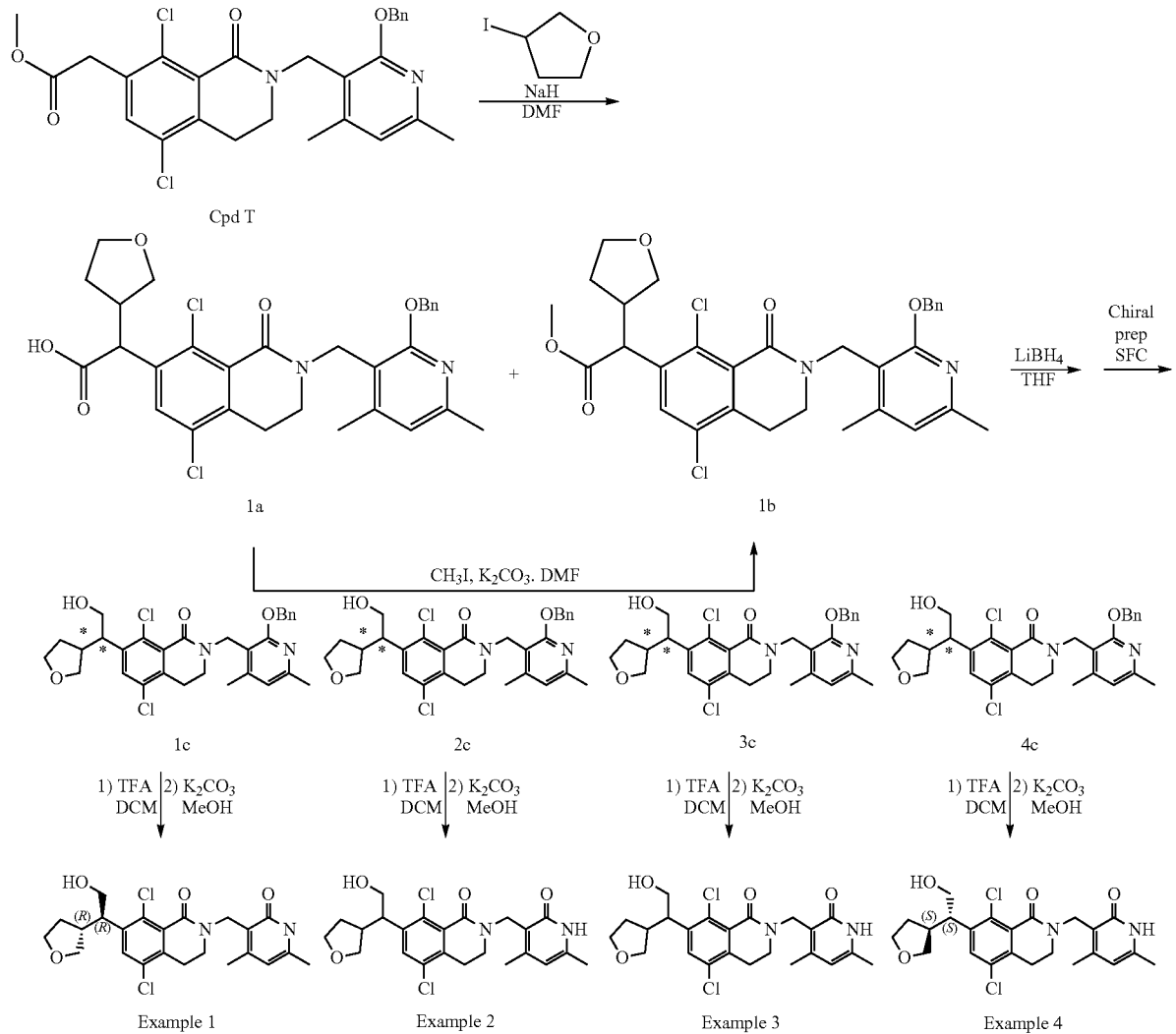

A cooled (0° C.) solution of methyl 2-(2-((2-(benzyloxy)-4,6-dimethylpyridin-3-yl)methyl)-5,8-dichloro-1-oxo-1,2,3,4-tetrahydroisoquinolin-7-yl)acetate (Cpd T, 800 mg, 0.487 mmol) in anhydrous N,N-dimethylformamide (70 mL) was treated with sodium hydride (60 wt % dispersion in mineral oil, 125 mg, 3.12 mmol), then stirred at 10° C. for 15 minutes. The mixture was cooled again to 0° C. and 3-iodotetrahydrofuran (463 mg, 2.34 mmol) was added. After stirring at room temperature for 12 hours, glacial acetic acid (2 drops) and water (10 mL) were added, and the mixture extracted with ethyl acetate (3×20 mL). The combined organic extracts were washed with brine (10 mL), dried over sodium sulfate, concentrated, and purified by column chromatography (silica gel, Petroleum ether/EtOAc=5:1~1:1) to obtain 2-(2-((2-(benzyloxy)-4,6-dimethylpyridin-3-yl)methyl)-5,8-dichloro-1-oxo-1,2,3,4-tetrahydroisoquinolin-7-yl)-2-(tetrahydrofuran-3-yl)acetic acid (1a, 500 mg, 56.3%) as a white solid; and methyl 2-(2-((2-(benzyloxy)-4,6-dimethylpyridin-3-yl)methyl)-5,8-dichloro-1-oxo-1,2,3,4-tetrahydroisoquinolin-7-yl)-2-(tetrahydrofuran-3-yl)acetate (1b, 150 mg, 16.5%) as a yellow solid.

A solution of 2-(2-((2-(benzyloxy)-4,6-dimethylpyridin-3-yl)methyl)-5,8-dichloro-1-oxo-1,2,3,4-tetrahydroisoquinolin-7-yl)-2-(tetrahydrofuran-3-yl)acetic acid (1a, 650 mg, 1.14 mmol), potassium carbonate (315 mg, 2.28 mmol), and iodomethane (324 mg, 2.28 mmol) in N,N-dimethylformamide (8 mL) was stirred at room temperature for 12 hours. The mixture was diluted with water (20 mL) and ethyl acetate (50 mL). The organic layer was separated and the aqueous layer was extracted with ethyl acetate (2×15 mL). The organic layers were combined, washed with brine (3×10 mL), dried over sodium sulfate, filtered and concentrated in vacuo to give the crude product, which was purified by column chromatography (silica gel, Petroleum ether/EtOAc=1:1) to obtain methyl 2-(2-((2-(benzyloxy)-4,6-dimethylpyridin-3-yl)methyl)-5,8-dichloro-1-oxo-1,2,3,4-tet rahydroisoquinolin-7-yl)-2-(tetrahydrofuran-3-yl)acetate (1b 600 mg, 90.1%) as a white solid.

Lithium borohydride (28 mg, 1.29 mmol) was added in one portion to a room temperature solution of methyl 2-(2-((2-(benzyloxy)-4,6-dimethylpyridin-3-yl)methyl)-5,8-dichloro-1-oxo-1,2,3,4-tetrahydroisoquinolin-7-yl)-2-(tetrahydrofuran-3-yl)acetate (1b, 250 mg, 0.428 mmol) in anhydrous tetrahydrofuran (25 mL). The resulting mixture was heated at 60° C. for 2 hours. The mixture was quenched with water (5 mL) and then extracted with ethyl acetate (3×15 mL). The organic layers were combined, washed with brine (5 mL), dried over sodium sulfate, filtered and concentrated in vacuo to give the crude product, which was purified by prep. TLC (Petroleum ether/EtOAc=1:1) to obtain 2-((2-(benzyloxy)-4,6-dimethylpyridin-3-yl)methyl)-5,8-dichloro-7-(2-hydroxy-1-(tetrahydrofuran-3-yl)ethyl)-3,4-dihydroisoquinolin-1(2H)-one (mixture of 4 stereoisomers, 160 mg, 67.2%) as a white solid. Combined batches (500 mg total) of this stereoisomer mixture was resolved by preparative chiral SFC (Chiralpak AD, 250×30 mm I.D., 5 μm, mobile phase 35% EtOH NH$_3$ H$_2$O, flow rate 50 mL/min) to obtain separated isomers 1c (peak one, 80 mg, 15.9%), 2c (peak two, 90 mg, 17.9%), 3c (peak three, 110 mg, 21.9%) and 4c (peak four, 100 mg, 19.9%) as white solids. Absolute stereochemistry of each isomer was not determined at this stage.

A solution of 2-((2-(benzyloxy)-4,6-dimethylpyridin-3-yl)methyl)-5,8-dichloro-7-(2-hydroxy-1-(tetrahydrofuran-3-yl)ethyl)-3,4-dihydroisoquinolin-1(2H)-one stereoisomer 1c (80 mg, 0.144 mmol) in dichloromethane (3 mL) and trifluoroacetic acid (3 mL) was stirred at 35° C. for 5 hours, and then evaporated to dryness. The residue was taken up in methanol (10 mL), cooled to 10° C., and potassium carbonate (99.5 mg, 0.720 mmol) added. After stirring for 30 minutes at 10° C., the reaction mixture was filtered, and the filter pad washed with dichloromethane/methanol (10:1, 10 mL). The filtrate was concentrated in vacuo and the residue, purified by prep. TLC (CH2Cl2/MeOH=10:1, Rf=0.4 in CH2Cl2/MeOH=10:1) to obtain Example 1 (38 mg, 57%) as a white solid.

By the same procedure, stereoisomer 2c (90 mg, 0.162 mmol) afforded Example 2 (44 mg, 59%); stereoisomer 3c (110 mg, 0.198 mmol) afforded Example 3 (61 mg, 66%); and stereoisomer 4c (100 mg, 0.18 mmol) afforded Example 4 (35 mg, 41%); all as white solids.

A small-molecule X-Ray crystal structure of Example 4 shows it to have absolute (S,S) stereochemistry. Absolute (R,R) stereochemistry was attributed to Example 1 because its $^1$HNMR spectrum is identical to that of Example 4. The $^1$HNMR spectra of Example 2 and Example 3 are identical to each other, and clearly different from that of Example 4, suggesting they are the (R,S) and (S,R) stereoisomers, though the absolute configuration of each was not determined.

Example 1: 5,8-dichloro-2-[(4,6-dimethyl-2-oxo-1,2-dihydropyridin-3-yl)methyl]-7-{(1R)-2-hydroxy-1-[(3R)-tetrahydrofuran-3-yl]ethyl}-3,4-dihydroisoquinolin-1(2H)-one (Absolute Stereochemistry Assigned Based on Crystal Structure of Enantiomeric Compound)

$^1$H NMR (400 MHz, CD3OD) δ 7.63 (s, 1H), 6.12 (s, 1H), 4.77 (s, 2H), 3.94-3.90 (m, 1H), 3.81-3.80 (m, 3H), 3.59-3.57 (m, 2H), 3.51-3.49 (m, 2H), 3.17-3.10 (m, 1H), 2.98-2.95 (m, 2H), 2.71 (br s, 1H), 2.30 (s, 3H), 2.29-2.25 (m, 1H), 2.25 (s, 3H), 1.83-1.78 (m, 1H). MS: 465 [M+H]$^+$. Chiral analysis: 95.66% ee/de; retention time: 6.867 min; column: Chiralpak AD-3 150×4.6 mm I.D., 3 μm; mobile phase: ethanol (0.05% DEA) in CO2 from 5% to 40%; flow rate: 2.5 mL/min; wavelength 220 nm.

Example 2: 5,8-dichloro-2-[(4,6-dimethyl-2-oxo-1,2-dihydropyridin-3-yl)methyl]-7-{(1R*)-2-hydroxy-1-[(3S*)-tetrahydrofuran-3-yl]ethyl}-3,4-dihydroisoquinolin-1(2H)-one (Relative Stereochemistry Known, Absolute Stereochemistry Undetermined)

$^1$H NMR (400 MHz, CD3OD) δ 7.62 (s, 1H), 6.11 (s, 1H), 4.76 (s, 2H), 4.13-4.11 (m, 1H), 3.78-3.75 (m, 1H), 3.69-3.68 (m, 2H), 3.61-3.59 (m, 3H), 3.51-3.50 (m, 2H), 2.98-2.95 (m, 2H), 2.65 (br s, 1H), 2.30 (s, 3H), 2.25 (s, 3H), 1.77-1.75 (m, 1H), 1.42-1.37 (m, 1H).). MS: 465 [M+H]$^+$. Chiral analysis: 98.70% ee/de; retention time: 7.309 min; column: Chiralpak AD-3 150×4.6 mm I.D., 3 μm; mobile phase: ethanol (0.05% DEA) in CO2 from 5% to 40%; flow rate: 2.5 mL/min; wavelength 220 nm.

Example 3: 5,8-dichloro-2-[(4,6-dimethyl-2-oxo-1,2-dihydropyridin-3-yl)methyl]-7-{(1S*)-2-hydroxy-1-[(3R*)-tetrahydrofuran-3-yl]ethyl}-3,4-dihydroisoquinolin-1(2H)-one (Relative Stereochemistry Known, Absolute Stereochemistry Undetermined)

$^1$H NMR (400 MHz, CD3OD) δ 7.62 (s, 1H), 6.11 (s, 1H), 4.76 (s, 2H), 4.12-4.11 (m, 1H), 3.80-3.78 (m, 1H), 3.69-3.67 (m, 3H), 3.67-3.62 (m, 2H), 3.61-3.50 (m, 2H), 2.98-2.95 (m, 2H), 2.65 (br s, 1H), 2.29 (s, 3H), 2.25 (s, 3H), 1.77-1.74 (m, 1H), 1.42-1.37 (m, 1H). MS: 465 [M+H]$^+$. Chiral analysis: 96.48% ee/de; retention time: 8.021 min; column: Chiralpak AD-3 150×4.6 mm I.D., 3 μm; mobile phase: ethanol (0.05% DEA) in CO2 from 5% to 40%; flow rate: 2.5 mL/min; wavelength 220 nm.

Example 4: 5,8-dichloro-2-[(4,6-dimethyl-2-oxo-1,2-dihydropyridin-3-yl)methyl]-7-{(1S)-2-hydroxy-1-[(3S)-tetrahydrofuran-3-yl]ethyl}-3,4-dihydroisoquinolin-1(2H)-one (Absolute Stereochemistry Determined by X-Ray Crystal Structure)

$^1$H NMR (400 MHz, CD3OD) δ 7.64 (s, 1H), 6.13 (s, 1H), 4.78 (s, 2H), 3.95-3.90 (m, 1H), 3.83-3.81 (m, 3H), 3.60-3.55 (m, 2H), 3.55-3.52 (m, 2H), 3.32-3.19, (m, 1H), 2.99-2.96 (m, 2H), 2.75 (br s, 1H), 2.32 (s, 3H), 2.31-2.29 (m, 1H), 2.27 (s, 3H), 1.84-1.79 (m, 1H). MS: 465 [M+H]$^+$. Chiral analysis: 99.18% ee/de; retention time: 8.429 min; column: Chiralpak AD-3 150×4.6 mm I.D., 3 μm; mobile phase: ethanol (0.05% DEA) in CO2 from 5% to 40%; flow rate: 2.5 mL/min; wavelength 220 nm.

Method B

Example 5: 5,8-dichloro-2-[(4,6-dimethyl-2-oxo-1,2-dihydropyridin-3-yl)methyl]-7-{1-[(3R)-3-fluoropyrrolidin-1-yl]-2-hydroxyethyl}-3,4-dihydroisoquinolin-1(2H)-one Example 6: 5,8-dichloro-2-[(4,6-dimethyl-2-oxo-1,2-dihydropyridin-3-yl)methyl]-7-{(1)-1-[(3R)-3-fluoropyrrolidin-1-yl]-2-hydroxyethyl}-3,4-dihydroisoquinolin-1(2H)-one isomer A Example 7: 5,8-dichloro-2-[(4,6-dimethyl-2-oxo-1,2-dihydropyridin-3-yl)methyl]-7-{(1)-1-[(3R)-3-fluoropyrrolidin-1-yl]-2-hydroxyethyl}-3,4-dihydroisoquinolin-1(2H)-one isomer B

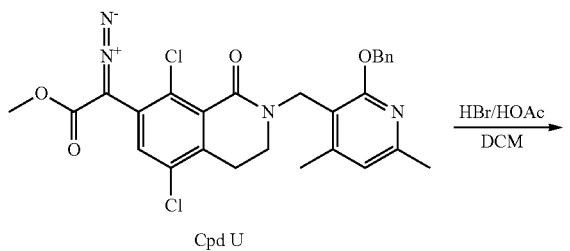

Cpd U

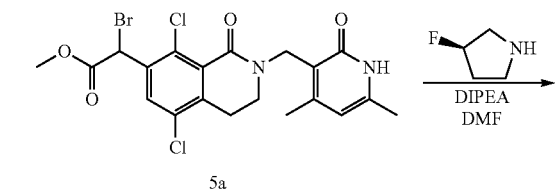

5a

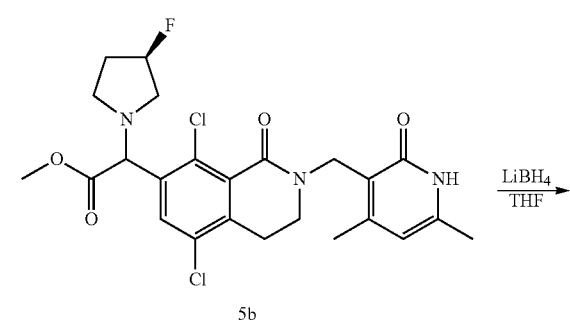

Example 5

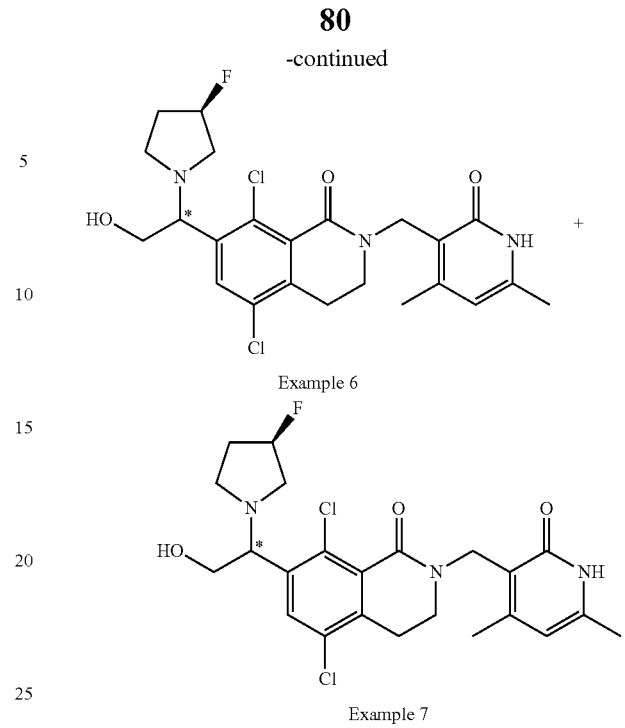

Example 6

Example 7

To an ice bath-cooled solution of methyl 2-(2-((2-(benzyloxy)-4,6-dimethylpyridin-3-yl)methyl)-5,8-dichloro-1-oxo-1,2,3,4-tetrahydroisoquinolin-7-yl)-2-diazoacetate (Cpd U, 800 mg, 1.48 mmol) in anhydrous dichloromethane (10 mL) was added HBr (800 uL, 4.42 mmol, 33% wt in HOAc), causing gas evolution. The solution was allowed to warm to room temperature and stirred overnight. The reaction mixture was carefully quenched with saturated aqueous sodium hydrogen carbonate, and extracted with ethyl acetate (2×50 mL). The combined organic phases were dried over sodium sulfate, concentrated to dryness, and purified by a silica gel column with a gradient elution of 0→10% MeOH/EA to afford racemic methyl 2-bromo-2-(5,8-dichloro-2-((4,6-dimethyl-2-oxo-1,2-dihydropyridin-3-yl)methyl)-1-oxo-1,2,3,4-tetrahydroisoquinolin-7-yl)acetate (5a, 655 mg, 88%) as a solid. MS: 501.00/502.05. $^1$H NMR (400 MHz, CDCl3) δ 7.91 (s, 1H), 6.18 (s, 1H), 6.03 (s, 1H), 4.76 (s, 2H), 3.81 (s, 3H), 3.68 (t, J=6.24 Hz, 2H), 2.98 (t, J=6.24 Hz, 2H), 2.45 (s, 3H), 2.37 (s, 3H).

A mixture of methyl 2-bromo-2-(5,8-dichloro-2-((4,6-dimethyl-2-oxo-1,2-dihydropyridin-3-yl)methyl)-1-oxo-1,2,3,4-tetrahydroisoquinolin-7-yl)acetate (5a, 162 mg, 0.323 mmol), (3R)-3-fluoropyrrolidine hydrochloride (144 mg, 1.15 mmol), N,N-diisopropylethylamine (0.35 mL, 2.01 mmol), and anhydrous N,N-dimethylformamide (4 mL) was stirred at room temperature overnight. The reaction mixture was partitioned between ethyl acetate (20 mL) and water (20 mL). The organic phase was separated, washed sequentially with water (20 mL) and brine (20 mL), dried over sodium sulfate, and concentrated to dryness to give crude methyl 2-(5,8-dichloro-2-((4,6-dimethyl-2-oxo-1,2-dihydropyridin-3-yl)methyl)-1-oxo-1,2,3,4-tetrahydroisoquinolin-7-yl)-2-((R)-3-fluoropyrrolidin-1-yl)acetate, as a mixture of diastereomers (5b, 162 mg, 98% yield), which was used in the next step without further purification. LCMS: T=510.15/511.10/512.20.

The crude mixture of methyl 2-(5,8-dichloro-2-((4,6-dimethyl-2-oxo-1,2-dihydropyridin-3-yl)methyl)-1-oxo-1,2,3,4-tetrahydroisoquinolin-7-yl)-2-((R)-3-fluoropyrrolidin-1- yl)acetate diastereomers (5b, 152 mg, 0.298 mmol) in anhydrous tetrahydrofuran (4.0 mL) was treated with lithium borohydride (2.0 M solution in THF, 0.45 mL, 0.90 mmol) followed by a few drops of methanol. The process of addition was repeated 4 times, then the reaction was quenched with 2 M NH$_4$Cl (20 mL) and extracted with ethyl acetate (2×20 mL). The combined organic phases were dried over sodium sulfate, concentrated to dryness, and purified by preparative HPLC to afford 5,8-dichloro-2-[(4,6-dimethyl-2-oxo-1,2-dihydropyridin-3-yl)methyl]-7-{1-[(3R)-3-fluoropyrrolidin-1-yl]-2-hydroxyethyl}-3,4-dihydroisoquinolin-1(2H)-one as a mixture of diastereomers at the benzylic carbon (Example 5, 32.2 mg, 22% yield over two steps). $^1$H NMR (400 MHz, DMSO-d6) δ 11.66 (br. s., 1H), 7.80 (d, J=3.67 Hz, 1H), 6.00 (s, 1H), 5.15-5.43 (m, 1H), 4.85 (br. s., 1H), 4.69 (s, 2H), 4.03-4.13 (m, 1H), 3.66-3.84 (m, 2H), 3.50-3.63 (m, 2H), 3.02-3.10 (m, 1H), 2.94-3.02 (m, 2H), 2.71-2.90 (m, 2H), 2.42-2.55 (m, 1H), 2.28 (s, 3H), 2.24 (s, 3H), 2.09-2.23 (m, 1H), 1.87-2.08 (m, 1H). MS: 482 [M+H]$^+$.

The mixture of diastereomers of 5,8-dichloro-2-[(4,6-dimethyl-2-oxo-1,2-dihydropyridin-3-yl)methyl]-7-{1-[(3R)-3-fluoropyrrolidin-1-yl]-2-hydroxyethyl}-3,4-dihydroisoquinolin-1(2H)-one (Example 5, 20.0 mg, 0.0415 mmol) was separated by chiral preparative SFC on a Chiralcel OJ-3 4.6×100 mm 3 u column, eluting with 10% MeOH/DEA @ 120 bar, 4 mL/min, affording, after lyophilization, Example 6 (Peak 1, retention time 1.18 min, 5.65 mg, 28%) and Example 7 (Peak 2, retention time 1.42 min, 6.23 mg, 31%). The absolute configuration of the benzylic carbon in each isomer was not determined.

Example 6: 5,8-dichloro-2-[(4,6-dimethyl-2-oxo-1,2-dihydropyridin-3-yl)methyl]-7-{(1ξ)-1-[(3R)-3-fluoropyrrolidin-1-yl]-2-hydroxyethyl}-3,4-dihydroisoquinolin-1(2H)-one—Isomer A MS: 482 [M+H]$^+$. Chiral analysis: ~88% de, [α]D=+62.1° (c 0.01 MeOH)

Example 7: 5,8-dichloro-2-[(4,6-dimethyl-2-oxo-1,2-dihydropyridin-3-yl)methyl]-7-{(1ξ)-1-[(3R)-3-fluoropyrrolidin-1-yl]-2-hydroxyethyl}-3,4-dihydroisoquinolin-1(2H)-one—Isomer B MS: 482 [M+H]$^+$. Chiral analysis: ~98% de; [α]D=−58.9° (c 0.01 MeOH)
Method C Example 8: (+)-5,8-dichloro-2-[(4,6-dimethyl-2-oxo-1,2-dihydropyridin-3-yl)methyl]-7-{fluoro[1-(hydroxyacetyl)piperidin-4-yl]methyl}-3,4-dihydroisoquinolin-1 (2H)-one Example 9: (−)-5,8-dichloro-2-[(4,6-dimethyl-2-oxo-1,2-dihydropyridin-3-yl)methyl]-7-{fluoro[1-(hydroxyacetyl)piperidin-4-yl]methyl}-3,4-dihydroisoquinolin-1 (2H)-one

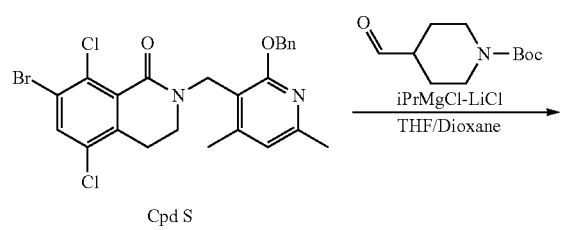

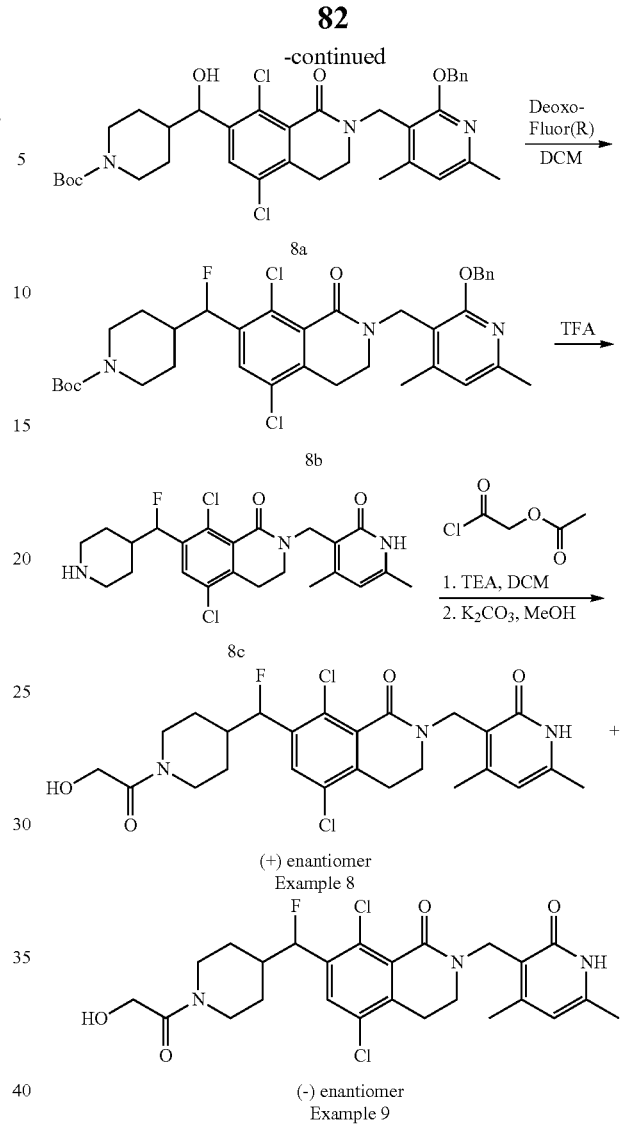

To a solution 2-{[2-(benzyloxy)-4,6-dimethylpyridin-3-yl]methyl}-7-bromo-5,8-dichloro-3,4-dihydroisoquinolin-1 (2H)-one (Cpd S, 311.0 mg, 0.598 mmol) in tetrahydrofuran (5.0 mL) and 1,4-dioxane (0.5 mL) at −40° C. (in an acetonitrile/dry ice bath) was added iPrMgCl-LiCl (1.3 M in THF, 0.850 mL, 1.10 mmol) and the reaction was stirred for 1 hour. N-Boc-4-formylpiperidine (0.242 g, 1.14 mmol) was then added, and the flask was warmed to 0° C. in an ice bath. After 1 hour at 0° C., the solution was quenched with sat. aq. NH$_4$Cl and extracted with MTBE. The MTBE layer was concentrated, and the resulting oil purified on silica gel (Isco RediSepRf, 12 g, 10-70% gradient of ethyl acetate in heptane) to give racemic tert-butyl 4-((2-((2-(benzyloxy)-4,6-dimethylpyridin-3-yl)methyl)-5,8-dichloro-1-oxo-1,2,3,4-tetrahydroisoquinolin-7-yl)(hydroxy)methyl) piperidine-1-carboxylate (8a, 0.229 g, 59%) as a white solid. $^1$H NMR (400 MHz, CD3OD) δ 7.66 (s, 1H), 7.36-7.44 (m, 2H), 7.18-7.31 (m, 3H), 6.71 (s, 1H), 5.42 (s, 2H), 5.04 (d, J=5.14 Hz, 1H), 4.83 (d, J=1.96 Hz, 2H), 4.08 (d, J=12.72 Hz, 2H), 3.23 (t, J=6.24 Hz, 2H), 2.73 (t, J=6.11 Hz, 2H), 2.53-2.71 (m, 2H), 2.39 (s, 3H), 2.35 (s, 3H), 1.76-1.90 (m, 1H), 1.32-1.62 (m, 13H); MS 654, 656 [M+H]$^+$.

To a solution of racemic tert-butyl 4-((2-((2-(benzyloxy)-4,6-dimethylpyridin-3-yl)methyl)-5,8-dichloro-1-oxo-1,2,3, 4-tetrahydroisoquinolin-7-yl)(hydroxy)methyl)piperidine-1-carboxylate (8a, 88 mg, 0.13 mmol) in dichloromethane (4 ML) cooled in a dry ice/acetone bath was added Deoxo-Fluor™ (50% in THF, 0.165 mL, 0.39 mmol). After stirring at −78° C. for 5 minutes, the cooling bath was removed and the mixture stirred for 5 minutes. The reaction was quenched with the addition of sat. aq. $NaHCO_3$, the layers were separated, and the dichloromethane layer was concentrated. The resulting oil was purified on silica gel (Biotage SNAP, HP-Sil, 10 g, 0-40% gradient of ethyl acetate in heptane) to give racemic tert-butyl 4-((2-((2-(benzyloxy)-4,6-dimethyl-pyridin-3-yl)methyl)-5,8-dichloro-1-oxo-1,2,3,4-tetrahydroisoquinolin-7-yl)fluoromethyl)piperidine-1-carboxylate (8b, 0.075 g, 85%) as a white, sticky solid. MS: 656, 658 [M+H]$^+$.

A solution of racemic tert-butyl 4-((2-((2-(benzyloxy)-4,6-dimethylpyridin-3-yl)methyl)-5,8-dichloro-1-oxo-1,2,3,4-tetrahydroisoquinolin-7-yl)fluoromethyl)piperidine-1-carboxylate (8b, (0.075 g, 0.11 mmol) in trifluoroacetic acid (5.0 mL) was heated to 50° C. for 1 hour. The reaction mixture was diluted with heptane and concentrated under vacuum. The residue was dissolved in ethanol and concentrated again. The remaining white solid was dried under vacuum to give crude, racemic 5,8-dichloro-2-((4,6-dimethyl-2-oxo-1,2-dihydropyridin-3-yl)methyl)-7-(fluoro(piperidin-4-yl)methyl)-3,4-dihydroisoquinolin-1(2H)-one (8c 0.085 g) as the TFA salt. MS 466, 468 [M+H]$^+$. This material was dissolved in dichloromethane (5 mL) and cooled to 0° C. Triethylamine (0.060 mL, 0.43 mmol) and then 2-acetoxyacetyl chloride (0.017 mL, 0.16 mmol) were added, the mixture stirred for 30 minutes, and then a few drops of methanol were added to quench the excess reagent. The solution was concentrated under vacuum, and the residue was dissolved in methanol (5 mL) and treated with potassium carbonate (0.100 g, 0.724 mmol). After 4 hours at room temperature, the reaction was filtered, concentrated, and purified by preparative chiral SFC (OJ-H, 21×250 mm column, 32 mL MeOH: 8 mL $CO_2$, 100 bar, 40 mL/min) to give separated enantiomers Example 8 (peak 1, 9.6 mg, 15%) and Example 9 (peak 2, 8.1 mg, 13%) as white solids.

The absolute stereochemistry of each isomer was not determined, but optical rotation measurements were obtained.

Example 8: (+)-5,8-dichloro-2-[(4,6-dimethyl-2-oxo-1,2-dihydropyridin-3-yl)methyl]-7-{fluoro[1-(hydroxyacetyl)piperidin-4-yl]methyl}-3,4-dihydroisoquinolin-1(2H)-one MS 524, 526 [M+H]$^+$. Optical rotation: $[\alpha]_D$=+9.9° (c, 0.1, DMSO). Chiral analysis: >99% ee; Retention time 8.13 min on Lux Cellulose-2 4.6×100 mm 3 u column, 60% MeOH @ 120 bar, 4 mL/min.

Example 9: (−)-5,8-dichloro-2-[(4,6-dimethyl-2-oxo-1,2-dihydropyridin-3-yl)methyl]-7-{fluoro[1-(hydroxyacetyl)piperidin-4-yl]methyl}-3,4-dihydroisoquinolin-1(2H)-one $^1$H NMR (600 MHz, DMSO-d$_6$) δ 11.55 (s, 1H), 7.58 (d, J=4.95 Hz, 1H), 5.88 (s, 1H), 5.72-5.84 (m, 1H), 4.55 (q, J=13.75 Hz, 2H), 4.46 (br. s., 1H), 4.30-4.42 (m, 1H), 4.05-4.13 (m, 1H), 3.97-4.04 (m, 1H), 3.69 (t, J=13.39 Hz, 1H), 3.45 (t, J=5.78 Hz, 2H), 2.80-2.98 (m, 3H), 2.20 (d, J=18.71 Hz, 1H), 2.11 (s, 3H), 1.61 (br. s., 1H), 1.46 (br. s., 1H), 1.34-1.42 (m, 1H), 1.23 (s, 5H); MS 524, 526 [M+H]$^+$. Optical rotation: $[\alpha]_D$=−6.5° (c, 0.1, DMSO). Chiral analysis: ~95% ee; Retention time 10.29 min on Lux Cellulose-2 4.6×100 mm 3 u column, 60% MeOH @ 120 bar, 4 mL/min.
Method D Example 10: 5,8-dichloro-2-[(4,6-dimethyl-2-oxo-1,2-dihydropyridin-3-yl)methyl]-7-(2-hydroxy-1-methoxyethyl)-3,4-dihydroisoquinolin-1(2H)-one—Isomer A Example 11: 5,8-dichloro-2-[(4,6-dimethyl-2-oxo-1,2-dihydropyridin-3-yl)methyl]-7-(2-hydroxy-1-methoxyethyl)-3,4-dihydroisoquinolin-1(2H)-one—Isomer B

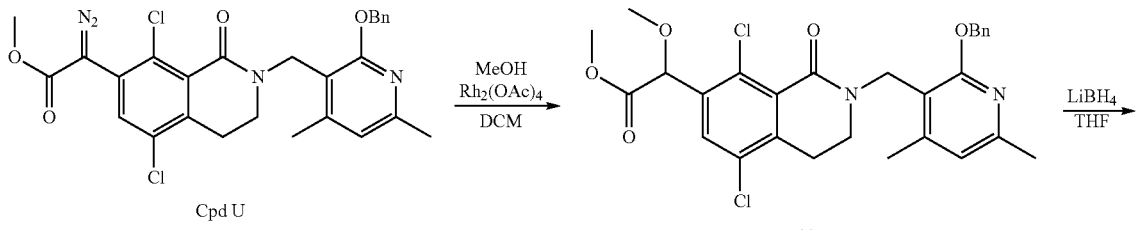

Cpd U

11a

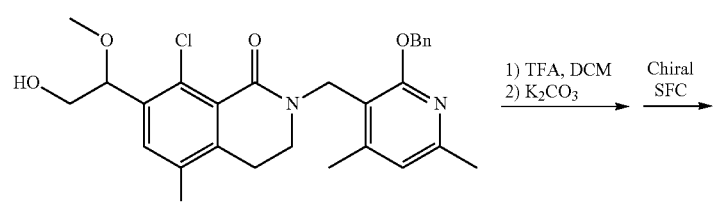

11b

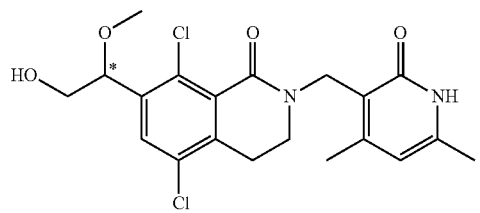

Example 10

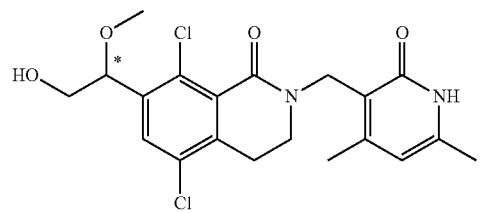

Example 11

To a stirred solution of dry methanol (12 mg, 0.36 mmol) and dirhodium tetraacetate (1.2 mg, 0.0028 mmol) in dichloromethane (5 mL) was added a solution of methyl 2-(2-((2-(benzyloxy)-4,6-dimethylpyridin-3-yl)methyl)-5,8-dichloro-1-oxo-1,2,3,4-tetrahydroisoquinolin-7-yl)-2-diazoacetate (Cpd U, 150 mg, 0.278 mmol) in dichloromethane (5 mL) dropwise over a period of 60 minutes at room temperature. After the addition, the reaction was heated to reflux for 18 hours. The mixture was concentrated and purified by flash chromatography (eluting with petroleum ether/EtOAc=10:1, Rf~0.3) to afford racemic methyl 2-(2-((2-(benzyloxy)-4,6-dimethylpyridin-3-yl)methyl)-5,8-dichloro-1-oxo-1,2,3,4-tetrahydroisoquinolin-7-yl)-2-methoxyacetate (11a, 100 mg, 66%) as brown oil.

To a stirred solution of racemic methyl 2-(2-((2-(benzyloxy)-4,6-dimethylpyridin-3-yl)methyl)-5,8-dichloro-1-oxo-1,2,3,4-tetrahydroisoquinolin-7-yl)-2-methoxyacetate (11a, 100 mg, 0.184 mmol) in anhydrous tetrahydrofuran (10 mL) was added solid lithium borohydride (12 mg, 0.55 mmol) in one portion at room temperature. The resulting mixture was heated at 60° C. for 1 hour. The mixture was quenched with water (15 mL) and extracted with ethyl acetate (3×15 mL). The combined organic extracts were washed with saturated aq. NaCl (15 mL), dried over sodium sulfate, filtered and concentrated to afford the crude product (91 mg). Purification was accomplished using flash chromatography (eluting with petroleum ether/EtOAc=1:1) to afford racemic 2-((2-(benzyloxy)-4,6-dimethylpyridin-3-yl)methyl)-5,8-dichloro-7-(2-hydroxy-1-methoxyethyl)-3,4-dihydroisoquinolin-1(2H)-one (11b, 60 mg, 63%) as a white solid.

A solution of racemic 2-((2-(benzyloxy)-4,6-dimethylpyridin-3-yl)methyl)-5,8-dichloro-7-(2-hydroxy-1-methoxyethyl)-3,4-dihydroisoquinolin-1(2H)-one (11b 60 mg, 0.12 mmol) in dichloromethane (2 mL) and trifluoroacetic acid (2 mL) was stirred at room temperature for 18 hours. Analysis by LC-MS showed complete deprotection of the benzyl group, but some trifluoroacetate ester at the pyridone oxygen, so the mixture was concentrated and then methanol (10 mL) and potassium carbonate (80.9 mg, 0.585 mmol) were added. The resulting mixture was stirred at room temperature for 30 minutes, at which time analysis by LC-MS showed complete deprotection of the TFA-ester. The mixture was filtered, the collected solid was washed with DCM/MeOH (10:1, 10 mL) and the filtrate was concentrated. Purification was accomplished using flash chromatography (eluting with DCM/MeOH=10:1, Rf 0.6) to obtain a racemic 5,8-dichloro-2-[(4,6-dimethyl-2-oxo-1,2-dihydropyridin-3-yl)methyl]-7-(2-hydroxy-1-methoxyethyl)-3,4-dihydroisoquinolin-1(2H)-one (37 mg, 75%) as a white solid.

Combined batches of racemic 5,8-dichloro-2-[(4,6-dimethyl-2-oxo-1,2-dihydropyridin-3-yl)methyl]-7-(2-hydroxy-1-methoxyethyl)-3,4-dihydroisoquinolin-1(2H)-one (total 100 mg, 0.235 mmol) were separated by chiral SFC on a Chiralpak IC 250 mm×30 mm, 10 μm column, eluting with 50% EtOH/NH$_4$OH at a flow rate of 70 mL/min. After lyophilization, Example 10 (peak 1, 33 mg, 33%) and Example 11 (peak 2, 35 mg, 35%) were obtained as off-white solids. Absolute stereochemistry for each isomer was not determined.

Example 10: 5,8-dichloro-2-[(4,6-dimethyl-2-oxo-1,2-dihydropyridin-3-yl)methyl]-7-(2-hydroxy-1-methoxyethyl)-3,4-dihydroisoquinolin-1(2H)-one—Isomer A $^1$H NMR (400 MHz, CDCl3) δ 12.23 (br. s., 1H), 7.53 (s, 1H), 5.95 (s, 1H), 4.92-4.89 (m, 1H), 4.78 (s, 2H), 3.80-3.71 (m, 1H), 3.68-3.62 (m, 2H), 3.53-3.51 (m, 1H), 3.33 (s, 3H), 2.94 (t, J=6.0 Hz, 2H), 2.35 (s, 3H), 2.29 (s, 3H). MS: 425 [M+H]$^+$. Chiral analysis: 100% ee, retention time 7.717 min, column: Chiralpak IC-3 150×4.6 mm I.D., 3 μm; mobile phase: 40% ethanol (0.05% DEA) in CO2; flow rate: 2.35 mL/min.

Example 11 5,8-dichloro-2-[(4,6-dimethyl-2-oxo-1,2-dihydropyridin-3-yl)methyl]-7-(2-hydroxy-1-methoxyethyl)-3,4-dihydroisoquinolin-1(2H)-one—Isomer B $^1$H NMR (400 MHz, CDCl3) δ 12.15 (br. s., 1H), 7.53 (s, 1H), 5.95 (s, 1H), 4.92-4.89 (m, 1H), 4.78 (s, 2H), 3.80-3.71 (m, 1H), 3.68-3.63 (m, 2H), 3.55-3.51 (m, 1H), 3.34 (s, 3H), 2.94 (t, J=5.6 Hz, 2H), 2.35 (s, 3H), 2.29 (s, 3H). MS: 425 [M+H]$^+$. Chiral analysis: 100% ee, retention time 11.063 min, column: Chiralpak IC-3 150×4.6 mm I.D., 3 μm; mobile phase: 40% ethanol (0.05% DEA) in CO2; flow rate: 2.35 mL/min.

Method E

Example 12: 5,8-dichloro-2-[(4,6-dimethyl-2-oxo-1,2-dihydropyridin-3-yl)methyl]-7-{(1R)-2-hydroxy-1-[(2S)-tetrahydrofuran-2-yl]ethyl}-3,4-dihydroisoquinolin-1(2H)-one Example 13: 5,8-dichloro-2-[(4,6-dimethyl-2-oxo-1,2-dihydropyridin-3-yl)methyl]-7-{(1R)-2-hydroxy-1-[(2R)-tetrahydrofuran-2-yl]ethyl}-3,4-dihydroisoquinolin-1(2H)-one

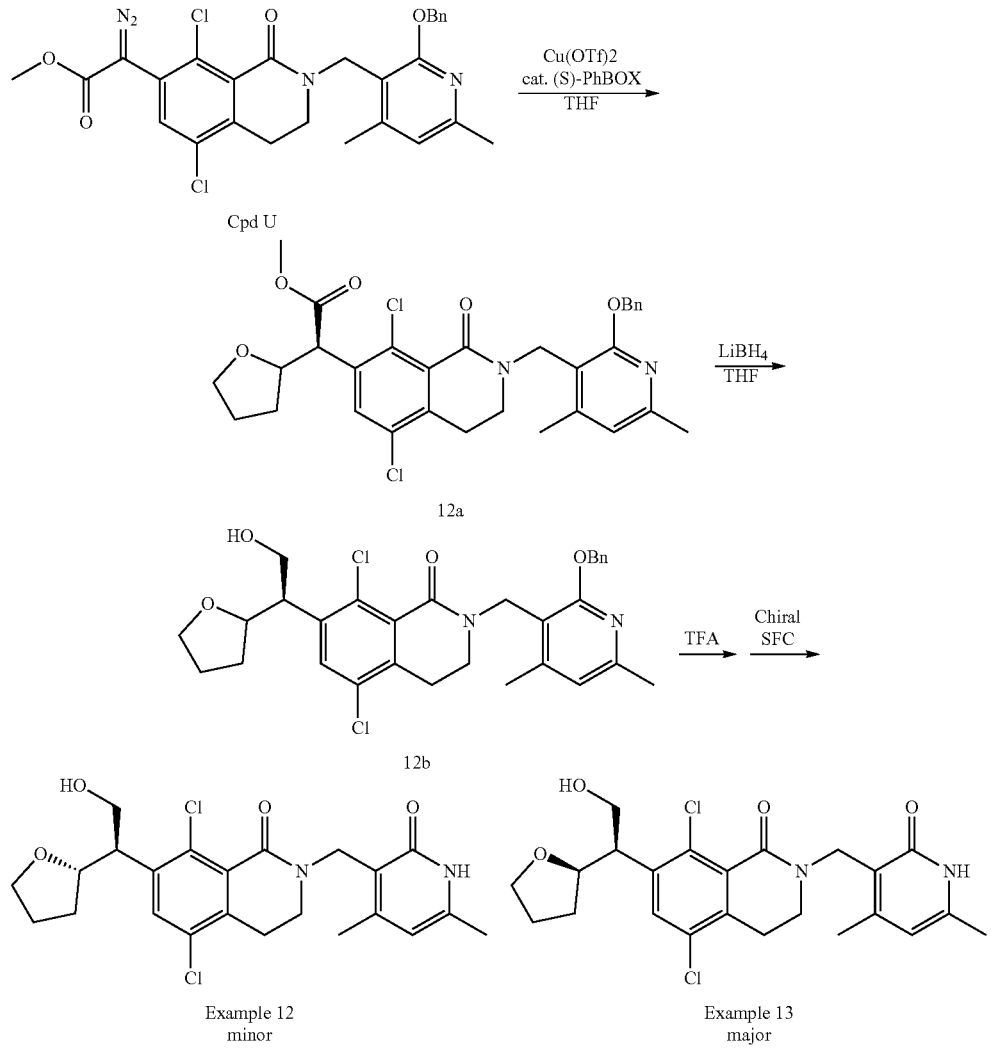

Example 12
minor

Example 13
major

To a solution methyl 2-(2-((2-(benzyloxy)-4,6-dimethylpyridin-3-yl)methyl)-5,8-dichloro-1-oxo-1,2,3,4-tetrahydroisoquinolin-7-yl)-2-diazoacetate (Cpd U, 1.78 g, 3.29 mmol) in anhydrous tetrahydrofuran (20 mL) was added a solution of copper (II) triflate (120 mg, 0.332 mmol) and (S)-(−)-2,2'-isopropylidene-bis(4-phenyl-2-oxazoline) (130 mg, 0.389 mmol) in anhydrous tetrahydrofuran (4 mL). The resulting solution was heated to reflux overnight in an 80° C. oil bath. After cooling to room temperature, the reaction mixture was concentrated to dryness and purified by a silica gel column with a gradient elution of 0→40% EA/HEP to afford a mixture of diastereomers with (S) geometry at the benzylic carbon (stereochemical assignment by analogy to Jiménez-Osés, G. et al., *J. Org. Chem.* 2013, 78, 5851-5857), methyl (2S)-2-(2-((2-(benzyloxy)-4,6-dimethylpyridin-3-yl)methyl)-5,8-dichloro-1-oxo-1,2,3,4-tetrahydroisoquinolin-7-yl)-2-(tetrahydrofuran-2-yl)acetate (12a, 333 mg, 17%). MS: 583.10/584.20 [M+H]$^+$. $^1$H NMR (400 MHz, CDCl3) δ 7.69 (d, J=2.20 Hz, 1H), 7.45 (d, J=7.58 Hz, 2H), 7.30-7.39 (m, 3H), 6.64 (s, 1H), 5.45 (s, 2H), 4.80-4.92 (m, 2H), 4.41-4.59 (m, 1H), 3.79-4.02 (m, 1H), 3.72-3.80 (m, 1H), 3.70 (d, J=5.01 Hz, 3H), 3.23-3.31 (m, 2H), 2.69-2.76 (m, 2H), 2.44 (s, 3H), 2.34 (d, J=3.79 Hz, 3H), 1.93-2.18 (m, 1H), 1.80-1.94 (m, 2H), 1.55-1.80 (m, 2H).

[Under the same conditions, use of the enantiomeric (R)-(−)-2,2'-isopropylidene-bis(4-phenyl-2-oxazoline) ligand produces a mixture of diastereomers with (R) geometry at the benzylic position, methyl (2R)-2-(2-((2-(benzyloxy)-4,6-dimethylpyridin-3-yl)methyl)-5,8-dichloro-1-oxo-1,2,3,4-tetrahydroisoquinolin-7-yl)-2-(tetrahydrofuran-2-yl)acetate.]

Lithium borohydride (2.0 M solution in THF, 1.0 mL, 2.0 mmol) was added to a solution of methyl (2S)-2-(2-((2-(benzyloxy)-4,6-dimethylpyridin-3-yl)methyl)-5,8-dichloro-1-oxo-1,2,3,4-tetrahydroisoquinolin-7-yl)-2-(tetrahydrofuran-2-yl)acetate (12a 333 mg, 0.571 mmol) in anhydrous tetrahydrofuran (10 mL), followed by a few drops of methanol. Gas was evolved. The mixture was stirred at room temperature for 1 hour, then quenched with 10 mL 2 M NH4Cl, diluted with water, and extracted with ether (3×50 mL). The combined organic phases were dried over sodium sulfate, concentrated to dryness, to give crude 2-((2-(benzyloxy)-4,6-dimethylpyridin-3-yl)methyl)-5,8-dichloro-7-((1R)-2-hydroxy-1-(tetrahydrofuran-2-yl)ethyl)-3,4-dihydroisoquinolin-1(2H)-one (12b, 280 mg, 88%), as a mixture of diastereomers with (R) geometry at the benzylic carbon. This mixture was used in the next step without further purification. MS: 555.20/557.20.

A solution of the crude mixture of diastereomers, 2-((2-(benzyloxy)-4,6-dimethylpyridin-3-yl)methyl)-5,8-dichloro-7-((1R)-2-hydroxy-1-(tetrahydrofuran-2-yl)ethyl)-3,4-dihydroisoquinolin-1(2H)-one (12b, 280 mg, 0.504 mmol) in trifluoroacetic acid (8 mL) was stirred at 50° C. for 1 hour. After removing excess trifluoroacetic acid, the residue was dissolved in methanol (10 mL) and treated with 4 M NaOH for 30 minutes at 50° C. The reaction mixture was partitioned between ethyl acetate (50 mL) and water (50 mL). The organic phase was separated. The aqueous phase was acidified to pH~2-3, and extracted with ethyl acetate (2×50 mL). The combined organic phases were dried over sodium sulfate, concentrated to dryness, and purified by chiral SFC (Chiralpak AD-3 4.6×100 mm 3 u column; eluting with 5-60% MeOH in 3 minutes, 120 bar, 4 mL/min) yielding the separated diastereomeric products, Example 12 (peak 1, 32 mg, 14%) and Example 13 (peak 2, 77 mg, 33%). Stereochemistry of the isolated products were assigned by analogy to Jiménez-Osés, G. et al., *J. Org. Chem.* 2013, 78, 5851-5857.

Example 12: 5,8-dichloro-2-[(4,6-dimethyl-2-oxo-1,2-dihydropyridin-3-yl)methyl]-7-{(1R)-2-hydroxy-1-[(2S)-tetrahydrofuran-2-yl]ethyl}-3,4-dihydroisoquinolin-1(2H)-one $^1$H NMR (400 MHz, CD3OD) δ 7.58 (s, 1H), 6.11 (s, 1H), 4.76 (s, 2H), 4.10-4.21 (m, 1H), 3.86-3.99 (m, 3H), 3.75-3.84 (m, 1H), 3.64-3.72 (m, 1H), 3.46-3.55 (m, 2H), 2.91-3.01 (m, 2H), 2.29 (s, 3H), 2.25 (s, 3H), 1.73-1.97 (m, 3H), 1.44-1.58 (m, 1H). MS: 465 {M+H}$^+$. Chiral analysis: 91% ee/de; retention time 2.91 min on Chiralpak AD-3 4.6×100 mm 3p column; eluting with 5-60% MeOH in 3 minutes, 120 bar, 4 mL/min.

Example 13: 5,8-dichloro-2-[(4,6-dimethyl-2-oxo-1,2-dihydropyridin-3-yl)methyl]-7-{(1R)-2-hydroxy-1-[(2R)-tetrahydrofuran-2-yl]ethyl}-3,4-dihydroisoquinolin-1(2H)-one $^1$H NMR (400 MHz, CD3OD) δ 7.66 (s, 1H), 6.10 (s, 1H), 4.77 (s, 2H), 4.27 (dt, J=7.86, 6.16 Hz, 1H), 3.72-3.91 (m, 3H), 3.67 (t, J=6.79 Hz, 2H), 3.49 (t, J=6.24 Hz, 2H), 2.95 (t, J=6.17 Hz, 2H), 2.28 (s, 3H), 2.24 (s, 3H), 2.01-2.13 (m, 1H), 1.68-1.92 (m, 2H), 1.49-1.62 (m, 1H). MS: 465 {M+H}$^+$. Chiral analysis: 93% ee/de; retention time 3.21 minutes on Chiralpak AD-3 4.6×100 mm 3p column; eluting with 5-60% MeOH in 3 minutes, 120 bar, 4 mL/min.

Method F

Example 14: 5,8-dichloro-2-[(4,6-dimethyl-2-oxo-1,2-dihydropyridin-3-yl)methyl]-7-(propan-2-yl)-3,4-dihydroisoquinolin-1(2H)-one

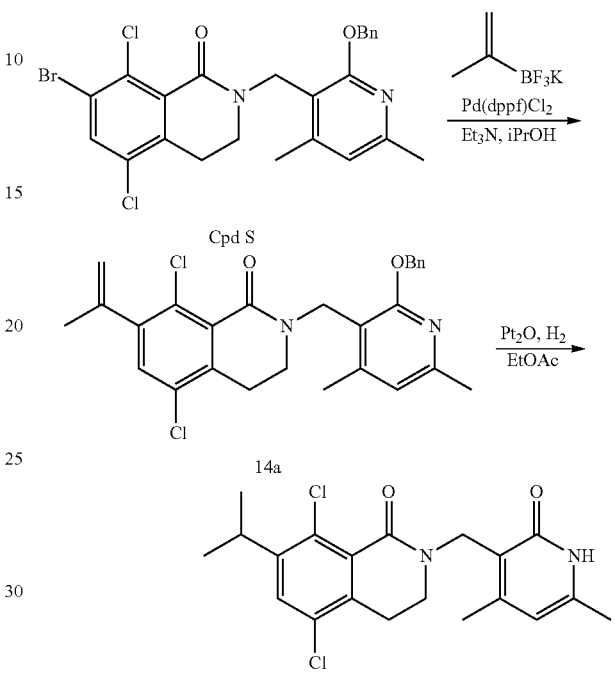

Example 14

A solution of 2-{[2-(benzyloxy)-4,6-dimethylpyridin-3-yl]methyl}-7-bromo-5,8-dichloro-3,4-dihydroisoquinolin-1(2H)-one (Cpd S, 500 mg, 0.961 mmol), triethylamine (0.30 mL, 2.2 mmol), and [1,1'-bis(diphenylphosphino)ferrocene]dichloropalladium(II)-dichloromethane complex (24 mg, 0.028 mmol) in 2-propanol (15 mL) under nitrogen in a capped microwave tube was heated at 100° C. for 1 hour in a microwave reactor. After removal of the solvent, the product was extracted into ether (3×10 mL) and the combined organic extracts were washed with water (2×), dried over magnesium sulfate, concentrated, and purified by flash chromatography (silica gel, 0-60% EtOAc in heptane) to afford 2-((2-(benzyloxy)-4,6-dimethylpyridin-3-yl)methyl)-5,8-dichloro-7-(prop-1-en-2-yl)-3,4-dihydroisoquinolin-1(2H)-one (14a, 240 mg, 52%) as a white foam. $^1$H NMR (400 MHz, CDCl3) δ 7.37 (d, J=6.8 Hz, 2H), 7.30-7.20 (m, 3H), 7.18 (d, J=2.6 Hz, 1H), 6.55 (s, 1H), 5.35 (s, 2H), 5.16 (d, J=1.5 Hz, 1H), 4.85 (d, J=1.5 Hz, 1H), 4.80 (s, 2H), 3.20 (t, J=6.2 Hz, 2H), 2.65 (t, J=6.2 Hz, 2H), 2.34 (s, 3H), 2.26 (s, 3H), 2.01 (s, 3H). MS: 481 [M+H]$^+$.

A solution of 2-((2-(benzyloxy)-4,6-dimethylpyridin-3-yl)methyl)-5,8-dichloro-7-(prop-1-en-2-yl)-3,4-dihydroisoquinolin-1(2H)-one (14a, 75 mg, 0.16 mmol) and platinum (IV) oxide (71 mg, 0.31 mmol) in ethyl acetate (5 mL) was stirred under a hydrogen balloon for 2 hours. The catalyst was filtered off and the solvent removed in vacuo. The crude product was purified via supercritical fluid chromatography (SFC/ZymorSpher HAP 150×21.2 mm column with 8% MeOH @ 100 bar, 58 mL/min) to afford 5,8-dichloro-2-[(4,6-dimethyl-2-oxo-1,2-dihydropyridin-3-yl)methyl]-7-(propan-2-yl)-3,4-dihydroisoquinolin-1(2H)-one (Example 14 (7 mg, 10%), as a white solid. $^1$H NMR (400 MHz, CDCl3) δ 7.35 (s, 1H), 5.90 (s, 1H), 4.78 (s, 2H), 3.63 (t, J=6.30 Hz, 2H), 3.5-3.6 (m, 1H), 2.90 (t, J=6.11 Hz, 2H), 2.35 (s, 3H), 2.24 (s, 3H), 1.24 (d, J=6.85 Hz, 6H). MS: 393 [M+H]. Method G Example 15: 5,8-dichloro-2-[(4,6-dimethyl-2-oxo-1,2-dihydropyridin-3-yl)methyl]-7-(1-methoxypropyl)-3,4-dihydroisoquinolin-1 (2H)-one—isomer A Example 16: 5,8-dichloro-2-[(4,6-dimethyl-2-oxo-1,2-dihydropyridin-3-yl)methyl]-7-(1-methoxypropyl)-3,4-dihydroisoquinolin-1 (2H)-one—isomer B

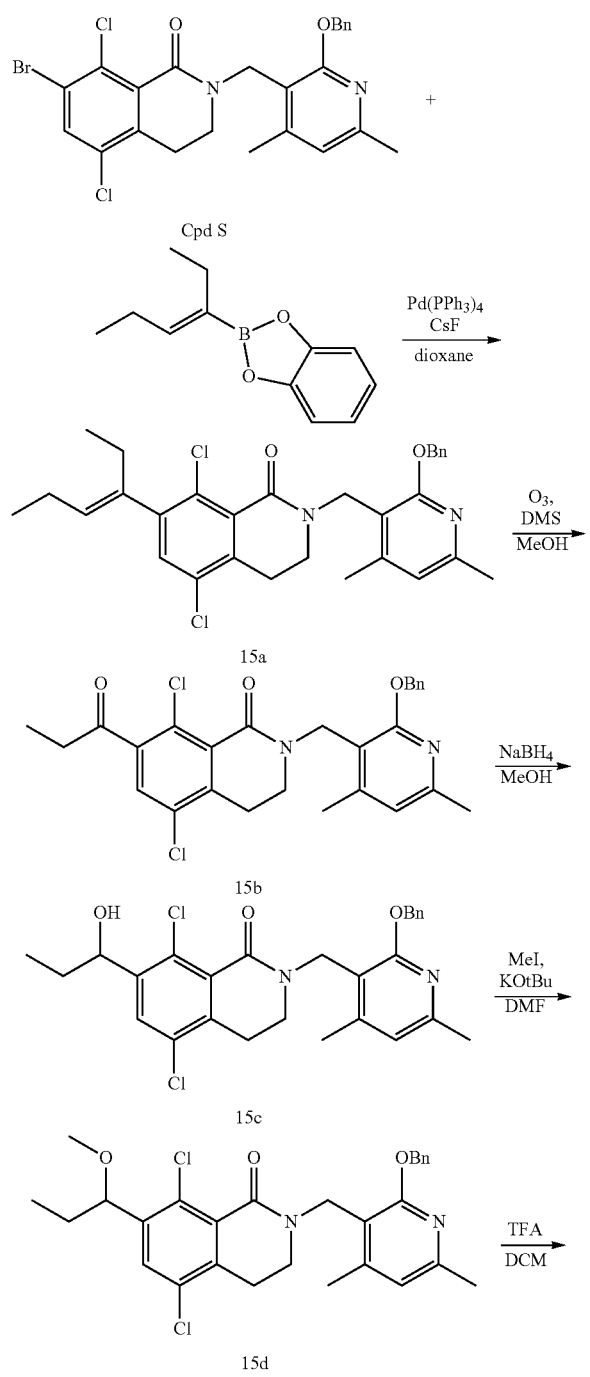

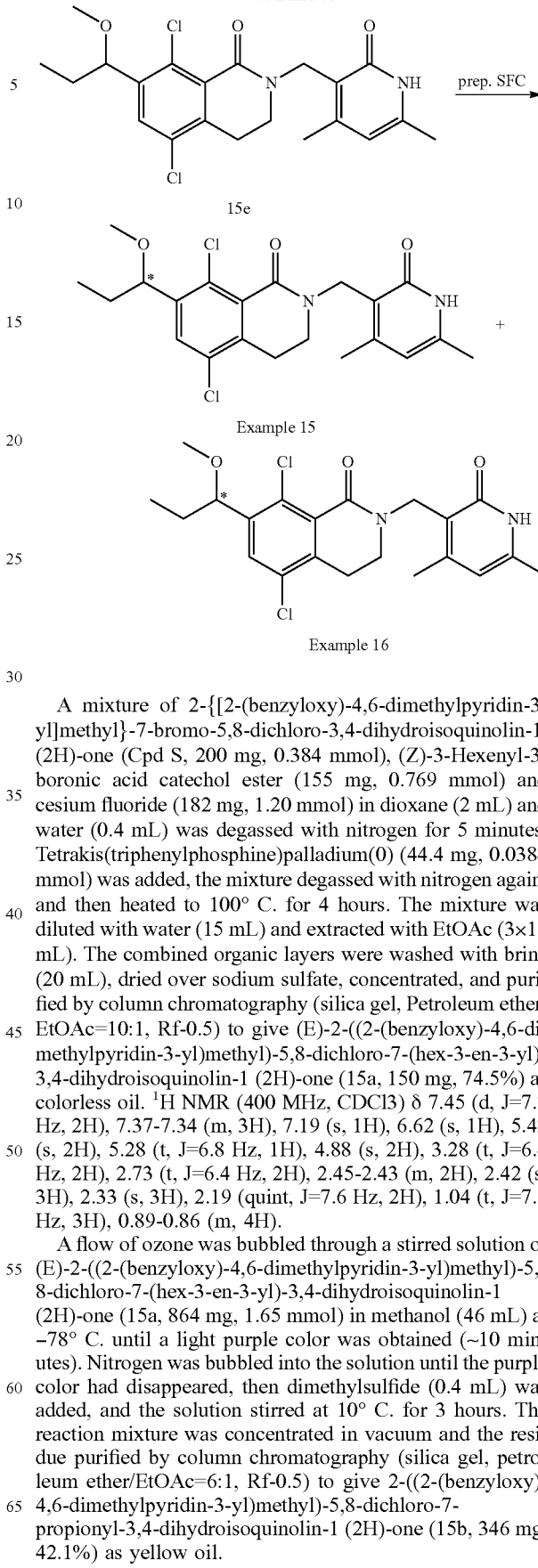

A mixture of 2-{[2-(benzyloxy)-4,6-dimethylpyridin-3-yl]methyl}-7-bromo-5,8-dichloro-3,4-dihydroisoquinolin-1 (2H)-one (Cpd S, 200 mg, 0.384 mmol), (Z)-3-Hexenyl-3-boronic acid catechol ester (155 mg, 0.769 mmol) and cesium fluoride (182 mg, 1.20 mmol) in dioxane (2 mL) and water (0.4 mL) was degassed with nitrogen for 5 minutes. Tetrakis(triphenylphosphine)palladium(0) (44.4 mg, 0.0384 mmol) was added, the mixture degassed with nitrogen again, and then heated to 100° C. for 4 hours. The mixture was diluted with water (15 mL) and extracted with EtOAc (3×15 mL). The combined organic layers were washed with brine (20 mL), dried over sodium sulfate, concentrated, and purified by column chromatography (silica gel, Petroleum ether/EtOAc=10:1, Rf-0.5) to give (E)-2-((2-(benzyloxy)-4,6-dimethylpyridin-3-yl)methyl)-5,8-dichloro-7-(hex-3-en-3-yl)-3,4-dihydroisoquinolin-1 (2H)-one (15a, 150 mg, 74.5%) as colorless oil. $^1$H NMR (400 MHz, CDCl3) δ 7.45 (d, J=7.7 Hz, 2H), 7.37-7.34 (m, 3H), 7.19 (s, 1H), 6.62 (s, 1H), 5.43 (s, 2H), 5.28 (t, J=6.8 Hz, 1H), 4.88 (s, 2H), 3.28 (t, J=6.4 Hz, 2H), 2.73 (t, J=6.4 Hz, 2H), 2.45-2.43 (m, 2H), 2.42 (s, 3H), 2.33 (s, 3H), 2.19 (quint, J=7.6 Hz, 2H), 1.04 (t, J=7.6 Hz, 3H), 0.89-0.86 (m, 4H).

A flow of ozone was bubbled through a stirred solution of (E)-2-((2-(benzyloxy)-4,6-dimethylpyridin-3-yl)methyl)-5,8-dichloro-7-(hex-3-en-3-yl)-3,4-dihydroisoquinolin-1 (2H)-one (15a, 864 mg, 1.65 mmol) in methanol (46 mL) at −78° C. until a light purple color was obtained (~10 minutes). Nitrogen was bubbled into the solution until the purple color had disappeared, then dimethylsulfide (0.4 mL) was added, and the solution stirred at 10° C. for 3 hours. The reaction mixture was concentrated in vacuum and the residue purified by column chromatography (silica gel, petroleum ether/EtOAc=6:1, Rf-0.5) to give 2-((2-(benzyloxy)-4,6-dimethylpyridin-3-yl)methyl)-5,8-dichloro-7-propionyl-3,4-dihydroisoquinolin-1 (2H)-one (15b, 346 mg, 42.1%) as yellow oil.

Sodium borohydride (52.6 mg, 1.39 mmol) was added to a cooled (0° C.) solution of 2-((2-(benzyloxy)-4,6-dimethylpyridin-3-yl)methyl)-5,8-dichloro-7-propionyl-3,4-dihydroisoquinolin-1(2H)-one (15b, 346 mg, 0.696 mmol) in methanol (20 mL), and stirring continued for 1 hour at 10° C. The reaction was quenched with Sat.NH4Cl (30 mL), extracted with ethyl acetate (3×25 mL). The combined organic layers were washed with brine (25 mL), dried over sodium sulfate, and concentrated in vacuum. The residue was purified by column chromatography (silica gel, Petroleum ether/EtOAc=2:1, Rf~0.6), affording racemic 2-((2-(benzyloxy)-4,6-dimethylpyridin-3-yl)methyl)-5,8-dichloro-7-(1-hydroxypropyl)-3,4-dihydroisoquinolin-1(2H)-one (15c, 300 mg, 86.4%) as colorless oil.

Potassium tert-butoxide (111 mg, 0.985 mmol) and iodomethane (140 mg, 0.985 mmol) were added to a cooled (10° C.) solution of 2-((2-(benzyloxy)-4,6-dimethylpyridin-3-yl)methyl)-5,8-dichloro-7-(1-hydroxypropyl)-3,4-dihydroisoquinolin-1(2H)-one (15c, 246 mg, 0.493 mmol) in N,N-dimethylformamide (25 mL), and stirred at 10° C. overnight. The reaction was quenched with water (30 mL), extracted with EtOAc (3×35 mL). The combined organic layers were washed with brine (35 mL), dried over sodium sulfate, concentrated, and purified by column chromatography (silica gel, Petroleum ether/EtOAc=5:1), yielding racemic 2-((2-(benzyloxy)-4,6-dimethylpyridin-3-yl)methyl)-5,8-dichloro-7-(1-methoxypropyl)-3,4-dihydroisoquinolin-1(2H)-one (15d, 148 mg, 58.5%) as yellow oil.

Trifluoroacetic acid (9 mL) was added dropwise to a stirred solution of 2-((2-(benzyloxy)-4,6-dimethylpyridin-3-yl)methyl)-5,8-dichloro-7-(1-methoxypropyl)-3,4-dihydroisoquinolin-1 (2H)-one (15d, 218 mg, 0.423 mmol) in dichloromethane (9 mL) at 10° C. The resulting mixture was stirred at 25° C. overnight. The mixture was concentrated in vacuum and the residue purified by column chromatography (silica gel, CH2Cl2/MeOH=10:1, Rf-0.55) to give racemic 5,8-dichloro-2-((4,6-dimethyl-2-oxo-1,2-dihydropyridin-3-yl)methyl)-7-(1-methoxypropyl)-3,4-dihydroisoquinolin-1 (2H)-one (15e, 150 mg, 83.8%) as pink oil. This racemic mixture was separated by preparatory SFC [column: (AD (250 mm*30 mm, 5 um)), mobile phase: 25% MeOH NH3H2O, Flow rate: 50 mL/min, wavelength: 220 nm, workup: lyophilization] to give Isomer A (Example 15, 45.65 mg, 31.4%) as a white solid and Isomer B (Example 16, 31.8 mg, 21.2%) as an off-white solid. The absolute stereochemistry of each isomer was not determined.

Example 15: 5,8-dichloro-2-[(4,6-dimethyl-2-oxo-1, 2-dihydropyridin-3-yl)methyl]-7-(1-methoxypropyl)-3,4-dihydroisoquinolin-1(2H)-one—Isomer A ¹H NMR (400 MHz, CDCl3) δ 11.88 (br s, 1H), 7.53 (s, 1H), 5.94 (s, 1H), 4.78 (s, 2H), 4.69-4.66 (m, 1H), 3.65 (t, J=4.8 Hz, 2H), 3.24 (s, 3H), 2.93 (t, J=6.2 Hz, 2H), 2.36 (s, 3H), 2.29 (s, 3H), 1.76-1.72 (m, 1H), 1.65-1.60 (m, 1H), 0.96 (t, J=7.0 Hz, 3H). MS: 423 [M+H]⁺. Chiral analysis: 100% ee; column: Chiralpak AD-H 250×4.6 mm I.D., 5 um; retention time: 8.04 min; mobile phase: methanol (0.05% DEA) in CO2 from 5% to 40%; flow rate: 2.5 mL/min; wavelength: 220 nm.

Example 16: 5,8-dichloro-2-[(4,6-dimethyl-2-oxo-1, 2-dihydropyridin-3-yl)methyl]-7-(1-methoxypropyl)-3,4-dihydroisoquinolin-1(2H)-one—Isomer B ¹H NMR (400 MHz, CDCl3) δ 10.88 (br s, 1H), 7.53 (s, 1H), 5.93 (s, 1H), 4.77 (s, 2H), 4.69-4.66 (m, 1H), 3.67-3.63 (m, 2H), 3.24 (s, 3H), 2.93 (t, J=5.8 Hz, 2H), 2.36 (s, 3H), 2.28 (s, 3H), 1.78-1.73 (m, 1H), 1.65-1.58 (m, 1H), 0.96 (t, J=7.2 Hz, 3H). MS: 423 [M+H]⁺. Chiral analysis: 99.6% ee; column: Chiralpak AD-H 250×4.6 mm I.D., 5 um; retention time: 8.34 min; mobile phase: methanol (0.05% DEA) in CO2 from 5% to 40%; flow rate: 2.5 mL/min; wavelength: 220 nm.

Method H

Example 75: 5,8-dichloro-2-[(4,6-dimethyl-2-oxo-1, 2-dihydropyridin-3-yl)methyl]-7-{1-[1-(hydroxyacetyl)azetidin-3-ylidene]ethyl}-3,4-dihydroisoquinolin-1(2H)-one

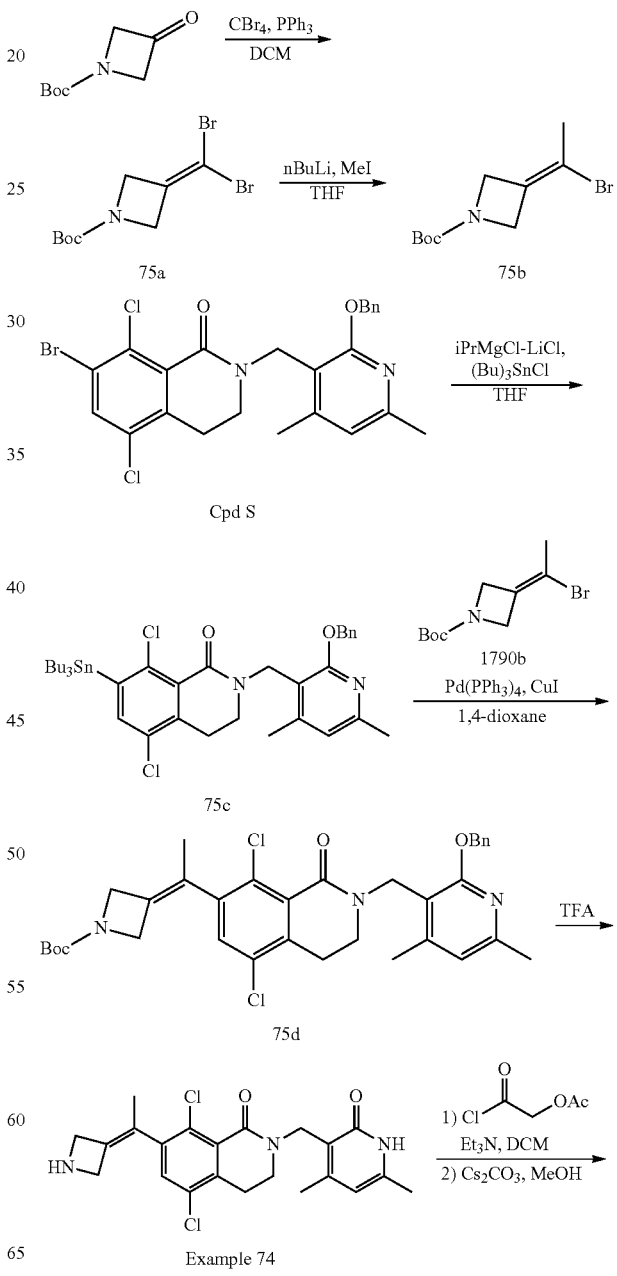

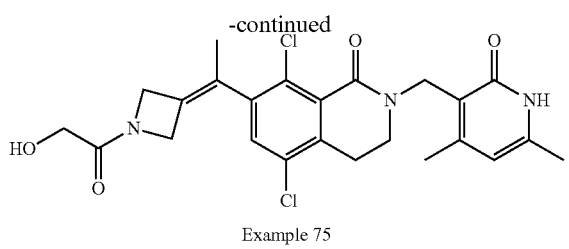

Example 75

A solution of triphenylphosphine (15.83 g, 60.35 mmol) in anhydrous dichloromethane (16 mL) was cooled to 0° C. and degassed by sparging with nitrogen for 5 minutes. Carbon tetrabromide (9.98 g, 30.1 mmol) was added, and the solution stirred at 0° C. for 5 minutes before a solution of 3-oxo-azetidine-1-carboxylic acid tert-butyl ester (2.52 g, 14.7 mmol) in anhydrous dichloromethane (7 mL) was added dropwise via syringe, over 1 minutes. After stirring at 0° C. for 20 minutes, the reaction was allowed to stir at room temperature for 22.5 hours. Heptane (100 mL) was added and the resulting precipitate removed by filtration. The filtrate was concentrated to give 7.82 g off-white solid. This solid was stirred in 100 mL heptane with sonication, and then residual solids removed by suction filtration. The filtrate was concentrated to give tert-butyl 3-(dibromomethylene)azetidine-1-carboxylate (75a, 4.59 g, 95% yield) as a white solid. $^1$H NMR (400 MHz, CDCl3) δ 4.32 (s, 4H), 1.46 (s, 9H). MS: 226, 228, 230 [M-Boc+H]$^+$.

To a solution of tert-butyl 3-(dibromomethylene)azetidine-1-carboxylate (75a, 542 mg, 1.66 mmol) in THF (16.6 mL) at −78° C. was added n-butyllithium (1.6M solution in hexanes, 1.86 mL, 2.98 mmol). After 30 minutes, the reaction was treated with iodomethane (325 uL, 5.22 mmol) and stirring continued at −78° C. for one hour. The reaction was quenched with sat. aq. NH$_4$Cl and extracted with MTBE. The organic layer was concentrated and purified on silica gel (Eluting with 0-25% ethyl acetate in heptane) to give tert-butyl 3-(1-bromoethylidene)azetidine-1-carboxylate (75b 0.230 g, 53% yield) as a clear oil. $^1$H NMR (400 MHz, CDCl3) δ 4.38-4.43 (m, 2H), 4.31-4.37 (m, 2H), 2.14 (quint, J=1.74 Hz, 3H), 1.46 (s, 9H).

Isopropylmagnesium chloride lithium chloride complex (1.3M solution in THF, 2.00 mL, 2.60 mmol, 2.00 mL) was added to a cooled (~40° C., acetonitrile/dry ice bath) solution of 2-{[2-(benzyloxy)-4,6-dimethylpyridin-3-yl]methyl}-7-bromo-5,8-dichloro-3,4-dihydroisoquinolin-1(2H)-one (Cpd S, 657 mg, 1.26 mmol) in THF (12.6 mL), and the mixture stirred for one hour. Tri-n-butyltin chloride (600 uL, 72.2 mmol) was added, and the flask was warmed to 0° C. in an ice bath for 30 minutes. The reaction was quenched with sat. aq. NH$_4$Cl and extracted with MTBE. The MTBE layer was washed with brine, concentrated, and the resulting crude oil purified on silica gel (eluting with 0-30% ethyl acetate in heptane) to give 2-((2-(benzyloxy)-4,6-dimethylpyridin-3-yl)methyl)-5,8-dichloro-7-(tributylstannyl)-3,4-dihydroisoquinolin-1(2H)-one (75c, 0.699 g, 76%) as a clear, thick oil. $^1$H NMR (400 MHz, DMSO-d$_6$) δ 7.42 (d, J=7.09 Hz, 2H), 7.37 (s, 1H), 7.22-7.34 (m, 3H), 6.74 (s, 1H), 5.37 (s, 2H), 4.69 (s, 2H), 3.22 (t, J=5.99 Hz, 2H), 2.72 (t, J=5.87 Hz, 2H), 2.35 (s, 3H), 2.30 (s, 3H), 1.51 (quint, J=7.76 Hz, 6H), 1.08-1.35 (m, 12H), 0.85 (t, J=7.34 Hz, 9H). MS: 731 [M+H]$^+$=731.

A mixture of 2-((2-(benzyloxy)-4,6-dimethylpyridin-3-yl)methyl)-5,8-dichloro-7-(tributylstannyl)-3,4-dihydroisoquinolin-1(2H)-one (75c, 251 mg, 0.344 mmol) and tert-butyl 3-(1-bromoethylidene)azetidine-1-carboxylate (75b, 103 mg, 0.393 mmol) 1,4-dioxane (4.00 mL) was treated with tetrakis(triphenylphosphino)palladium(0) (60.8 mg, 0.0526 mmol), and copper (I) iodide (10.0 mg, 0.0525 mmol). Nitrogen was bubbled through the mixture for 10 minutes, then the vial was sealed and irradiated in a microwave reactor at 120° C. for 2 hours. Dioxane was removed under vacuum, and the resulting oil was purified on silica gel (eluting with 0-40% ethyl acetate in heptane) to give tert-butyl 3-(1-(2-((2-(benzyloxy)-4,6-dimethylpyridin-3-yl)methyl)-5,8-dichloro-1-oxo-1,2,3,4-tetrahydroisoquinolin-7-yl)ethylidene)azetidine-1-carboxylate (75d, 49 mg, 23% yield) as a clear gum. $^1$H NMR (400 MHz, CDCl3) δ 7.43-7.49 (m, 2H), 7.30-7.39 (m, 3H), 7.21 (s, 1H), 6.65 (s, 1H), 5.47 (s, 2H), 4.87 (s, 2H), 4.57 (br. s., 2H), 4.24 (br. s., 2H), 3.29 (t, J=6.24 Hz, 2H), 2.73 (t, J=6.24 Hz, 2H), 2.45 (s, 3H), 2.36 (s, 3H), 1.87 (s, 3H), 1.45 (s, 9H). MS: 622, 624 [M+H]$^+$.

A solution of tert-butyl 3-(1-(2-((2-(benzyloxy)-4,6-dimethylpyridin-3-yl)methyl)-5,8-dichloro-1-oxo-1,2,3,4-tetrahydroisoquinolin-7-yl)ethylidene)azetidine-1-carboxylate (75d, 49 mg, 0.079 mmol) in trifluoroacetic acid (5 mL, 70 mmol) was stirred at room temperature for 6 hours. The solution was concentrated to dryness. The residue was dissolved in methanol and purified by SCX column (Varian Bond elute SCX, 2 g, 100% MeOH to 3.5M NH$_3$ in MeOH) to give crude 7-(1-(azetidin-3-ylidene)ethyl)-5,8-dichloro-2-((4,6-dimethyl-2-oxo-1,2-dihydropyridin-3-yl)methyl)-3,4-dihydroisoquinolin-1(2H)-one (Example 74, 38 mg, 100% yield) as a clear gum, which was used without further purification in the next step. MS: 432, 434 [M+H]$^+$.

To a cooled (0° C.) solution of crude 7-(1-(azetidin-3-ylidene)ethyl)-5,8-dichloro-2-((4,6-dimethyl-2-oxo-1,2-dihydropyridin-3-yl)methyl)-3,4-dihydroisoquinolin-1(2H)-one (Example 74, 24 mg, 0.056 mmol) in dichloromethane (3.0 mL) was added triethylamine (10 uL, 0.072 mmol) and then acetoxy acetyl chloride (6.5 uL, 0.060 mmol). The reaction was stirred for 30 minutes and then quenched with methanol. The mixture was concentrated, re-dissolved in methanol (5 mL), treated with cesium carbonate (45 mg, 0.14 mmol), and stirred at room temperature overnight. The resulting solution was concentrated to dryness. The residue was dissolved in DMF, filtered, and purified by preparative HPLC to give 5,8-dichloro-2-[(4,6-dimethyl-2-oxo-1,2-dihydropyridin-3-yl)methyl]-7-{1-[1-(hydroxyacetyl)azetidin-3-ylidene]ethyl}-3,4-dihydroisoquinolin-1(2H)-one (Example 75, 9.38 mg, 34% yield) as a white powder. $^1$H NMR (400 MHz, DMSO-d$_6$) δ 11.54 (br. s., 1H), 7.51 (s, 1H), 5.89 (s, 1H), 4.81-4.99 (m, 2H), 4.51-4.60 (m, 3H), 4.48 (br. s., 1H), 4.19 (br. s., 1H), 3.83-4.01 (m, 2H), 3.46 (t, J=6.11 Hz, 2H), 2.88 (t, J=5.87 Hz, 2H), 2.17 (s, 3H), 2.12 (s, 3H), 1.85 (br. s., 3H). MS: 490, 492 [M+H]$^+$.

Method I

Example 34: (±)-5,8-dichloro-2-[(4,6-dimethyl-2-oxo-1,2-dihydropyridin-3-yl)methyl]-7-{[1-(hydroxyacetyl)piperidin-4-yl](methoxy)methyl}-3,4-dihydroisoquinolin-1(2H)-one Example 35: 5,8-dichloro-2-[(4,6-dimethyl-2-oxo-1,2-dihydropyridin-3-yl)methyl]-7-{[1-(hydroxyacetyl)piperidin-4-yl](methoxy)methyl}-3,4-dihydroisoquinolin-1(2H)-one—Isomer B Example 36: 5,8-dichloro-2-[(4,6-dimethyl-2-oxo-1,2-dihydropyridin-3-yl)methyl]-7-{[1-(hydroxyacetyl)piperidin-4-yl](methoxy)methyl}-3,4-dihydroisoquinolin-1(2H)-one—Isomer A

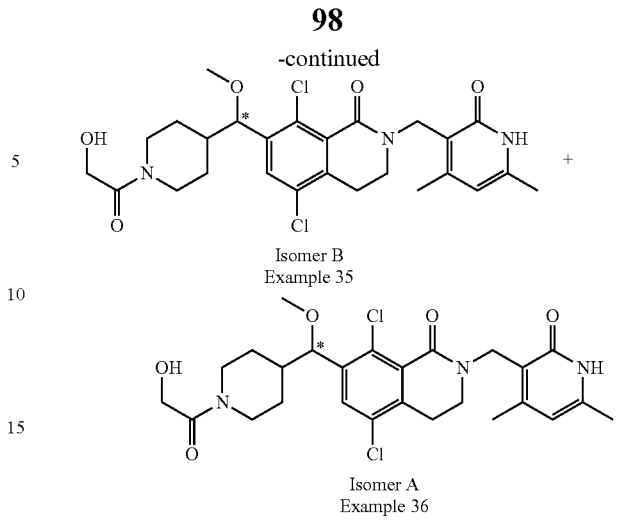

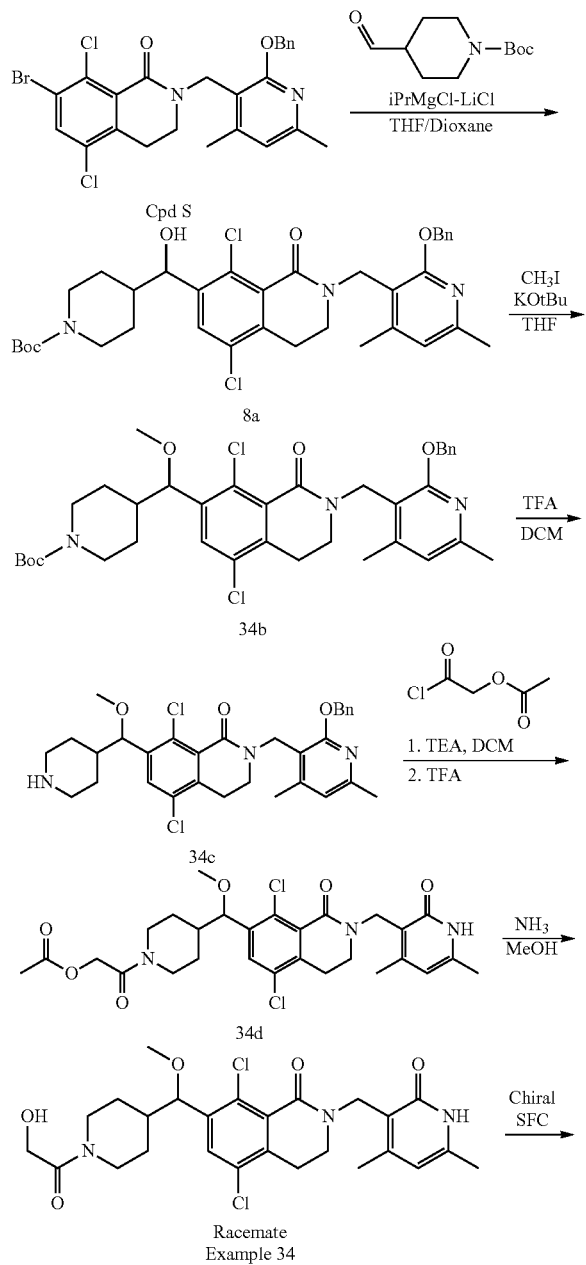

To a solution of 2-{[2-(benzyloxy)-4,6-dimethylpyridin-3-yl]methyl}-7-bromo-5,8-dichloro-3,4-dihydroisoquinolin-1(2H)-one (Cpd S, 311.0 mg, 0.598 mmol) in tetrahydrofuran (5.0 mL) and 1,4-dioxane (0.5 mL) at −40° C. (in an acetonitrile/dry ice bath) was added isopropylmagnesium chloride lithium chloride complex (1.3 M in THF, 0.850 mL, 1.10 mmol) and the reaction was stirred for 1 hour. N-Boc-4-formylpiperidine (0.242 g, 1.14 mmol) was then added, and the flask was warmed to 0° C. in an ice bath. After 1 hour at 0° C., the solution was quenched with sat. aq. $NH_4Cl$ and extracted with MTBE. The MTBE layer was concentrated, and the resulting oil purified on silica gel (Isco RediSepRf, 12 g, 10-70% gradient of ethyl acetate in heptane) to give racemic tert-butyl 4-((2-((2-(benzyloxy)-4,6-dimethylpyridin-3-yl)methyl)-5,8-dichloro-1-oxo-1,2,3,4-tetrahydroisoquinolin-7-yl)(hydroxy)methyl) piperidine-1-carboxylate (8a, 0.229 g, 59%) as a white solid. $^1$H NMR (400 MHz, CD3OD) δ 7.66 (s, 1H), 7.36-7.44 (m, 2H), 7.18-7.31 (m, 3H), 6.71 (s, 1H), 5.42 (s, 2H), 5.04 (d, J=5.14 Hz, 1H), 4.83 (d, J=1.96 Hz, 2H), 4.08 (d, J=12.72 Hz, 2H), 3.23 (t, J=6.24 Hz, 2H), 2.73 (t, J=6.11 Hz, 2H), 2.53-2.71 (m, 2H), 2.39 (s, 3H), 2.35 (s, 3H), 1.76-1.90 (m, 1H), 1.32-1.62 (m, 13H); MS 654, 656 [M+H]$^+$.

A cooled (0° C.) solution of racemic tert-butyl 4-((2-((2-(benzyloxy)-4,6-dimethylpyridin-3-yl)methyl)-5,8-dichloro-1-oxo-1,2,3,4-tetrahydroisoquinolin-7-yl)(hydroxy)methyl) piperidine-1-carboxylate (8a, 91.0 mg, 0.139 mmol) in THF (3.0 mL) was treated with iodomethane (34 mg, 0.24 mmol) and potassium tert-butoxide (0.155 mL of a 1.0M solution in THF, 0.155 mmol). Stirring was continued at 0° C. for 30 minutes, then the mixture partitioned between brine and MTBE. The organic phase was concentrated to dryness, to give crude racemic tert-butyl 4-((2-((2-(benzyloxy)-4,6-dimethylpyridin-3-yl)methyl)-5,8-dichloro-1-oxo-1,2,3,4-tetrahydroisoquinolin-7-yl)(methoxy)methyl) piperidine-1-carboxylate (34b, 97 mg, 100%) as a gum. MS: 612, 614 [M+H−tBu]+.

Trifluoroacetic acid (0.10 mL, 1.35 mmol) was added to a room temperature solution of crude racemic tert-butyl 4-((2-((2-(benzyloxy)-4,6-dimethylpyridin-3-yl)methyl)-5,8-dichloro-1-oxo-1,2,3,4-tetrahydroisoquinolin-7-yl)(methoxy)methyl)piperidine-1-carboxylate (34b, 97 mg, 0.139 mmol) in dichloromethane (5.0 mL). The mixture was stirred at room temperature for 2 hours, at 35° C. for 4 hours, at room temperature overnight, then at 40° C. for 6 hours. The solution was diluted with heptane and concentrated to dryness, leaving crude racemic 2-((2-(benzyloxy)-4,6-dimethylpyridin-3-yl)methyl)-5,8-dichloro-7-(methoxy(piperidin-4-yl)methyl)-3,4-dihydroisoquinolin-1(2H)-one (34c, 124 mg, 100%) as a gum. MS: 568, 570 [M+H]$^+$.

To a cooled (0° C.) solution of crude racemic 2-((2-(benzyloxy)-4,6-dimethylpyridin-3-yl)methyl)-5,8-dichloro-7-(methoxy(piperidin-4-yl)methyl)-3,4-dihydroisoquinolin-1 (2H)-one (34c, 124 mg, 0.139 mmol) in dichloromethane (3.0 mL) was added triethylamine (75 uL, 0.54 mmol) and 2-acetoxyacetyl chloride (16 uL, 0.15 mmol). The mixture was stirred at 0° C. for 30 minutes. Trifluoroacetic acid (2.0 mL) was then added and the mixture stirred at room temperature for 1 hour, then at 40° C. for 7 hours. The solution was concentrated to dryness and further dried under high vacuum for 2 days, giving crude racemic 2-(4-((5,8-dichloro-2-((4,6-dimethyl-2-oxo-1,2-dihydropyridin-3-yl)methyl)-1-oxo-1,2,3,4-tetrahydroisoquinolin-7-yl)(methoxy)methyl)piperidin-1-yl)-2-oxoethyl acetate (34d, 204 mg, 100%) as a golden oil. MS: 578, 580 [M+H]$^+$.

The crude racemic 2-(4-((5,8-dichloro-2-((4,6-dimethyl-2-oxo-1,2-dihydropyridin-3-yl)methyl)-1-oxo-1,2,3,4-tetrahydroisoquinolin-7-yl)(methoxy)methyl)piperidin-1-yl)-2-oxoethyl acetate (34d, 204 mg, 0.139 mmol) was dissolved in a 7N solution of ammonia in methanol (4 mL, 28 mmol NH3), stirred at room temperature for 1 hour, then stirred at 40° C. for 4 hours. The solution was concentrated to dryness and the residue purified by preparative HPLC to give (±)-5,8-dichloro-2-[(4,6-dimethyl-2-oxo-1,2-dihydropyridin-3-yl)methyl]-7-{[1-(hydroxyacetyl)piperidin-4-yl](methoxy)methyl}-3,4-dihydroisoquinolin-1(2H)-one (Example 34, 19.87 mg, 27% yield from 8a) as a white solid. $^1$H NMR (400 MHz, CD3OD) δ 7.44 (s, 1H), 6.01 (s, 1H), 4.66 (s, 2H), 4.56 (d, J=5.62 Hz, 1H), 4.35-4.45 (m, 1H), 4.02-4.17 (m, 2H), 3.57-3.68 (m, 1H), 3.43 (t, J=6.24 Hz, 2H), 3.10 (s, 3H), 2.86-2.92 (m, 2H), 2.75-2.85 (m, 1H), 2.40-2.54 (m, 1H), 2.20 (s, 3H), 2.15 (s, 3H), 1.78-1.87 (m, 1H), 1.60-1.69 (m, 1H), 1.18-1.47 (m, 3H). MS: 536, 538 [M+H]$^+$.

The racemate (Example 34) was further purified by chiral preparative SFC, affording, after lyophilization, Example 35 (Isomer B, retention time 13.019 min, 9.09 mg, 12% yield from 8a) and Example 36 (Isomer A, retention time 10.712 min, 8.36 mg, 11% yield from 8a) as white solids. The absolute configuration of the benzylic carbon in each isomer was not determined.

Example 35: 5,8-dichloro-2-[(4,6-dimethyl-2-oxo-1,2-dihydropyridin-3-yl)methyl]-7-{[1-(hydroxyacetyl)piperidin-4-yl](methoxy)methyl}-3,4-dihydroisoquinolin-1(2H)-one—Isomer B MS: 536, 538 [M+H]$^+$. Chiral analysis: ~97% ee, retention time 13.019 min on a Lux Cellulose-4 4.6×100 mm 3 u column, eluting with 50% MeOH, 120 bar, 4 mL/min.

Example 36: 5,8-dichloro-2-[(4,6-dimethyl-2-oxo-1,2-dihydropyridin-3-yl)methyl]-7-{[1-(hydroxyacetyl)piperidin-4-yl](methoxy)methyl}-3,4-dihydroisoquinolin-1(2H)-one—Isomer A MS: 536, 538 [M+H]$^+$. Chiral analysis: >99% ee, retention time 10.712 min on a Lux Cellulose-4 4.6×100 mm 3 u column, eluting with 50% MeOH, 120 bar, 4 mL/min.

Example 81: 5,8-dichloro-2-[(4-methoxy-6-methyl-2-oxo-1,2-dihydropyridin-3-yl)methyl]-7-[(R)-methoxy(oxetan-3-yl)methyl]-3,4-dihydroisoquinolin-1(2H)-one Example 82: 5,8-dichloro-2-[(4-methoxy-6-methyl-2-oxo-1,2-dihydropyridin-3-yl)methyl]-7-[(S)-methoxy(oxetan-3-yl)methyl]-3,4-dihydroisoquinolin-1(2H)-one

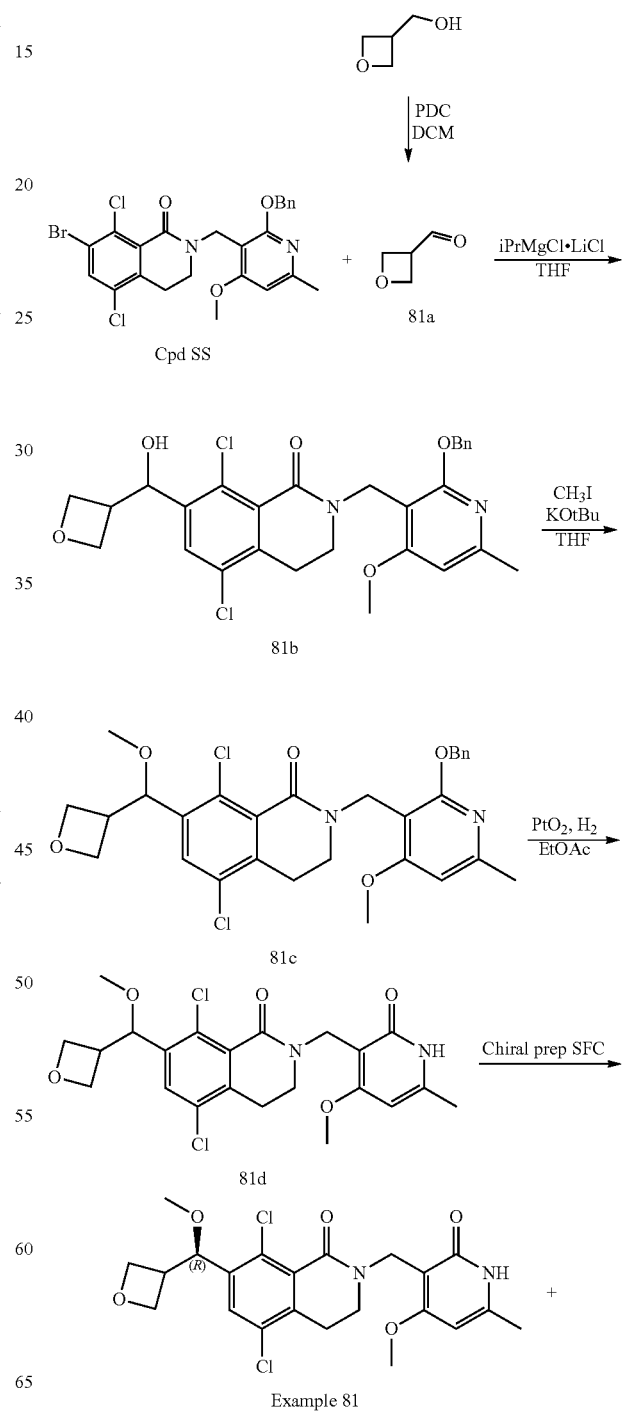

-continued

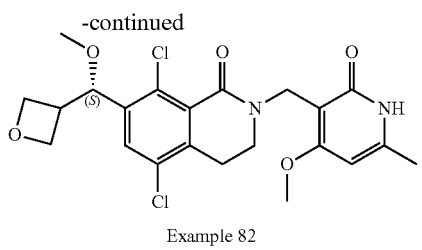

Example 82

To a stirred, room temperature solution of oxetan-3-ylmethanol (2.20 g, 24.97 mmol) in dichloromethane (110 mL) was added solid pyridinium dichromate (5.87 g, 15.6 mmol) in five portions. The resulting black mixture was stirred at room temperature for 16 hours. The deep brown suspension was then filtered through a silica gel pad and the filter cake rinsed with dichloromethane (8×120 mL). The combined dichloromethane filtrates were partially concentrated under reduced pressure at room temperature (27~30° C.) to afford oxetane-3-carbaldehyde (81a, 3 g, ~26% yield) as a colorless solution, 18.7 wt % solution in dichloromethane by NMR. The solution was dried over magnesium sulfate, filtered and used immediately in the next step. 1H NMR (400 MHz, CDCl3) δ 9.95 (d, J=2.4 Hz, 1H), 4.87 (m, 4H), 3.81 (m, 1H).

A solution of 2-((2-(benzyloxy)-4-methoxy-6-methylpyridin-3-yl)methyl)-7-bromo-5,8-dichloro-3,4-dihydroisoquinolin-1(2H)-one (Cpd SS, 500 mg, 0.932 mmol) in anhydrous THF (7 mL) was cooled to −65° C., then isopropylmagnesium chloride lithium chloride complex (1.3 M solution in THF, 2.15 mL, 2.80 mmol) was added dropwise over 3 minutes. The resulting brown solution was stirred at −65° C. for 10 minutes, then warmed to −10° C. for 30 minutes. To this was oxetane-3-carbaldehyde (81a, ~2.2 g, ~4.8 mmol, ~18.7 wt % solution in dichloromethane) dropwise over 2 minutes, causing the color to change to light yellow. Stirring was continued at −5° C. for 30 minutes. The reaction was quenched with glacial acetic acid (0.5 mL) and diluted with ethyl acetate (10 mL), then washed with sat. aq. NaHCO₃/sat. aq. NaCl (1/1 v/v, 3×15 mL). The organic layer was dried over sodium sulfate, filtered, concentrated, and purified by silica gel chromatography (eluting with 1/1 petroleum ether/ethyl acetate) to give 2-((2-(benzyloxy)-4-methoxy-6-methylpyridin-3-yl)methyl)-5,8-dichloro-7-(hydroxy(oxetan-3-yl)methyl)-3,4-dihydroisoquinolin-1(2H)-one (81b, 300 mg, 59% yield, racemate) as a white solid. MS: 543 [M+H]⁺.

Iodomethane (133 mg, 0.938 mmol) was added dropwise to a cooled (−5° C.) suspension of 2-((2-(benzyloxy)-4-methoxy-6-methylpyridin-3-yl)methyl)-5,8-dichloro-7-(hydroxy(oxetan-3-yl)methyl)-3,4-dihydroisoquinolin-1(2H)-one (81b, 300 mg, 0.552 mmol) in anhydrous THF (5 mL). Potassium tert-butoxide (1.0M solution in THF, 0.938 mL, 0.938 mmol) was added, and the mixture stirred at 0° C. for 1 hour. The reaction mixture was partitioned between sat. aq. NaCl (15 mL) and MTBE (3×15 mL). The combined organic extracts were washed with sat. aq. NaCl (30 mL), dried over sodium sulfate, concentrated, and purified by silica gel chromatography (eluting with 1/1 petroleum ether/ethyl acetate) to give racemic 2-((2-(benzyloxy)-4-methoxy-6-methylpyridin-3-yl)methyl)-5,8-dichloro-7-(methoxy(oxetan-3-yl)methyl)-3,4-dihydroisoquinolin-1(2H)-one (81c, 280 mg, 91% yield) as a yellow gum. MS: 557 [M+H]⁺.

A room-temperature mixture of 2-((2-(benzyloxy)-4-methoxy-6-methylpyridin-3-yl)methyl)-5,8-dichloro-7-(methoxy(oxetan-3-yl)methyl)-3,4-dihydroisoquinolin-1(2H)-one (81c, 100 mg, 0.179 mmol) and PtO2 (21 mg, 0.092 mmol) in ethyl acetate (4 mL) was stirred under a hydrogen balloon for 3 days. The solution was filtered through a Celite pad. The flask and filter pad were rinsed with ethyl acetate (2×10 mL). The combined filtrates were concentrated and purified by preparative thin layer chromatography (silica gel, eluting with 10/1 dichloromethane/methanol) to give racemic 5,8-dichloro-2-[(4-methoxy-6-methyl-2-oxo-1,2-dihydropyridin-3-yl)methyl]-7-[methoxy(oxetan-3-yl)methyl]-3,4-dihydroisoquinolin-1(2H)-one (81d, 45 mg, 54% yield) as a white solid.

Multiple batches of racemic 5,8-dichloro-2-[(4-methoxy-6-methyl-2-oxo-1,2-dihydropyridin-3-yl)methyl]-7-[methoxy(oxetan-3-yl)methyl]-3,4-dihydroisoquinolin-1(2H)-one (81d, 140 mg total) were combined for chiral separation by preparative SFC [Column: (R,R)Whelk O1 250 mm*30 mm, 5 um; mobile phase: base-ETOH; wavelength: 220 nm; workup: lyophilization] to give Example 81 (50.34 mg, 36% yield) as a gray solid, and, after further purification by preparative TLC (silica gel, eluting with 10/1 dichloromethane/methanol), Example 82 (22.83 g, 16% yield) as a brown solid. A small-molecule X-Ray crystal structure of Example 82 shows it to have absolute (S) stereochemistry, so absolute (R) stereochemistry was attributed to its enantiomer, Example 81.

Example 81: 5,8-dichloro-2-[(4-methoxy-6-methyl-2-oxo-1,2-dihydropyridin-3-yl)methyl]-7-[(R)-methoxy(oxetan-3-yl)methyl]-3,4-dihydroisoquinolin-1(2H)-one ¹H NMR (400 MHz, CDCl3) δ 12.34 (brs, 1H), 7.49 (s, 1H), 5.93 (s, 1H), 5.05 (d, J=6.0 Hz, 1H), 4.78-4.61 (m, 6H), 3.88 (s, 3H), 3.50-3.48 (m, 2H), 3.38-3.37 (m, 1H), 3.31 (s, 3H), 2.94 (t, J=6.2 Hz, 2H), 2.35 (s, 3H). MS: 489 [M+Na]+. Chiral analysis: 100% ee; retention time 9.85 min; column (R,R)Whelk O1, 250×4.6 mm I.D., 5 um; mobile phase 50% ethanol (0.05% DEA) in CO2; wavelength 220 nm.

Example 82: 5,8-dichloro-2-[(4-methoxy-6-methyl-2-oxo-1,2-dihydropyridin-3-yl)methyl]-7-[(S)-methoxy(oxetan-3-yl)methyl]-3,4-dihydroisoquinolin-1(2H)-one ¹H NMR (400 MHz, CDCl3) δ 12.38 (brs, 1H), 7.49 (s, 1H), 5.92 (s, 1H), 5.05 (d, J=6.0 Hz, 1H), 4.78-4.64 (m, 6H), 3.87 (s, 3H), 3.50-3.47 (m, 2H), 3.38-3.37 (m, 1H), 3.31 (s, 3H), 2.93 (t, J=6.2 Hz, 2H), 2.35 (s, 3H). MS: 467 [M+H]⁺. Chiral analysis: 98% ee; retention time 8.65 min; column: (R,R)Whelk 01, 250×4.6 mm I.D., 5 um; mobile phase 50% ethanol (0.05% DEA) in CO2; wavelength 220 nm.

Example 83: 8-chloro-2-[(4-methoxy-6-methyl-2-oxo-1,2-dihydropyridin-3-yl)methyl]-7-{(R)-methoxy[(3R)-tetrahydrofuran-3-yl]methyl}-5-methyl-3,4-dihydroisoquinolin-1(2H)-one Example 84: 8-chloro-2-[(4-methoxy-6-methyl-2-oxo-1,2-dihydropyridin-3-yl)methyl]-7-{(R*)-methoxy[(3S*)-tetrahydrofuran-3-yl]-5-methyl}-5-methyl-3,4-dihydroisoquinolin-1(2H)-one Example 85: 8-chloro-2-[(4-methoxy-6-methyl-2-oxo-1,2-dihydropyridin-3-yl)methyl]-7-{(S*)-methoxy[(3R*)-tetrahydrofuran-3-yl]methyl}-5-methyl-3,4-dihydroisoquinolin-1(2H)-one Example 86: 8-chloro-2-[(4-methoxy-6-methyl-2-oxo-1,2-dihydropyridin-3-yl)methyl]-7-{(S)-methoxy[(3S)-tetrahydrofuran-3-yl]methyl}-5-methyl-3,4-dihydroisoquinolin-1(2H)-one

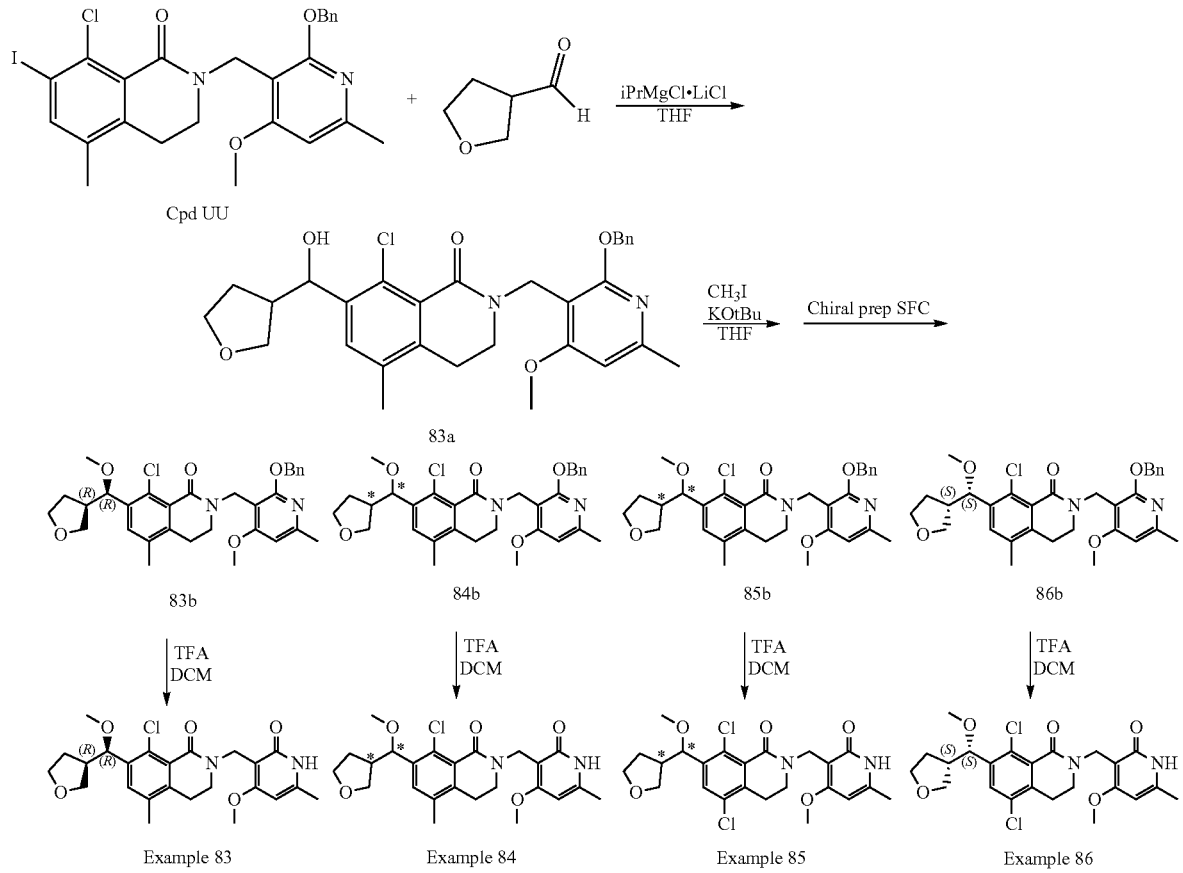

Aqueous tetrahydrofuran-3-carboxaldehyde solution (~4.0 mL of 50 wt % in water, 4.0 g) was extracted with dichloromethane (2×2.5 mL). The combined organic layers were cooled (15° C.) and phosphorus pentoxide slowly added. The resulting dark solution was filtered to remove solids and the yellow filtrate (~16 wt % tetrahydrofuran-3-carboxaldehyde in dichloromethane by NMR) was promptly used as described below.

Isopropylmagnesium chloride lithium chloride complex (1.3 M solution in THF, 3.73 mL, 4.85 mmol) was added dropwise to a cooled (−70° C.) solution of 2-((2-(benzyloxy)-4-methoxy-6-methylpyridin-3-yl)methyl)-8-chloro-7-iodo-5-methyl-3,4-dihydroisoquinolin-1(2H)-one (Cpd UU, 910 mg, 1.617 mmol) in anhydrous THF (10 mL) over 5 minutes. The resulting brown mixture was stirred at −70° C. for 30 minutes, then the tetrahydrofuran-3-carboxaldehyde solution prepared above (3.98 g of ~16 wt % in dichloromethane, ~636 mg tetrahydrofuran-3-carboxaldehyde, ~16.35 mmol) was added dropwise over 5 minutes. Stirring was continued at −70° C. for 30 minutes. The reaction was quenched with glacial acetic acid (0.5 mL) and diluted with ethyl acetate (80 mL), then washed with sat. aq. NaHCO₃/sat. aq. NaCl (1/1 v/v, 3×35 mL). The organic layer was dried over sodium sulfate, filtered, concentrated, and purified by silica gel chromatography (eluting with 1/1 petroleum ether/ethyl acetate) to give 2-((2-(benzyloxy)-4-methoxy-6-methylpyridin-3-yl)methyl)-8-chloro-7-(hydroxy(tetrahydrofuran-3-yl)methyl)-5-methyl-3,4-dihydroisoquinolin-1(2H)-one (83a, 450 mg, 52% yield, mixture of 4 diastereomers) as a white solid. $^1$H NMR (400 MHz, CDCl3) δ 7.37-7.46 (m, 3H), 7.20-7.31 (m, 3H), 6.39 (s, 1H), 5.44 (s, 2H), 5.22-5.31 (m, 1H), 4.87 (s, 2H), 3.88-4.02 (m, 1H), 3.83 (s, 3H), 3.65-3.82 (m, 3H), 3.16 (t, J=5.99 Hz, 2H), 2.71-2.89 (m, 1H), 2.55 (t, J=6.17 Hz, 2H), 2.44 (s, 3H), 2.20 (s, 3H), 1.66-1.95 (m, 3H).

Iodomethane (225 mg, 1.58 mmol) was added dropwise to a cooled (−5° C.) suspension of 2-((2-(benzyloxy)-4-methoxy-6-methylpyridin-3-yl)methyl)-8-chloro-7-(hydroxy(tetrahydrofuran-3-yl)methyl)-5-methyl-3,4-dihydroisoquinolin-1(2H)-one (83a, 500 mg, 0.931 mmol in THF (15 mL), followed by potassium tert-butoxide (1.0M solution in THF, 1.58 mL, 1.58 mmol). The mixture was stirred at 0° C. for 1 hour. Glacial acetic acid (0.5 mL) and ethyl acetate (100 mL) were added, and the solution washed with sat. aq. NaHCO₃ (3×20 mL) and brine (30 mL). The organic layer was dried over sodium sulfate, filtered, concentrated, and purified by silica gel chromatography (eluting with 1/1 petroleum ether/ethyl acetate), to give 2-((2-(benzyloxy)-4-methoxy-6-methylpyridin-3-yl)methyl)-8-chloro- 7-(methoxy(tetrahydrofuran-3-yl)methyl)-5-methyl-3,4-dihydroisoquinolin-1(2H)-one as a mixture of 4 diastereomers (400 mg, 70% yield).

The stereoisomers were separated by preparative chiral SFC (column: AD, 250*30 mm, 5 um, mobile phase: 30% IPA+NH3H2O 60 mL/min, wavelength: 220 nm, workup: lyophilization) to give 140 mg of peak 12 (mixture of peak 1 and 2) and 120 mg of peak 34 (mixture of peak 3 and 4) as white solids.

The peak 12 mixture (140 mg) was re-separated by preparative SFC (column: AD, 250*30 mm, 5 um, mobile phase: 25% MeOH+NH3H2O 60 mL/min, wavelength: 220 nm, workup: lyophilization) to give enantio-enriched peak 1 (60 mg, 81% chiral purity, further purified as described below) and pure peak 2 (1610b, 60 mg, 12% yield, 96% chiral purity, used without further purification).

The peak 34 mixture (120 mg) was re-separated by preparative SFC (Column: AD, 250*30 mm, 5 um, mobile phase: 25% MeOH+NH3H2O 60 mL/min, wavelength: 220 nm, workup: lyophilization) to give pure peak 3 (1613b, 50 mg, 9.8% yield, 95% chiral purity, used without further purification) and enantio-enriched peak 4 (50 mg, 88% chiral purity, further purified as described below).

The enantio-enriched peak 1 material (60 mg, 81% chiral purity) was further purified by preparative SFC (column: AD, 250*30 mm, 5 um, mobile phase: 25% MeOH+ NH3H2O 70 mL/min, wavelength: 220 nm, workup: lyophilization) to give pure peak 1 (83b, 45 mg, 8.7% yield, 98% chiral purity).

The enantio-enriched peak 4 material (50 mg, 88% chiral purity) was further purified by preparative SFC (column: AD, 250*30 mm, 5 um, mobile phase: 25% MeOH+NH3H2O 70 mL/min, wavelength: 220 nm, workup: lyophilization) to give pure peak 4 (1613b, 45 mg, 8.7% yield, 99% chiral purity). Absolute or relative stereochemistry of each isomer was not determined at this stage.

A stirred solution of 2-((2-(benzyloxy)-4-methoxy-6-methylpyridin-3-yl)methyl)-8-chloro-7-(methoxy(tetrahydrofuran-3-yl)methyl)-5-methyl-3,4-dihydroisoquinolin-1(2H)-one peak 1 (83b, 45 mg, 0.082 mmol) in dichloromethane (2 mL) was treated with TFA (2 mL) at room temperature. The mixture was heated to 30° C. for 16 hours, then the solution was diluted with dichloromethane (20 mL) and concentrated to dryness. The residue was purified by silica gel chromatography (eluting with 10/1 dichloromethane/methanol) to give 8-chloro-2-[(4-methoxy-6-methyl-2-oxo-1,2-dihydropyridin-3-yl)methyl]-7-{(R)-methoxy[(3R)-tetrahydrofuran-3-yl]methyl}-5-methyl-3,4-dihydroisoquinolin-1(2H)-one (Example 83, 18.55 mg, 50% yield, 100% ee) as a white solid. A small molecule X-Ray crystal structure of Example 83 confirms it has absolute (R,R) configuration. $^1$H NMR (400 MHz, CDCl3) δ 12.36 (brs, 1H), 7.29 (s, 1H), 5.91 (s, 1H), 4.85-4.75 (m, 3H), 3.89-3.83 (m, 6H), 3.71-3.69 (m, 1H), 3.47-3.44 (m, 2H), 3.16 (s, 3H), 2.76-2.73 (m, 2H), 2.58-2.54 (m, 1H), 2.34 (s, 3H), 2.26 (s, 3H), 1.73-1.70 (m, 2H). MS: 461 [M+H]$^+$. Chiral analysis: 100% ee; retention time 34.91 min; column: Chiralpak IC 250×4.6 mm I.D., 5 um; mobile phase: 50% ethanol (0.05% DEA) in CO2; flow rate: 2.0 mL/min; wavelength: 220 nm.

By the same procedure, the peak 2 stereoisomer (1610b, 60.0 mg, 0.109 mmol) afforded 8-chloro-2-[(4-methoxy-6-methyl-2-oxo-1,2-dihydropyridin-3-yl)methyl]-7-{(R*)-methoxy[(3S*)-tetrahydrofuran-3-yl]methyl}-5-methyl-3,4-dihydroisoquinolin-1(2H)-one (Example 84, 30 mg, 60% yield, 97% ee) as a white solid. The absolute stereochemistry of this isomer was not determined, but the $^1$HNMR spectrum shows clear differences from that of Example 83, suggesting that Example 84 is either the R,S or S,R isomer. $^1$H NMR (400 MHz, CDCl3) δ 12.33 (br. s, 1H), 7.30 (s, 1H), 5.91 (s, 1H), 4.84-4.77 (m, 3H), 3.89-3.86 (m, 4H), 3.73-3.68 (m, 2H), 3.60-3.58 (m, 1H), 3.46-3.44 (m, 2H), 3.19 (s, 3H), 2.75-2.73 (m, 2H), 2.64-2.62 (m, 1H), 2.34 (s, 3H), 2.24 (s, 3H), 1.98-1.95 (m, 2H). MS: 461 [M+H]$^+$. Chiral analysis: 97% ee, retention time 39.01 min; column: Chiralpak IC 250×4.6 mm I.D., 5 um; mobile phase: 50% ethanol (0.05% DEA) in CO2; flow rate: 2.0 mL/min; wavelength: 220 nm.

By the same procedure, the peak 3 stereoisomer (85b, 50.0 mg, 0.091 mmol) afforded 8-chloro-2-[(4-methoxy-6-methyl-2-oxo-1,2-dihydropyridin-3-yl)methyl]-7-{(S*)-methoxy[(3R*)-tetrahydrofuran-3-yl]methyl}-5-methyl-3,4-dihydroisoquinolin-1(2H)-one (Example 85, 16.06 mg, 38% yield, 100% ee) as a white solid. The absolute stereochemistry of this isomer was not determined, but the $^1$HNMR spectrum shows clear differences from that of Example 83, and is identical to that of Example 84, suggesting that Example 85 is either the S,R or R,S isomer. $^1$H NMR (400 MHz, CDCl3) δ 12.30 (br s, 1H), 7.30 (s, 1H), 5.91 (s, 1H), 4.84-4.77 (m, 3H), 3.89-3.86 (m, 4H), 3.74-3.66 (m, 2H), 3.59-3.58 (m, 1H), 3.46-3.44 (m, 2H), 3.19 (s, 3H), 2.75-2.73 (m, 2H), 2.65-2.63 (m, 1H), 2.34 (s, 3H), 2.24 (s, 3H), 1.98-1.95 (m, 2H). MS: 461 [M+H]$^+$. Chiral analysis: 100% ee, retention time 29.05 min; column: Chiralpak IC 250×4.6 mm I.D., 5 um; mobile phase; 50% ethanol (0.05% DEA) in CO2; flow rate: 2.0 mL/min; wavelength: 220 nm.

By the same procedure, the peak 4 stereoisomer (86b, 45.0 mg, 0.082 mmol) afforded 8-chloro-2-[(4-methoxy-6-methyl-2-oxo-1,2-dihydropyridin-3-yl)methyl]-7-{(S)-methoxy[(3S)-tetrahydrofuran-3-yl]methyl}-5-methyl-3,4-dihydroisoquinolin-1(2H)-one (Example 86, 14.79 mg, 39% yield, 100% ee) as a white solid. Though it has a different retention time on the chiral column, the $^1$HNMR spectrum of this compound is identical to that of Example 83, which was shown to have R,R configuration by X-Ray crystal structure. This suggests that Example 86 is the S,S stereoisomer. $^1$H NMR (400 MHz, CDCl3) δ 12.29 (br. s, 1H), 7.30 (s, 1H), 5.91 (s, 1H), 4.84-4.75 (m, 3H), 3.89-3.83 (m, 6H), 3.71-3.69 (m, 1H), 3.47-3.44 (m, 2H), 3.16 (s, 3H), 2.76-2.73 (m, 2H), 2.58-2.56 (m, 1H), 2.34 (s, 3H), 2.25 (s, 3H), 1.73-1.70 (m, 2H). MS: 461 [M+H]$^+$. Chiral analysis: 100% ee, retention time 32.28 min; column: Chiralpak IC 250×4.6 mm I.D., 5 um; mobile phase: 50% ethanol (0.05% DEA) in CO2; flow rate: 2.0 mL/min; wavelength: 220 nm.

Method J

Example 87: 5,8-dichloro-2-[(4-methoxy-6-methyl-2-oxo-1,2-dihydropyridin-3-yl)methyl]-7-[1-(1-methylazetidin-3-yl)ethyl]-3,4-dihydroisoquinolin-1(2H)-one—Isomer A Example 88: 5,8-dichloro-2-[(4-methoxy-6-methyl-2-oxo-1,2-dihydropyridin-3-yl)methyl]-7-[1-(1-methylazetidin-3-yl)ethyl]-3,4-dihydroisoquinolin-1(2H)-one—Isomer B

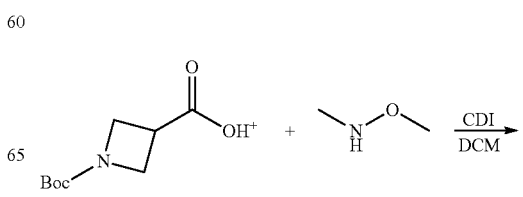

-continued

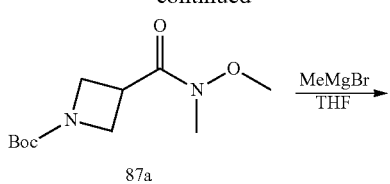
87a

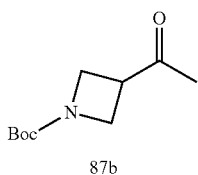
87b

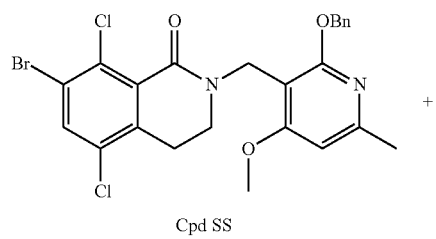
Cpd SS

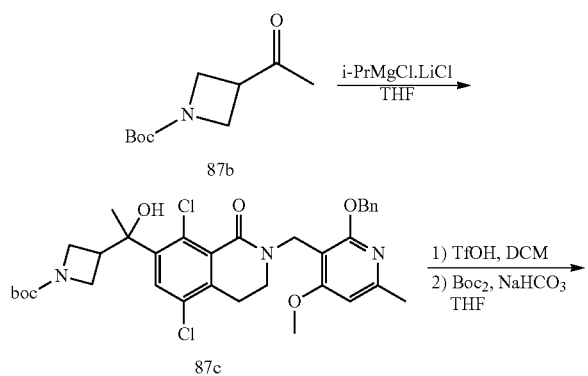
87c

87d

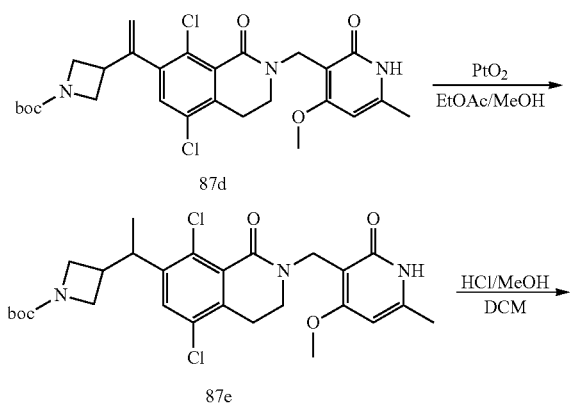
87e

87f

-continued

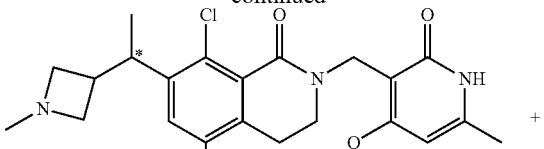
Isomer A
Example 87

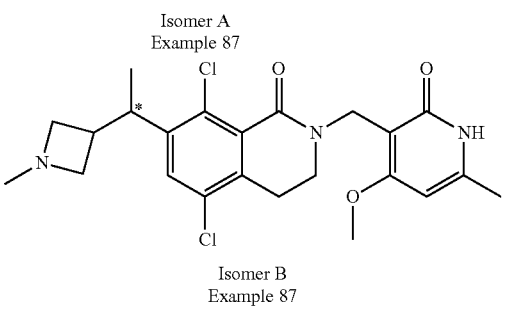
Isomer B
Example 87

A solution of 1-boc-azetidine-3-carboxylic acid (5.00 g, 24.8 mmol, and CDI (4.23 g, 26.1 mmol) in dichloromethane (100 mL) was stirred at room temperature for 1 hour, then N,O-dimethylhydroxylamine hydrochloride (4.0 g, 29.8 mmol) was added and stirring continued at room temperature for 16 hours. The resulting suspension was washed with water (3×30 mL), sat. aq. NaHCO$_3$ (3×30 mL), and brine (3×30 mL). The organic layer was dried over sodium sulfate, filtered, and concentrated to give tert-butyl 3-(methoxy(methyl)carbamoyl)azetidine-1-carboxylate (87a, 5.1 g, 84% yield) as a colorless oil. $^1$H NMR (400 MHz, CDCl3) δ 4.14 (br s, 2H), 4.05 (t, J=8.6 Hz, 2H), 3.66 (s, 3H), 3.65 (m, 1H), 3.20 (s, 3H), 1.43 (s, 9H).

Methylmagnesium bromide (3M solution in THF, 10.4 mL, 31.3 mmol) was added dropwise to a cooled (0° C.) solution of tert-butyl 3-(methoxy(methyl)carbamoyl)azetidine-1-carboxylate (87a, 5.1 g, 20.88 mmol) in anhydrous THF (100 mL). Stirring was continued at 0° C. for one hour, then at room temperature for 16 hours. The mixture was cooled to 0° C. and quenched with sat. aq. NaHCO$_3$ (35 mL), then extracted with ethyl acetate (3×40 mL). The combined organic extracts were washed with brine (3×40 mL), dried over sodium sulfate, filtered, concentrated, and purified by silica gel chromatography (eluting with petroleum ether/ethyl acetate from 10:1 to 3:1) to give tert-butyl 3-acetylazetidine-1-carboxylate (87b, (3.20 g, 77% yield) as light yellow oil. $^1$H NMR (400 MHz, CDCl3) δ 4.05 (d, J=7.6 Hz, 4H), 3.41 (quint, J=7.6 Hz, 1H), 2.18 (s, 3H), 1.43 (s, 9H).

A solution of 2-((2-(benzyloxy)-4-methoxy-6-methylpyridin-3-yl)methyl)-7-bromo-5,8-dichloro-3,4-dihydroisoquinolin-1(2H)-one (Cpd SS, 1.20 g, 2.238 mmol) in anhydrous THF (15 mL) was cooled to −60° C., then isopropylmagnesium chloride lithium chloride complex (1.3 M solution in THF, 5.16 mL, 6.71 mmol) was added dropwise via syringe over 3 minutes. Stirring was continued at −60° C. for 10 minutes, then at 0° C. for 20 minutes. To this was added tert-butyl 3-(methoxy(methyl)carbamoyl)azetidine-1-carboxylate (87a, 892 mg, 4.48 mmol) dropwise, then the mixture stirred at 0° C. for 1 hour. The mixture was quenched with glacial acetic acid (1 mL) and diluted with ethyl acetate (100 mL). The organic phase was washed with NaHCO$_3$/brine (v/v=1/1, 3×50 mL) and brine (50 mL), dried over sodium sulfate, and filtered. The filtrate was concentrated to give the crude product (2.0 g, yellow oil), which was purified by silica gel chromatography (eluting with petroleum ether/ethyl acetate=1:1) to give racemic tert-butyl 3-(1-(2-((2-(benzyloxy)-4-methoxy-6-methylpyridin-3-yl)methyl)-5,8-dichloro-1-oxo-1,2,3,4-tetrahydroisoquinolin-7-yl)-1-hydroxyethyl)azetidine-1-carboxylate (87c, 450 mg, 31% yield) as a white solid. MS: 656 [M+H]$^+$.

Trifluoromethanesulfonic acid (0.54 mL, 6.15 mmol) was added dropwise to a cooled (0° C.) solution of racemic tert-butyl 3-(1-(2-((2-(benzyloxy)-4-methoxy-6-methylpyridin-3-yl)methyl)-5,8-dichloro-1-oxo-1,2,3,4-tetrahydroisoquinolin-7-yl)-1-hydroxyethyl)azetidine-1-carboxylate (87c, 450 mg, 0.685 mmol) in anhydrous dichloromethane (10 mL). The mixture was stirred at 5-10° C. for 1 hour, then re-cooled to 0° C. and more trifluoromethanesulfonic acid (0.54 mL, 6.15 mmol) was added. After stirring at 2-5° C. for 12 hours, sat. aq. sodium bicarbonate was added to bring the solution to pH~8. The mixture was concentrated to remove dichloromethane, and the aqueous residue diluted with THF (20 mL). Solid sodium bicarbonate (288 mg, 3.43 mmol) and di-tert-butyl dicarbonate (448 mg, 2.06 mmol) were added and the mixture stirred at 2-5° C. for 16 hours, then let stand at 15° C. for 18 hours. The solution was extracted with ethyl acetate (2×50 mL). The combined organic layers were washed with brine (2×20 mL), dried over sodium sulfate, and filtered. The filtrate was concentrated to give the crude product (1 g, yellow solid), which was purified first by silica gel chromatography (eluting with 10% methanol in dichloromethane) and then re-purified by preparative SFC (column: AD 250 mm*30 mm, 5 um; mobile phase: 35% Base-ETOH; wavelength: 220 nm; workup: concentration) to give tert-butyl 3-(1-(5,8-dichloro-2-((4-methoxy-6-methyl-2-oxo-1,2-di hydropyridin-3-yl) methyl)-1-oxo-1,2,3,4-tetrahydroisoquinolin-7-yl)vinyl) azetidine-1-carboxylate (87d, 256 mg, 68.1%) as a yellow solid. MS: 548 [M+H]$^+$.

A suspension of tert-butyl 3-(1-(5,8-dichloro-2-((4-methoxy-6-methyl-2-oxo-1,2-di hydropyridin-3-yl)methyl)-1-oxo-1,2,3,4-tetrahydroisoquinolin-7-yl)vinyl)azetidine-1-carboxylate (87d, 236 mg, 0.43 mmol) and platinum oxide (80 mg, 0.35 mmol) in ethyl acetate (15 mL) and methanol (5 mL) was stirred at room temperature under a hydrogen balloon for 3 hours. After filtration to remove solids, the filtrate was concentrated and purified by preparative TLC (silica gel, dichloromethane/methanol=15:1 to give racemic tert-butyl 3-(1-(5,8-dichloro-2-((4-methoxy-6-methyl-2-oxo-1,2-dihydropyridin-3-yl)methyl)-1-oxo-1,2,3,4-tetrahydroisoquinolin-7-yl)ethyl)azetidine-1-carboxylate (87e, 180 mg, 76% yield) as a white solid. MS: 549 [M+H]$^+$.

A solution of give racemic tert-butyl 3-(1-(5,8-dichloro-2-((4-methoxy-6-methyl-2-oxo-1,2-di hydropyridin-3-yl) methyl)-1-oxo-1,2,3,4-tetrahydroisoquinolin-7-yl)ethyl) azetidine-1-carboxylate (87e, 180 mg, 0.327 mmol) in dichloromethane (10 mL) was stirred with HCl (4.0 M solution in methanol, 5 mL, 20 mmol) at 14° C. for 30 minutes. The solution was concentrated to dryness, and the residue dissolved in methanol (5 mL). Concentrated NH$_4$OH was added to bring the pH to ~8, and the mixture was again concentrated to dryness, leaving crude, racemic 7-(1-(azetidin-3-yl)ethyl)-5,8-dichloro-2-((4-methoxy-6-methyl-2-oxo-1,2-dihydropyridin-3-yl)methyl)-3,4-dihydroisoquinolin-1(2H)-one (87f, 180 mg, 100%) as a white solid, which was used without further purification.

Glacial acetic acid (0.1 mL) was added to a 15° C. solution of crude, racemic 7-(1-(azetidin-3-yl)ethyl)-5,8-dichloro-2-((4-methoxy-6-methyl-2-oxo-1,2-dihydropyridin-3-yl)methyl)-3,4-dihydroisoquinolin-1(2H)-one (87f, 180 mg, 0.327 mmol) and formaldehyde (37 wt % in water, 79.5 mg, 0.980 mmol) in methanol (5 mL), and the mixture stirred at 15° C. for 45 minutes. Sodium cyanoborohydride (41 mg, 0.653 mmol) was added and stirring continued at room temperature for 12 hours. The mixture was quenched with saturated NH4Cl solution (2 mL) and stirred at 15° C. for 30 minutes, then concentrated to remove the solvent. The residue was dissolved in dichloromethane/methanol (v/v=10:1, 50 mL) and filtered. The filtrate was concentrated and purified by preparative HPLC [column: Phenomenex Gemini C18 250*50 10 u; mobile phase: from 4% to 34% acetonitrile (with 0.225% formic acid) in water; wavelength: 220 nm; workup: lyophilization] to give the formate salt of (±)-5,8-dichloro-2-((4-methoxy-6-methyl-2-oxo-1,2-dihydropyridin-3-yl)methyl)-7-(1-(1-methylazetidin-3-yl)ethyl)-3,4-dihydroisoquinolin-1(2H)-one (110 mg, 66%) as a white solid. The enantiomers of this racemic salt were separated by preparative SFC [column: AD (250 mm*30 mm, 5 um); mobile phase: 30% base-ETOH; wavelength: 220 nm; workup: lyophilization], and each enantiomer separately re-purified by preparative HPLC [column: Phenomenex Gemini C18 250*50 10 u; mobile phase: from 28% MeCN (0.05% ammonia) in water to 48% MeCN (0.05% ammonia) in water; wavelength: 220 nm; workup: lyophilization], affording isomer A (Example 87, 15.67 mg, 16% yield) and isomer B (Example 88, 13.35 mg, 13% yield) as white solids. The absolute stereochemistry was not determined for either isomer.

Example 87: 5,8-dichloro-2-[(4-methoxy-6-methyl-2-oxo-1,2-dihydropyridin-3-yl)methyl]-7-[1-(1-methylazetidin-3-yl)ethyl]-3,4-dihydroisoquinolin-1(2H)-one—Isomer A $^1$H NMR (400 MHz, CD3OD) δ 7.44 (s, 1H), 6.27 (s, 1H), 4.73 (s, 2H), 3.91 (m, 3H), 3.77-3.68 (m, 2H), 3.41-3.37 (m, 3H), 3.16 (t, J=7.4 Hz, 1H), 2.95-2.92 (m, 2H), 2.90-2.83 (m, 2H), 2.39 (s, 3H), 2.34 (s, 3H), 1.16 (d, J=6.4 Hz, 3H). MS: 464 [M+H]$^+$. Chiral analysis: 99% ee; retention time 5.511 min on Chiralpak AD-3 150×4.6 mm I.D., 3 um column [mobile phase: A: CO2 B: ethanol (0.05% DEA); gradient: from 5% to 40% of B in 5.0 min and hold 40% for 2.5 min, then 5% of B for 2.5 min; wavelength: 220 nm].

Example 88: 5,8-dichloro-2-[(4-methoxy-6-methyl-2-oxo-1,2-dihydropyridin-3-yl)methyl]-7-[1-(1-methylazetidin-3-yl)ethyl]-3,4-dihydroisoquinolin-1(2H)-one—Isomer B $^1$H NMR (400 MHz, CD3OD) δ 7.43 (s, 1H), 6.26 (s, 1H), 4.73 (s, 2H), 3.91 (m, 3H), 3.77-3.68 (m, 2H), 3.41-3.37 (m, 3H), 3.12 (brs, 1H), 2.95-2.92 (m, 2H), 2.90-2.83 (m, 2H), 2.36 (s, 3H), 2.33 (s, 3H), 1.16 (d, J=6.4 Hz, 3H). MS: 464 [M+H]$^+$. Chiral analysis: 100% ee; retention time 5.997 min on Chiralpak AD-3 150×4.6 mm I.D., 3 um column [mobile phase: A: CO2 B: ethanol (0.05% DEA); gradient: from 5% to 40% of B in 5.0 min and hold 40% for 2.5 min, then 5% of B for 2.5 min; wavelength: 220 nm].

Method K

Example 89: (±)-5,8-dichloro-2-[(4,6-dimethyl-2-oxo-1,2-dihydropyridin-3-yl)methyl]-7-[1-(morpholin-4-yl)ethyl]-3,4-dihydroisoquinolin-1(2H)-one Example 90: (+)-5,8-dichloro-2-[(4,6-dimethyl-2-oxo-1,2-dihydropyridin-3-yl)methyl]-7-[1-(morpholin-4-yl)ethyl]-3,4-dihydroisoquinolin-1(2H)-one Example 91: (−)-5,8-dichloro-2-[(4,6-dimethyl-2-oxo-1,2-dihydropyridin-3-yl)methyl]-7-[1-(morpholin-4-yl)ethyl]-3,4-dihydroisoquinolin-1(2H)-one

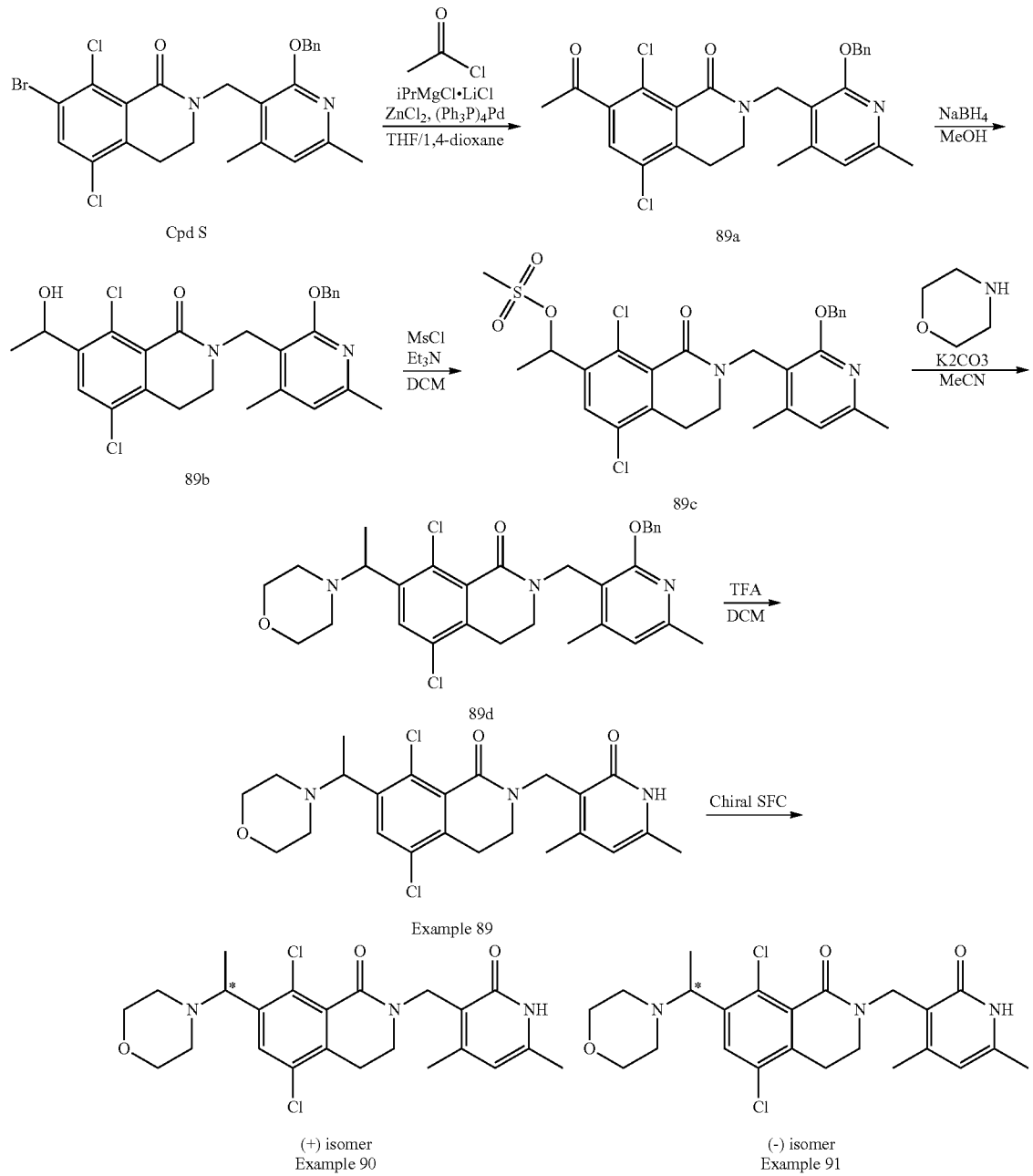

To a cooled (−40° C.) solution of 2-{[2-(benzyloxy)-4,6-dimethylpyridin-3-yl]methyl}-7-bromo-5,8-dichloro-3,4-dihydroisoquinolin-1(2H)-one (Cpd S, 5.00 g, 9.61 mmol) in anhydrous THF (50 mL) and 1,4-dioxane (5 mL) was added isopropylmagnesium chloride-lithium chloride complex (1.3 M solution in THF, 22.2 mL, 28.8 mmol) via syringe. After stirring at −40° C. for 30 minutes, zinc chloride (1.0 M solution in ether, 11.5 mL, 11.5 mmol) was added. Stirring was continued at −40° C. for 30 minutes, then tetrakis(triphenylphosphine)palladium(0) (1.11 g, 0.961 mmol) and acetyl chloride (1.51 g, 19.2 mmol) were added. The mixture was stirred and allowed to warm to room temperature over 18 hours. The reaction was quenched with sat. aq. NH4Cl (5 mL), diluted with ethyl acetate (30 mL), and washed with sat. aq. NH4Cl (40 mL) and brine (40 mL). The organic layer was dried over sodium sulfate, filtered, concentrated, and purified by silica gel chromatography (eluting with 0-30% ethyl acetate in petroleum ether) to give 7-acetyl-2-((2-(benzyloxy)-4,6-dimethylpyridin-3-yl)methyl)-5,8-dichloro-3,4-dihydroisoquinolin-1(2H)-one (89a, 4.00 g, 78% yield) as a yellow solid. $^1$H NMR (400 MHz, CDCl3) δ 7.45 (d, J=6.8 Hz, 2H), 7.39 (s, 1H), 7.38-7.27 (m, 3H), 6.63 (s, 1H), 5.43 (s, 2H), 4.86 (s, 2H), 3.29 (t, J=6.3 Hz, 2H), 2.75 (t, J=6.3 Hz, 2H), 2.63 (s, 3H), 2.42 (s, 3H), 2.34 (s, 3H). MS: 483 [M+H]+.

Sodium borohydride (47.0 mg, 1.24 mmol) was added to a room temperature solution of 7-acetyl-2-((2-(benzyloxy)-4,6-dimethylpyridin-3-yl)methyl)-5,8-dichloro-3,4-dihydroisoquinolin-1(2H)-one (89a, 200 mg, 0.414 mmol) in methanol (5 mL). After stirring at room temperature for 30 minutes, the reaction mixture was concentrated and purified by silica gel chromatography (eluting with 0-30% ethyl acetate in petroleum ether) to give 2-((2-(benzyloxy)-4,6-dimethylpyridin-3-yl)methyl)-5,8-dichloro-7-(1-hydroxyethyl)-3,4-dihydroisoquinolin-1 (2H)-one (89b, 190 mg, 95% yield) as a white solid.

A cooled (0° C.) solution of 2-((2-(benzyloxy)-4,6-dimethylpyridin-3-yl)methyl)-5,8-dichloro-7-(1-hydroxyethyl)-3,4-dihydroisoquinolin-1(2H)-one (89b, 190 mg, 0.391 mmol) and triethylamine (119 mg, 1.17 mmol) in dichloromethane (5 mL) was treated with methanesulfonyl chloride (67.3 mg, 0.587 mmol), then stirred at 0° C. for one hour. The reaction mixture was diluted with dichloromethane (30 mL); washed sequentially with sat. aq. NH4Cl, sat. aq. NaHCO3, and sat. aq. NaCl; dried over sodium sulfate, and concentrated to dryness, leaving crude racemic 1-(2-((2-(benzyloxy)-4,6-dimethylpyridin-3-yl)methyl)-5,8-dichloro-1-oxo-1,2,3,4-tetrahydroisoquinolin-7-yl)ethyl methanesulfonate (89c, 225 mg, 100% yield) as a white solid, which was used immediately without further purification.

A suspension of 1-(2-((2-(benzyloxy)-4,6-dimethylpyridin-3-yl)methyl)-5,8-dichloro-1-oxo-1,2,3,4-tetrahydroisoquinolin-7-yl)ethyl methanesulfonate (89c, 100 mg, 0.177 mmol), morpholine (46.4 mg, 0.532 mmol), and potassium carbonate (73.6 mg, 0.532 mmol) in acetonitrile (5 mL) was stirred at reflux (85° C.) for 2 hours. After cooling to room temperature, the suspension was filtered to remove solids. The filtrate was concentrated and purified by silica gel chromatography (eluting with 0-30% ethyl acetate in petroleum ether) to give racemic 2-((2-(benzyloxy)-4,6-dimethylpyridin-3-yl)methyl)-5,8-dichloro-7-(1-morpholinoethyl)-3,4-dihydroisoquinolin-1(2H)-one (89d, 90 mg, 91% yield, 80% pure by LCMS) as a gum. MS: 576 [M+Na]+.

A solution of racemic 2-((2-(benzyloxy)-4,6-dimethylpyridin-3-yl)methyl)-5,8-dichloro-7-(1-morpholinoethyl)-3,4-dihydroisoquinolin-1(2H)-one (89d, 90 mg, 0.16 mmol) in dichloromethane (5 mL) and trifluoroacetic acid (2 mL) was stirred at room temperature for 19 hours. The solution was evaporated to dryness, and then the residue was dissolved in toluene (10 mL) and basified to pH 8-9 by adding a few drops of conc. NH4OH. The solution was concentrated and purified by preparative HPLC to give (±)-5,8-dichloro-2-[(4,6-dimethyl-2-oxo-1,2-dihydropyridin-3-yl)methyl]-7-[1-(morpholin-4-yl)ethyl]-3,4-dihydroisoquinolin-1(2H)-one (Example 89, 29.49 mg, 39% yield) as a white solid. 1H NMR (400 MHz, CDCl3) δ 7.74 (s, 1H), 5.94 (s, 1H), 4.87-4.70 (m, 2H), 4.00 (q, J=6.3 Hz, 1H), 3.76-3.59 (m, 6H), 2.99-2.81 (m, 2H), 2.53 (br. s., 2H), 2.36 (m, 5H), 2.29 (s, 3H), 1.24 (d, J=6.5 Hz, 3H). MS: 464 [M+H]+.

The racemic material (Example 89) was further purified by chiral SFC separation conditions to provide the compounds of Example 90 and Example 91.

Additional compounds of the invention were prepared by modifications of the methods exemplified herein. Selected compounds prepared and corresponding characterization data are presented in Table 1 below.

TABLE 1

| Ex. No. | Structure/IUPAC name | Method | 1H NMR (ppm); LCMs [M + H]+ | Stereochemistry Note |
|---|---|---|---|---|
| 1 | 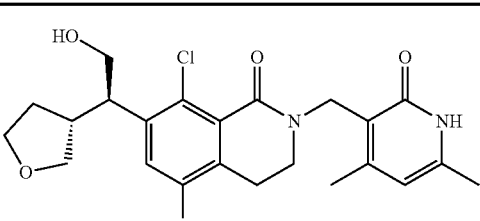<br>5,8-dichloro-2-[4,6-dimethyl-2-oxo-1,2-dihydropyridin-3-yl)methyl]-7-{(1R)-2-hydroxy-1-[(3R)-tetrahydrofuran-3-yl]ethyl}-3,4-dihydroisoquinolin-1(2H)-one | A | 1H NMR (400 MHz, CD3OD) δ 7.63 (s, 1H), 6.12 (s, 1H), 4.77 (s, 2H), 3.94-3.90 (m, 1H), 3.81-3.80 (m, 3H), 3.59-3.57 (m, 2H), 3.51-3.49 (m, 2H), 3.17-3.10 (m, 1H), 2.98-2.95 (m, 2H), 2.71 (br s, 1H), 2.30 (s, 3H), 2.29-2.25 (m, 1H), 2.25 (s, 3H), 1.83-1.78 (m, 1H); LCMs [M + H]+ 465 | R,R isomer; stereochemistry determined from x-ray crystal structure of enantiomeric compound (Ex. 4); Chiral purity: 95.66%; retention time: 6.867 min; column: Chiralpak AD-3 150 × 4.6 mm I.D., 3 um; mobile phase: 5-40% ethanol (0.05% DEA) in CO2; flow rate: 2.5 mL/min |
| 2 | 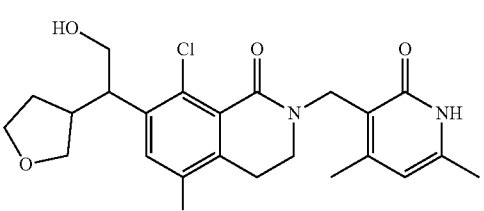<br>5,8-dichloro-2-[(4,6-dimethyl-2-oxo-1,2-dihydropyridin-3-yl)methyl]-7-{(1R*)-2-hydroxy-1-[(3S*)-tetrahydrofuran-3-yl]ethyl}-3,4-dihydroisoquinolin-1(2H)-one | A | 1H NMR (400 MHz, CD3OD) δ 7.62 (s, 1H), 6.11 (s, 1H), 4.76 (s, 2H), 4.13-4.11 (m, 1H), 3.78-3.75 (m, 1H), 3.69-3.68 (m, 2H), 3.61-3.59 (m, 3H), 3.51-3.50 (m, 2H), 2.98-2.95 (m, 2H), 2.65 (br s, 1H), 2.30 (s, 3H), 2.25 (s, 3H), 1.77-1.75 (m, 1H), 1.42-1.37 (m, 1H); LCMs [M + H]+ 465 | Single enantiomer, either R,S or S,R but absolute stereochemistry unknown; Enantiomer of Ex. 3; Chiral purity: 98.70%; retention time: 7.309 min; column: Chiralpak AD-3 150 × 4.6 mm I.D., 3 um; mobile phase: 5-40% ethanol (0.05% DEA) in CO2; flow rate: 2.5 mL/min |

TABLE 1-continued

| Ex. No. | Structure/IUPAC name | Method | ¹H NMR (ppm); LCMs [M + H]⁺ | Stereochemistry Note |
|---|---|---|---|---|
| 3 | 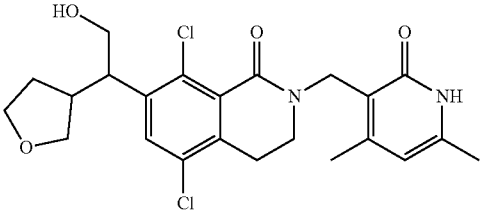<br>5,8-dichloro-2-[(4,6-dimethyl-2-oxo-1,2-dihydropyridin-3-yl)methyl]-7-{(1S*)-2-hydroxy-1-[(3R*)-tetrahydrofuran-3-yl]ethyl}-3,4-dihydroisoquinolin-1(2H)-on | A | ¹H NMR (400 MHz, CD3OD) δ 7.62 (s, 1H), 6.11 (s, 1H), 4.76 (s, 2H), 4.12-4.11 (m, 1H), 3.80-3.78 (m, 1H), 3.69-3.67 (m, 3H), 3.67-3.62 (m, 2H), 3.61-3.50 (m, 2H), 2.98-2.95 (m, 2H), 2.65 (br s, 1H), 2.29 (s, 3H), 2.25 (s, 3H), 1.77-1.74 (m, 1H), 1.42-1.37 (m, 1H); LCMs [M + H]⁺ 465 | Single enantiomer, either S,R or R,S isomer but absolute stereochemistry unknown; Enantiomer of Ex. 2 Chiral purity: 96.48%; retention time: 8.021 min; column: Chiralpak AD-3 150 × 4.6 mm I.D., 3 um; mobile phase: 5-40% ethanol (0.05% DEA) in CO2; flow rate 2.5 mL/min |
| 4 | 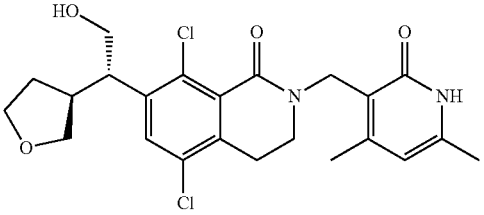<br>5,8-dichloro-2-[(4,6-dimethyl-2-oxo-1,2-dihydropyridin-3-yl)methyl]-7-{(1S)-2-hydroxy-1-[(3S)-tetrahydrofuran-3-yl]ethyl}-3,4-dihydroisoquinolin-1(2H)-one | A | ¹H NMR (400 MHz, CD3OD) δ 7.64 (s, 1H), 6.13 (s, 1H), 4.78 (s, 2H), 3.95-3.90 (m, 1H), 3.83-3.81 (m, 3H), 3.60-3.55 (m, 2H), 3.55-3.52 (m, 2H), 3.32-3.19, (m, 1H), 2.99-2.96 (m, 2H), 2.75 (br s, 1H), 2.32 (s, 3H), 2.31-2.29 (m, 1H), 2.27 (s, 3H), 1.84-1.79 (m, 1H); LCMs [M + H]⁺ 465 | Known to be S,S by X-ray crystal structure; Enantiomer of Ex. 1; Chiral purity: 99.18%; retention time: 8.429 min; column: Chiralpak AD-3 150 × 4.6 mm I.D., 3 um; mobile phase: 5-40% ethanol (0.05% DEA) in CO2; flow rate 2.5 mL/min |
| 5 | 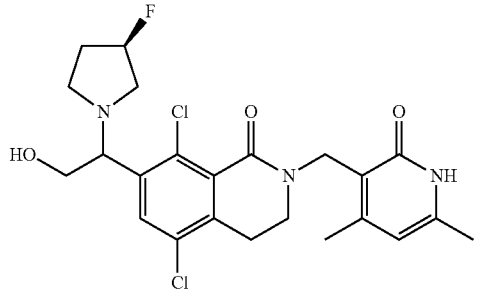<br>5,8-dichloro-2-[(4,6-dimethyl-2-oxo-1,2-dihydropyridin-3-yl)methyl]-7-{1-[(3R)-3-fluoropyrrolidin-1-yl]-2-hydroxyethyl}-3,4-dihydroisoquinolin-1(2H)-one | B | ¹H NMR (400 MHz, DMSO-d6) δ 11.66 (br. s., 1H), 7.80 (d, J = 3.67 Hz, 1H), 6.00 (s, 1H), 5.15-5.43 (m, 1H), 4.85 (br. s., 1H), 4.69 (s, 2H), 4.03-4.13 (m, 1H), 3.66-3.84 (m, 2H), 3.50-3.63 (m, 2H), 3.02-3.10 (m, 1H), 2.94-3.02 (m, 2H), 2.71-2.90 (m, 2H), 2.42-2.55 (m, 1H), 2.28 (s, 3H), 2.24 (s, 3H), 2.09-2.23 (m, 1H), 1.87-2.08 (m, 1H); LCMs [M + H]⁺ 482 | Mixture of diastereomers containing (R)-3-fluoropyrrolidine Mixture separated to Ex. 6 and Ex. 7 |
| 6 | 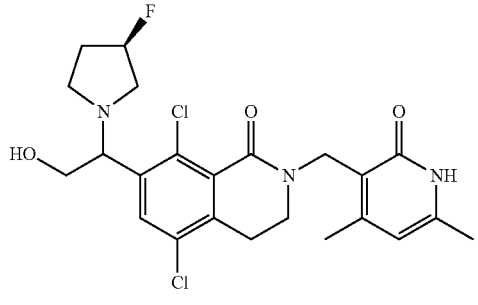<br>5,8-dichloro-2-[(4,6-dimethyl-2-oxo-1,2-dihydropyridin-3-yl)methyl]-7-{(1ε)-1-[(3R)-3-fluoropyrrolidin-1-yl]-2-hydroxyethyl}-3,4-dihydroisoquinolin-1(2H)-one - Isomer A | B | HNMR was not taken due to limited quantity. See Ex. 5; LCMs [M + H]⁺ 482 | One component of the Ex. 5 mixture. Single diastereomer, containing (R)-3-fluoropyrrolidine, other chiral center undetermined; >99% de (−), [α]D = −51.3° (c 0.01 MeOH) 1st peak; RT 1.18 min Chiralcel OJ-3 4.6 × 100 mm 3u column; 10% MeOH/DEA @ 120 bar, 4 mL/min |

TABLE 1-continued

| Ex. No. | Structure/IUPAC name | Method | ¹H NMR (ppm); LCMs [M + H]⁺ | Stereochemistry Note |
|---|---|---|---|---|
| 7 | 5,8-dichloro-2-[(4,6-dimethyl-2-oxo-1,2-dihydropyridin-3-yl)methyl]-7-{(1ε)-1-[(3R)-3-fluoropyrrolidin-1-yl]-2-hydroxyethyl}-3,4-dihydroisoquinolin-1(2H)-one - Isomer B | B | HNMR was not taken due to limited quantity. See Ex. 5; LCMs [M + H]⁺ 482 | One component of the Ex. 5 mixture; single diasteromer containing (R)-3-fluoropyrrolidine, other chiral center undetermined; ~88% de (+) [α]D = +62.1° (c 0.01 MeOH) 2nd peak; RT 1.42 min Chiralcel OJ-3 4.6 × 100 mm 3u column; 10% MeOH/DEA @ 120 bar, 4 mL/min; |
| 8 | (+)-5,8-dichloro-2-[(4,6-dimethyl-2-oxo-1,2-dihydropyridin-3-yl)-methyl]-7-{fluoro[1-(hydroxyacetyl)piperidin-4-yl]methyl}-3,4-dihydroisoquinolin-1(2H)-one | C | ¹H NMR (600 MHz, DMSO-d6) δ ppm 11.55 (s, 1 H), 7.58 (d, J = 4.95 Hz, 1 H), 5.88 (s, 1 H), 5.72-5.84 (m, 1 H), 4.55 (q, J = 13.75 Hz, 2 H), 4.46 (br. s., 1 H), 4.30-4.42 (m, 1 H), 4.05-4.13 (m, 1 H), 3.97-4.04 (m, 1 H), 3.69 (t, J = 13.39 Hz, 1 H), 3.45 (t, J = 5.78 Hz, 2 H), 2.80-2.98 (m, 3 H), 2.20 (d, J = 18.71 Hz, 1 H), 2.11 (s, 3 H), 1.61 (br. s., 1 H), 1.46 (br. s., 1 H), 1.34-1.42 (m, 1 H), 1.23 (s, 5 H); LCMs [M + H]⁺ 524 | >99% ee (+), [α]D = +9.9° (c 0.1 DMSO) First peak off column: Lux Cellulose-2 4.6 × 100 mm 3u column 60% MeOH @ 120 bar, 4 mL/min Peak 1 @ 8.13 min (prep: OJ-H, 21 × 250 mm column, 32 mL MeOH: 8 mL CO2, 100 bar, 40 mL/min) |
| 9 | (−)-5,8-dichloro-2-[(4,6-dimethyl-2-oxo-1,2-dihydropyridin-3-yl)-methyl]-7-{fluoro[1-(hydroxyacetyl)piperidin-4-yl]methyl}-3,4-dihydroisoquinolin-1(2H)-one | C | ¹H NMR (600 MHz, DMSO-d6) δ ppm 11.55 (s, 1 H), 7.58 (d, J = 4.95 Hz, 1 H), 5.88 (s, 1 H), 5.72-5.84 (m, 1 H), 4.55 (q, J = 13.75 Hz, 2 H), 4.46 (br. s., 1 H), 4.30-4.42 (m, 1 H), 4.05-4.13 (m, 1 H), 3.97-4.04 (m, 1 H), 3.69 (t, J = 13.39 Hz, 1 H), 3.45 (t, J = 5.78 Hz, 2 H), 2.80-2.98 (m, 3 H), 2.20 (d, J = 18.71 Hz, 1 H), 2.11 (s, 3 H), 1.61 (br. s., 1 H), 1.46 (br. s., 1 H), 1.34-1.42 (m, 1 H), 1.23 (s, 5 H); LCMs [M + H]⁺ 524 | ~95% ee (−), [α]D = −6.5° (c 0.1 DMSO) Second peak off column: Lux Cellulose-2 4.6 × 100 mm 3u column 60% MeOH @ 120 bar, 4 mL/min Peak 2 @ 10.29 min (prep: OJ-H, 21 × 250 mm column, 32 mL MeOH: 8 mL CO2, 100 bar, 40 mL/min) |
| 10 | 5,8-dichloro-2-[(4,6-dimethyl-2-oxo-1,2-dihydropyridin-3-yl)methyl]-7-(2-hydroxy-1-methoxyethyl)-3,4-dihydroisoquinolin-1(2H)-one - Isomer A | D | ¹H NMR (400 MHz, CDCl3) δ 12.23 (br. s., 1H), 7.53 (s, 1H), 5.95 (s, 1H), 4.92-4.89 (m, 1H), 4.78 (s, 2H), 3.80-3.71 (m, 1H), 3.68-3.62 (m, 2H), 3.53-3.51 (m, 1H), 3.33 (s, 3H), 2.94 (t, J = 6.0 Hz, 2H), 2.35 (s, 3H), 2.29 (s, 3H); LCMs [M + H]⁺ 425 | Single isomer, absolute stereochemistry unknown; Enantiomer of Ex. 11; 100% ee; retention time 7.717 min; column: Chiralpak IC-3 150 × 4.6 mm I.D., 3 um; mobile phase: 40% ethanol (0.05% DEA) in CO2; flow rate: 2.35 mL/min |

TABLE 1-continued

| Ex. No. | Structure/IUPAC name | Method | $^1$H NMR (ppm); LCMs [M + H]$^+$ | Stereochemistry Note |
|---|---|---|---|---|
| 11 | 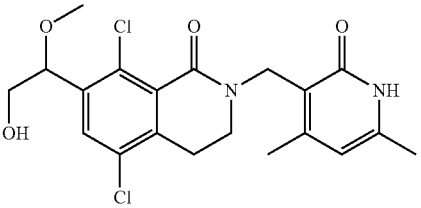<br>5,8-dichloro-2-[(4,6-dimethyl-2-oxo-1,2-dihydropyridin-3-yl)methyl]-7-(2-hydroxy-1-methoxyethyl)-3,4-dihydroisoquinolin-1(2H)-one - Isomer B | D | $^1$H NMR (400 MHz, CDCl3) δ 12.15 (br. s., 1H), 7.53 (s, 1H), 5.95 (s, 1H), 4.92-4.89 (m, 1H), 4.78 (s, 2H), 3.80-3.71 (m, 1H), 3.68-3.63 (m, 2H), 3.55-3.51 (m, 1H), 3.34 (s, 3H), 2.94 (t, J = 5.6 Hz, 2H), 2.35 (s, 3H), 2.29 (s, 3H); LCMs [M + H]$^+$ 425 | Single isomer, absolute stereochemistry unknown; Enantiomer of Ex. 10; 100% ee;: retention time 11.063 min; column: Chiralpak IC-3 150 × 4.6 mm I.D., 3 um; mobile phase: 40% ethanol (0.05% DEA) in CO2; flow rate: 2.35 mL/min |
| 12 | 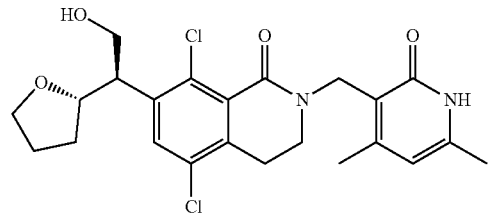<br>5,8-dichloro-2-[(4,6-dimethyl-2-oxo-1,2-dihydropyridin-3-yl)methyl]-7-{(1R)-2-hydroxy-1-[(2S)-tetrahydrofuran-2-yl]ethyl}-3,4-dihydroisoquinolin-1(2H)-one | E | $^1$H NMR (400 MHz, CD3OD) δ 7.58 (s, 1H), 6.11 (s, 1H), 4.76 (s, 2H), 4.10-4.21 (m, 1H), 3.86-3.99 (m, 3H), 3.75-3.84 (m, 1H), 3.64-3.72 (m, 1H), 3.46-3.55 (m, 2H), 2.91-3.01 (m, 2H), 2.29 (s, 3H), 2.25 (s, 3H), 1.73-1.97 (m, 3H), 1.44-1.58 (m, 1H); LCMs [M + H]$^+$ 465 | Single enantiomer: (R) at benzylic carbon and (S) at THF 91% ee 1st peak; RT 2.91 min Chiralpak AD-3 4.6 × 100 mm 3u column; 5-60% MeOH in 3 minutes, 120 bar, 4 mL/min |
| 13 | 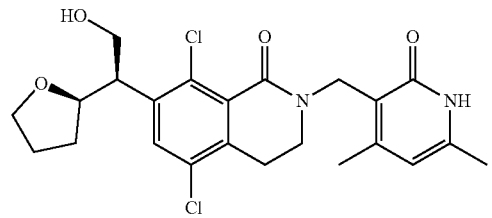<br>5,8-dichloro-2-[(4,6-dimethyl-2-oxo-1,2-dihydropyridin-3-yl)methyl]-7-{(1R)-2-hydroxy-1-[(2R)-tetrahydrofuran-2-yl]ethyl}-3,4-dihydroisoquinolin-1(2H)-one | E | $^1$H NMR (400 MHz, CD3OD) δ 7.66 (s, 1H), 6.10 (s, 1H), 4.77 (s, 2H), 4.27 (dt, J = 7.86, 6.16 Hz, 1H), 3.72-3.91 (m, 3H), 3.67 (t, J = 6.79 Hz, 2H), 3.49 (t, J = 6.24 Hz, 2H), 2.95 (t, J = 6.17 Hz, 2H), 2.28 (s, 3H), 2.24 (s, 3H), 2.01-2.13 (m, 1H), 1.68-1.92 (m, 2H), 1.49-1.62 (m, 1H); LCMs [M + H]$^+$ 465 | Single enantiomer (R,R); 93% ee 2nd Peak; RT 3.21 min Chiralpak AD-3 4.6 × 100 mm 3u column; 5-60% MeOH in 3 minutes, 120 bar, 4 mL/min |
| 14 | 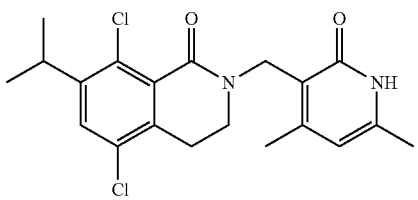<br>5,8-dichloro-2-[(4,6-dimethyl-2-oxo-1,2-dihydropyridin-3-yl)methyl]-7-(propan-2-yl)-3,4-dihydroisoquinolin-1(2H)-one | F | $^1$H NMR (400 MHz, CDCl3) δ 7.35 (s, 1H), 5.90 (s, 1H), 4.78 (s, 2H), 3.63 (t, J = 6.30 Hz, 2H), 3.5-3.6 (m, 1H), 2.90 (t, J = 6.11 Hz, 2H), 2.35 (s, 3H), 2.24 (s, 3H), 1.24 (d, J = 6.85 Hz, 6H); LCMs [M + H]$^+$ 393 | N/A |
| 15 | 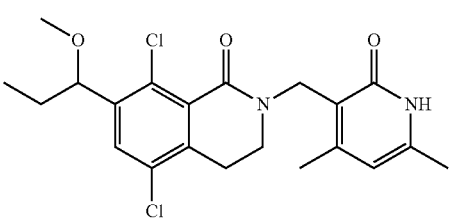<br>5,8-dichloro-2-[(4,6-dimethyl-2-oxo-1,2-dihydropyridin-3-yl)methyl]-7-(1-methoxypropyl)-3,4-dihydroisoquinolin-1(2H)-one - Isomer A | G | $^1$H NMR (400 MHz, CDCl3) δ 11.88 (br. s., 1H), 7.53 (s, 1H), 5.94 (s, 1H), 4.78 (s, 2H), 4.69-4.66 (m, 1H), 3.65 (t, J = 4.8 Hz, 2H), 3.24 (s, 3H), 2.93 (t, J = 6.2 Hz, 2H), 2.36 (s, 3H), 2.29 (s, 3H), 1.76-1.72 (m, 1H), 1.65-1.60 (m, 1H), 0.96 (t, J = 7.0 Hz, 3H); LCMs [M + H]$^+$ 423 | Single isomer, absolute stereochemistry unknown; Enantiomer of Ex. 16; 100% Chiral Purity; 1st peak, RT 8.04 min; column: Chiralpak AD-H 250 × 4.6 mm I.D., 5 um; mobile phase: 5-40% methanol (0.05% DEA) in CO2; flow rate: 2.5 mL/min |

TABLE 1-continued

| Ex. No. | Structure/IUPAC name | Method | ¹H NMR (ppm); LCMs [M + H]⁺ | Stereochemistry Note |
|---|---|---|---|---|
| 16 | 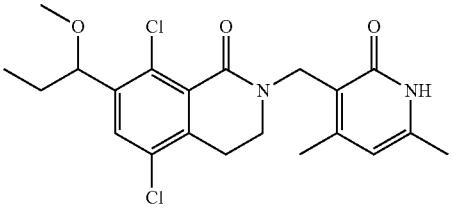<br>5,8-dichloro-2-[(4,6-dimethyl-2-oxo-1,2-dihydropyridin-3-yl)methyl]-7-(1-methoxypropyl)-3,4-dihydroisoquinolin-1(2H)-one - Isomer B | G | ¹H NMR (400 MHz, CDCl3) δ 10.88 (br s, 1H), 7.53 (s, 1H), 5.93 (s, 1H), 4.77 (s, 2H), 4.69-4.66 (m, 1H), 3.67-3.63 (m, 2H), 3.24 (s, 3H), 2.93 (t, J = 5.8 Hz, 2H), 2.36 (s, 3H), 2.28 (s, 3H), 1.78-1.73 (m, 1H), 1.65-1.58 (m, 1H), 0.96 (t, J = 7.2 Hz, 3H); LCMs [M + H]⁺ 423 | Single isomer, absolute stereochemistry unknown; Enantiomer of Ex. 15; 99.6194% Chiral Purity; 2nd peak, RT 8.34 min; column: Chiralpak AD-H 250 × 4.6 mm I.D., 5 um; mobile phase: 5-40% methanol (0.05% DEA) in CO2; flow rate: 2.5 mL/min |
| 17 | 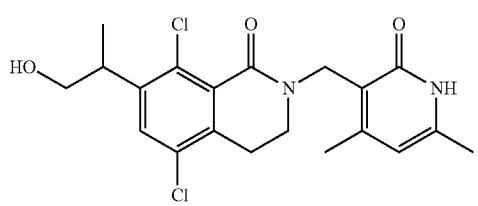<br>(±)-5,8-dichloro-2-[(4,6-dimethyl-2-oxo-1,2-dihydropyridin-3-yl)methyl]-7-(1-hydroxypropan-2-yl)-3,4-dihydroisoquinolin-1(2H)-one | A | ¹H NMR (400 MHz, CDCl3) δ 11.54 (s, 1H), 7.37 (s, 1H), 5.93 (s, 1H), 4.78 (s, 2H), 3.79-3.71 (m, 3H), 3.64-3.61 (m, 2H), 2.91 (t, J = 6 Hz, 2H), 2.34 (s, 3H), 2.28 (s, 3H), 1.43 (s, 1H), 1.27 (t, J = 6.4 Hz, 3H); LCMs [M + H]⁺ 409 | Racemic mixture |
| 18 | 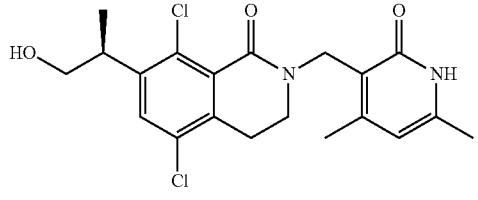<br>5,8-dichloro-2-[(4,6-dimethyl-2-oxo-1,2-dihydropyridin-3-yl)methyl]-7-[(2S)-1-hydroxypropan-2-yl]-3,4-dihydroisoquinolin-1(2H)-one | A | ¹H NMR (400 MHz, CDCl3) δ 11.54 (s, 1H), 7.37 (s, 1H), 5.93 (s, 1H), 4.78 (s, 2H), 3.79-3.71 (m, 3H), 3.64-3.61 (m, 2H), 2.91 (t, J = 6 Hz, 2H), 2.34 (s, 3H), 2.28 (s, 3H), 1.43 (s, 1H), 1.27 (t, J = 6.4 Hz, 3H); LCMs [M + H]⁺ 409 | Single isomer, known; (S) stereochemistry determined from x-ray crystal structure; 1st peak under the following SFC conditions: Chiralpak AS-H 4.6 × 100 mm 5u column; 20% MeOH @ 120 bar CO2, 4 mL/min |
| 19 | 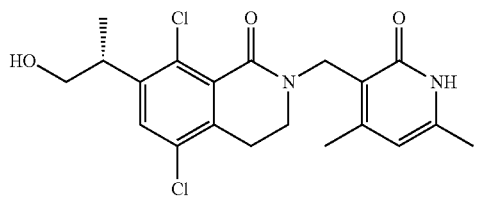<br>5,8-dichloro-2-[(4,6-dimethyl-2-oxo-1,2-dihydropyridin-3-yl)methyl]-7-[(2R)-1-hydroxypropan-2-yl]-3,4-dihydroisoquinolin-1(2H)-one | A | ¹H NMR (400 MHz, CDCl3) δ 11.54 (s, 1H), 7.37 (s, 1H), 5.93 (s, 1H), 4.78 (s, 2H), 3.79-3.71 (m, 3H), 3.64-3.61 (m, 2H), 2.91 (t, J = 6 Hz, 2H), 2.34 (s, 3H), 2.28 (s, 3H), 1.43 (s, 1H), 1.27 (t, J = 6.4 Hz, 3H); LCMs [M + H]⁺ 409 | Single isomer, known; (R) stereochemistry determined from x-ray crystal structure of enantiomeric compound (Ex. 18); 2nd peak under the following SFC conditions: Chiralpak AS-H 4.6 × 100 mm 5u column; 20% MeOH @ 120 bar CO2, 4 mL/min |
| 20 | 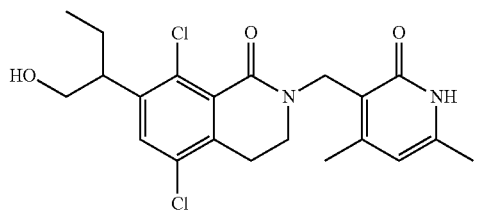<br>(±)-5,8-dichloro-2-[(4,6-dimethyl-2-oxo-1,2-dihydropyridin-3-yl)methyl]-7-(1-hydroxybutan-2-yl)-3,4-dihydroisoquinolin-1(2H)-one | A | ¹H NMR (400 MHz, CD3OD) δ 7.49 (s, 1H), 6.11 (s, 1H), 4.76 (s, 2H), 3.94 (s, 2H), 3.71-3.66 (m, 2H), 3.52-3.50 (m, 3H), 2.95 (t, J = 6.4 Hz, 2H), 2.29 (s, 3H), 2.25 (s, 3H), 1.90-1.82 (m, 1H), 1.65-1.55 (m, 1H), 0.85 (t, J = 7.6 Hz, 3H); LCMs [M + H]⁺ 423 | Racemic mixture |

TABLE 1-continued

| Ex. No. | Structure/IUPAC name | Method | ¹H NMR (ppm); LCMs [M + H]⁺ | Stereochemistry Note |
|---|---|---|---|---|
| 21 | 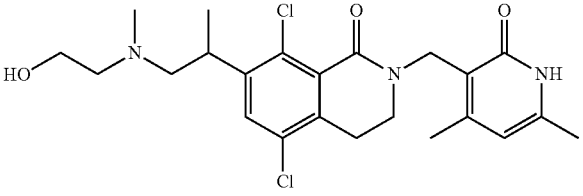<br>(±)-5,8-dichloro-2-[(4,6-dimethyl-2-oxo-1,2-dihydropyridin-3-yl)methyl]-7-{1-[(2-hydroxyethyl)(methyl)amino]propan-2-yl}-3,4-dihydroisoquinolin-1(2H)-one | A | ¹H NMR (400 MHz, CD3OD) δ 7.63 (s, 1H), 6.10 (s, 1H), 4.75 (s, 2H), 3.97 (sxt, J = 6.94 Hz, 1H), 3.79 (t, J = 5.38 Hz, 2H), 3.52 (t, J = 6.17 Hz, 2H), 3.33-3.40 (m, 1H), 3.00-3.19 (m, 3H), 2.92-3.00 (m, 2H), 2.72 (s, 3H), 2.30 (s, 3H), 2.25 (s, 3H), 1.33 (d, J = 6.85 Hz, 3H); LCMs [M + H]⁺ 466 | Racemic mixture |
| 22 | 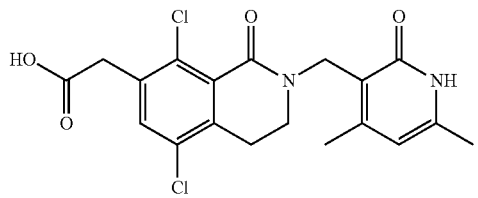<br>{5,8-dichloro-2-[(4,6-dimethyl-2-oxo-1,2-dihydropyridin-3-yl)methyl]-1-oxo-1,2,3,4-tetrahydroisoquinolin-7-yl}-acetic acid | A | ¹H NMR (400 MHz, DMSO-d6) δ 12.50 (br. s., 1H), 11.54 (br. s., 1H), 7.66 (s, 1H), 5.88 (s, 1H), 4.57 (s, 2H), 3.77 (s, 2H), 3.45 (t, J = 5.50 Hz, 2H), 2.88 (t, J = 5.07 Hz, 2H), 2.16 (s, 3H), 2.12 (s, 3H); LCMs [M + H]⁺ 409 | N/A |
| 23 | 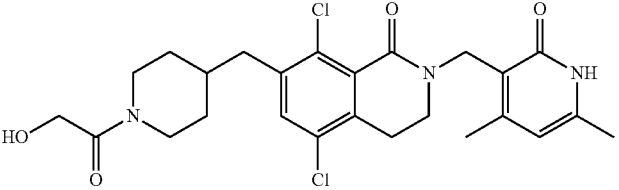<br>5,8-dichloro-2-[(4,6-dimethyl-2-oxo-1,2-dihydropyridin-3-yl)methyl]-7-{[1-(hydroxyacetyl)piperidin-4-yl]methyl}-3,4-dihydroisoquinolin-1(2H)-one | F | ¹H NMR (400 MHz, CD3OD) δ 7.48 (s, 1H), 6.12 (s, 1H), 4.77 (s, 2H), 4.50 (d, J = 13.57 Hz, 1H), 4.14-4.29 (m, 2H), 3.73 (d, J = 13.45 Hz, 1H), 3.48-3.56 (m, 2H), 2.92-3.03 (m, 3H), 2.79 (d, J = 7.09 Hz, 2H), 2.66 (t, J = 12.53 Hz, 1H), 2.31 (s, 3H), 2.26 (s, 3H), 1.93-2.06 (m, 1H), 1.70 (d, J = 13.57 Hz, 2H), 1.21-1.34 (m, 2H); LCMs [M + H]⁺ 506 | N/A |
| 24 | 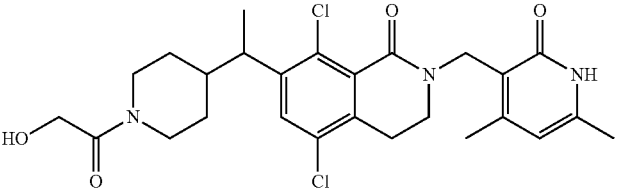<br>(±)-5,8-dichloro-2-[(4,6-dimethyl-2-oxo-1,2-dihydropyridin-3-yl)-methyl]-7-{1-[1-(hydroxyacetyl)piperidin-4-yl]ethyl}-3,4-dihydroisoquinolin-1(2H)-one | J | ¹H NMR (400 MHz, CD3OD) δ 7.40 (s, 1H), 6.01 (s, 1H), 4.66 (s, 2H), 4.27-4.49 (m, 1H), 4.00-4.18 (m, 2H), 3.49-3.73 (m, 1H), 3.41 (t, J = 6.24 Hz, 2H), 3.23-3.30 (m, 1H), 2.75-2.95 (m, 3H), 2.41-2.63 (m, 1H), 2.19 (s, 3H), 2.15 (s, 3H), 1.80-1.89 (m, 1H), 1.67-1.79 (m, 1H), 1.28-1.36 (m, 1H), 0.97-1.22 (m, 5H); LCMs [M + H]⁺ 520 | Racemic mixture |

TABLE 1-continued

| Ex. No. | Structure/IUPAC name | Method | ¹H NMR (ppm); LCMs [M + H]⁺ | Stereochemistry Note |
|---|---|---|---|---|
| 25 | (±)-5,8-dichloro-2-[(4,6-dimethyl-2-oxo-1,2-dihydro-pyridin-3-yl)methyl]-7-(1-hydroxypropyl)-3,4-dihydroisoquinolin-1(2H)-one | G | ¹H NMR (400 MHz, CDCl3) δ 13.22 (br. s., 1H), 7.41 (s, 1H), 6.01 (s, 1H), 5.13 (dd, J = 7.76, 3.36 Hz, 1H), 4.85 (d, J = 13.94 Hz, 1H), 4.53 (d, J = 13.94 Hz, 1H), 3.70 (dt, J = 12.50, 4.94 Hz, 1H), 3.41-3.53 (m, 1H), 2.79 (t, J = 5.99 Hz, 2H), 2.42 (s, 3H), 2.31 (s, 3H), 1.67-1.82 (m, 1H), 1.41-1.57 (m, 1H), 0.96 (t, J = 7.34 Hz, 3H); LCMs [M + H]⁺ 409 | Racemic mixture |
| 26 | (±)-5,8-dichloro-2-[(4,6-dimethyl-2-oxo-1,2-dihydropyridin-3-yl)methyl]-7-[(2S*3R*)-3-hydroxybutan-2-yl]-3,4-dihydroisoquinolin-1(2H)-one | A | ¹H NMR (400 MHz, CD3OD) δ 7.52 (s, 1H), 6.13 (s, 1H), 4.78 (s, 2H), 3.91-3.84 (m, 1H), 3.53-3.48 (m, 3H), 2.97 (t, J = 6.2 Hz, 2H), 2.31 (s, 3H), 2.27 (s, 3H), 1.29 (d, J = 7.2 Hz, 3H), 1.14 (d, J = 6.0 Hz, 3H); LCMs [M + H]⁺ 423 | Racemic mixture of (2R,3S) and (2S,3R) isomers separated enantiomers are Ex. 47 and Ex. 48 |
| 27 | (+)-5,8-dichloro-2-[(4,6-dimethyl-2-oxo-1,2-dihydropryridin-3-yl)methyl]-7-(1-hydroxy-propyl)-3,4-dihydroisoquinolin-1(2H)-one | G | ¹H NMR (400 MHz, CDCl3) δ 13.22 (br.s., 1H), 7.41 (s, 1H), 6.01 (s, 1H), 5.13 (dd, J = 7.76, 3.36 Hz, 1H), 4.85 (d, J = 13.94 Hz, 1H), 4.53 (d, J = 13.94 Hz, 1H), 3.70 (dt, J = 12.50, 4.94 Hz, 1H), 3.41-3.53 (m, 1H), 2.79 (t, J = 5.99 Hz, 2H), 2.42 (s, 3H), 2.31 (s, 3H), 1.67-1.82 (m, 1H), 1.41-1.57 (m, 1H), 0.96 (t, J = 7.34 Hz, 3H); LCMs [M + H]⁺ 409 | Single isomer, absolute stereochemistry unknown; Enantiomer of Ex. 28; [α]D = +48.8° (c 0.1 MeOH) >99% ee (+); RT 1.407 min; column: Chiralpak AS-3 4.6 × 100 mm 3u; 20% MeOH/DEA @ 120 bar CO2, 4 mL/min; |
| 28 | (−)-5,8-dichloro-2-[(4,6-dimethyl-2-oxo-1,2-dihydropyridin-3-yl)methyl]-7-(1-hydroxy-propyl)-3,4-dihydroisoquinolin-1(2H)-one | G | ¹H NMR (400 MHz, CDCl3) δ 13.22 (br. s., 1H), 7.41 (s, 1H), 6.01 (s, 1H), 5.13 (dd, J = 7.76, 3.36 Hz, 1H), 4.85 (d, J = 13.94 Hz, 1H), 4.53 (d, J = 13.94 Hz, 1H), 3.70 (dt, J = 12.50, 4.94 Hz, 1H), 3.41-3.53 (m, 1H), 2.79 (t, J = 5.99 Hz, 2H), 2.42 (s, 3H), 2.31 (s, 3H), 1.67-1.82 (m, 1H), 1.41-1.57 (m, 1H), 0.96 (t, J = 7.34 Hz, 3H); LCMs [M + H]⁺ 409 | Single isomer, absolute stereochemistry unknown; Enantiomer of Ex. 27; [α]D = −47.5° (c 0.1 MeOH) ~99% ee (−); RT 1.893 min; column: Chiralpak AS-3 4.6 × 100 mm 3u; 20% MeOH/DEA @ 120 bar CO2, 4 mL/min; |

TABLE 1-continued

| Ex. No. | Structure/IUPAC name | Method | ¹H NMR (ppm); LCMs [M + H]⁺ | Stereochemistry Note |
|---|---|---|---|---|
| 29 | 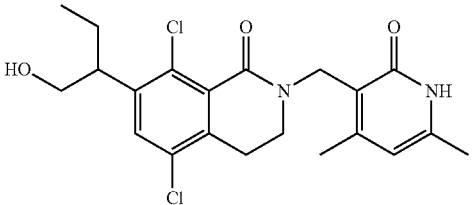<br>5,8-dichloro-2-[(4,6-dimethyl-2-oxo-1,2-dihydropyridin-3-yl)methyl]-7-(1-hydroxybutan-2-yl)-3,4-dihydroisoquinolin-1(2H)-one - Isomer A | A | ¹H NMR (400 MHz, CD3OD) δ 7.49 (s, 1H), 6.11 (s, 1H), 4.76 (s, 2H), 3.71-3.66 (m, 2H), 3.52-3.50 (m, 3H), 2.95 (t, J = 6.4 Hz, 2H), 2.29 (s, 3H), 2.25 (s, 3H), 1.90-1.82 (m, 1H), 1.65-1.55 (m, 1H), 0.85 (t, J = 7.6 Hz, 3H); LCMs [M + H]⁺ 423 | Single isomer, absolute stereochemistry unknown; Enantiomer of Ex. 30; 1st peak under the following SFC conditions: Chiralpak AD-3 4.6 × 100 mm 3u column; 30% MeOH @ 120 bar CO2, 4 mL/min |
| 30 | 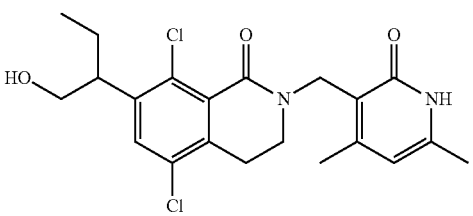<br>5,8-dichloro-2-[(4,6-dimethyl-2-oxo-1,2-dihydropyridin-3-yl)methyl]-7-(1-hydroxybutan-2-yl)-3,4-dihydroisoquinolin-1(2H)-one - Isomer B | A | ¹H NMR (400 MHz, CD3OD) δ 7.49 (s, 1H), 6.11 (s, 1H), 4.76 (s, 2H), 3.71-3.66 (m, 2H), 3.52-3.50 (m, 3H), 2.95 (t, J = 6.4 Hz, 2H), 2.29 (s, 3H), 2.25 (s, 3H), 1.90-1.82 (m, 1H), 1.65-1.55 (m, 1H), 0.85 (t, J = 7.6 Hz, 3H); LCMs [M + H]⁺ 423 | Single isomer, absolute stereochemistry unknown; Enantiomer of Ex. 29; 2nd peak under the following SFC conditions: Chiralpak AD-3 4.6 × 100 mm 3u column; 30% MeOH @ 120 bar CO, 4 mL/min |
| 31 | 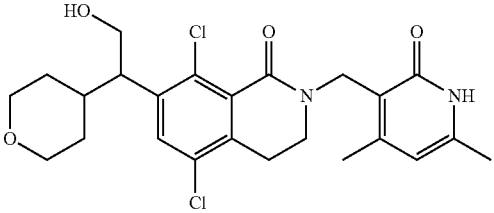<br>(±)-5,8-dichloro-2-[(4,6-dimethyl-2-oxo-1,2-dihydropyridin-3-yl)methyl]-7-[2-hydroxy-1-(tetrahydro-2H-pyran-4-yl)ethyl]-3,4-dihydroisoquinolin-1(2H)-one | A | ¹H NMR (400 MHz, CD3OD) δ 11.65 (bs, 1H), 7.43 (s, 1H), 5.95 (s, 1H), 4.77 (s, 2H), 4.04-3.87 (m, 4H), 3.68-3.40 (m, 3H), 3.31-3.30 (m, 2H), 2.92 (t, J = 6.4 Hz, 2H), 2.37 (s, 3H), 2.29 (s, 3H), 2.05-1.82 (m, 2H), 1.32-1.28 (m, 4H); LCMs [M + H]⁺ 479 | Racemic mixture |
| 32 | 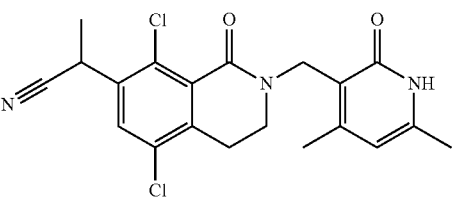<br>(±)-2-{5,8-dichloro-2-[(4,6-dimethyl-2-oxo-1,2-dihydropyridin-3-yl)methyl]-1-oxo-1,2,3,4-tetrahydroisoquinolin-7-yl}propanenitrile | G | ¹H NMR (400 MHz, DMSO-d6) δ 11.55 (br. s. 1H), 7.77 (s, 1H), 5.89 (s, 1H), 4.61-4.68 (m, 1H), 4.58 (s, 2H), 3.42-3.50 (m, 2H), 2.87-2.95 (m, 2H), 2.16 (s, 3H), 2.12 (s, 3H), 1.56-1.63 (m, 3H); LCMs [M + H]⁺ 404 | Racemic mixture |
| 33 | 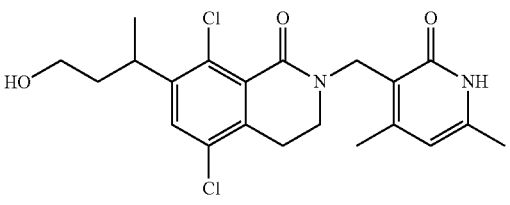<br>(±)-5,8-dichloro-2-[(4,6-dimethyl-2-oxo-1,2-dihydropyridin-3-yl)methyl]-7-(4-hydroxybutan-2-yl)-3,4-dihydroisoquinolin-1(2H)-one | A | ¹H NMR (400 MHz, DMSO-d6) δ 7.53 (s, 1H), 5.92 (s, 1H), 4.57 (s, 2H), 3.48-3.47 (m, 1H), 3.41 (t, J = 6.2 Hz, 2H), 3.34 (t, J = 6.6 Hz, 2H), 2.85 (t, J = 6.0 Hz, 2H), 2.16 (s, 3H), 2.13 (s, 3H), 1.78-1.68 (m, 2H), 1.15 (d, J = 6.8 Hz, 3H); LCMs [M + H]⁺ 423 | Racemic mixture |

TABLE 1-continued

| Ex. No. | Structure/IUPAC name | Method | ¹H NMR (ppm); LCMs [M + H]⁺ | Stereochemistry Note |
|---|---|---|---|---|
| 34 | (±)-5,8-dichloro-2-[(4,6-dimethyl-2-oxo-1,2-dihydropyridin-3-yl)methyl]-7-{[1-(hydroxyacetyl)piperidin-4-yl](methoxy)methyl}-3,4-dihydroisoquinolin-1(2H)-one | I | ¹H NMR (400 MHz, CD3OD) δ 7.44 (s, 1H), 6.01 (s, 1H), 4.66 (s, 2H), 4.56 (d, J = 5.62 Hz, 1H), 4.35-4.45 (m, 1H), 4.02-4.17 (m, 2H), 3.57-3.68 (m, 1H), 3.43 (t, J = 6.24 Hz, 2H), 3.10 (s, 3H), 2.86-2.92 (m, 2H), 2.75-2.85 (m, 1H), 2.40-2.54 (m, 1H), 2.20 (s, 3H), 2.15 (s, 3H), 1.78-1.87 (m, 1H), 1.60-1.69 (m, 1H), 1.18-1.47 (m, 3H); LCMs [M + H]⁺ 536 | Racemic mixture |
| 35 | 5,8-dichloro-2-[(4,6-dimethyl-2-oxo-1,2-dihydropyridin-3-yl)methyl]-7-{[1-(hydroxyacetyl)piperidin-4-yl](methoxy)methyl}-3,4-dihydroisoquinolin-1(2H)-one - Isomer B | I | NMR of Racemate, Ex. 34: ¹H NMR (400 MHz, CD3OD) δ 7.44 (s, 1H), 6.01 (s, 1H), 4.66 (s, 2H), 4.56 (d, J = 5.62 Hz, 1H), 4.35-4.45 (m, 1H), 4.02-4.17 (m, 2H), 3.57-3.68 (m, 1H), 3.43 (t, J = 6.24 Hz, 2H), 3.10 (s, 3H), 2.86-2.92 (m, 2H), 2.75-2.85 (m, 1H), 2.40-2.54 (m, 1H), 2.20 (s, 3H), 2.15 (s, 3H), 1.78-1.87 (m, 1H), 1.60-1.69 (m, 1H), 1.18-1.47 (m, 3H); LCMs [M + H]⁺ 536 | Single isomer, absolute stereochemistry unknown; Enantiomer of Ex. 36; ~97% ee; retention time 13.019 min; Lux Cellulose-4 4.6 × 100 mm 3u column; 50% MeOH @ 120 bar CO2, 4 mL/min |
| 36 | 5,8-dichloro-2-[(4,6-dimethyl-2-oxo-1,2-dihydropyridin-3-yl)methyl]-7-{[1-(hydroxyacetyl)piperidin-4-yl](methoxy)methyl}-3,4-dihydroisoquinolin-1(2H)-one - Isomer A | I | NMR of Racemate, Ex. 34: ¹H NMR (400 MHz, CD3OD) δ 7.44 (s, 1H), 6.01 (s, 1H), 4.66 (s, 2H), 4.56 (d, J = 5.62 Hz, 1H), 4.35-4.45 (m, 1H), 4.02-4.17 (m, 2H), 3.57-3.68 (m, 1H), 3.43 (t, J = 6.24 Hz, 2H), 3.10 (s, 3H), 2.86-2.92 (m, 2H), 2.75-2.85 (m, 1H), 2.40-2.54 (m, 1H), 2.20 (s, 3H), 2.15 (s, 3H), 1.78-1.87 (m, 1H), 1.60-1.69 (m, 1H), 1.18-1.47 (m, 3H); LCMs [M + H]⁺ 536 | Single isomer, absolute stereochemistry unknown; Enantiomer of Ex. 35; >99% ee; retention time 10.712 min; Lux Cellulose-4 4.6 × 100 mm 3u column; 50% MeOH @ 120 bar CO2, 4 mL/min |
| 37 | 5,8-dichloro-2-[(4,6-dimethyl-2-oxo-1,2-dihydropyridin-3-yl)methyl]-7-[2-hydroxy-1-(tetrahydro-2H-pyran-4-yl)ethyl]-3,4-dihydroisoquinolin-1(2H)-one - Isomer A | A | ¹H NMR (400 MHz, CD3OD) δ 11.65 (bs, 1H), 7.43 (s, 1H), 5.95 (s, 1H), 4.77 (s, 2H), 4.04-3.87 (m, 4H), 3.68-3.40 (m, 3H), 3.31-3.30 (m, 2H), 2.92 (t, J = 6.4 Hz, 2H), 2.37 (s, 3H), 2.29 (s, 3H), 2.05-1.82 (m, 2H), 1.32-1.28 (m, 4H); LCMs [M + H]⁺ 479 | Single isomer, absolute stereochemistry unknown; Enantiomer of Ex. 38; 1st peak under the following SFC conditions: Chiralpak AD-3 4.6 × 100 mm 3u column; 30% MeOH @ 120 bar CO2, 4 mL/min |

TABLE 1-continued

| Ex. No. | Structure/IUPAC name | Method | $^1$H NMR (ppm); LCMs [M + H]$^+$ | Stereochemistry Note |
|---|---|---|---|---|
| 38 | 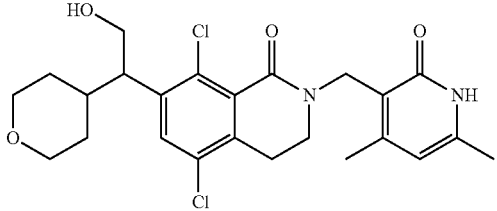<br>5,8-dichloro-2-[(4,6-dimethyl-2-oxo-1,2-dihydropyridin-3-yl)-methyl]-7-[2-hydroxy-1-(tetrahydro-2H-pyran-4-yl)-ethyl]-3,4-dihydroisoquinolin-1(2H)-one - Isomer B | A | $^1$H NMR (400 MHz, CD3OD) δ 11.65 (bs, 1H), 7.43 (s, 1H), 5.95 (s, 1H), 4.77 (s, 2H), 4.04-3.87 (m, 4H), 3.68-3.40 (m, 3H), 3.31-3.30 (m, 2H), 2.92 (t, J = 6.4 Hz, 2H), 2.37 (s, 3H), 2.29 (s, 3H), 2.05-1.82 (m, 2H), 1.32-1.28 (m, 4H); LCMs [M + H]$^+$ 479 | Single isomer, absolute stereochemistry unknown; Enantiomer of Ex. 37; 2nd peak under the following SFC conditions: Chiralpak AD-3 4.6 × 100 mm 3u column; 30% MeOH @ 120 bar CO2, 4 mL/min |
| 39 | 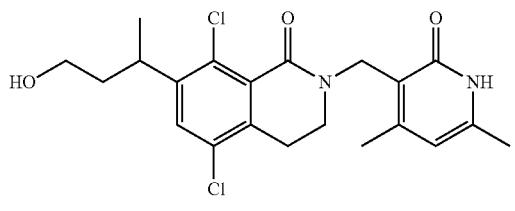<br>5,8-dichloro-2-[(4,6-dimethyl-2-oxo-1,2-dihydropyridin-3-yl)-methyl]-7-(4-hydroxybutan-2-yl)-3,4-dihydroisoquinolin-1(2H)-one - Isomer A | A | $^1$H NMR (400 MHz, DMSO-d6) δ 7.53 (s, 1H), 5.92 (s, 1H), 4.57 (s, 2H), 3.48-3.47 (m, 1H), 3.41 (t, J = 6.2 Hz, 2H), 3.34 (t, J = 6.6 Hz, 2H), 2.85 (t, J = 6.0 Hz, 2H), 2.16 (s, 3H), 2.13 (s, 3H), 1.78-1.68 (m, 2H), 1.15 (d, J = 6.8 Hz, 3H); LCMs [M + H]$^+$ 423 | Single enantiomer, absolute stereochemistry unknown; 1st peak under the following SFC conditions: Lux Cellulose-4 4.6 × 100 mm 3u column; 50% MeOH @ 120 bar, 4 mL/min |
| 40 | 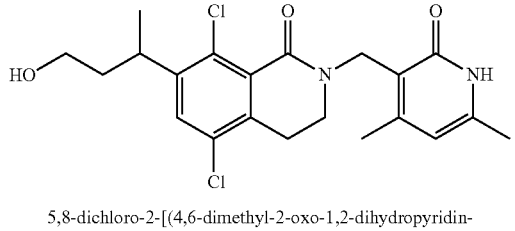<br>5,8-dichloro-2-[(4,6-dimethyl-2-oxo-1,2-dihydropyridin-3-yl)methyl]-7-(4-hydroxybutan-2-yl)-3,4-dihydro-isoquinolin-1(2H)-one - Isomer B | A | $^1$H NMR (400 MHz, DMSO-d6) δ 7.53 (s, 1H), 5.92 (s, 1H), 4.57 (s, 2H), 3.48-3.47 (m, 1H), 3.41 (t, J = 6.2 Hz, 2H), 3.34 (t, J = 6.6 Hz, 2H), 2.85 (t, J = 6.0 Hz, 2H), 2.16 (s, 3H), 2.13 (s, 3H), 1.78-1.68 (m, 2H), 1.15 (d, J = 6.8 Hz, 3H); LCMs [M + H]$^+$ 423 | Single enantiomer, absolute stereochemistry unknown; 2nd peak under the following SFC conditions: Lux Cellulose-4 4.6 ×100 mm 3u column; 50% MeOH @ 120 bar, 4 mL/min |
| 41 | 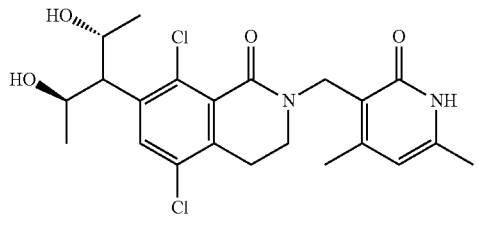<br>(±)-5,8-dichloro-7-[(2R*,3ε,4R*),-2,4-dihydroxypentan-3-yl]-2-[(4,6-dimethyl-2-oxo-1,2-dihydropyridin-3-yl)-methyl]-3,4-dihydroisoquinolin-1(2H)-one | G | $^1$H NMR (400 MHz, CDCl3) δ 12.02 (br. s., 1H), 7.78 (s, 1H), 6.28 (s, 1H), 4.74 (s, 2H), 4.58 (dq, J = 3.06, 6.48 Hz, 1H), 4.24 (qd, J = 6.21, 7.79 Hz, 1H), 3.68 (t, J = 6.11 Hz, 2H), 3.54 (dd, J = 2.93, 8.07 Hz, 1H), 2.97 (t, J = 6.11 Hz, 2H), 2.52 (s, 3H), 2.40 (s, 3H), 1.18 (d, J = 6.36 Hz, 3H), 1.05 (d, J = 6.36 Hz, 3H); LCMs [M + H]$^+$ 423 | Racemic mixture of 2,4-anti diols, stereochemistry at 3-position unknown. |
| 42 | 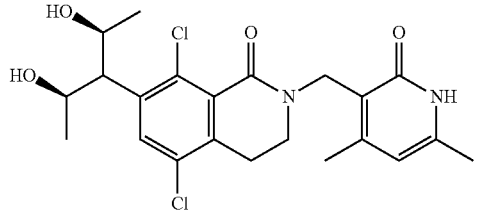<br>5,8-dichloro-7-[(2R*,3ε,4S*)-2,4-dihydroxypentan-3-yl]-2-[4,6-dimethyl-2-oxo-1,2-dihydropyridin-3-yl)methyl-3,4-dihydroisoquinolin-1(2H)-one | G | $^1$H NMR (400 MHz, DMSO-d6) δ 11.54 (br. s., 1H), 7.74 (s, 1H), 5.88 (s, 1H), 4.57 (s, 2H), 4.54 (br. s., 2H), 4.07 (quin, J = 5.81 Hz, 2H), 3.44 (t, J = 6.11 Hz, 2H), 3.24 (t, J = 5.87 Hz, 1H), 2.86 (t, J = 5.99 Hz, 2H), 2.17 (s, 3H), 2.12 (s, 3H), 1.02 (d, J = 6.11 Hz, 6H); LCMs [M + H]$^+$ 453 | Single achiral/meso 2,4-syn diol, stereochemistry at 3-position unknown |

TABLE 1-continued

| Ex. No. | Structure/IUPAC name | Method | ¹H NMR (ppm); LCMs [M + H]⁺ | Stereochemistry Note |
|---|---|---|---|---|
| 43 | 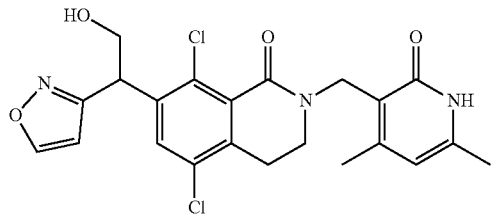<br>(±)-5,8-dichloro-2-[(4,6-dimethyl-2-oxo-1,2-dihydro-pyridin-3-yl)methyl]-7-[2-hydroxy-1-(1,2-oxazol-3-yl)ethyl]-3,4-dihydroisoquinolin-1(2H)-one | A | ¹H NMR (700 MHz, DMSO-d6) δ 8.84 (d, J =1.51 Hz, 1H), 7.60 (s, 1H), 6.65 (d, J = 1.51 Hz, 1H), 5.88 (s, 1H), 5.14 (br. s, 1H), 4.88 (t, J = 6.99 Hz, 1H), 4.57 (s, 2H), 3.93-4.00 (m, 2H), 3.43 (t, J = 6.24 Hz, 2H), 2.86 (t, J = 6.24 Hz, 2H), 2.15 (s, 3H), 2.12 (s, 3H); LCMs [M + H]⁺462 | Racemic mixture |
| 44 | 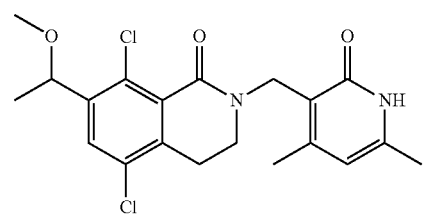<br>(±)-5,8-dichloro-2-[(4,6-dimethyl-2-oxo-1,2-dihydropyridin-3-yl)methyl]-7-(1-methoxy-ethyl)-3,4-dihydroisoquinolin-1(2H)-one | G | ¹H NMR (400 MHz, DMSO-d6) δ 11.53 (br. s, 1H), 7.52 (s, 1H), 5.88 (s, 1H), 4.78 (q, J = 6.24 Hz, 1H), 4.57 (s, 2H), 3.45 (t, J = 6.24 Hz, 2H), 3.18 (s, 3H), 2.89 (t, J = 6.11 Hz, 2H), 2.16 (s, 3H), 2.12 (s, 3H), 1.32 (d, J = 6.36 Hz, 3H); LCMs [M + H]⁺ 409 | Racemic mixture |
| 45 | 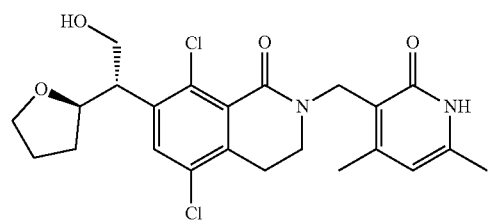<br>5,8-dichloro-2-[4,6-dimethyl-2-oxo-1,2-dihydropyridin-3-yl)methyl]-7-{(1S)-2-hydroxy-1-[(2R)-tetrahydrofuran-2-yl]ethyl}-3,4-dihydroisoquinolin-1(2H)-one | E | ¹H NMR (400 MHz, CD3OD) δ 7.58 (s, 1H), 6.10 (s, 1H), 4.76 (s, 2H), 4.09-4.22 (m, 1H), 3.86-4.00 (m, 3H), 3.75-3.84 (m, 1H), 3.62-3.72 (m, 1H), 3.45-3.55 (m, 2H), 2.95 (t, J = 6.17 Hz, 2H), 2.29 (s, 3H), 2.25 (s, 3H), 1.72-1.98 (m, 3H), 1.44-1.58 (m, 1H); LCMs [M + H]⁺ 465 | Single enantiomer, S at benzyl, R at THF 91% ee 1st peak; RT 2.91 min Chiralpak AD-3 4.6 × 100 mm 3u column, 5-60% MeOH in 3 minutes, 120 bar, 4 mL/min |
| 46 | 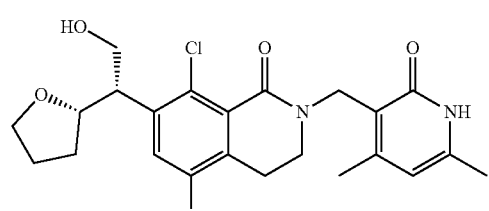<br>5,8-dichloro-2-[(4,6-dimethyl-2-oxo-1,2-dihydropyridin-3-yl)methyl]-7-{(1S)-2-hydroxy-[(2S)-tetrahydrofuran-2-yl]-ethyl}-3,4-dihydroisoquinolin-1(2H)-one | E | ¹H NMR (400 MHz, CD3OD) δ 7.66 (s, 1H), 6.10 (s, 1H), 4.76 (s, 2H), 4.23-4.32 (m, 1H), 3.73-3.91 (m, 3H), 3.67 (t, J = 6.79 Hz, 2H), 3.50 (t, J = 6.24 Hz, 2H), 2.95 (t, J = 6.17 Hz, 2H), 2.29 (s, 3H), 2.25 (s, 3H), 2.01-2.11 (m, 1H), 1.80-1.92 (m, 1H), 1.69-1.80 (m, 1H), 1.49-1.62 (m, 1H); LCMs [M + H]⁺ 465 | Single enantiomer, S,S 92% ee 2nd peak; RT 3.21 min Chiralpak AD-3 4.6 × 100 mm 3u column, 5-60% MeOH in 3 minutes, 120 bar, 4 mL/min |
| 47 | 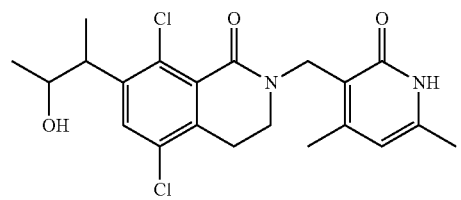<br>5,8-dichloro-2-[(4,6-dimethyl-2-oxo-1,2-dihydropyridin-3-yl)methyl]-7-[(2S*,3R*)-3-hydroxybutan-2-yl]-3,4-dihydroisoquinolin-1(2H)-one - Isomer A | A | ¹H NMR (400 MHz, CD3OD) δ 7.52 (s, 1H), 6.13 (s, 1H), 4.78 (s, 2H), 3.89-3.86 (m, 1H), 3.54-3.48 (m, 3H), 2.97 (t, J = 6.2 Hz, 2H), 2.31 (s, 3H), 2.27 (s, 3H), 1.29 (d, J = 7.2 Hz, 3H), 1.14 (d, J = 6.4 Hz, 3H); LCMs [M + H]⁺ 423 | Single enantiomer; relative stereochemistry known; absolute stereochemistry unknown; 99.08% ee; 1st peak, RT 9.67 min Column: Chiralpak AD-H 250 × 4.6 mm I.D., 5 um; mobile phase; 5-40% isopropanol (0.05% DEA) in CO2; flow rate: 2.5 mL/min |

TABLE 1-continued

| Ex. No. | Structure/IUPAC name | Method | ¹H NMR (ppm); LCMs [M + H]⁺ | Stereochemistry Note |
|---|---|---|---|---|
| 48 | 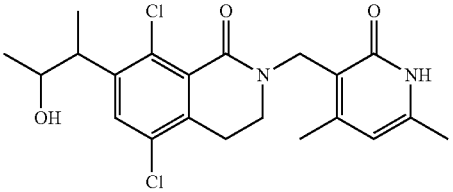<br>5,8-dichloro-2-[(4,6-dimethyl-2-oxo-1,2-dihydropyridin-3-yl)methyl]-7-[(2R*,3S*)-3-hydroxybutan-2-yl]-3,4-dihydroisoquinolin-1(2H)-one - Isomer B | A | ¹H NMR (400 MHz, CD3OD) δ 7.52 (s, 1H), 6.13 (s, 1H), 4.78 (s, 2H), 3.91-3.84 (m, 1H), 3.53-3.48 (m, 3H), 2.97 (t, J = 6.0 Hz, 2H), 2.31 (s, 3H), 2.27 (s, 3H), 1.29 (d, J = 7.2 Hz, 3H), 1.14 (d, J = 6.0 Hz, 3H); LCMs [M + H]⁺ 423 | Single enantiomer; relative stereochemistry known; absolute stereochemistry unknown; 96.73% ee; 2nd peak, RT 10.21 min; Column: Chiralpak AD-H 250 × 4.6 mm I.D., 5 um; mobile phase: 5-40% isopropanol (0.05% DEA) in CO2; flow rate: 2.5 mL/min |
| 49 | 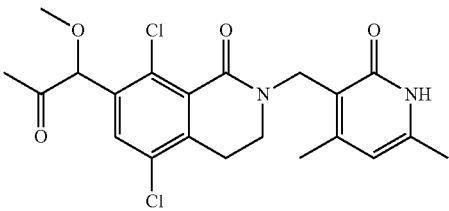<br>(±)-5,8-dichloro-2-[(4,6-dimethyl-2-oxo-1,2-dihydropyridin-3-yl)methyl]-7-(1-methoxy-2-oxopropyl)-3,4-dihydroisoquinolin-1(2H)-one | D | ¹H NMR (400 MHz, CDCl3) δ 7.51 (s, 1H), 5.93 (s, 1H), 5.32 (s, 1H), 4.76 (s, 2H), 3.75-3.60 (m, 2H), 3.39 (s, 3H), 3.00-2.90 (m, 2H), 2.36 (s, 3H), 2.27 (s, 3H), 2.19 (s, 3H), 1.26 (s, 1H); LCMs [M + H]⁺ 437 | Racemic mixture |
| 50 | 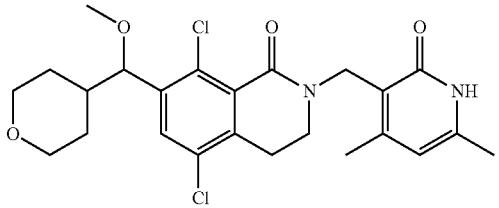<br>(−)-5,8-dichloro-2-[(4,6-dimethyl-2-oxo-1,2-dihydropyridin-3-yl)methyl]-7-[methoxy(tetrahydro-2H-pyran-4-yl)methyl]-3,4-dihydroisoquinolin-1(2H)-one | I | ¹H NMR (400 MHz, DMSO-d6) δ 11.54 (br. s., 1H), 7.45 (s, 1H), 5.88 (s, 1H), 4.56 (s, 3H), 3.74-3.89 (m, 2H), 3.46 (t, J = 6.11 Hz, 2H), 3.14-3.24 (m, 2H), 3.13 (s, 3H), 2.89 (t, J = 6.11 Hz, 2H), 2.17 (s, 3H), 2.12 (s, 3H), 1.76-1.90 (m, 1H), 1.32-1.56 (m, 3H), 1.17-1.27 (m, 1H); LCMs [M + H]⁺ 479 | [α]D = −56.4° (c 0.1, MeOH) ~96% ee (−); retention time 3.17 min; Lux Cellulose-4 4.6 × 100 mm 3u column; mobile phase: 50% MeOH @ 120 bar, 4 mL/min |
| 51 | 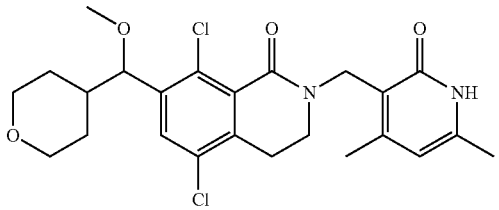<br>(+)-5,8-dichloro-2-[(4,6-dimethyl-2-oxo-1,2-dihydropyridin-3-yl)methyl]-7-[methoxy(tetrahydro-2H-pyran-4-yl)methyl]-3,4-dihydroisoquinolin-1(2H)-one | I | ¹H NMR (400 MHz, DMSO-d6) δ 11.54 (br. s., 1H), 7.45 (s, 1H), 5.89 (s, 1H), 4.56 (s, 3H), 3.75-3.89 (m, 2H), 3.46 (t, J = 6.11 Hz, 2H), 3.14-3.23 (m, 2H), 3.13 (s, 3H), 2.89 (t, J = 6.24 Hz, 2H), 2.17 (s, 3H), 2.12 (s, 3H), 1.76-1.89 (m, 1H), 1.32-1.57 (m, 3H), 1.16-1.26 (m, 1H); LCMs [M + H]⁺ 479 | [α]D = +80.9° (c 0.1, MeOH) ~99% ee (+); retention time 4.15 min; Lux Cellulose-4 4.6 × 100 mm 3u column; mobile phase 50% MeOH @ 120 bar CO2, 4 mL/min |
| 52 | 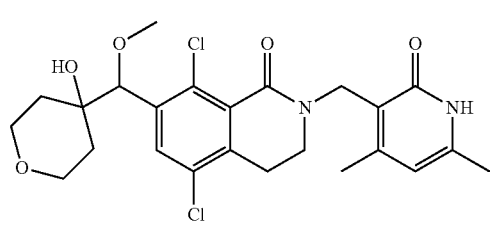<br>(−)-5,8-dichloro-2-[(4,6-dimethyl-2-oxo-1,2-dihydropyridin-3-yl)methyl]-7-[(4-hydroxytetrahydro-2H-pyran-4-yl)(methoxy)methyl]-3,4-dihydroisoquinolin-1(2H)-one | I | ¹H NMR (400 MHz, DMSO-d6) δ 11.54 (br. s., 1H), 7.62 (s, 1H), 5.88 (s, 1H), 4.65 (s, 1H), 4.62 (s, 1H), 4.56 (s, 2H), 3.61-3.69 (m, 1H), 3.43-3.59 (m, 5H), 3.12 (s, 3H), 2.86-2.92 (m, 2H), 2.18 (s, 3H), 2.12 (s, 3H), 1.57-1.75 (m, 3H), 0.92 (d, J = 12.72 Hz, 1H); LCMs [M + H]⁺ 495 | [α]D = −51.3° (c 0.1, MeOH) >99% ee (−); retention time 2.51 min; Lux Cellulose-4 4.6 × 100 mm 3u column; mobile phase: 50% MeOH @ 120 bar CO2; 4 mL/min |

TABLE 1-continued

| Ex. No. | Structure/IUPAC name | Method | ¹H NMR (ppm); LCMs [M + H]⁺ | Stereochemistry Note |
|---|---|---|---|---|
| 53 | 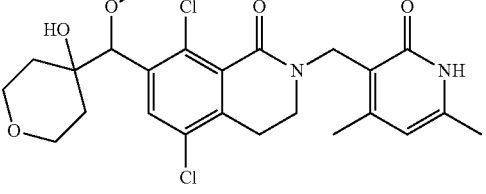<br>(+)-5,8-dichloro-2-[(4,6-dimethyl-2-oxo-1,2-dihydropyridin-3-yl)methyl]-7-[(4,hydroxytetrahydro-2H-pyran-4-yl)-(methoxy)methyl]-3,4-dihydroisoquinolin-1(2H)-one | I | ¹H NMR (400 MHz, DMSO-d6) δ 11.54 (br. s., 1H), 7.62 (s, 1H), 5.88 (s, 1H), 4.65 (s, 1H), 4.62 (s, 1H), 4.56 (s, 2H), 3.62-3.68 (m, 1H), 3.43-3.59 (m, 5H), 3.12 (s, 3H), 2.85-2.93 (m, 2H), 2.18 (s, 3H), 2.12 (s, 3H), 1.57-1.74 (m, 3H), 0.92 (d, J = 13.45 Hz, 1H); LCMs [M + H]⁺ 495 | [α]D = +73.8° (c 0.1, MeOH) ~99% ee (+); retention time 3.85 min; Lux Cellulose-4 4.6 × 100 mm 3u column; mobile phase: 50% MeOH @ 120 bar CO2, 4 mL/min |
| 54 | 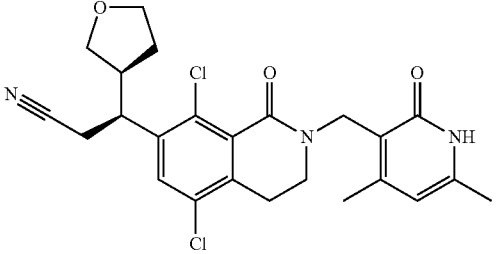<br>(3S)-3-{5,8-dichloro-2-[(4,6-dimethyl-2-oxo-1,2-dihydro-pyridin-3-yl)methyl]-1-oxo-1,2,3,4-tetrahydroisoquinolin-7-yl}-3-[(3S)-tetrahydrofuran-3-yl]propanenitrile | A | ¹H NMR (400 MHz, CDCl3) δ 11.80-13.19 (m, 1H), 7.49 (s, 1H), 6.01 (s, 1H), 4.78 (s, 2H), 4.09 (t, J = 7.76 Hz, 1H), 3.82-3.90 (m, 1H), 3.73-3.81 (m, 2H), 3.64-3.73 (m, 2H), 3.57-3.64 (m, 1H), 2.87-3.03 (m, 2H), 2.73-2.87 (m, 1H), 2.59-2.73 (m, 2H), 2.38 (s, 3H), 2.32 (s, 3H), 1.84-1.97 (m, 1H), 1.34-1.47 (m, 1H); LCMs [M + H]⁺ 474 | single enantiomer from chiral reagents; absolute stereochemistry S,S |
| 55 | 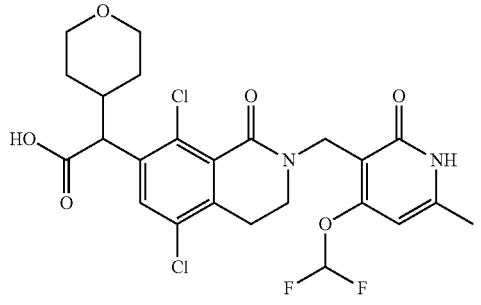<br>5,8-dichloro-2-{[4-(difluoromethoxy)-6-methyl-2-oxo-1,2-dihydropyridin-3-yl]methyl}-7-[2-hydroxy-1-(tetrahydro-2H-pyran-4-yl)ethyl]-3,4-dihydro-isoquinolin-1(2H)-one - Isomer B | A | ¹H NMR (400 MHz, CD3OD) δ 7.59 (s, 1H), 7.21-6.85 (m, 1H), 6.21 (s, 1H), 4.71 (s, 2H), 3.98-3.96 (m, 1H), 3.85-3.81 (m, 3H), 3.52-3.49 (m, 5H), 2.98 (t, J = 6.2 Hz, 2H), 2.31 (s, 3H), 1.92-1.89 (m, 2H), 1.46-1.43 (m, 1H), 1.29-1.23 (m, 3H); LCMs [M + H]⁺ 531 | Single isomer, absolute stereochemistry unknown; Enantiomer of Ex. 56: 98.46% ee; retention time: 3.767 min; column: Chiralpak AS-H 150* 4.6 mm I.D., 5 um; mobile phase: 5-40% ethanol (0.05% DEA) in CO2; flow rate: 3 mL/min |
| 56 | 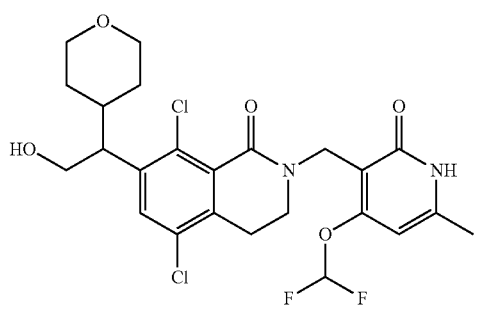<br>5,8-dichloro-2-{[4-(difluoromethoxy)-6-methyl-2-oxo-1,2-dihydropyridin-3-yl]methyl}-7-[2-hydroxy-1-(tetra-hydro-2H-pyran-4-yl)ethyl]-3,4-dihydroisoquinolin-1(2H)-one - Isomer A | A | ¹H NMR (400 MHz, CD3OD) δ 7.59 (s, 1H), 7.21-6.85 (m, 1H), 6.21 (s, 1H), 4.71 (s, 2H), 3.96-3.94 (m, 1H), 3.85-3.81 (m, 3H), 3.52-3.43 (m, 5H), 2.98 (t, J = 6.2 Hz, 2H), 2.31 (s, 3H), 1.92-1.89 (m, 2H), 1.46-1.42 (m, 1H), 1.29-1.23 (m, 3H); LCMs [M + H]⁺ 531 | Single isomer, absolute stereochemistry unknown; Enantiomer of Ex. 55: 99.02% ee; retention time: 3.585 min; column: Chiralpak AS-H 150* 4.6 mm I.D., 5 um; mobile phase: 5-40% ethanol (0.05% DEA) in CO2; flow rate: 3 mL/min |

TABLE 1-continued

| Ex. No. | Structure/IUPAC name | Method | ¹H NMR (ppm); LCMs [M + H]⁺ | Stereochemistry Note |
|---|---|---|---|---|
| 57 | (±)-5,8-dichloro-2-[(4,6-dimethyl-2-oxo-1,2-dihydro-pyridin-3-yl)methyl]-7-[2-hydroxy-1-(pyrrolidin-1-yl)ethyl]-3,4-dihydroisoquinolin-1(2H)-one | B | ¹H NMR (400 MHz, DMSO-d6) δ 11.50 (br. s., 1H), 7.68 (s, 1H), 5.89 (s, 1H), 4.65 (br. s., 1H), 4.58 (s, 2H), 3.90 (t, J = 4.52 Hz, 1H), 3.56-3.76 (m, 2H), 3.40-3.49 (m, 2H), 2.87 (t, J = 6.11 Hz, 2H), 2.33-2.44 (m, 2H), 2.17 (s, 3H), 2.13 (s, 3H), 1.67 (br. s., 4H), two Hs obscured by DMSO peak; LCMs [M + H]⁺ 464 | Racemic mixture |
| 58 | 5,8-dichloro-2-[(4,6-dimethyl-2-oxo-1,2-dihydropyridin-3-yl)methyl]-7-{1-[(3S)-3-fluoropyrrolidin-1-yl]-2-hydroxyethyl}-3,4-dihydroisoquinolin-1(2H)-one | B | ¹H NMR (400 MHz, DMSO-d6) δ 11.51 (br. s., 1H), 7.68 (d, J = 3.55 Hz, 1H), 5.89 (s, 1H), 5.03-5.31 (m, 1H), 4.75 (br. s., 1H), 4.58 (s, 2H), 3.92-4.01 (m, 1H), 3.54-3.73 (m, 2H), 3.38-3.52 (m, 2H), 2.91-2.99 (m, 1H), 2.84-2.91 (m, 2H), 2.59-2.78 (m, 2H), 2.29-2.43 (m, 1H), 2.17 (s, 3H), 2.13 (s, 3H), 1.99-2.12 (m, 1H), 1.76-1.97 (m, 1H); LCMs [M + H]⁺ 482 | Mixture of diastereomers containing (S)-3-fluoro-pyrrolidine Mixture separated to give Ex. 62 and Ex. 63 |
| 59 | (±)-5,8-dichloro-7-[1-(3,3-difluoropyrrolidin-1-yl)-2-hydroxyethyl]-2-[(4,6-dimethyl-2-oxo-1,2-dihydropyridin-3-yl)methyl]-3,4-dihydroisoquinolin-1(2H)-one | B | ¹H NMR (400 MHz, DMSO-d6) δ 11.51 (br. s., 1H), 7.66 (s, 1H), 5.88 (s, 1H), 4.83 (br. s., 1H), 4.57 (s, 2H), 4.03 (t, J = 4.52 Hz, 1H), 3.54-3.70 (m, 2H), 3.38-3.50 (m, 2H), 3.04 (dt, J = 14.37, 11.10 Hz, 1H), 2.79-2.94 (m, 3H), 2.62-2.78 (m, 2H), 2.18-2.30 (m, 2H), 2.16 (s, 3H), 2.12 (s, 3H); LCMs [M + H]⁺ 500 | Racemic Mixture |
| 60 | (±)-5,8-dichloro-2-[(4,6-dimethyl-2-oxo-1,2-dihydro-pyridin-3-yl)methyl]-7-[2-hydroxy-1-(morpholin-4-yl)ethyl]-3,4-dihydroisoquinolin-1(2H)-one | B | ¹H NMR (400 MHz, DMSO-d6) δ 11.54 (br. s., 1H), 7.72 (s, 1H), 5.89 (s, 1H), 4.71 (br. s., 1H), 4.58 (s, 2H), 3.95 (t, J = 4.65 Hz, 1H), 3.68-3.78 (m, 1H), 3.51-3.67 (m, 5H), 3.45 (t, J = 6.54 Hz, 2H), 2.87 (t, J = 6.11 Hz, 2H), 2.54 (br. s., 2H), 2.27-2.39 (m, 2H), 2.17 (s, 3H), 2.13 (s, 3H); LCMs [M + H]⁺ 480 | Racemic mixture |

TABLE 1-continued

| Ex. No. | Structure/IUPAC name | Method | $^1$H NMR (ppm); LCMs [M + H]$^+$ | Stereochemistry Note |
|---|---|---|---|---|
| 61 | 3-{4-[{5,8-dichloro-2-[(4,6-dimethyl-2-oxo-1,2-dihydropyridin-3-yl)methyl]-1-oxo-1,2,3,4-tetrahydroisoquinolin-7-yl}(methoxy)-methyl]piperidin-1-yl}-3-oxopropanenitrile - Isomer B | I | $^1$H NMR (400 MHz, CD3OD) δ 11.40 (br. s., 1H) 7.46 (s, 1H), 5.95 (s, 1H), 4.82-4.73 (m, 2H), 4.64-4.57 (m, 2H), 3.68 (t, J = 5.4 Hz, 3H), 3.47 (s, 2H), 3.20 (s, 3H), 3.09-3.02 (m, 1H), 2.95 (t, J = 6 Hz, 2H), 2.52-2.48 (m, 1H), 2.37 (s, 3H), 2.29 (s, 3H), 1.89-1.87 (m, 1H), 1.75-1.68 (m, 2H), 1.61-1.51 (m, 2H); LCMs [M + H]$^+$ 545 | Single isomer, absolute stereochemistry unknown; Enantiomer of Ex. 71; 96.42% ee; retention time: 9.135 min; column: Chiralpak AS-H 250 × 4.6 mm I.D., 5 um; mobile phase: 5-40% methanol (0.05% DEA) in CO2; flow rate: 2.35 mL/min |
| 62 | 5,8-dichloro-2-[(4,6-dimethyl-2-oxo-1,2-dihydro-pyridin-3-yl)methyl]-7-{1ε)-1-[(3S)-3-fluoro-pyrrolidin-1-yl]-2-hydroxyethyl}-3,4-dihydroisoquinolin-1(2H)-one - Isomer A | B | HNMR was not taken due to limited quantity. See Ex. 58; LCMs [M + H]$^+$ 482 | One component of the Ex. 58 mixture. Single diasteromer containing (S)-3-fluoropyrrolidine, other chiral center undetermined; [α]D = −58.9° (c 0.01 MeOH) ~98% de (−); 1st peak; RT 1.233 min; Chiralcel OJ-3 4.6 × 100 mm 3u column; 10% MeOH/DEA @ 120 bar, 4 mL/min |
| 63 | 5,8-dichloro-2-[(4,6-dimethyl-2-oxo-1,2-dihydro-pyridin-3-yl)methyl]-7-{(1ε)-1-[(3S)-3-fluoro-pyrrolidin-1-yl]-2-hydroxyethyl}-3,4-dihydroisoquinolin-1(2H)-one - Isomer B | B | HNMR was not taken due to limited quantity. See Ex. 58; LCMs [M + H]$^+$ 482 | One component of the Ex. 58 mixture. Single diasteromer containing (S)-3-fluoropyrrolidine, other chiral center undetermined; ~90% de (+); 2nd peak; RT 1.489 min; Chiralcel OJ-3 4.6 × 100 mm 3u column; 10% MeOH/DEA @ 120 bar, 4 mL/min |
| 64 | (±)-8-chloro-2-[(4,6-dimethyl-2-oxo-1,2-dihydropyridin-3-yl)methyl]-7-{(1S*)-2-hydroxy-1-[(3S*)-tetrahydro-furan-3-yl]ethyl}-3,4-dihydroisoquinolin-1(2H)-one | A | $^1$H NMR (400 MHz, CD3OD) δ 7.50 (d, J = 7.83 Hz, 1H), 7.20 (d, J = 7.83 Hz, 1H), 6.13 (s, 1H), 4.79 (s, 2H), 3.95 (dt, J = 3.67, 8.31 Hz, 1H), 3.76-3.87 (m, 3H), 3.58 (t, J = 7.95 Hz, 2H), 3.43-3.52 (m, 2H), 3.18 (t, J = 8.44 Hz, 1H), 2.87 (dd, J = 5.14, 7.09 Hz, 2H), 2.75 (dd, J = 7.83, 15.89 Hz, 1H), 2.33-2.25 (m, 1H), 2.30 (s, 3H), 2.26 (s, 3H), 1.83 (qd, J = 8.60, 12.10 Hz, 1H); LCMs [M + H]$^+$ 431 | Racemic Mixture of R,R and S,S isomers (Assigned by analogy to Ex. 4, which had a crystal structure showing S,S stereochemistry) |

TABLE 1-continued

| Ex. No. | Structure/IUPAC name | Method | $^1$H NMR (ppm); LCMs [M + H]$^+$ | Stereochemistry Note |
|---|---|---|---|---|
| 65 | 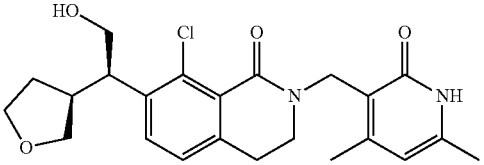<br>(±)-8-chloro-2-[(4,6-dimethyl-2-oxo-1,2-dihydropyridin-3-yl)methyl]-7-{(1R*)-2-hydroxy-1-[(3S*)-tetrahydrofuran-3-yl]ethyl}-3,4-dihydroisoquinolin-1(2H)-one | A | $^1$H NMR (400 MHz, CD3OD) δ 7.48 (d, J = 8.07 Hz, 1H), 7.19 (d, J = 7.83 Hz, 1H), 6.11 (s, 1H), 4.78 (s, 2H), 4.13 (t, J = 7.95 Hz, 1H), 3.78 (dt, J = 4.16, 8.31 Hz, 1H), 3.55-3.73 (m, 5H), 3.47 (t, J =5.26 Hz, 2H), 2.86 (dd, J = 4.40, 6.85 Hz, 2H), 2.60-2.74 (m, 1H), 2.29 (s, 3H), 2.25 (s, 3H), 1.68-1.80 (m, 1H), 1.40 (qd, J = 8.56, 12.23 Hz, 1H); LCMs [M + H]$^+$ 431 | Racemic Mixture of R,S and S,R isomers |
| 66 | 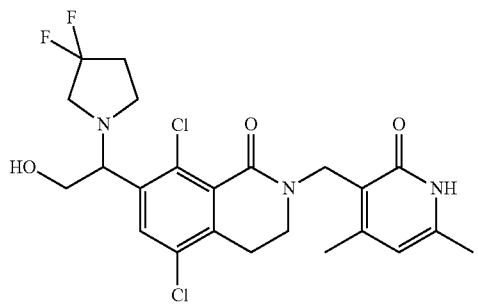<br>(−)-5,8-dichloro-7-[1-(3,3-difluoropyrrolidin-1-yl)-2-hydroxyethyl]-2-[(4,6-dimethyl-2-oxo-1,2-dihydropyridin-3-yl)methyl]-3,4-dihydroisoquinolin-1(2H)-one | B | $^1$H NMR (400 MHz, DMSO-d6) δ 11.51 (br. s., 1H), 7.66 (s, 1H), 5.88 (s, 1H), 4.83 (br. s., 1H), 4.57 (s, 2H), 4.03 (t, J = 4.52 Hz, 1H), 3.54-3.70 (m, 2H), 3.38-3.50 (m, 2H), 3.04 (dt, J = 14.37, 11.10 Hz, 1H), 2.79-2.94 (m, 3H), 2.62-2.78 (m, 2H), 2.18-2.30 (m, 2H), 2.16 (s, 3H), 2.12 (s, 3H); LCMs [M + H]$^+$ 500 | Single isomer, absolute stereochemistry unknown; Enantiomer of Ex. 67; [α]D = −65.35° (c 0.01 MeOH) >99% ee (−); 1st peak; RT 2.120 min; Chiralpak IC-3 4.6 × 100 mm 3u column; 40% MeOH @ 120 bar, 4 mL/min |
| 67 | 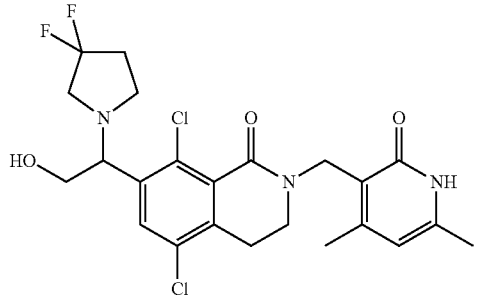<br>(+)-5,8-dichloro-7-[1-(3,3-difluoropyrrolidin-1-yl)-2-hydroxyethyl]-2-[(4,6-dimethyl-2-oxo-1,2-dihydropyridin-3-yl)methyl]-3-4-dihydroisoquinolin-1(2H)-one | B | $^1$H NMR (400 MHz, DMSO-d6) δ 11.51 (br. s., 1H), 7.66 (s, 1H), 5.88 (s, 1H), 4.83 (br. s., 1H), 4.57 (s, 2H), 4.03 (t, J = 4.52 Hz, 1H), 3.54-3.70 (m, 2H), 3.38-3.50 (m, 2H), 3.04 (dt, J = 14.37, 11.10 Hz, 1H), 2.79-2.94 (m, 3H), 2.62-2.78 (m, 2H), 2.18-2.30 (m, 2H), 2.16 (s, 3H), 2.12 (s, 3H); LCMs [M + H]$^+$ 500 | Single isomer, absolute stereochemistry unknown; Enantiomer of Ex. 66; [α]D = +92.77° (c 0.01 MeOH) ~99% ee (+); 2nd peak; RT 2.866 min; Chiralpak IC-3 4.6 × 100 mm 3u column; 40% MeOH @ 120 bar, 4 mL/min |
| 68 | 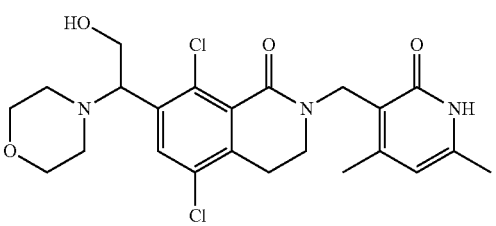<br>(−)-5,8-dichloro-2-[(4,6-dimethyl-2-oxo-1,2-dihydropyridin-3-yl)methyl]-7-[2-hydroxy-1-(morpholin-4-yl)ethyl]-3,4-dihydroisoquinolin-1(2H)-one | B | $^1$H NMR (400 MHz, DMSO-d6) δ 11.54 (br. s., 1H), 7.72 (s, 1H), 5.89 (s, 1H), 4.71 (br. s., 1H), 4.58 (s, 2H), 3.95 (t, J = 4.65 Hz, 1H), 3.68-3.78 (m, 1H), 3.51-3.67 (m, 5H), 3.45 (t, J = 6.54 Hz, 2H), 2.87 (t, J = 6.11 Hz, 2H), 2.54 (br. s., 2H), 2.27-2.39 (m, 2H), 2.17 (s, 3H), 2.13 (s, 3H); LCMs [M + H]$^+$ 480 | Single isomer, absolute stereochemistry unknown; Enantiomer of Ex. 69; [α]D = −52.63° (c 0.01 MeOH) >99% ee (−); 1st peak; RT 3.039 min; Chiralpak AD-3 4.6 × 100 mm 3u column; 20% MeOH/DEA @ 120 bar, 4 mL/min |

TABLE 1-continued

| Ex. No. | Structure/IUPAC name | Method | ¹H NMR (ppm); LCMs [M + H]⁺ | Stereochemistry Note |
|---|---|---|---|---|
| 69 | 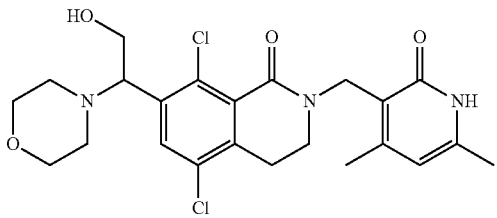<br>(+)-5,8-dichloro-2-[(4,6-dimethyl-2-oxo-1,2-dihydro-pyridin-3-yl)methyl]-7-[2-hydroxy-1-(morpholin-4-yl)ethyl]-3,4-dihydroisoquinolin-1(2H)-one | B | ¹H NMR (400 MHz, DMSO-d6) δ 11.54 (br. s., 1H), 7.72 (s, 1H), 5.89 (s, 1H), 4.71 (br. s., 1H), 4.58 (s, 2H), 3.95 (t, J = 4.65 Hz, 1H), 3.68-3.78 (m, 1H), 3.51-3.67 (m, 5H), 3.45 (t, J = 6.54 Hz, 2H), 2.87 (t, J = 6.11 Hz, 2H), 2.54 (br. s., 2H), 2.27-2.39 (m, 2H), 2.17 (s, 3H), 2.13 (s, 3H);<br><br>LCMs [M + H]⁺ 480 | Single isomer, absolute stereochemistry unknown; Enantiomer of Ex. 68; [α]D = +75.09° (c 0.01 MeOH) ~97.6% ee (+); 2nd peak; RT 4.327 min; Chiralpak AD-3 4.6 × 100 mm 3u column; 20% MeOH/DEA @ 120 bar, 4 mL/min; |
| 70 | 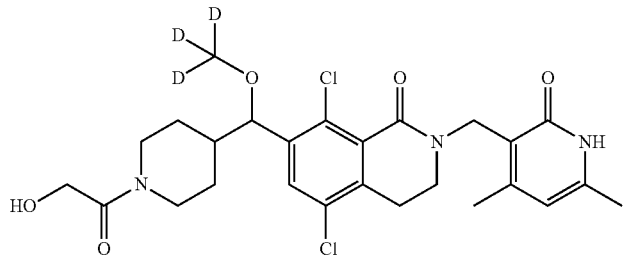<br>(±)-5,8-dichloro-2-[(4,6-dimethyl-2-oxo-1,2-dihydropyridin-3-yl)methyl]-7-{[1-(hydroxyacetyl)piperidin-4-yl][(²H₃)-methyloxy]methyl}-3,4-dihydroisoquinolin-1(2H)-one | I | ¹H NMR (400 MHz, CD3OD) δ 7.54 (s, 1H), 6.11 (s, 1H), 4.76 (s, 2H), 4.66 (d, J = 5.62 Hz, 1H), 4.43-4.56 (m, 1H), 4.11-4.28 (m, 2H), 3.66-3.80 (m, 1H), 3.53 (t, J = 6.11 Hz, 2H), 2.99 (t, J = 6.11 Hz, 2H), 2.84-2.96 (m, 1H), 2.50-2.64 (m, 1H), 2.30 (s, 3H), 2.25 (s, 3H), 1.86-2.01 (m, 1H), 1.74 (dd, J = 2.20, 13.20 Hz, 1H), 1.28-1.58 (m, 3H);<br><br>LCMs [M + H]⁺ 539 | Racemic Mixture |
| 71 | 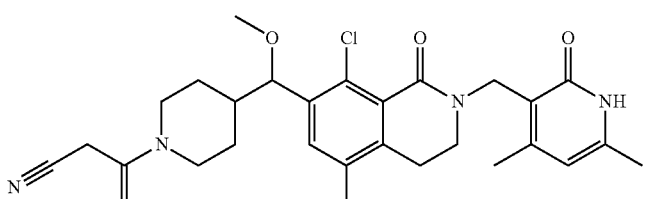<br>3-{4-[{5,8-dichloro-2-[(4,6-dimethyl-2-oxo-1,2-dihydropyridin-3-yl)-methyl]-1-oxo-1,2,3,4-tetrahydroisoquinolin-7-yl}(methoxy)methyl]-piperidin-1-yl}-3-oxopropanenitrile - Isomer A | I | ¹H NMR (400 MHz, CD3OD) δ 11.61 (br. s., 1H) 7.46 (s, 1H), 5.95 (s, 1H), 4.82-4.73 (m, 2H), 4.64-4.57 (m, 2H), 3.68 (t, J = 5.4 Hz, 3H), 3.47 (s, 2H), 3.20 (s, 3H), 3.09-3.02 (m, 1H), 2.95 (t, J = 6 Hz, 2H), 2.52-2.49 (m, 1H), 2.37 (s, 3H), 2.29 (s, 3H), 1.89-1.87 (m, 1H), 1.75-1.68 (m, 2H), 1.62-1.51 (m, 2H); LCMs [M + H]⁺ 545 | Single isomer, absolute stereochemistry unknown; Enantiomer of Ex. 61; 97.43% ee; retention time: 8.742 min; column: Chiralpak AS-H 250 × 4.6 mm I.D., 5 um; mobile phase: 5-40% methanol (0.05% DEA) in CO2; flow rate: 2.35 mL/min |
| 72 | 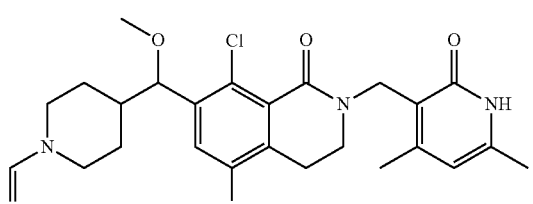<br>4-[{5,8-dichloro-2-[(4,6-dimethyl-2-oxo-1,2-dihydropyridin-3-yl)methyl]-1-oxo-1,2,3,4-tetrahydroisoquinolin-7-yl}-(methoxy)methyl]piperidine-1-carbaldehyde - Isomer A | I | ¹H NMR (400 MHz, CDCl3) δ 11.52 (br s, 1H), 7.99 (s, 1H), 7.47 (s, 1H), 5.96 (s, 1H), 4.77 (s, 2H), 4.63 (d, J = 4.8 Hz, 1H), 4.42 (d, J = 11.6 Hz, 1H), 3.68 (t, J = 6 Hz, 2H), 3.61 (t, J = 13.2 Hz, 1H), 3.20 (s, 3H), 2.97-2.94 (m, 3H), 2.49-2.47 (m, 1H), 2.38 (s, 3H), 2.29 (s, 3H), 1.89-1.87 (m, 1H), 1.36-1.26 (m, 4H);<br><br>LCMs [M + H]⁺ 506 | Single isomer, absolute stereochemistry unknown; Enantiomer of Ex. 73; 94.43% ee; retention time: 8.623 min; column: Chiralpak AS-H 250 × 4.6 mm I.D., 5 um; mobile phase: 5-40% methanol (0.05% DEA) in CO2; flow rate: 2.35 mL/min. |

TABLE 1-continued

| Ex. No. | Structure/IUPAC name | Method | ¹H NMR (ppm); LCMs [M + H]⁺ | Stereochemistry Note |
|---|---|---|---|---|
| 73 | 4-[{5,8-dichloro-2-[(4,6-dimethyl-2-oxo-1,2-dihydropyridin-3-yl)methyl]-1-oxo-1,2,3,4-tetrahydroisoquinolin-7-yl}-(methoxy)methyl]piperidine-1-carbaldehyde - Isomer B | I | ¹H NMR (400 MHz, CDCl3) δ 11.29 (br s, 1H), 7.99 (s, 1H), 7.47 (s, 1H), 5.95 (s, 1H), 4.77 (s, 2H), 4.63 (d, J = 4.8 Hz, 1H), 4.42 (d, J = 12.0 Hz, 1H), 3.68 (t, J = 6 Hz, 2H), 3.61 (t, J = 12.8 Hz, 1H), 3.20 (s, 3H), 2.97-2.94 (m, 3H), 2.49-2.47 (m, 1H), 2.37 (s, 3H), 2.29 (s, 3H), 1.89-1.87 (m, 1H), 1.36-1.26 (m, 4H); LCMs [M + H]⁺ 506 | Single isomer, absolute stereochemistry unknown; Enantiomer of Ex. 72; 92.36% ee; retention time: 9.05 min; column: Chiralpak AS-H 250 × 4.6 mm I.D., 5 um; mobile phase: 5-40% methanol (0.05% DEA) in CO2; flow rate: 2.35 mL/min |
| 74 | 7-[1-(azetidin-3-ylidene)ethyl]-5,8-dichloro-2-[(4,6-dimethyl-2-oxo-1,2-dihydropyridin-3-yl)-methyl]-3,4-dihydroisoquinolin-1(2H)-one | H | N/A; LCMs [M + H]⁺ 432 | N/A |
| 75 | 5,8-dichloro-2-[(4,6-dimethyl-2-oxo-1,2-dihydropyridin-3-yl)-methyl]-7-{1-[1-(hydroxyacetyl)azetidin-3-ylidene]ethyl}-3,4-dihydroisoquinolin-1(2H)-one | H | ¹H NMR (400 MHz, DMSO-d6) δ 11.54 (br. s., 1H), 7.51 (s, 1H), 5.89 (s, 1H), 4.81-4.99 (m, 2H), 4.51-4.60 (m, 3H), 4.48 (br. s., 1H), 4.19 (br. s., 1H), 3.83-4.01 (m, 2H), 3.46 (t, J = 6.11 Hz, 2H), 2.88 (t, J = 5.87 Hz, 2H), 2.17 (s, 3H), 2.12 (s, 3H), 1.85 (br. s., 3H); LCMs [M + H]⁺ 490 | N/A |
| 76 | 7-[1-(1-acetylazetidin-3-ylidene)ethyl]-5,8-dichloro-2-[(4,6-dimethyl-2-oxo-1,2-dihydropyridin-3-yl)methyl]-3,4-dihydroisoquinolin-1(2H)-one | H | ¹H NMR (400 MHz, DMSO-d6) δ 11.46 (br. s., 1H), 7.44 (s, 0.56H), 7.43 (s, 0.44H), 5.81 (s, 1H), 4.72 (br. s., 0.88H), 4.49 (s, 2H), 4.40 (br. s., 1.12H), 4.36 (br. s., 1.12H), 4.05 (br. s., 0.88H), 3.39 (t, J = 6.24 Hz, 2H), 2.81 (t, J = 6.11 Hz, 2H), 2.10 (s, 3H), 2.05 (s, 3H), 1.78 (br. s., 3H), 1.76 (s, 1.32H), 1.68 (s, 1.68H) Rotamers (~4:5 ratio); LCMs [M + H]⁺ 474 | N/A |

TABLE 1-continued

| Ex. No. | Structure/IUPAC name | Method | $^1$H NMR (ppm); LCMs [M + H]$^+$ | Stereochemistry Note |
|---|---|---|---|---|
| 77 | 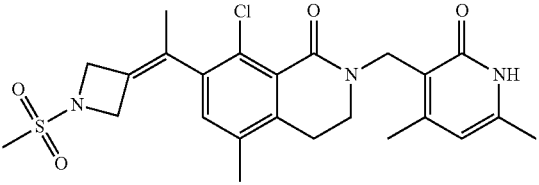<br>8-chloro-2-[(4,6-dimethyl-2-oxo-1,2-dihydropyridin-3-yl)methyl]-5-methyl-7-{1-[1-(methylsulfonyl)azetidin-3-ylidene]ethyl}-3,4-dihydroisoquinolin-1(2H)-one | H | $^1$H NMR (400 MHz, CDCl3) δ 11.72 (br. s., 1H), 6.98 (s, 1H), 5.93 (s, 1H), 4.79 (s, 2H), 4.65 (br. s., 2H), 4.29 (br. s., 2H), 3.62 (t, J = 6.15 Hz, 2H), 2.89 (s, 3H), 2.73 (t, J = 6.15 Hz, 2H), 2.36 (s, 3H), 2.23-2.30 (m, 3H), 2.21 (s, 3H), 1.87 (s, 3H); LCMs [M + H]$^+$ 490 | N/A |
| 78 | 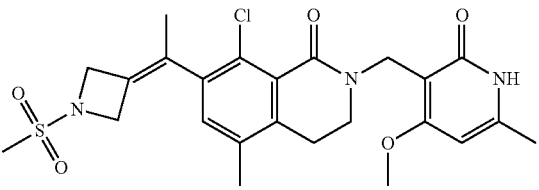<br>8-chloro-2-[(4-methoxy-6-methyl-2-oxo-1,2-dihydropyridin-3-yl)methyl]-5-methyl-7-{1-[1-(methylsulfonyl)azetidin-3-ylidene]ethyl}-3,4-hydroisoquinolin-1(2H)-one | H | $^1$H NMR (400 MHz, CD3OD) δ 7.17 (s, 1H), 6.28 (s, 1H), 4.74 (s, 2H), 4.68 (br. s., 2H), 4.24-4.33 (m, 2H), 3.91 (s, 3H), 3.38 (t, J = 6.27 Hz, 2H), 2.99 (s, 3H), 2.80 (t, J = 6.27 Hz, 2H), 2.34 (s, 3H), 2.27 (s, 3H), 1.91 (t, J = 1.51 Hz, 3H); [M + Na]$^+$ 528 | N/A |
| 79 | 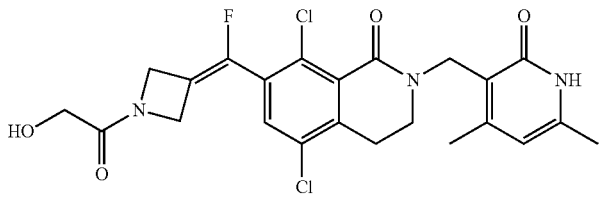<br>5,8-dichloro-2-[(4,6-dimethyl-2-oxo-1,2-dihydropyridin-3-yl)-methyl]-7-{fluoro[1-(hydroxyacetyl)azetidin-3-ylidene]-methyl}-3,4-dihydroisoquinolin-1(2H)-one | H | $^1$H NMR (400 MHz, DMSO-d6) δ 11.58 (brs, 1H), 7.84 (d, J = 5.6 Hz, 1H), 5.89 (s, 1H), 5.15-5.00 (m, 1H), 5.00-4.95 (m, 1H), 4.80-4.75 (m, 1H), 4.65-4.60 (m, 1H), 4.57 (s, 2H), 4.50-4.45 (m, 1H), 4.00-3.95 (m, 2H), 3.47 (t, J = 6.0 Hz, 2H), 2.93 (t, J = 4.8 Hz, 2H), 2.16 (s, 3H), 2.12 (s, 3H); [M + H]$^+$ 494 | N/A |
| 80 | 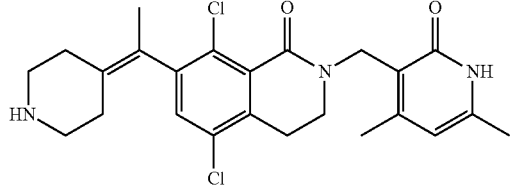<br>5,8-dichloro-2-[(4,6-dimethyl-2-oxo-1,2-dihydropyridin-3-yl)methyl]-7-[1-(piperidin-4-ylidene)ethyl]-3,4-dihydroisoquinolin-1(2H)-one | H | $^1$H NMR (400 MHz, CD3OD) δ 7.36 (s, 1H), 6.18 (s, 1H), 4.78-4.83 (m, 2H), 3.60 (t, J = 6.24 Hz, 2H), 2.98-3.12 (m, 4H), 2.91 (t, J = 5.14 Hz, 2H), 2.58-2.69 (m, 1H), 2.47-2.58 (m, 1H), 2.37 (s, 3H), 2.32 (s, 3H), 2.05 (d, J = 7.58 Hz, 2H), 1.97-2.01 (m, 3H); [M + H]$^+$ 460 | N/A |
| 81 | 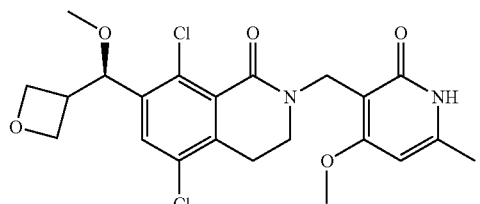<br>5,8-dichloro-2-[(4-methoxy-6-methyl-2-oxo-1,2-dihydropyridin-3-yl)methyl]-7-[(R)-methoxy(oxetan-3-yl)methyl]-3,4-dihydroisoquinolin-1(2H)-one | I | $^1$H NMR (400 MHz, CDCl3) δ 12.34 (brs, 1H), 7.49 (s, 1H), 5.93 (s, 1H), 5.05 (d, J = 6.0 Hz, 1H), 4.61-4.78 (m, 6H), 3.88 (s, 3H), 3.48-3.50 (m, 2H), 3.37-3.38 (m, 1H), 3.31 (s, 3H), 2.94 (t, J = 6.2 Hz, 2H), 2.35 (s, 3H); [M + Na]$^+$ 489 | R isomer; stereochemistry determined from X-ray crystal structure of enantiomeric compound Ex. 82; 100% ee; retention time 9.85 min; Column: (R,R) Whelk O1, 250 × 4.6mm I.D., 5 um; Mobile phase: 50% ethanol (0.05% DEA) in CO2; wavelength 220 nm |

TABLE 1-continued

| Ex. No. | Structure/IUPAC name | $^1$H NMR (ppm); Method | LCMs [M + H]$^+$ | Stereochemistry Note |
|---|---|---|---|---|
| 82 | 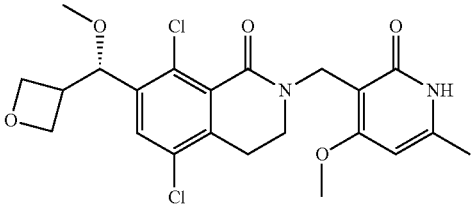<br>5,8-dichloro-2-[(4-methoxy-6-methyl-2-oxo-1,2-dihydro-pyridin-3-yl)methyl]-7-[(S)-methoxy(oxetan-3-yl)methyl]-3,4-dihydroisoquinolin-1(2H)-one | I | $^1$H NMR (400 MHz, CDCl3) δ 12.38 (brs, 1H), 7.49 (s, 1H), 5.92 (s, 1H), 5.05 (d, J = 6.0 Hz, 1H), 4.64-4.78 (m, 6H), 3.87 (s, 3H), 3.47-3.50 (m, 2H), 3.37-3.38 (m, 1H), 3.31 (s, 3H), 2.93 (t, J = 6.2 Hz, 2H), 2.35 (s, 3H); [M + H]$^+$ 467 | Known to be S isomer by X-ray crystal structure; Enantiomer of Ex. 81; 98% ee; retention time 8.65 min; column: (R,R) Whelk O1, 250 ×4.6 mm I.D., 5 um; mobile phase: 50% ethanol (0.05% DEA) in CO2; wavelength 220 nm |
| 83 | 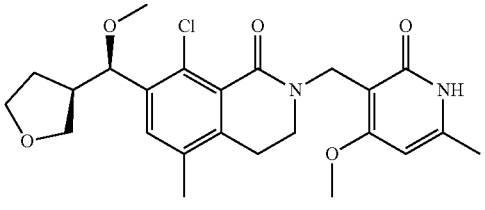<br>8-chloro-2-[(4-methoxy-6-methyl-2-oxo-1,2-dihydropyridin-3-yl)methyl]-7-{(R)-methoxy-[(3R)-tetrahydrofuran-3-yl]methyl}-5-methyl-3,4-dihydroisoquinolin-1(2H)-one | I | $^1$H NMR (400 MHz, CDCl3) δ 12.36 (brs, 1H), 7.29 (s, 1H), 5.91 (s, 1H), 4.75-4.85 (m, 3H), 3.83-3.89 (m, 6H), 3.69-3.71 (m, 1H), 3.44-3.47 (m, 2H), 3.16 (s, 3H), 2.73-2.76 (m, 2H), 2.54-2.58 (m, 1H), 2.34 (s, 3H), 2.26 (s, 3H), 1.70-1.73 (m, 2H); [M + H]$^+$ 461 | Known to be R,R isomer by X-ray crystal structure; Enantiomer of Ex. 86; Diastereomer of Ex. 84 and Ex. 85; 100% ee; retention time 34.91 min; column: Chiralpak IC 250 × 4.6 mm I.D., 5 um; mobile phase: 50% ethanol (0.05% DEA) in CO2; flow rate: 2.0 mL/min |
| 84 | 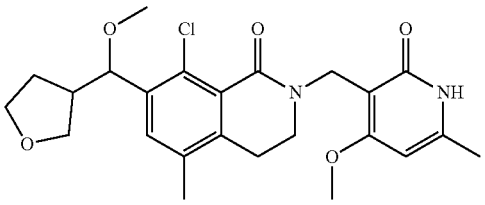<br>8-chloro-2-[(4-methoxy-6-methyl-2-oxo-1,2-dihydro-pyridin-3-yl)methyl]-7-{(R*)-methoxy[(3S*)-tetrahydrofuran-3-yl]methyl}-5-methyl-3,4-dihydroisoquinolin-1(2H)-one | I | $^1$H NMR (400 MHz, CDCl3) δ 12.33 (brs, 1H), 7.30 (s, 1H), 5.91 (s, 1H), 4.77-4.84 (m, 3H), 3.86-3.89 (m, 4H), 3.68-3.73 (m, 2H), 3.58-3.60 (m, 1H), 3.44-3.46 (m, 2H), 3.19 (s, 3H), 2.73-2.75 (m, 2H), 2.62-2.64 (m, 1H), 2.34 (s, 3H), 2.24 (s, 3H), 1.95-1.98 (m, 2H); [M + H]$^+$ 461 | Single enantiomer, either R,S or S,R, but absolute stereochemistry unknown; Enantiomer of Ex. 85; Diastereomer of Ex. 83 and Ex. 86; 97% ee; retention time 39.01 min; column: Chiralpak IC 250 × 4.6 mm I.D., 5 um; mobile phase: 50% ethanol (0.05% DEA) in CO2; flow rate: 2.0 mL/min |
| 85 | 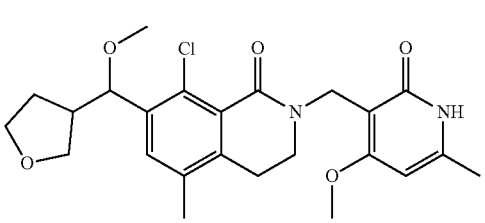<br>8-chloro-2-[(4-methoxy-6-methyl-2-oxo-1,2-dihydropyridin-3-yl)methyl]-7-{(S*)-methoxy[(3R*)-tetrahydrofuran-3-yl]methyl}-5-methyl-3,4-dihydroisoquinolin-1(2H)-one | I | $^1$H NMR (400 MHz, CDCl3) δ 12.30 (brs, 1H), 7.30 (s, 1H), 5.91 (s, 1H), 4.77-4.84 (m, 3H), 3.86-3.89 (m, 4H), 3.66-3.74 (m, 2H), 3.58-3.59 (m, 1H), 3.44-3,46 (m, 2H), 3.19 (s, 3H), 2.73-2.75 (m, 2H), 2.63-2.65 (m, 1H), 2.34 (s, 3H), 2.24 (s, 3H), 1.95-1.98 (m, 2H); [M + H]$^+$ 461 | Single enantiomer, either R,S or S,R, but absolute stereochemistry unknown; Enantiomer of Ex. 84; Diastereomer of Ex. 83 and Ex. 86; 100% ee; retention time 29.05 min; column: Chiralpak IC 250 × 4.6 mm I.D., 5 um; mobile phase: 50% ethanol (0.05% DEA) in CO2; flow rate: 2.0 mL/min |
| 86 | 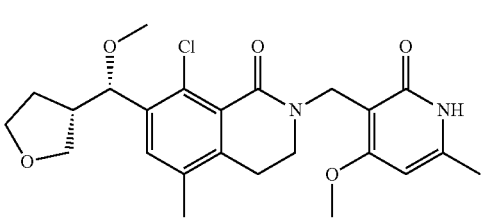<br>8-chloro-2-[(4-methoxy-6-methyl-2-oxo-1,2-dihydropyridin-3-yl)methyl]-7-{(S)-methoxy[(3S)-tetrahydrofuran-3-yl]methyl}-5-methyl-3,4-dihydroisoquinolin-1(2H)-one | I | $^1$H NMR (400 MHz, CDCl3) δ 12.29 (brs, 1H), 7.30 (s, 1H), 5.91 (s, 1H), 4.75-4.84 (m, 3H), 3.83-3.89 (m, 6H), 3.69-3.71 (m, 1H), 3.44-3.47 (m, 2H), 3.16 (s, 3H), 2.73-2.76 (m, 2H), 2.56-2.58 (m, 1H), 2.34 (s, 3H), 2.25 (s, 3H), 1.70-1.73 (m, 2H);[M + H]$^+$ 461 | S,S isomer; stereochemistry determined by X-ray crystal structure of enantiomeric compound Ex. 83; Diastereomer of Ex. 84 and Ex. 85; 100% ee; retention time 32.28 min; column: Chiralpak IC 250 × 4.6 mm I.D., 5 um; mobile phase: 50% ethanol (0.05% DEA) in CO2; flow rate: 2.0 mL/min |

TABLE 1-continued

| Ex. No. | Structure/IUPAC name | Method | ¹H NMR (ppm); LCMs [M + H]⁺ | Stereochemistry Note |
|---|---|---|---|---|
| 87 | 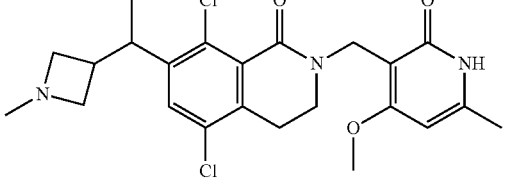<br>5,8-dichloro-2-[(4-methoxy-6-methyl-2-oxo-1,2-dihydropyridin-3-yl)methyl]-7-[1-(1-methyl-azetidin-3-yl)ethyl]-3,4-dihydroisoquinolin-1(2H)-one - Isomer A | J | ¹H NMR (400 MHz, CD3OD) δ 7.44 (s, 1H), 6.27 (s, 1H), 4.73 (s, 2H), 3.91 (s, 3H), 3.67-3.78 (m, 2H), 3.36-3.42 (m, 3H), 3.16 (t, J = 7.40 Hz, 1H), 2.90-2.96 (m, 2H), 2.82-2.90 (m, 2H), 2.39 (s, 3H), 2.33 (s, 3H), 1.16 (d, J = 6.78 Hz, 3H); [M + H]⁺ 464 | Single isomer, absolute stereochemistry unknown; Enantiomer of Ex. 88; 99% ee; retention time 5.511 min; Column: Chiralpak AD-3 150 × 4.6 mm I.D., 3 um; mobile phase; ethanol (0.05% DEA) in CO2 |
| 88 | 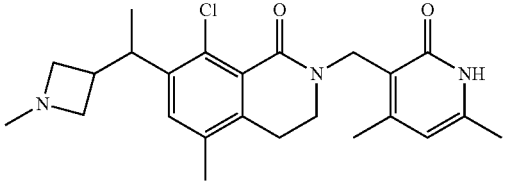<br>5,8-dichloro-2-[(4-methoxy-6-methyl-2-oxo-1,2-dihydro-pyridin-3-yl)methyl]-7-[1-(1-methylazetidin-3-yl)ethyl]-3,4-dihydroisoquinolin-1(2H)-one - Isomer B | J | ¹H NMR (400 MHz, CD3OD) δ 7.43 (s, 1H), 6.26 (s, 1H), 4.73 (s, 2H), 3.91 (s, 3H), 3.64-3.75 (m, 2H), 3.34-3.42 (m, 3H), 3.12 (br. s., 1H), 2.93 (t, J = 6.02 Hz, 2H), 2.83 (br. s., 2H), 2.35-2.40 (m, 3H), 2.33 (s, 3H), 1.16 (d, J = 6.78 Hz, 3H); [M + H]⁺ 464 | Single isomer, absolute stereochemistry unknown; Enantiomer of Ex. 87; 100% ee; retention time 55.997 min; Column: Chiralpak AD-3 150 × 4.6 mm I.D., 3 um; mobile phase; ethanol (0.05% DEA) in CO2 |
| 89 | 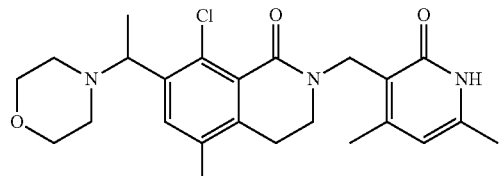<br>(±)-5,8-dichloro-2-[(4,6-dimethyl-2-oxo-1,2-dihydro-pyridin-3-yl)methyl]-7-[1-(morpholin-4-yl)ethyl]-3,4-dihydroisoquinolin-1(2H)-one | K | ¹H NMR (400 MHz, CDCl3) δ 7.74 (s, 1H), 5.94 (s, 1H), 4.87-4.70 (m, 2H), 4.00 (q, J = 6.3 Hz, 1H), 3.76-3.59 (m, 6H), 2.99-2.81 (m, 2H), 2.53 (br. s., 2H), 2.36 (m, 5H), 2.29 (s, 3H), 1.24 (d, J = 6.5 Hz, 3H); [M + H]⁺ 464 | racemic mixture |
| 90 | 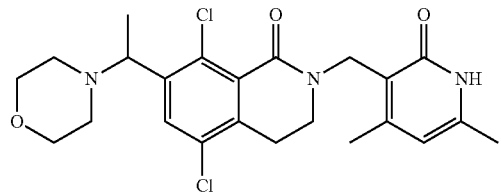<br>(+)-5,8-dichloro-2-[(4,6-dimethyl-2-oxo-1,2-dihydro-pyridin-3-yl)methyl]-7-[1-(morpholin-4-yl)ethyl]-3,4-dihydroisoquinolin-1(2H)-one | K | [M + H]⁺ 464 | (+) isomer of Ex. 89 |
| 91 | 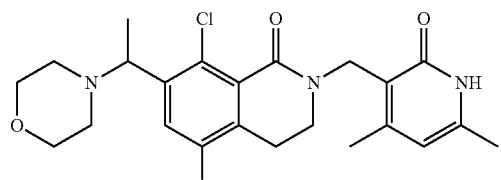<br>(−)-5,8-dichloro-2-[(4,6-dimethyl-2-oxo-1,2-dihydropyridin-3-yl)methyl]-7-[1-(morpholin-4-yl)ethyl]-3,4-dihydroisoquinolin-1(2H)-one | K | [M + H]⁺ 464 | (−) isomer of Ex. 89 |

TABLE 1-continued

| Ex. No. | Structure/IUPAC name | Method | $^1$H NMR (ppm); LCMs [M + H]$^+$ | Stereochemistry Note |
|---|---|---|---|---|
| 92 | 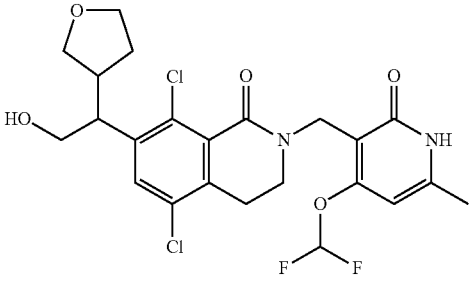<br>5,8-dichloro-2-{[4-(difluoromethoxy)-6-methyl-2-oxo-1,2-dihydropyridin-3-yl]methyl}-7-[2-hydroxy-1-(tetrahydrofuran-3-yl)ethyl]-3,4-dihydroisoquinolin-1(2H)-one - Isomer A | A | $^1$H NMR (400 MHz, CDCl3) δ 12.31 (br. s., 1H), 7.42 (s, 1H), 6.72 (t, J = 72 Hz, 1H), 6.09 (s, 1H), 4.70 (s, 2H), 3.82-3.96 (m, 4H), 3.61-3.65 (m, 4H), 3.20 (t, J = 8.4 Hz, 2H), 2.97 (t, J = 6.2 Hz, 2H), 2.70-2.72 (m, 1H), 2.35 (s, 3H), 2.21-2.23 (m, 1H), 1.75-1.81 (m, 1H); [M + H]$^+$ 517 | Single isomer, absolute stereochemistry unknown; Enantiomer of Ex. 93; Diastereomer of Ex. 94 and Ex. 95; 100% ee; retention time 5.37 min; column: Chiralcel OJ-H 250 × 4.6 mm I.D., 5 um; mobile phase: methanol (0.05% DEA) in CO2 from 5% to 40%; flow rate; 2.5 mL/min |
| 93 | 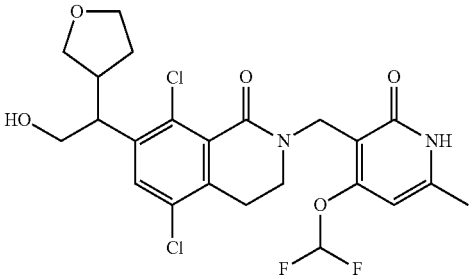<br>5,8-dichloro-2-{[4-(difluoromethoxy)-6-methyl-2-oxo-1,2-dihydropyridin-3-yl]methyl}-7-[2-hydroxy-1-(tetrahydrofuran-3-yl)ethyl]-3,4-dihydroisoquinolin-1(2H)-one - Isomer B | A | $^1$H NMR (400 MHz, CDCl3) δ 12.25 (br. s., 1H), 7.42 (s, 1H), 6.72 (t, J = 72 Hz, 1H), 6.09 (s, 1H), 4.70 (s, 2H), 3.82-3.89 (m, 4H), 3.61-3.66 (m, 4H), 3.20 (t, J = 8.4 Hz, 2H), 2.98 (t, J = 6.2 Hz, 2H), 2.70-2.72 (m, 1H), 2.35 (s, 3H), 2.21-2.23 (m, 1H), 1.76-1.81 (m, 1H); [M + H]$^+$ 517 | Single isomer, absolute stereochemistry unknown; Enantiomer of Ex. 92; Diastereomer of Ex. 94 and Ex. 95; 100% ee; retention time 5.54 min; column: Chiralcel OJ-H 250 × 4.6 mm I.D., 5 um; mobile phase: methanol (0.05% DEA) in CO2 from 5% to 40%; flow rate; 2.5 mL/min |
| 94 | 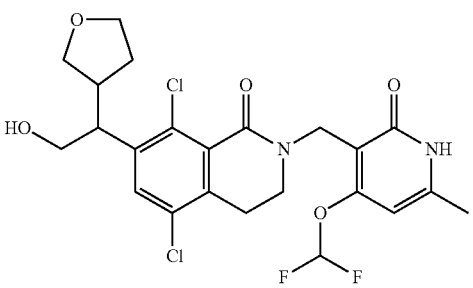<br>5,8-dichloro-2-{[4-(difluoromethoxy)-6-methyl-2-oxo-1,2-dihydropyridin-3-yl]methyl}-7-[2-hydroxy-1-(tetrahydrofuran-3-yl)ethyl]-3,4-dihydroisoquinolin-1(2H)-one - Isomer C | A | $^1$H NMR (400 MHz, CDCl3) δ 12.12 (br. s., 1H), 7.45 (s, 1H), 6.73 (t, J = 72 Hz, 1H), 6.10 (s, 1H), 4.71 (t, J = 13.3 Hz, 2H), 4.07-4.10 (m, 1H), 3.82-3.70 (m, 4H), 3.60-3.65 (m, 4H), 2.99 (t, J = 6.2 Hz, 2H), 2.63-2.65 (m, 1H), 2.35 (s, 3H), 1.78-1.8 (m, 1H), 1.40-1.45 (m, 1H); [M + H]$^+$ 517 | Single isomer, absolute stereochemistry unknown; Enantiomer of Ex. 95; Diastereomer of Ex. 92 and Ex. 93; 100% ee; retention time 5.80 min; column: Chiralcel OJ-H 250 × 4.6 mm I.D., 5 um; mobile phase: methanol (0.05% DEA) in CO2 from 5% to 40%; flow rate; 2.5 mL/min |
| 95 | 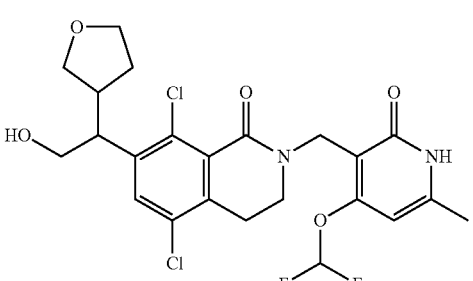<br>5,8-dichloro-2-{[4-(difluoromethoxy)-6-methyl-2-oxo-1,2-dihydropyridin-3-yl]methyl}-7-[2-hydroxy-1-(tetrahydrofuran-3-yl)ethyl]-3,4-dihydroisoquinolin-1(2H)-one - Isomer D | A | $^1$H NMR (400 MHz, CDCl3) δ 12.36 (br. s., 1H), 7.45 (s, 1H), 6.72 (t, J = 73 Hz, 1H), 6.09 (s, 1H), 4.71 (q, J = 13.9 Hz, 2H), 4.06-4.08 (m, 1H), 3.70-3.83 (m, 4H), 3.59-3.63 (m, 4H), 2.98 (t, J =5.4 Hz, 2H), 2.63-2.65 (m, 1H), 2.35 (s, 3H), 1.78-1.8 (m, 1H), 1.39-1.45 (m, 1H); [M + H]$^+$ 517 | Single isomer, absolute stereochemistry unknown; Enantiomer of Ex. 94; Diastereomer of Ex. 92 and Ex. 93; 100% ee; retention time 5.98 min; column: Chiralcel OJ-H 250 × 4.6 mm I.D., 5 um; mobile phase: methanol (0.05% DEA) in CO2 from 5% to 40%; flow rate; 2.5 mL/min |

TABLE 1-continued

| Ex. No. | Structure/IUPAC name | Method | $^1$H NMR (ppm); LCMs [M + H]$^+$ | Stereochemistry Note |
|---|---|---|---|---|
| 96 | 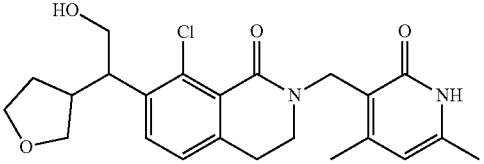<br>(+)-8-chloro-2-[(4,6-dimethyl-2-oxo-1,2-dihydropyridin-3-yl)methyl]-7-{(1S*)-2-hydroxy-1-[(3S*)-tetrahydrofuran-3-yl]ethyl}-3,4-dihydroisoquinolin-1(2H)-one | A | $^1$H NMR (400 MHz, CD3OD) δ 7.48 (d, J = 7.34 Hz, 1H), 7.18 (d, J = 7.83 Hz, 1H), 6.10 (s, 1H), 4.77 (s, 2H), 3.89-3.98 (m, 1H), 3.74-3.86 (m, 3H), 3.57 (t, J = 7.70 Hz, 2H), 3.42-3.51 (m, 2H), 3.16 (t, J = 8.31 Hz, 1H), 2.82-2.89 (m, 2H), 2.64-2.80 (m, 1H), 2.32-2.23 (m, 1H), 2.28 (s, 3H), 2.24 (s, 3H), 1.74-1.89 (m, 1H); [M + H]$^+$ 431 | [α]$_D$ = +51.7° (c 0.2 MeOH); (+) isomer of Ex. 64 racemate; either R,R or S,S isomer; absolute stereochemistry undetermined; Enantiomer of Ex. 97 |
| 97 | 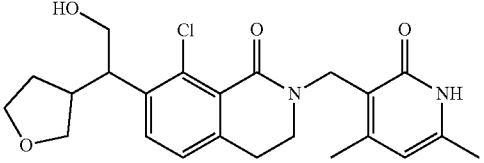<br>(−)-8-chloro-2-[(4,6-dimethyl-2-oxo-1,2-dihydropyridin-3-yl)methyl]-7-{(1R*)-2-hydroxy-1-[(3R*)-tetrahydrofuran-3-yl]ethyl}-3,4-dihydroisoquinolin-1(2H)-one | A | $^1$H NMR (400 MHz, CD3OD) δ 7.48 (d, J = 7.58 Hz, 1H), 7.18 (d, J = 7.83 Hz, 1H), 6.10 (s, 1H), 4.77 (s, 2H), 3.93 (dt, J = 3.79, 8.13 Hz, 1H), 3.74-3.86 (m, 3H), 3.57 (t, J = 7.83 Hz, 2H), 3.43-3.51 (m, 2H), 3.16 (t, J = 8.44 Hz, 1H), 2.85 (t, J = 5.75 Hz, 2H), 2.65-2.80 (m, 1H), 2.32-2.23 (m, 1H), 2.28 (s, 3H), 2.24 (s, 3H), 1.75-1.89 (m, 1H); [M + H]$^+$ 431 | [α]$_D$ = −27.4° (c 0.1 MeOH); (−) isomer of Ex. 64 racemate; either R,R or S,S isomer; absolute stereochemistry undetermined; Enantiomer of Ex. 96 |
| 98 | 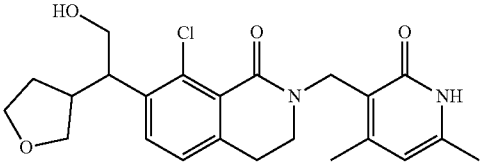<br>(+)-8-chloro-2-[(4,6-dimethyl-2-oxo-1,2-dihydropyridin-3-yl)methyl]-7-{(1R*)-2-hydroxy-1-[(3S*)-tetrahydrofuran-3-yl]ethyl}-3,4-dihydroisoquinolin-1(2H)-one | A | $^1$H NMR (400 MHz, CD3OD) δ 7.48 (d, J = 7.83 Hz, 1H), 7.19 (d, J = 7.82 Hz, 1H), 6.10 (s, 1H), 4.78 (s, 2H), 4.13 (t, J = 7.83 Hz, 1H), 3.78 (dt, J = 4.16, 8.31 Hz, 1H), 3.55-3.73 (m, 5H), 3.43-3.50 (m, 2H), 2.83-2.89 (m, 2H), 2.61-2.74 (m, 1H), 2.29 (s, 3H), 2.24 (s, 3H), 1.69-1.79 (m, 1H), 1.34-1.45 (m, 1H); [M + H]$^+$ 431 | [α]$_D$ = +20.5° (c 0.1 MeOH); (+) isomer of Ex. 65 racemate; either R,S or S,R isomer; absolute stereochemistry undetermined; Enantiomer of Ex. 99 |
| 99 | 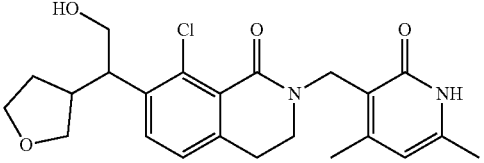<br>(−)-8-chloro-2-[(4,6-dimethyl-2-oxo-1,2-dihydropyridin-3-yl)methyl]-7-{(1S*)-2-hydroxy-1-[(3R*)-tetrahydrofuran-3-yl]ethyl}-3,4-dihydroisoquinolin-1(2H)-one | A | $^1$H NMR (400 MHz, CD3OD) δ 7.48 (d, J = 7.83 Hz, 1H), 7.19 (d, J = 8.07 Hz, 1H), 6.10 (s, 1H), 4.78 (s, 2H), 4.13 (t, J = 7.83 Hz, 1H), 3.78 (dt, J = 4.16, 8.31 Hz, 1H), 3.56-3.74 (m, 5H), 3.42-3.52 (m, 2H), 2.82-2.89 (m, 2H), 2.59-2.75 (m, 1H), 2.29 (s, 3H), 2.24 (s, 3H), 1.68-1.79 (m, 1H), 1.40 (qd, J = 8.57, 12.20 Hz, 1H); [M + H]$^+$ 431 | [α]$_D$ = −33.1° (c 0.1 MeOH); (−) isomer of Ex. 65 racemate; either R,S or S,R isomer; absolute stereochemistry undetermined; Enantiomer of Ex. 98 |

TABLE 1-continued

| Ex. No. | Structure/IUPAC name | Method | $^1$H NMR (ppm); LCMs [M + H]$^+$ | Stereochemistry Note |
|---|---|---|---|---|
| 100 | 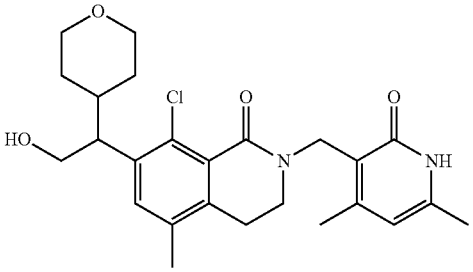<br>(+)-8-chloro-2-[(4,6-dimethyl-2-oxo-1,2-dihydropyridin-3-yl)methyl]-7-[2-hydroxy-1-(tetrahydro-2H-pyran-4-yl)-ethyl]-5-methyl-3,4-dihydroisoquinolin-1(2H)-one | A | $^1$H NMR (700 MHz, DMSO-d6) δ 7.27 (br. s., 1H), 5.89 (s, 1H), 4.50-4.61 (m, 2H), 3.84 (d, J = 8.88 Hz, 1H), 3.21-3.74 (m, 7H), 3.15 (td, J = 10.76, 3.59 Hz, 1H), 2.67 (t, J = 5.81 Hz, 2H), 2.19 (s, 3H), 2.15 (s, 3H), 2.12 (s, 3H), 1.82-1.91 (m, 1H), 1.78 (d, J = 12.64 Hz, 1H), 1.20-1.31 (m, 1H), 1.05-1.15 (m, 2H); [M + H]$^+$ 459 | [α]$_D$ = +10.8° (c 0.1 MeOH); 99% ee; absolute stereochemistry undetermined; Enantiomer of Ex. 101 |
| 101 | 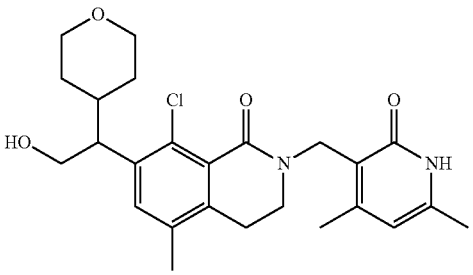<br>(−)-8-chloro-2-[(4,6-dimethyl-2-oxo-1,2-dihydropyridin-3-yl)methyl]-7-[2-hydroxy-1-(tetrahydro-2H-pyran-4-yl)ethyl]-5-methyl-3,4-dihydroisoquinolin-1(2H)-one | A | $^1$H NMR (700 MHz, DMSO-d6) δ 7.27 (br. s., 1H), 5.89 (s, 1H), 4.50-4.63 (m, 2H), 3.84 (d, J = 11.10 Hz, 1H), 3.20-3.75 (m, 7H), 3.15 (td, J = 10.89, 3.67 Hz, 1H), 2.67 (t, J = 5.89 Hz, 2H), 2.19 (s, 3H), 2.15 (s, 3H), 2.12 (s, 3H), 1.82-1.91 (m, 1H), 1.78 (d, J = 12.98 Hz, 1H), 1.20-1.30 (m, 1H), 1.06-1.15 (m, 2H); [M + H]$^+$ 459 | [α]$_D$ = −9.7° (c 0.1 MeOH); >99% ee; absolute stereochemistry undetermined; Enantiomer of Ex. 100 |
| 102 | 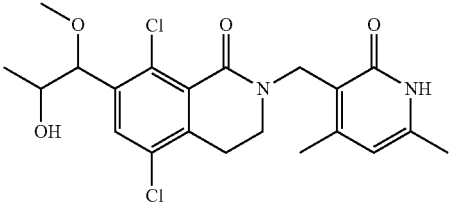<br>5,8-dichloro-2-[(4,6-dimethyl-2-oxo-1,2-dihydropyridin-3-yl)methyl]-7-(2-hydroxy-1-methoxypropyl)-3,4-dihydroisoquinolin-1(2H)-one | D | $^1$H NMR (400 MHz, CDCl3) δ 11.52 (br. s., 1H), 7.54 (s, 1H), 5.96 (s, 1H), 4.88 (br. s., 1H), 4.77 (s, 2H), 4.08-4.11 (m, 1H), 3.65-3.70 (m, 2H), 3.31 (s, 3H), 2.99-2.91 (m, 2H), 2.37 (s, 3H), 2.29 (s, 3H), 1.05 (d, J = 6.4 Hz, 3H); [M + H]$^+$ 439 | Mixture of 4 possible diastereomers |
| 103 | 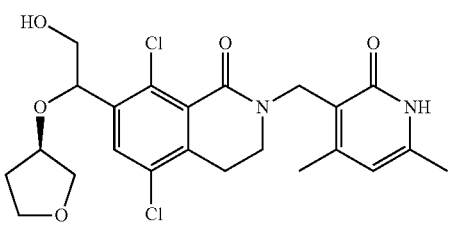<br>5,8-dichloro-2-[(4,6-dimethyl-2-oxo-1,2-dihydropyridin-3-yl)methyl]-7-{2-hydroxy-1-[(3R)-tetrahydrofuran-3-yloxy]ethyl}-3,4-dihydroisoquinolin-1(2H)-one | D | $^1$H NMR (400 MHz, CD3OD) δ 7.52 (s, 1H), 6.00 (s, 1H), 4.97 (dd, J = 7.15, 2.87 Hz, 1H), 4.66 (s, 2H), 4.00-4.05 (m, 1H), 3.83-3.91 (m, 1H), 3.72 (td, J = 8.34, 4.10 Hz, 1H), 3.56-3.66 (m, 3H), 3.37-3.45 (m, 3H), 2.88 (t, J = 6.24 Hz, 2H), 2.19 (s, 3H), 2.15 (s, 3H), 2.05-2.13 (m, 1H), 1.85-1.97 (m, 1H); [M + H]$^+$ 481 | Single isomer, (R) at THF center, other chiral center undetermined; Diastereomer of Ex. 104; 99% de; retention time 1.088 min on Chiralcel OJ-3 4.6 × 100 mm 3u column; 10% MeOH @ 120 bar, 4 mL/min |

TABLE 1-continued

| Ex. No. | Structure/IUPAC name | Method | $^1$H NMR (ppm); LCMs [M + H]$^+$ | Stereochemistry Note |
|---|---|---|---|---|
| 104 | 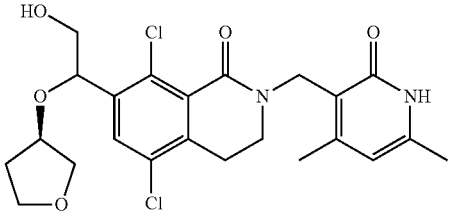<br>5,8-dichloro-2-[(4,6-dimethyl-2-oxo-1,2-dihydropyridin-3-yl)methyl]-7-{2-hydroxy-1-[(3R)-tetrahydrofuran-3-yloxy]ethyl}-3,4-dihydroisoquinolin-1(2H)-one | D | $^1$H NMR (400 MHz, CD3OD) δ 7.57 (s, 1H), 6.00 (s, 1H), 4.91 (dd, J = 7.03, 2.87 Hz, 1H), 4.65 (s, 2H), 4.04-4.11 (m, 1H), 3.90 (d, J = 9.66 Hz, 1H), 3.78 (q, J = 8.07 Hz, 1H), 3.62-3.69 (m, 2H), 3.59 (dd, J = 11.86, 2.93 Hz, 1H), 3.37-3.45 (m, 3H), 2.88 (t, J = 6.24 Hz, 2H), 2.19 (s, 3H), 2.15 (s, 3H), 1.74-1.96 (m, 2H); [M + H]$^+$ 481 | Single isomer, (R) at THF center, other chiral center undetermined; Diastereomer of Ex. 103; 94% de; retention time 1.558 min on Chiralcel OJ-3 4.6 × 100 mm 3u column; 10% MeOH @ 120 bar, 4 mL/min |
| 105 | 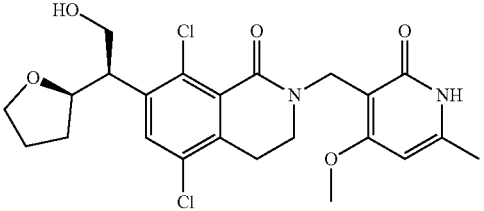<br>5,8-dichloro-7-{(1R)-2-hydroxy-1[(2R)-tetrahydrofuran-2-yl]ethyl}-2-[(4-methoxy-6-methyl-2-oxo-1,2-dihydropyridin-3-yl)methyl]-3,4-dihydroisoquinolin-1(2H)-one | E | $^1$H NMR (400 MHz, CD3OD) δ 7.67 (s, 1H), 6.27 (s, 1H), 4.74 (s, 2H), 4.28-4.29 (m, 1H), 3.90-3.79 (m, 6H), 3.69 (t, J = 6.8 Hz, 2H), 3.40 (t, J = 6.0 Hz, 2H), 2.94 (t, J = 6.0 Hz, 2H), 2.34 (s, 3H), 2.10-2.07 (m, 1H), 1.90-1.86 (m, 1H), 1.77-1.75 (m, 1H), 1.60-1.56 (m, 1H); [M + H]$^+$ 481 | 1R,2R isomer; Diastereomer of Ex. 106; retention time: 3.480 min; column: Chiralpak AD-3 150 × 4.6 mm I.D., 3 um; mobile phase 40% ethanol (0.05% DEA) in CO2 |
| 106 | 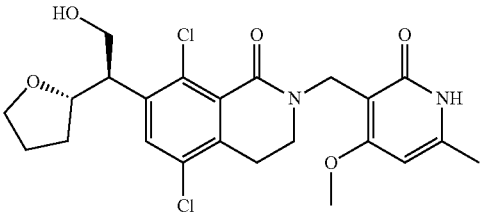<br>5,8-dichloro-7-{(1R)-2-hydroxy-1-[(2S)-tetrahydrofuran-2-yl]ethyl}-2-[(4-methoxy-6-methyl-2-oxo-1,2-dihydropyridin-3-yl)methyl]-3,4-dihydroisoquinolin-1(2H)-one | E | $^1$H NMR (400 MHz, CD3OD) δ 7.60 (s, 1H), 6.27 (s, 1H), 4.74 (s, 2H), 4.20-4.18 (m, 1H), 3.97-3.92 (m, 6H), 3.91-3.80 (m, 1H), 3.70 (s, 1H), 3.40 (t, J = 5.6 Hz, 2H), 2.95 (t, J = 6.0 Hz, 2H), 2.34 (s, 3H), 1.96-1.82 (m, 3H), 1.55-1.50 (m, 1H); [M + H]$^+$ 481 | 1R,2S isomer; Diastereomer of Ex. 105; retention time: 2.507 min; column: Chiralpak AD-3 150 × 4.6 mm I.D., 3 um; mobile phase 40% ethanol (0.05% DEA) in CO2 |
| 107 | 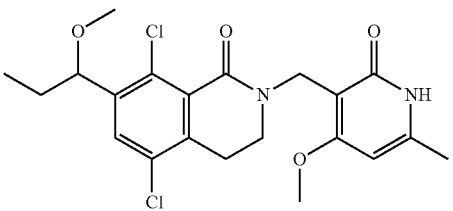<br>5,8-dichloro-2-[(4-methoxy-6-methyl-2-oxo-1,2-dihydropyridin-3-yl)methyl]-7-(1-methoxypropyl)-3,4-dihydroisoquinolin-1(2H)-one - Isomer A | G | $^1$H NMR (400 MHz, CD3OD) δ 7.56 (s, 1H), 6.27 (s, 1H), 4.73 (s, 2H), 4.70-4.72 (m, 1H), 3.91 (s, 3H), 3.40-3.43 (m, 2H), 3.26 (s, 3H), 2.95-2.99 (m, 2H), 2.34 (s, 3H), 1.74-1.79 (m, 1H), 1.62-1.67 (m, 1H), 0.99 (t, J = 7.2 Hz, 3H); [M + H]$^+$ 439 | Single isomer, absolute stereochemistry unknown; Enantiomer of Ex. 108; 100% ee; retention time 11.41 min; column: Pheno Lux Cellulose-2, 150 × 4.6 mm I.D., 5 um; mobile phase: 50% MeOH (0.05% DEA) in CO2; Flow rate: 2.0 mL/min |

TABLE 1-continued

| Ex. No. | Structure/IUPAC name | Method | $^1$H NMR (ppm); LCMs [M + H]$^+$ | Stereochemistry Note |
|---|---|---|---|---|
| 108 | 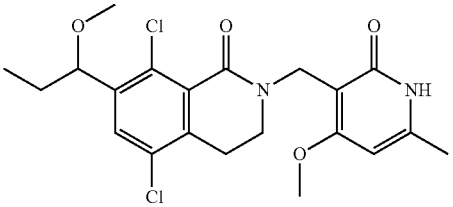

5,8-dichloro-2-[(4-methoxy-6-methyl-2-oxo-1,2-dihydropyridin-3-yl)methyl]-7-(1-methoxypropyl)-3,4-dihydroisoquinolin-1(2H)-one - Isomer B | G | $^1$H NMR (400 MHz, CD3OD) δ 7.56 (s, 1H), 6.27 (s, 1H), 4.74 (s, 2H), 4.70-4.72 (m, 1H), 3.91 (s, 3H), 3.40-3.43 (m, 2H), 3.26 (S, 3H), 2.95-2.99 (m, 2H), 2.34 (s, 3H), 1.73-1.77 (m, 1H), 1.62-1.67 (m, 1H), 0.99 (t, J = 7.4 Hz, 3H); [M + H]$^+$ 439 | Single isomer, absolute stereochemistry unknown; Enantiomer of Ex. 107; 99% ee; retention time 15.01 min; column: Pheno Lux Cellulose-2, 150 × 4.6 mm I.D., 5 um; mobile phase: 50% MeOH (0.05% DEA) in CO2; Flow rate: 2.0 mL/min |
| 109 | 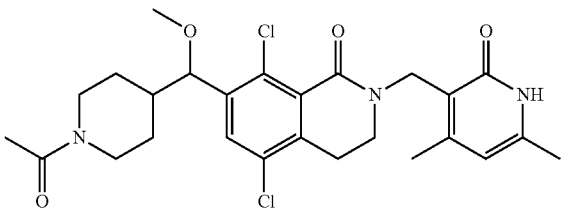

7-[(1-acetylpiperidin-4-yl)(methoxy)methyl]-5,8-dichloro-2-[(4,6-dimethyl-2-oxo-1,2-dihydropyridin-3-yl)methyl]-3,4-dihydroisoquinolin-1(2H)-one - Isomer A | I | $^1$H NMR (400 MHz, CDCl3) δ 12.03 (br. s., 1H), 7.46 (s, 1H), 5.95 (s, 1H), 4.74-4.82 (m, 2H), 4.64-4.65 (m, 2H), 3.77-3.79 (m, 1H), 3.68 (t, J = 5.8 Hz, 2H), 3.19 (s, 3H), 2.90-2.96 (m, 3H), 2.41-2.47 (m, 1H), 2.37 (s, 3H), 2.29 (s, 3H), 2.07 (s, 3H), 1.83-1.86 (m, 1H), 1.52-1.57 (m, 2H), 1.34-1.41 (m, 2H); [M + H]$^+$ 520 | Single isomer, absolute stereochemistry unknown; Enantiomer of Ex. 110; 100% ee; retention time: 10.42 min; column: Chiralpak AD-H 250 × 4.6 mm I.D., 5 um; mobile phase: 5-40% methanol (0.05% DEA) in CO2; flow rate: 2.5 mL/min |
| 110 | 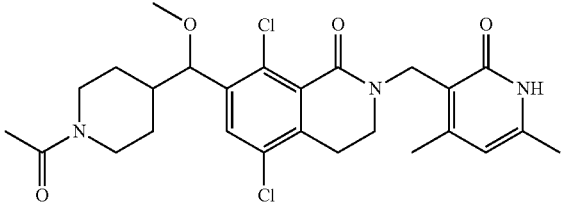

7-[(1-acetylpiperidin-4-yl)(methoxy)methyl]-5,8-dichloro-2-[4,6-dimethyl-2-oxo-1,2-dihydropyridin-3-yl)methyl]-3,4-dihydroisoquinolin-1(2H)-one - Isomer B | I | $^1$H NMR (400 MHz, CDCl3) δ 12.01 (br. s., 1H), 7.47 (s, 1H), 5.95 (S, 1H), 4.74-4.82 (m, 2H), 4.62-4.65 (m, 2H), 3.76-3.79 (m, 1H), 3.69 (t, J = 6 Hz, 2H), 3.19 (s, 3H), 2.90-2.96 (m, 3H), 2.41-2.47 (m, 1H), 2.37 (s, 3H), 2.29 (s, 3H), 2.07 (s, 3H), 1.83-1.86 (m, 1H), 152-1.58 (m, 2H), 1.34-1.40 (m, 2H); [M + H]$^+$ 520 | Single isomer, absolute stereochemistry unknown; Enantiomer of Ex. 109; 93% ee; retention time: 11.08 min; column: Chiralpak AD-H 250 × 4.6 mm I.D., 5 um; mobile phase: 5-40% methanol (0.05% DEA) in CO2; flow rate: 2.5 mL/min |
| 111 | 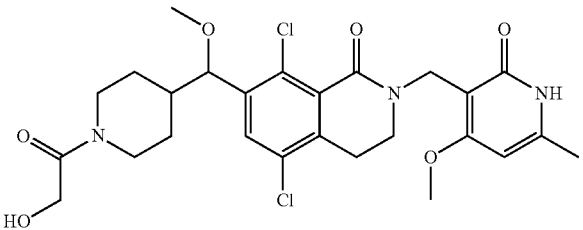

5,8-dichloro-7-{[1-(hydroxyacetyl)piperidin-4-yl](methoxy)-methyl}-2-[(4-methoxy-6-methyl-2-oxo-1,2-dihydropyridin-3-yl)methyl]-3,4-dihydroisoquinolin-1(2H)-one - Isomer A | I | $^1$H NMR (400 MHz, CDCl3) δ 12.06 (s, 1H), 7.44 (d, J = 3.2 Hz, 1H), 5.93 (s, 1H), 4.78 (s, 2H), 462-4.64 (m, 2H), 4.10-4.14 (m, 2H), 3.88 (s, 3H), 3.72 (s, 1H), 347-3.53 (m, 3H), 3.20 (s, 3H), 2.84-296 (m, 3H), 2.46-2.60 (m, 1H) (m, 2.35 (s, 3H), 1.70-1.72 (m, 1H), 1.58-1.59 (m, 2H), 1.33-1.46 (m, 2H); [M + Na]$^+$ 574 | Single isomer, absolute stereochemistry unknown; Enantiomer of Ex. 112; 100% ee; retention time: 9.21 min; column: Chiralpak AD-3 150 × 4.6 mm I.D., 3 um; mobile phase: 30% ethanol (0.1% ethanolamine) in CO2 |

TABLE 1-continued

| Ex. No. | Structure/IUPAC name | $^1$H NMR (ppm); LCMs Method [M + H]$^+$ | Stereochemistry Note |
|---|---|---|---|
| 112 | 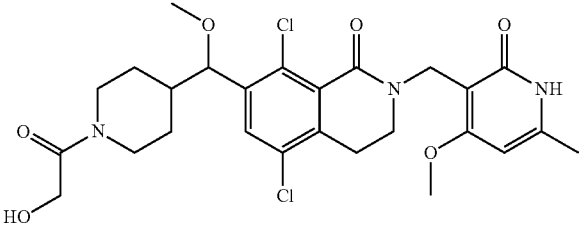<br>5,8-dichloro-7-{[1-(hydroxyacetyl)piperidin-4-yl](methoxy)methyl}-2-[(4-methoxy-6-methyl-2-oxo-1,2-dihydropyridin-3-yl)methyl]-3,4-dihydroisoquinolin-1(2H)-one - Isomer B | I $^1$H NMR (400 MHz, CDCl3) δ 11.98 (s, 1H), 7.44 (d, J = 3.6 Hz, 1H), 5.93 (s, 1H), 4.77-4.81 (m, 2H), 4.59-4.64 (m, 2H), 4.10-4.14 (m, 2H), 3.88 (s, 3H), 3.72 (s, 1H), 3.47-3.53 (m, 3H), 3.20 (s, 3H), 2.83-296 (m, 3H), 2.46-2.60 (m, 1H), 2.35 (s, 3H), 1.89-1.90 (m, 1H), 1.58-1.59 (m, 2H), 1.33-1.48 (m, 2H); [M + Na]$^+$ 574 | Single isomer, absolute stereochemistry unknown; Enantiomer of Ex. 111; 100% ee; retention time: 11.45 min; column: Chiralpak AD-3 150 × 4.6 mm I.D., 3 um; mobile phase: 30% ethanol (0.1% ethanolamine) in CO2 |
| 113 | 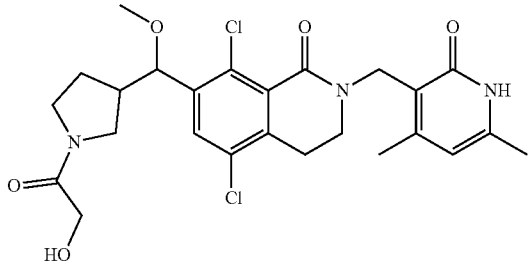<br>5,8-dichloro-2-[(4,6-dimethyl-2-oxo-1,2-dihydropyridin-3-yl)methyl]-7-{[1-(hydroxyacetyl)pyrrolidin-3-yl]-(methoxy)methyl}-3,4-dihydroisoquinolin-1(2H)-one | I $^1$H NMR (400 MHz, CD3OD) δ 7.63 (s, 1H), 6.13 (s, 1H), 4.78 (s, 2H), 4.09-4.17 (m, 2H), 3.67 (brs, 1H), 3.52-3.60 (m, 3H), 3.40-3.50 (m, 1H), 3.22-3.25 (m, 3H), 3.00-3.03 (m, 2H), 2.54-2.74 (m, 1H), 2.32 (s, 3H), 2.27 (s, 3H), 1.73-2.07 (m, 3H); [M + H]$^+$ 522 | mixture of diastereomers |
| 114 | 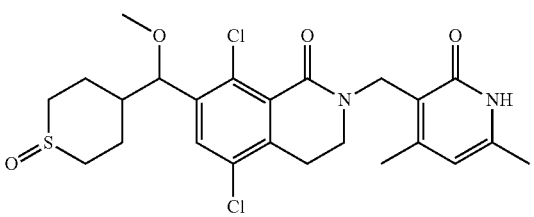<br>5,8-dichloro-2-[(4,6-dimethyl-2-oxo-1,2-dihydropyridin-3-yl)methyl]-7-[methoxy(1-oxidotetrahydro-2H-thiopyran-4-yl)methyl]-3,4-dihydroisoquinolin-1(2H)-one - Isomer A | I $^1$H NMR (400 MHz, CD3OD) δ 7.54 (s, 1H), 6.11 (s, 1H), 4.75-4.81 (m, 2H), 4.60-4.68 (m, 1H), 3.53 (t, J = 6.2 Hz, 2H), 3.31-3.37 (m, 2H), 3.20 (s, 3H), 2.98-2.99 (m, 2H), 2.59-2.66 (m, 2H), 2.30 (s, 3H), 2.25 (s, 3H), 2.06-2.15 (m, 1H), 1.71-1.92 (m, 4H); [M + H]$^+$ 511 | Single isomer, absolute stereochemistry unknown; Enantiomer of Ex. 115; 100% ee; retention time: 6.190 min; column: Chiralcel OJ-H 250 × 46 mm I.D., 5 um; mobile phase: 5-40% methanol (0.05% DEA) in CO2 |
| 115 | 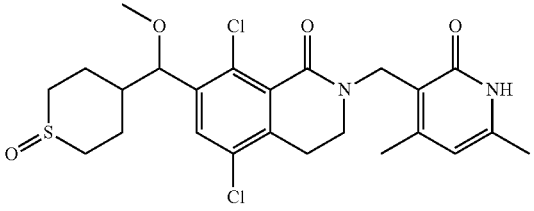<br>5,8-dichloro-2-[(4,6-dimethyl-2-oxo-1,2-dihydropyridin-3-yl)-methyl]-7-[methoxy(1-oxidotetrahydro-2H-thiopyran-4-yl)-methyl]-3,4-dihydroisoquinolin-1(2H)-one - Isomer B | I $^1$H NMR (400 MHz, CD3OD) δ 7.54 (s, 1H), 6.11 (s, 1H), 4.75-4.76 (m, 2H), 4.66-4.68 (m, 1H), 3.52 (t, J = 6.4 Hz, 2H), 3.37-3.51 (m, 2H), 3.20 (s, 3H), 2.99 (t, J = 6.0 Hz, 2H), 2.60-2.68 (m, 2H), 2.30 (s, 3H), 2.25 (s, 3H), 2.06-2.09 (m, 1H), 1.71-1.96 (m, 4H); [M + H]$^+$ 511 | Single isomer, absolute stereochemistry unknown; Enantiomer of Ex. 114; 98% ee; retention time: 6.995 min; column: Chiralcel OJ-H 250 × 4.6 mm I.D., 5 um; mobile phase: 5-40% methanol (0.05% DEA) in CO2 |

TABLE 1-continued

| Ex. No. | Structure/IUPAC name | Method | ¹H NMR (ppm); LCMs [M + H]⁺ | Stereochemistry Note |
|---|---|---|---|---|
| 116 | 5,8-dichloro-2-[(4,6-dimethyl-2-oxo-1,2-dihydro-pyridin-3-yl)methyl]-7-[(1,1-dioxidotetrahydro-2H-thiopyran-4-yl)(methoxy)methyl]-3,4-dihydroisoquinolin-1(2H)-one - Isomer A | I | ¹H NMR (400 MHz, CD3OD) δ 7.56 (s, 1H), 6.11 (s, 1H), 4.83 (s, 2H), 4.70-4.75 (m, 1H), 3.52 (t, J = 6.2 Hz, 2H), 3.23 (s, 3H), 2.99-3.20 (m, 6H), 2.30 (s, 3H), 2.24 (s, 3H), 1.97-1.99 (m, 2H), 1.91-1.95 (m, 3H); [M + H]⁺ 527 | Single isomer, absolute stereochemistry unknown; Enantiomer of Ex. 117; 100% ee; retention time: 1.170 min; column: Chiralcel OJ-3 50*4.6 mm I.D., 3 um; mobile phase: 5-40% methanol (0.05% DEA) in CO2 |
| 117 | 5,8-dichloro-2-[(4,6-dimethyl-2-oxo-1,2-dihydro-pyridin-3-yl)methyl]-7-[(1,1-dioxidotetrahydro-2H-thiopyran-4-yl)(methoxy)methyl]-3,4-dihydro-isoquinolin-1(2H)-one - Isomer B | I | ¹H NMR (400 MHz, CD3OD) δ 7.56 (s, 1H), 6.12 (s, 1H), 4.81 (s, 2H), 4.71-4.79 (m, 1H), 3.53 (t, J = 6.0 Hz, 2H), 3.23 (s, 3H), 2.99-3.20 (m, 6H), 2.30 (s, 3H), 2.25 (s, 3H), 2.10-2.16 (m, 2H), 1.92-2.00 (m, 3H); [M + H]⁺ 527 | Single isomer, absolute stereochemistry unknown; Enantiomer of Ex. 116; 92% ee; retention time: 1.364 min; column: Chiralcel OJ-3 50*4.6 mm I.D., 3 um; mobile phase: 5-40% methanol (0.05% DEA) in CO2 |
| 118 | 4-[{5,8-dichloro-2-[(4-methoxy-6-methyl-2-oxo-1,2-dihydropyridin-3-yl)methyl]-1-oxo-1,2,3,4-tetrahydroisoquinolin-7-yl}(methoxy)methyl]-piperidine-1-carbaldehyde - Isomer A | I | ¹H NMR (400 MHz, CDCl3) δ 12.40 (s, 1H), 7.99 (s, 1H), 7.45 (d, J = 2.0 Hz, 1H), 5.94 (s, 1H), 4.78-4.82 (m, 2H), 4.63 (d, J = 4.8 Hz, 1H), 4.40-4.44 (m, 1H), 3.88 (s, 3H), 3.59-3.62 (m, 1H), 3.49-3.52 (m, 2H), 3.20 (s, 3H), 2.91-2.96 (m, 3H), 2.46-2.50 (m, 1H), 2.36 (s, 3H), 1.88-1.89 (m, 1H), 1.26-1.57 (m, 4H); [M + H]⁺ 522 | Single isomer, absolute stereochemistry unknown; Enantiomer of Ex. 119; 100% ee; retention time: 7.866 min; column: Chiralpak AS-H 250 × 4.6 mm I.D., 5 um; mobile phase: 20% methanol (0.1% ethanolamine) in CO2 |
| 119 | 4-[{5,8-dichloro-2-[(4-methoxy-6-methyl-2-oxo-1,2-dihydropyridin-3-yl)methyl]-1-oxo-1,2,3,4-tetrahydroisoquinolin-7-yl}(methoxy)methyl]-piperidine-1-carbaldehyde - Isomer B | I | ¹H NMR (400 MHz, CDCl3) δ 12.29 (s, 1H), 8.00 (s, 1H), 7.45 (d, J = 2.4 Hz, 1H), 5.93 (s, 1H), 4.74-4.78 (m, 2H), 4.64 (d, J = 5.2 Hz, 1H), 4.41-4.44 (m, 1H), 3.88 (s, 3H), 3.59-3.63 (m, 1H), 3.51-3.52 (m, 2H), 3.20 (s, 3H), 2.93-3.01 (m, 3H), 2.47-2.53 (m, 1H), 2.35 (s, 3H), 1.89-1.90 (m, 1H), 1.75-1.77 (m, 1H), 1.26-1.57 (m, 3H); [M + H]⁺ 522 | Single isomer, absolute stereochemistry unknown; Enantiomer of Ex. 118; 94% ee; retention time: 9.458 min; column: Chiralpak AS-H 250 × 4.6 mm I.D., 5 um; mobile phase: 20% methanol (0.1% ethanolamine) in CO2 |

TABLE 1-continued

| Ex. No. | Structure/IUPAC name | Method | ¹H NMR (ppm); LCMs [M + H]⁺ | Stereochemistry Note |
|---|---|---|---|---|
| 120 | 5,8-dichloro-2-[(4,6-dimethyl-2-oxo-1,2-dihydropyridin-3-yl)methyl]-7-[(4-fluoro-1-methylpiperidin-4-yl)(methoxy)methyl]-3,4-dihydroisoquinolin-1(2H)-one - Isomer A | I | ¹H NMR (400 MHz, DMSO-d6) δ 11.58 (brs, 1H), 7.49 (s, 1H), 5.90 (s, 1H), 4.85 (d, J = 18.8 Hz, 1H), 4.57 (s, 2H), 3.51-3.46 (m, 2H), 3.16 (s, 3H), 2.91 (t, J = 6 Hz, 2H), 2.58-2.64 (m, 2H), 2.19 (s, 3H), 2.14 (s, 3H), 2.13 (s, 3H), 1.93-2.03 (m, 3H), 1.68-1.87 (m, 2H), 1.36 (t, J = 10.8 Hz, 1H); [M + H]⁺ 510 | Single isomer, absolute stereochemistry unknown; Enantiomer of Ex. 121; 90% ee; retention time: 7.533 min; column: AD-H 250 × 4.6 mm I.D., 5 um; mobile phase: 5-40% isopropanol (0.05% DEA) in CO2 |
| 121 | 5,8-dichloro-2-[(4,6-dimethyl-2-oxo-1,2-dihydropyridin-3-yl)methyl]-7-[(4-fluoro-1-methylpiperidin-4-yl)(methoxy)methyl]-3,4-dihydroisoquinolin-1(2H)-one - Isomer B | I | ¹H NMR (400 MHz, DMSO-d6) δ 11.59 (s, 1H), 10.77 (brs, 1H), 7.51 (S, 1H), 5.90 (s, 1H), 4.93 (d, J = 18.4 Hz, 1H), 4.57 (s, 2H), 3.50-3.52 (m, 3H), 3.19 (s, 3H), 2.92-3.05 (m, 4H), 2.72 (s, 3H), 2.13-2.34 (m, 9H), 1.65 (brs, 1H); [M + Na]⁺ 532 | Single isomer, absolute stereochemistry unknown; Enantiomer of Ex. 120; 91% ee; retention time: 7.810 min; column: AD-H 250 × 4.6 mm I.D., 5 um; mobile phase: 5-40% isopropanol (0.05% DEA) in CO2 |
| 122 | 7-[(1-acetylpiperidin-4-yl)(methoxy)methyl]-5,8-dichloro-2-[(4-methoxy-6-methyl-2-oxo-1,2-dihydropyridin-3-yl)-methyl]-3,4-dihydroisoquinolin-1(2H)-one - Isomer A | I | ¹H NMR (400 MHz, CDCl3) δ 12.40 (brs, 1H), 7.45 (d, J = 2 Hz, 1H), 5.94 (s, 1H), 4.77-4.79 (m, 2H), 4.63 (d, J = 5.2 Hz, 2H), 3.88 (s, 3H), 3.80-3.83 (m, 1H), 3.51 (s, 2H), 3.20 (s, 3H), 2.93-2.96 (m, 3H), 2.36-2.38 (m, 4H), 2.07 (s, 3H), 1.71-1.72 (m, 1H), 1.42-1.52 (m, 4H); [M + H]⁺ 536 | Single isomer, absolute stereochemistry unknown; Enantiomer of Ex. 123; 100% ee; retention time: 9.93 min; column: Chiralpak AD-H 250 × 4.6 mm I.D., 5 um; mobile phase: 5-40% methanol (0.05% DEA) in CO2 |
| 123 | 7-[(1-acetylpiperidin-4-yl)(methoxy)methyl]-5,8-dichloro-2-[(4-methoxy-6-methyl-2-oxo-1,2-dihydropyridin-3-yl)-methyl]-3,4-dihydroisoquinolin-1(2H)-one - Isomer B | I | ¹H NMR (400 MHz, CDCl3) δ 12.26 (brs, 1H), 7.45 (d, J = 2.4 Hz, 1H), 5.95 (s, 1H), 4.73-482 (m, 2H), 4.63 (d, J = 4.8 Hz, 2H), 3.89 (s, 3H), 3.79-3.82 (m, 1H), 3.51 (s, 2H), 3.20 (s, 3H), 2.91-2.96 (m, 3H), 2.36-2.44 (m, 4H), 2.07 (s, 3H), 1.38-1.71 (m, 5H); [M + H]⁺ 536 | Single isomer, absolute stereochemistry unknown; Enantiomer of Ex. 122; 97% ee; retention time: 10.60 min; column: Chiralpak AD-H 250 × 4.6 mm I.D., 5 um; mobile phase: 5-40% methanol (0.05% DEA) in CO2 |
| 124 | 5,8-dichloro-2-[4-methoxy-6-methyl-2-oxo-1,2-dihydropyridin-3-yl)methyl]-7-[methoxy(tetrahydrofuran-3-yl)methyl]-3,4-dihydroisoquinolin-1(2H)-one - Isomer A | I | ¹H NMR (400 MHz, CDCl3) δ 12.35 (s, 1H), 7.53 (s, 1H), 5.93 (s, 1H), 4.78-4.84 (m, 3H), 3.72-3.88 (m, 6H), 3.51-3.70 (m, 1H), 3.48-3.50 (m, 2H), 3.18 (s, 3H), 2.95-2.96 (m, 2H), 2.55-2.60 (m, 1H), 2.35 (s, 3H), 1.70-1.76 (m, 2H); [M + H]⁺ 481 | Single isomer, absolute stereochemistry unknown; Enantiomer of Ex. 126; Diastereomer of Ex. 125 and Ex. 127; 92% ee; retention time: 12.59 min; column: Chiralpak AD-H 250 × 4.6 mm I.D., 5 um; mobile phase: 40/60 hexane (0.1% DEA)/isopropanol (0.1% ethanolamine) |

TABLE 1-continued

| Ex. No. | Structure/IUPAC name | Method | $^1$H NMR (ppm); LCMs [M + H]$^+$ | Stereochemistry Note |
|---|---|---|---|---|
| 125 | 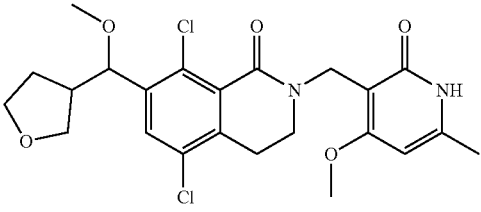<br>5,8-dichloro-2-[4-methoxy-6-methyl-2-oxo-1,2-dihydro-pyridin-3-yl)methyl]-7-[methoxy(tetrahydrofuran-3-yl)methyl]-3,4-dihydroisoquinolin-1(2H)-one - Isomer B | I | $^1$H NMR (400 MHz, DMSO-d6) δ 11.46 (s, 1H), 7.57 (s, 1H), 6.10 (s, 1H), 4.72 (d, J = 8.8 Hz, 1H), 4.51 (s, 2H), 3.78 (s, 3H), 3.74-3.69 (m, 3H), 3.59-3.57 (m, 1H), 3.30-3.29 (m, 2H), 3.09 (s, 3H), 2.89-2.87 (m, 2H), 2.51-2.50 (m, 1H), 2.19 (s, 3H), 1.51-1.47 (m, 2H); [M + H]$^+$ 481 | Single isomer, absolute stereochemistry unknown; Enantiomer of Ex. 127; Diastereomer of Ex. 124 and Ex. 126; 98% ee; retention time: 13.43 min; column: Chiralpak AD-H 250 × 4.6 mm I.D., 5 um; mobile phase: 70/30 hexane (0.1% DEA)/isopropanol (0.1% ethanolamine) |
| 126 | 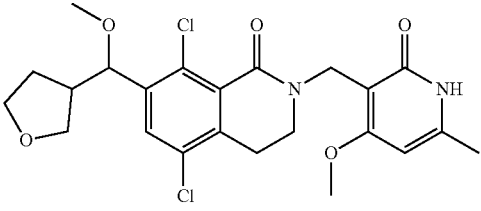<br>5,8-dichloro-2-[(4-methoxy-6-methyl-2-oxo-1,2-dihydropyridin-3-yl)methyl]-7-[methoxy(tetrahydrofuran-3-yl)methyl]-3,4-dihydroisoquinolin-1(2H)-one - Isomer C | I | $^1$H NMR (400 MHz, CDCl3) δ 12.62 (s, 1H), 7.52 (s, 1H), 5.93 (s, 1H), 4.77-4.83 (m, 3H), 3.87-3.91 (m, 4H), 3.72-3.76 (m, 2H), 3.62-3.63 (m, 1H), 3.48-3.51 (m, 2H), 3.22 (s, 3H), 2.94-2.96 (m, 2H), 2.63-2.65 (m, 1H), 2.35 (s, 3H), 1.95-1.96 (m, 1H), 1.80-1.82 (m, 1H); [M + H]$^+$ 481 | Single isomer, absolute stereochemistry unknown; Enantiomer of Ex. 124; Diastereomer of Ex. 125 and Ex. 127; 100% ee; retention time: 13.65 min; column: Chiralpak AD-H 250 × 4.6 mm I.D., 5 um; mobile phase: 40/60 hexane 0.1% DEA)/isopanol (0.1% ethanolamine) |
| 127 | 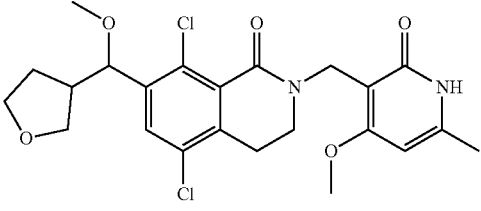<br>5,8-dichloro-2-[(4-methoxy-6-methyl-2-oxo-1,2-dihydropyridin-3-yl)methyl]-7-[methoxy(tetrahydrofuran-3-yl)methyl]-3,4-dihydroisoquinolin-1(2H)-one - Isomer D | I | $^1$H NMR (400 MHz, DMSO-d6) δ 11.44 (s, 1H), 7.53 (s, 1H), 6.09 (s, 1H), 4.70 (d, J = 6.4 Hz, 1H), 4.50 (s, 2H), 3.70-3.77 (m, 4H), 3.58-3.60 (m, 2H), 3.37-3.41 (m, 2H), 3.13 (s, 3H), 2.86-2.88 (m, 2H), 2.57-2.59 (m, 1H), 2.18 (s, 3H), 1.70-1.85 (m, 2H); [M + H]$^+$ 481 | Single isomer, absolute stereochemistry unknown; Enantiomer of Ex. 125; Diastereomer of Ex. 124 and Ex. 126; 99% ee; retention time: 14.76 min; column: Chiralpak AD-H 250 ×4.6 mm I.D., 5 um; mobile phase: 70/30 hexane (0.1% DEA)/isopropanol (0.1% ethanolamine) |
| 128 | 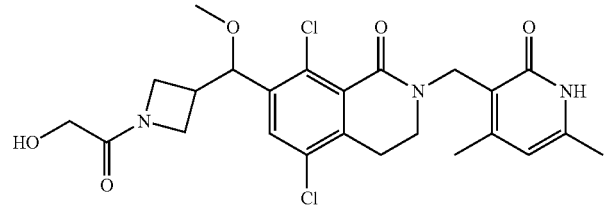<br>5,8-dichloro-2-[(4,6-dimethyl-2-oxo-1,2-dihydropyridin-3-yl)-methyl]-7-{[1-(hydroxyacetyl)azetidin-3-yl](methoxy)methyl}-3,4-dihydroisoquinolin-1(2H)-one - Isomer A | I | $^1$H NMR (400 MHz, DMSO-d6) δ 11.57 (s, 1H), 7.56 (s, 1H), 5.89 (s, 1H), 4.85-4.92 (m, 2H), 4.57 (s, 2H), 4.09-4.19 (m, 1H), 3.97-4.04 (m, 1H), 3.81-3.90 (m, 3H), 3.71-3.78 (m, 1H), 3.46 (t, J = 6.40 Hz, 2H), 3.22 (s, 3H), 2.95-3.05 (m, 1H), 2.90 (t, J = 5.9 Hz, 2H), 2.17 (s, 3H), 2.13 (s, 3H); [M + Na]$^+$ 530 | Single isomer, absolute stereochemistry unknown; Enantiomer of Ex. 129; 100% ee; retention time: 8.161 min; column: Chiracel OD-H 150 × 4.6 mm I.D., 5 um; mobile phase: 5-40% methanol (0.05% DEA) in CO2 |

TABLE 1-continued

| Ex. No. | Structure/IUPAC name | Method | ¹H NMR (ppm); LCMs [M + H]⁺ | Stereochemistry Note |
|---|---|---|---|---|
| 129 | 5,8-dichloro-2-[(4,6-dimethyl-2-oxo-1,2-dihydropyridin-3-yl)-methyl]-7-{[1-(hydroxyacetyl)azetidin-3-yl](methoxy)methyl}-3,4-dihydroisoquinolin-1(2H)-one - Isomer B | I | ¹H NMR (400 MHz, DMSO-d6) δ 11.46 (brs, 1H), 7.56 (s, 1H), 5.90 (s, 1H), 5.07-4.74 (m, 2H), 4.58 (s, 2H), 4.18-4.10 (m, 1H), 4.02-3.98 (m, 1H), 3.93-3.81 (m, 3H), 3.77-3.71 (m, 1H), 3.46 (t, J = 6 Hz, 2H), 3.22 (s, 3H), 3.03-2.96 (m, 1H), 2.90 (t, J = 6 Hz, 2H), 2.17 (s, 3H), 2.13 (s, 3H); [M + Na]⁺ 530 | Single isomer, absolute stereochemistry unknown; Enantiomer of Ex. 128; 96% ee; retention time: 8.511 min; column: Chiracel OD-H 150 × 4.6 mm I.D., 5 um; mobile phase: 5-40% methanol (0.05% DEA) in CO2 |
| 130 | 8-chloro-2-[(4,6-dimethyl-2-oxo-1,2-dihydropyridin-3-yl)-methyl]-7-[(1,1-dioxidotetrahydro-2H-thiopyran-4-yl)-(methoxy)methyl]-5-methyl-3,4-dihydroisoquinolin-1(2H)-one - Isomer A | I | ¹H NMR (400 MHz, CDCl3) δ 11.75 (brs, 1H), 7.24 (s, 1H), 5.94 (s, 1H), 4.78-4.83 (m, 2H), 4.69 (d, J = 5.20 Hz, 1H), 3.63 (t, J = 6.00 Hz, 2H), 3.18 (s, 3H), 3.02-3.10 (m, 2H), 2.79-2.94 (m, 2H), 2.75 (t, J = 6.00 Hz, 2H), 2.36 (s, 3H), 2.28 (s, 3H), 2.26 (s, 3H), 2.03-2.22 (m, 3H), 1.86-2.02 (m, 2H); [M + H]⁺ 507 | Single isomer, absolute stereochemistry unknown; Enantiomer of Ex. 131; 99% ee; retention time: 3.455 min; column: Chiralpak AD-H 250 × 4.6 mm I.D., 5 um; mobile phase; 40% methanol (0.05% DEA) in CO2 |
| 131 | 8-chloro-2-[(4,6-dimethyl-2-oxo-1,2-dihydropyridin-3-yl)methyl]-7-[(1,1-dioxidotetrahydro-2H-thiopyran-4-yl)methoxy)methyl]-5-methyl-3,4-dihydroisoquinolin-1(2H)-one - Isomer B | I | ¹H NMR (400 MHz, CDCl3) δ 11.75 (brs, 1H), 7.24 (s, 1H), 5.94 (s, 1H), 4.78-4.83 (m, 2H), 4.69 (d, J = 5.20 Hz, 1H), 3.63 (t, J = 6.00 Hz, 2H), 3.18 (s, 3H), 3.02-3.10 (m, 2H), 2.79-2.94 (m, 2H), 2.75 (t, J = 6.00 Hz, 2H), 2.36 (s, 3H), 2.28 (s, 3H), 2.26 (s, 3H), 2.03-2.22 (m, 3H), 1.86-2.02 (m, 2H); [M + H]⁺ 507 | Single isomer, absolute stereochemistry unknown; Enantiomer of Ex. 130; 99% ee; retention time: 6.221 min; column: Chiralpak AD-H 250 × 4.6 mm I.D., 5 um; mobile phase; 40% methanol (0.05% DEA) in CO2 |
| 132 | 8-chloro-2-[(4,6-dimethyl-2-oxo-1,2-dihydropyridin-3-yl)methyl]-7-[methoxy(tetrahydrofuran-3-yl)methyl]-3,4-dihydroisoquinolin-1(2H)-one - Isomer A | I | ¹H NMR (400 MHz, CDCl3) δ 12.11 (brs, 1H), 7. 47 (d, J = 8 Hz, 1H), 7.11 (d, J = 7.6 Hz, 1H), 5.95 (s, 1H), 4.81-483 (m, 3H), 3.83-3.89 (m, 1H), 3.70-3.73 (m, 2H), 3.61-3.64 (m, 3H), 3.19 (s, 3H), 2.82-2.85 (m, 2H), 2.64-2.66 (m, 1H), 2.37 (s, 3H), 2.29 (s, 3H), 1.95-1.97 (m, 1H), 1.81-1.84 (m, 1H); [M + H]⁺ 431 | Single isomer, absolute stereochemistry unknown; Enantiomer of Ex. 133; Diastereomer of Ex. 135 and Ex. 134; 99% ee; retention time: 6.84 min; column: Chiralpak AD-H 2504.6 mm I.D., 5 um; mobile phase: 5-40% methanol (0.05% DEA) in CO2 |

TABLE 1-continued

| Ex. No. | Structure/IUPAC name | Method | ¹H NMR (ppm); LCMs [M + H]⁺ | Stereochemistry Note |
|---|---|---|---|---|
| 133 | 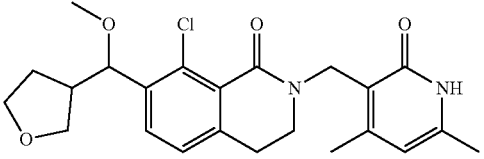<br>8-chloro-2-[(4,6-dimethyl-2-oxo-1,2-dihydropyridin-3-yl)methyl]-7-[methoxy(tetrahydrofuran-3-yl)methyl]-3,4-dihydroisoquinolin-1(2H)-one - Isomer B | I | ¹H NMR (400 MHz, CDCl3) δ 12.18 (brs, 1H), 7.47 (d, J = 7.6 Hz, 1H), 7.11 (d, J = 8 Hz, 1H), 5.96 (s, 1H), 4.81-4.83 (m, 3H), 3.87-3.89 (m, 1H), 3.70-3.73 (m, 2H), 3.61-3.64 (m, 3H), 3.19 (s, 3H), 2.82-2.85 (m, 2H), 2.64-2.65 (m, 1H), 2.37 (s, 3H), 2.29 (s, 3H), 1.95-1.97 (m, 1H), 1.80-1.6 (m, 1H); [M + H]⁺ 431 | Single isomer, absolute stereochemistry unknown; Enantiomer of Ex. 132; Diastereomer of Ex. 135 and Ex. 134; 100% ee; retention time: 7.13 min; column: Chiralpak AD-H 250 × 4.6 mm I.D., 5 um; mobile phase: 5-40% methanol (0.05% DEA) in CO2 |
| 134 | 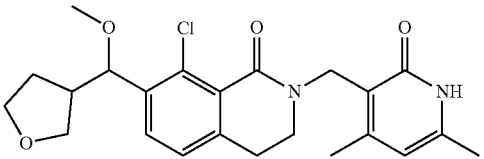<br>8-chloro-2-[(4,6-dimethyl-2-oxo-1,2-dihydropyridin-3-yl)methyl]-7-[methoxy(tetrahydrofuran-3-yl)methyl]-3,4-dihydroisoquinolin-1(2H)-one - Isomer C | I | ¹H NMR (400 MHz, CDCl3) δ 11.84 (brs, 1H), 7.47 (d, J = 8 Hz, 1H), 7.12 (d, J = 8 Hz, 1H), 5.96 (s, 1H), 4.80-4.88 (m, 3H), 3.71-3.88 (m, 3H), 3.63-3.65 (m, 3H), 3.16 (s, 3H), 2.83-2.86 (m, 2H), 2.51-2.60 (m, 1H), 2.38 (s, 3H), 2.29 (s, 3H), 1.69-1.74 (m, 2H); [M + H]⁺ 431 | Single isomer, absolute stereochemistry unknown; enantiomer of Ex. 135; diastereomer of Ex. 132 and Ex. 133; 100% ee; retention time: 7.21 min; column: Chiralpak AD-H 250 × 4.6 mm I.D., 5 um; mobile phase: 5-40% methanol (0.05% DEA) in CO2; wavelength: 220 nm |
| 135 | 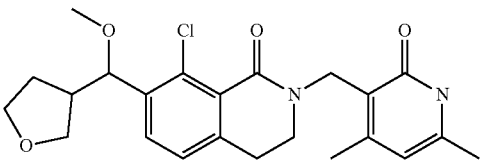<br>8-chloro-2-[(4,6-dimethyl-2-oxo-1,2-dihydropyridin-3-yl)methyl]-7-[methoxy(tetrahydrofuran-3-yl)methyl]-3,4-dihydroisoquinolin-1(2H)-one - Isomer D | I | ¹H NMR (400 MHz, CDCl3) δ 11.71 (brs, 1H), 7.47 (d, J = 7.6 Hz, 1H), 7.12 (d, J = 7.6 Hz, 1H), 5.95 (s, 1H), 4.80-4.88 (m, 3H), 3.83-3.88 (m, 3H), 3.64-3.72 (m, 3H), 3.16 (s, 3H), 2.83-2.86 (m, 2H), 2.55-2.60 (m, 1H), 2.38 (s, 3H), 2.28 (s, 3H), 1.69-1.74 (m, 2H); [M + H]⁺ 431 | Single isomer, absolute stereochemistry unknown; Enantiomer of Ex. 134; Diastereomer of Ex. 132 and Ex. 133; 99% ee; retention time: 7.32 min; column: Chiralpak AD-H 250 × 4.6 mm I.D., 5 um; mobile phase: 5-40% methanol (0.05% DEA) in CO2 |
| 136 | 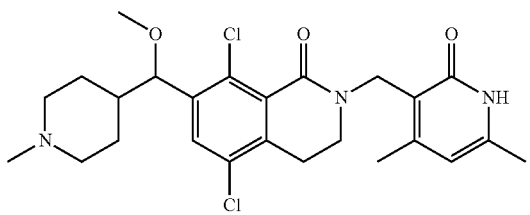<br>(+)-5,8-dichloro-2-[(4,6-dimethyl-2-oxo-1,2-dihydropyridin-3-yl)methyl]-7-[methoxy(1-methylpiperidin-4-yl)methyl]-3,4-dihydroisoquinolin-1(2H)-one | I | ¹H NMR (400 MHz, CD3OD) δ 7.58 (s, 1H), 6.16 (s, 1H), 4.81 (s, 2H), 4.72 (d, J = 4.65 Hz, 1H), 3.58 (t, J = 6.24 Hz, 2H), 3.26 (s, 3H), 2.99-3.10 (m, 4H), 2.40 (s, 3H), 2.35 (s, 3H), 2.30 (s, 3H), 2.17 (d, J = 11.86 Hz, 2H), 1.68-1.85 (m, 3H), 1.54 (d, J = 7.70 Hz, 2H); [M + H]⁺ 492 | [α]D22 = +70.1° (c = 0.2, MeOH); Single isomer, absolute stereochemistry unknown; Enantiomer of Ex. 137; ~99% ee; retention time 10.03 min; column: Lux Cellulose-4 4.6 × 100 mm 3u; mobile phase: 50% MeOH/DEA in CO2, 4 mL/min |
| 137 | 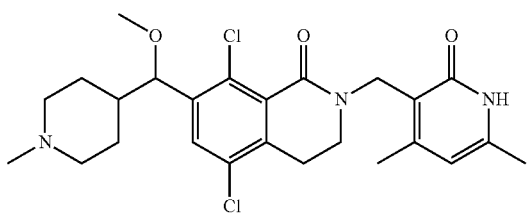<br>(−)-5,8-dichloro-2-[(4,6-dimethyl-2-oxo-1,2-dihydropyridin-3-yl)methyl]-7-[methoxy(1-methylpiperidin-4-yl)methyl]-3,4-dihydroisoquinolin-1(2H)-one | I | ¹H NMR (400 MHz, CD3OD) δ 7.58 (s, 1H), 6.16 (s, 1H), 4.81 (s, 2H), 4.72 (d, J = 4.65 Hz, 1H), 3.58 (t, J = 6.24 Hz, 2H), 3.26 (s, 3H), 2.99-3.10 (m, 4H), 2.40 (s, 3H), 2.35 (s, 3H), 2.30 (s, 3H), 2.17 (d, J = 11.86 Hz, 2H), 1.68-1.85 (m, 3H), 1.54 (d, J = 7.70 Hz, 2H); [M + H]⁺ 492 | [α]D22 = −59.5° (c = 0.2, MeOH); Single isomer, absolute stereochemistry unknown; Enantiomer of Ex. 136; >99% ee; retention time 7.25 min; column: Lux Cellulose-4 4.6 × 100 mm 3u; mobile phase: 50% MeOH/DEA in CO2, 4 mL/min |

TABLE 1-continued

| Ex. No. | Structure/IUPAC name | Method | $^1$H NMR (ppm); LCMs [M + H]$^+$ | Stereochemistry Note |
|---|---|---|---|---|
| 138 | 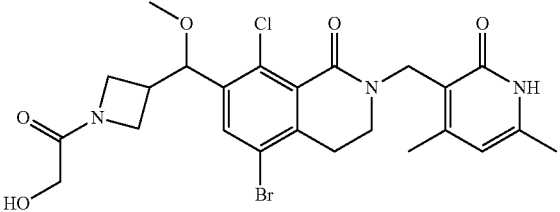<br>5-bromo-8-chloro-2-[(4,6-dimethyl-2-oxo-1,2-dihydropyridin-3-yl)methyl]-7-{[1-(hydroxyacetyl)azetidin-3-yl](methoxy)methyl}-3,4-dihydroisoquinolin-1(2H)-one - Isomer A | I | $^1$H NMR (400 MHz, CD3OD) δ 7.77 (d, J = 4.00 Hz, 1H), 6.11 (s, 1H), 4.97-4.98 (m, 2H), 4.75 (s, 2H), 4.22-4.27 (m, 2H), 3.98-4.09 (m, 5H), 3.84-3.86 (m, 1H), 3.52 (t, J = 6.40 Hz, 2H), 3.08-3.12 (m, 1H), 2.97-3.00 (m, 2H), 2.30 (s, 3H), 2.25 (s, 3H); [M + H]$^+$ 554 | Single isomer, absolute stereochemistry unknown; Enantiomer of Ex. 139; 96% ee; retention time: 6.104 min; column: Chiralcel OD-3 150 × 4.6 mm I.D., 3 um; mobile phase: 5-40% methanol (0.05% DEA) in CO2; flow rate: 2.5 mL/min |
| 139 | 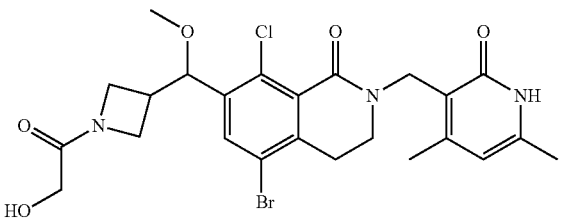<br>5-bromo-8-chloro-2-[(4,6-dimethyl-2-oxo-1,2-dihydropyridin-3-yl)methyl]-7-{[1-(hydroxyacetyl)azetidin-3-yl](methoxy)methyl}-3,4-dihydroisoquinolin-1(2H)-one - Isomer B | I | $^1$H NMR (400 MHz, CD3OD) δ 7.77 (d, J = 4.00 Hz, 1H), 6.11 (s, 1H), 4.92-4.98 (m, 2H), 4.57 (s, 2H), 4.22-4.27 (m, 2H), 3.98-4.08 (m, 5H), 3.84-3.86 (m, 1H), 3.52 (t, J = 6.40 Hz, 2H), 3.08-3.12 (m, 1H), 2.98-3.00 (m, 2H), 2.30 (s, 3H), 2.25 (s, 3H); [M + H]$^+$ 554 | Single isomer, absolute stereochemistry unknown; Enantiomer of Ex. 138; 98% ee; retention time: 6.403 min; column: Chiralcel OD-3 150 × 4.6 mm I.D., 3 um; mobile phase: 5-40% methanol (0.05% DEA) in CO2; flow rate: 2.5 mL/min |
| 140 | 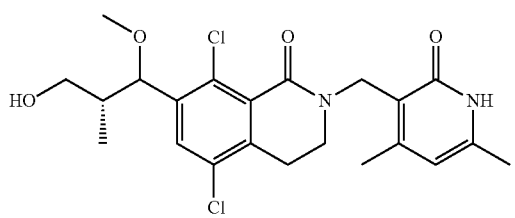<br>5,8-dichloro-2-[(4,6-dimethyl-2-oxo-1,2-dihydropyridin-3-yl)methyl]-7-[(2R)-3-hydroxy-1-methoxy-2-methylpropyl]-3,4-dihydroisoquinolin-1(2H)-one - Isomer A | I | $^1$H NMR (400 MHz, DMSO-d6) δ 11.55 (brs, 1H), 7.47 (s, 1H), 5.89 (s, 1H), 4.66 (d, J = 7.2 Hz, 1H), 4.57 (s, 2H), 4.38 (t, J = 5.6 Hz, 1H), 3.40-3.50 (m, 4H), 3.09 (s, 3H), 2.85-2.95 (m, 2H), 2.17 (s, 3H), 2.12 (s, 3H), 1.80-1.85 (m, 1H), 0.78 (d, J = 6.8 Hz, 3H); [M + Na]$^+$ 475 | Single (2R) isomer, other stereocenter unknown; Enantiomer of Ex. 142; Diastereomer of Ex. 143 and Ex. 141; 95% ee; retention time 6.36 min; column: Chiralpak AD-H 250 × 4.6 mm I.D., 5 um; mobile phase: 5-40% methanol (0.05% DEA) in CO2 |
| 141 | 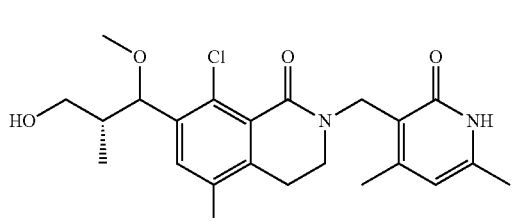<br>5,8-dichloro-2-[(4,6-dimethyl-2-oxo-1,2-dihydropyridin-3-yl)methyl]-7-[(2R)-3-hydroxy-1-methoxy-2-methylpropyl]-3,4-dihydroisoquinolin-1(2H)-one - Isomer B | I | $^1$H NMR (400 MHz, DMSO-d6) δ 11.58 (brs, 1H), 7.42 (s, 1H), 5.89 (s, 1H), 4.83 (d, J = 2.8 Hz, 1H), 4.65 (t, J = 5.2 Hz, 1H), 4.57 (s, 2H), 3.40-3.48 (m, 3H), 3.27-3.28 (m, 1H), 3.15 (s, 3H), 2.89 (t, J = 6.0 Hz, 2H), 2.16 (s, 3H), 2.12 (s, 3H), 1.85-1.89 (m, 1H), 0.66 (d, J = 6.8 Hz, 3H); [M + Na]$^+$ 475 | Single (2R) isomer, other stereocenter unknown; Enantiomer of Ex. 143; Diastereomer of Ex. 140 and Ex. 142; 99% ee; retention time 7.69 min; column: Chiralpak AD-H 250 × 4.6 mm I.D., 5 um; mobile phase: 5-40% isopropanol (0.05% DEA) in CO2 |
| 142 | 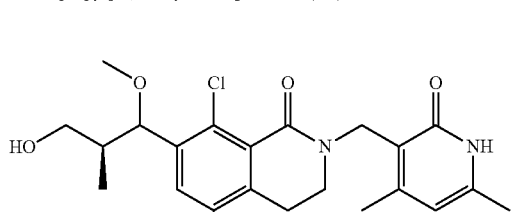<br>5,8-dichloro-2-[(4,6-dimethyl-2-oxo-1,2-dihydropyridin-3-yl)methyl]-7-[(2S)-3-hydroxy-1-methoxy-2-methylpropyl]-3,4-dihydroisoquinolin-1(2H)-one - Isomer A | I | $^1$H NMR (400 MHz, DMSO-d6) δ 11.56 (brs, 1H), 7.47 (s, 1H), 5.89 (s, 1H), 4.66 (d, J = 7.2 Hz, 1H), 4.56 (s, 2H), 3.40-3.50 (m, 5H), 3.09 (s, 3H), 2.89 (t, J = 5.6 Hz, 2H), 2.17 (s, 3H), 2.12 (s, 3H), 1.80-1.85 (m, 1H), 0.78 (d, J = 6.4 Hz, 3H); [M + Na]$^+$ 475 | Single (2S) isomer, other stereocenter unknown; Enantiomer of Ex. 140; Diastereomer of Ex. 143 and Ex. 141; 100% ee; retention time: 6.64 min; column: Chiralpak AD-H 250 × 4.6 mm I.D., 5 um; mobile phase: 5-40% methanol (0.05% DEA) in CO2 |

TABLE 1-continued

| Ex. No. | Structure/IUPAC name | Method | $^1$H NMR (ppm); LCMs [M + H]$^+$ | Stereochemistry Note |
|---|---|---|---|---|
| 143 | 5,8-dichloro-2-[(4,6-dimethyl-2-oxo-1,2-dihydropyridin-3-yl)methyl]-7-[(2S)-3-hydroxy-1-methoxy-2-methylpropyl]-3,4-dihydroisoquinolin-1(2H)-one - Isomer B | I | $^1$H NMR (400 MHz, DMSO-d6) δ 11.57 (brs, 1H), 7.42 (s, 1H), 5.89 (s, 1H), 4.83 (d, J = 2.8 Hz, 1H), 4.57 (s, 2H), 3.40-3.50 (m, 5H), 3.16 (s, 3H), 2.89 (t, J = 6.4 Hz, 2H), 2.16 (s, 3H), 2.12 (s, 3H), 1.86-1.89 (m, 1H), 0.66 (d, J = 6.8 Hz, 3H); [M + H]$^+$ 453 | Single (2S) isomer, other stereocenter unknown; Enantiomer of Ex. 141; Diastereomer of Ex. 142 and Ex. 140; 98% ee; retention time: 7.43 min; column: Chiralpak AD-H 250 × 4.6 mm I.D., 5 um; mobile phase: 5-40% isopropanol (0.05% DEA) in CO2 |
| 144 | 8-chloro-2-[(4-methoxy-6-methyl-2-oxo-1,2-dihydropyridin-3-yl)methyl]-7-[methoxy-(oxetan-3-yl)methyl]-5-methyl-3,4-dihydroisoquinolin-1(2H)-one - Isomer A | I | $^1$H NMR (400 MHz, CDCl3) δ 12.06 (brs, 1H), 7.26 (s, 1H), 5.92 (s, 1H), 5.11 (d, J = 6.8 Hz, 1H), 4.75-4.79 (m, 3H), 4.62-4.68 (m, 3H), 3.87 (s, 3H), 3.37-3.47 (m, 3H), 3.28 (s, 3H), 2.74 (d, J = 3.2 Hz, 2H), 2.34 (s, 3H), 2.24 (s, 3H); [M + H]$^+$ 447 | Single isomer, absolute stereochemistry unknown; Enantiomer of Ex. 145; 100% ee; retention time: 5.041 min; column: Chiralcel OD-3 150 × 4.6 mm I.D., 3 um; mobile phase: 5-40% ethanol (0.05% DEA) in CO2 |
| 145 | 8-chloro-2-[(4-methoxy-6-methyl-2-oxo-1,2-dihydropyridin-3-yl)methyl]-7-[methoxy-(oxetan-3-yl)methyl]-5-methyl-3,4-dihydroisoquinolin-1(2H)-one - Isomer B | I | $^1$H NMR (400 MHz, CDCl3) δ 7.26 (s, 1H), 5.92 (s, 1H), 5.11-5.12 (m, 1H), 4.76-4.78 (m, 3H), 4.62-4.68 (m, 3H), 3.87 (s, 3H), 3.37-3.47 (m, 3H), 3.28 (s, 3H), 2.74-2.75 (m, 2H), 2.33 (s, 3H), 2.24 (s, 3H); [M + H]$^+$ 447 | Single isomer, absolute stereochemistry unknown; Enantiomer of Ex. 144; 99% ee; retention time: 5.168 min; column: Chiralcel OD-3 150 × 4.6 mm I.D., 3 um; mobile phase: 5-40% ethanol (0.05% DEA) in CO2 |
| 146 | 5-bromo-8-chloro-2-[(4,6-dimethyl-2-oxo-1,2-dihydropyridin-3-yl)methyl]-7-[methoxy(1-methylpiperidin-4-yl)methyl]-3,4-dihydroisoquinolin-1(2H)-one - Isomer A | I | $^1$H NMR (400 MHz, CDCl3) δ 11.45 (brs, 1H), 7.55 (s, 1H), 5.88 (s, 1H), 4.70-4.73 (m, 2H), 4.58 (d, J = 4.40 Hz, 1H), 3.57-3.60 (m, 2H), 3.30-3.33 (m, 2H), 3.14 (s, 3H), 2.86-2.89 (m, 2H), 2.63 (s, 3H), 2.48-2.53 (m, 2H), 2.29 (s, 3H), 2.22 (s, 3H), 1.98-2.02 (m, 1H), 1.83-1.88 (m, 1H), 1.74-1.79 (m, 2H), 1.58-1.63 (m, 1H); [M + H]$^+$ 538 | Single isomer, absolute stereochemistry unknown; Enantiomer of Ex. 147; 100% ee; retention time: 4.177 min; column: Chiralcel OD-3 100 × 4.6 mm I.D., 3 um; mobile phase: 5-40% ethanol (0.05% DEA) in CO2 |

TABLE 1-continued

| Ex. No. | Structure/IUPAC name | Method | ¹H NMR (ppm); LCMs [M + H]⁺ | Stereochemistry Note |
|---|---|---|---|---|
| 147 | 5-bromo-8-chloro-2-[(4,6-dimethyl-2-oxo-1,2-dihydropyridin-3-yl)methyl]-7-[methoxy(1-methylpiperidin-4-yl)methyl]-3,4-dihydroisoquinolin-1(2H)-one - Isomer B | I | ¹H NMR (400 MHz, CDCl3) δ 11.82 (brs, 1H), 7.57 (s, 1H), 5.87 (s, 1H), 4.69 (s, 2H), 4.58 (d, J = 4.40 Hz, 1H), 3.57-3.60- (m, 2H), 3.12 (s, 3H), 3.01-3.07 (m, 2H), 2.85-2.88 (m, 2H), 2.38 (s, 3H), 2.29 (s, 3H), 2.22 (s, 3H), 2.08-2.13 (m, 2H), 1.82-1.88 (m, 1H), 1.69-1.75 (m, 2H), 1.58-1.63 (m, 1H), 1.40-1.46 (m, 1H); [M + H]⁺ 538 | Single isomer, absolute stereochemistry unknown; Enantiomer of Ex. 146; 100% ee; retention time; 4.202 min; column: Chiralcel OD-3 100 × 4.6 mm I.D., 3 um; mobile phase: 5-40% ethanol (0.05% DEA) in CO2 |
| 148 | 5,8-dichloro-2-[(4,6-dimethyl-2-oxo-1,2-dihydro-pyridin-3-yl)methyl]-7-[(1,1-dioxidotetrahydro-thiophen-3-yl)(methoxy)methyl]-3,4-dihydroisoquinolin-1(2H)-one - Isomer A | I | ¹H NMR (400 MHz, CDCl3) δ 11.25 (br. s., 1H), 7.43 (s, 1H), 5.95 (s, 1H), 4.71-4.85 (m, 3H), 3.60-3.76 (m, 2H), 3.27 (s, 3H), 3.18-3.25 (m, 1H), 2.88-3.16 (m, 5H), 2.79 (m, 1H), 2.37 (s, 3H), 2.29 (s, 3H), 2.16-2.27 (m, 2H); [M + Na]⁺ 535 | Single isomer, absolute stereochemistry unknown; Enantiomer of Ex. 151; Diastereomer of Ex. 149 and Ex. 150; 97% ee; retention time: 1.865 min; column: Chiralcel OJ-3 100 × 4.6 mm I.D., 3 um; mobile phase: 15% methanol (0.05% DEA) in CO2 |
| 149 | 5,8-dichloro-2-[(4,6-dimethyl-2-oxo-1,2-dihydro-pyridin-3-yl)methyl]-7-[(1,1-dioxidotetrahydro-thiophen-3-yl)(methoxy)methyl]-3,4-dihydro-isoquinolin-1(2H)-one - Isomer B | I | ¹H NMR (400 MHz, CDCl3) δ 10.79 (br. s., 1H), 7.48 (s, 1H), 5.93 (s, 1H), 4.70-4.84 (m, 3H), 3.61-3.74 (m, 2H), 3.26 (s, 3H), 3.18-3.25 (m, 1H), 3.14-3.16 (m, 2H), 2.96 (t, J = 6.27 Hz, 2H), 2.74-2.93 (m, 2H), 2.36 (s, 3H), 2.27 (s, 3H), 1.94-2.19 (m, 2H) [M + Na]⁺ 535 | Single isomer, absolute stereochemistry unknown; Enantiomer of Ex. 150; Diastereomer of Ex. 148 and Ex. 151; 100% ee; retention time: 1.949 min; column: Chiralcel OJ-3 100 × 4.6 mm I.D., 3 um; mobile phase: 15% methanol (0.05% DEA) in CO2 |
| 150 | 5,8-dichloro-2-[(4,6-dimethyl-2-oxo-1,2-dihydro-pyridin-3-yl)methyl]-7-[(1,1-dioxidotetrahydro-thiophen-3-yl)(methoxy)methyl]-3,4-dihydro-isoquinolin-1(2H)-one - Isomer C | I | ¹H NMR (400 MHz, CDCl3) δ 11.61 (br. s., 1H), 7.49 (s, 1H), 5.95 (s, 1H), 4.68-4.86 (m, 3H), 3.58-3.77 (m, 2H), 3.27 (s, 3H), 3.19-3.25 (m, 1H), 3.14-3.17 (m, 2H), 2.96 (t, J = 6.15 Hz, 2H), 2.75-2.94 (m, 2H), 2.37 (s, 3H), 2.29 (s, 3H), 1.96-2.21 (m, 2H); [M + Na]⁺ 535 | Single isomer, absolute stereochemistry unknown; Enantiomer of Ex. 149; Diastereomer of Ex. 148 and Ex. 151; 97% ee; retention time: 2.253 min; column: Chiralcel OJ-3 100 × 4.6 mm I.D., 3 um; mobile phase: 15% methanol (0.05% DEA) in CO2 |

TABLE 1-continued

| Ex. No. | Structure/IUPAC name | Method | ¹H NMR (ppm); LCMs [M + H]⁺ | Stereochemistry Note |
|---|---|---|---|---|
| 151 | 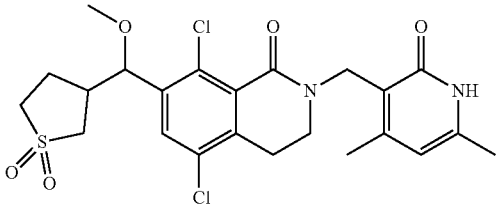<br>5,8-dichloro-2-[(4,6-dimethyl-2-oxo-1,2-dihydro-pyridin-3-yl)methyl]-7-[(1,1-dioxidotetrahydro-thiophen-3-yl)(methoxy)methyl]-3,4-dihydro-isoquinolin-1(2H)-one - Isomer D | I | ¹H NMR (400 MHz, CDCl3) δ 11.72 (br. s., 1H), 7.43 (s, 1H), 5.96 (s, 1H), 4.71-4.86 (m, 3H), 3.58-3.78 (m, 2H), 3.22-3.31 (m, 4H), 2.87-3.19 (m, 5H), 2.73-2.85 (m, 1H), 2.36 (s, 3H), 2.29 (s, 3H), 2.16-2.27 (m, 2H); [M + Na]⁺ 535 | Single isomer, absolute stereochemistry unknown; Enantiomer of Ex. 148; Diastereomer of Ex. 149 and Ex. 150; 100% ee; retention time: 2.596 min; column: Chiralcel OJ-3 100 × 4.6 mm I.D., 3 um; mobile phase: 15% methanol (0.05% DEA) in CO2 |
| 152 | 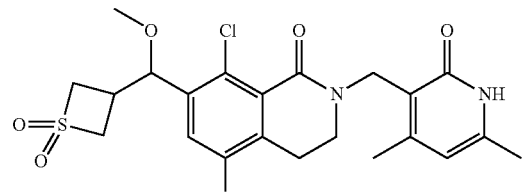<br>5,8-dichloro-2-[(4,6-dimethyl-2-oxo-1,2-dihydropyridin-3-yl)methyl]-7-[(1,1-dioxidothietan-3-yl)(methoxy)methyl]-3,4-dihydroisoquinolin-1(2H)-one - Isomer A | I | ¹H NMR (400 MHz, CDCl3) δ 7.47 (s, 1H), 5.96 (s, 1H), 4.93 (d, J = 4.8, 1H), 4.77 (s, 2H), 4.22-4.28 (m, 2H), 4.05-4.08 (m, 1H), 3.67-3.79 (m, 3H), 3.32 (s, 3H), 2.92-2.98 (m, 3H), 2.37 (s, 3H), 2.29 (s, 3H); [M + H]⁺ 499 | Single isomer, absolute stereochemistry unknown; Enantiomer of Ex. 153; 100% ee; retention time 5.106 min; column: Chiralpak AD-3 100 × 4.6 mm I.D., 3 um; mobile phase: 5-40% ethanol (0.05% DEA) in CO2 |
| 153 | 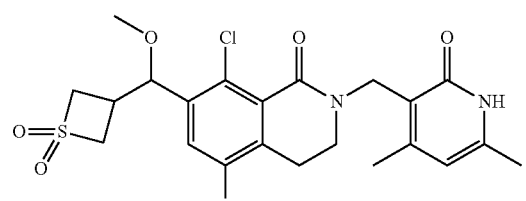<br>5,8-dichloro-2-[(4,6-dimethyl-2-oxo-1,2-dihydropyridin-3-yl)methyl]-7-[(1,1-dioxidothietan-3-yl)(methoxy)methyl]-3,4-dihydroisoquinolin-1(2H)-one - Isomer B | I | ¹H NMR (400 MHz, CDCl3) δ 7.47 (s, 1H), 5.96 (s, 1H), 4.93 (d, J = 4.8, 1H), 4.77 (s, 2H), 4.22-4.28 (m, 2H), 4.05-4.08 (m, 1H), 3.67-3.78 (m, 3H), 3.32 (s, 3H), 2.92-2.98 (m, 3H), 2.37 (s, 3H), 2.29 (s, 3H); [M + H]⁺ 499 | Single isomer, absolute stereochemistry unknown; Enantiomer of Ex. 152; 100% ee; retention time 4.69 min; column: Chiralpak AD-3 100 × 4.6 mm I.D., 3 um; mobile phase: 5-40% ethanol (0.05% DEA) in CO2 |
| 154 | 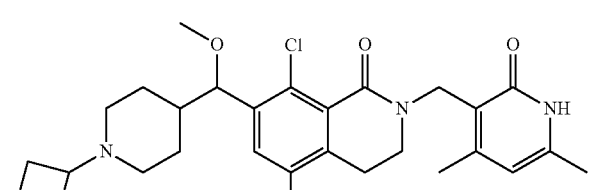<br>8-chloro-2-[(4,6-dimethyl-2-oxo-1,2-dihydropyridin-3-yl)methyl]-7-{methoxy[1-(oxetan-3-yl)piperidin-4-yl]methyl}-5-methyl-3,4-dihydroisoquinolin-1(2H)-one - Isomer A | I | ¹H NMR (400 MHz, CD3OD) δ 7.35 (s, 1H), 6.13 (s, 1H), 4.79 (s, 2H), 4.56-4.70 (m, 6H), 3.42-3.53 (m, 3H), 3.19 (s, 3H), 2.72-2.87 (m, 5H), 2.31 (s, 6H), 2.25-2.28 (m, 3H), 1.64-1.83 (m, 5H) [M + H]⁺ 514 | Single isomer, absolute stereochemistry unknown; Enantiomer of Ex. 155; 99% ee; retention time: 4.001 min; column: Chiralpak AD-3 100 × 4.6 mm I.D., 3 um; mobile phase: 5-40% methanol (0.05% DEA) in CO2 |
| 155 | 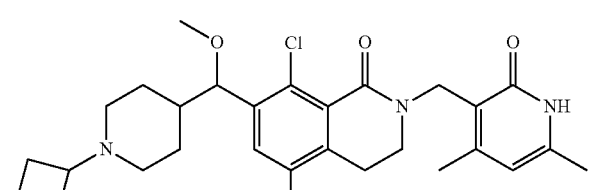<br>8-chloro-2-[(4,6-dimethyl-2-oxo-1,2-dihydropyridin-3-yl)methyl]-7-{methoxy[1-(oxetan-3-yl)piperidin-4-yl]methyl}-5-methyl-3,4-dihydroisoquinolin-1(2H)-one - Isomer B | I | ¹H NMR (400 MHz, CD3OD) δ 7.35 (s, 1H), 6.13 (s, 1H), 4.79 (s, 2H), 4.54-4.69 (m, 6H), 3.41-3.51 (m, 4H), 3.19 (s, 3H), 2.73-2.86 (m, 4H), 2.30 (s, 6H), 2.26 (s, 3H), 1.64-1.86 (m, 5H); [M + H]⁺ 514 | Single isomer, absolute stereochemistry unknown; Enantiomer of Ex. 154; 96% ee; retention time: 4.312 min; column: Chiralpak AD-3 100 × 4.6 mm I.D., 3 um; mobile phase: 5-40% methanol (0.05% DEA) in CO2 |

TABLE 1-continued

| Ex. No. | Structure/IUPAC name | Method | $^1$H NMR (ppm); LCMs [M + H]$^+$ | Stereochemistry Note |
|---|---|---|---|---|
| 156 | 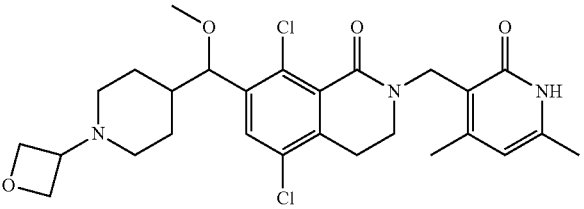<br>5,8-dichloro-2-[(4,6-dimethyl-2-oxo-1,2-dihydropyridin-3-yl)-methyl]-7-{methoxy[1-(oxetan-3-yl)piperidin-4-yl]methyl}-3,4-dihydroisoquinolin-1(2H)-one - Isomer A | I | $^1$H NMR (400 MHz, DMSO-d6) δ 11.57 (brs, 1H), 7.44 (s, 1H), 5.89 (s, 1H), 4.50-4.65 (m, 3H), 4.45-4.50 (m, 2H), 4.35-4.40 (m, 2H), 3.46 (t, J = 6.0 Hz, 2H), 3.30-3.35 (m, 3H), 3.12 (s, 3H), 2.89 (t, J = 6.0 Hz, 2H), 2.60-2.70 (m, 2H), 2.17 (s, 3H), 2.12 (s, 3H), 1.50-1.65 (m, 4H), 1.35-1.45 (m, 1H); [M + H]$^+$ 534 | Single isomer, absolute stereochemistry unknown; Enantiomer of Ex. 157; 100% ee; retention time: 2.263 min; column: Chiralpak AY 100 × 4.6 mm I.D., 3 um; mobile phase: 5-40% methanol (0.05% DEA) in CO2 |
| 157 | 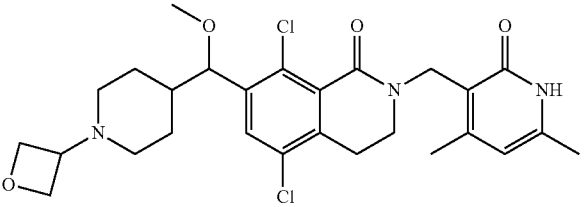<br>5,8-dichloro-2-[(4,6-dimethyl-2-oxo-1,2-dihydropyridin-3-yl)-methyl]-7-{methoxy[1-(oxetan-3-yl)piperidin-4-yl]methyl}-3,4-dihydroisoquinolin-1(2H)-one - Isomer B | I | $^1$H NMR (400 MHz, DMSO-d6) δ 11.58 (brs, 1H), 7.44 (s, 1H), 5.89 (s, 1H), 4.50-4.65 (m, 3H), 4.45-4.50 (m, 2H), 4.35-4.40 (m, 2H), 3.46 (t, J = 6.0 Hz, 2H), 3.30-3.35 (m, 3H), 3.12 (s, 3H), 2.89 (t, J = 5.6 Hz, 2H), 2.60-2.70 (m, 2H), 2.17 (s, 3H), 2.12 (s, 3H), 1.50-1.65 (m, 4H), 1.35-1.45 (m, 1H); [M + H]$^+$ 534 | Single isomer, absolute stereochemistry unknown; Enantiomer of Ex. 156; 100% ee; retention time: 3.339 min; column: Chiralpak AY 100 × 4.6 mm ID., 3 um; mobile phase: 5-40% methanol (0.05% DEA) in CO2 |
| 158 | 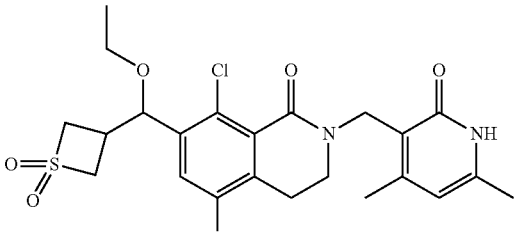<br>5,8-dichloro-2-[(4,6-dimethyl-2-oxo-1,2-dihydropyridin-3-yl)methyl]-7-[(1,1-dioxidothietan-3-yl)(ethoxy)methyl]-3,4-dihydroisoquinolin-1(2H)-one - Isomer A | I | $^1$H NMR (400 MHz, CDCl3) δ 11.26 (brs, 1H), 7.49 (s, 1H), 5.94 (s, 1H), 5.03 (d, J = 4.4 Hz, 1H), 4.77 (s, 2H), 4.21-4.26 (m, 2H), 4.03-4.04 (m, 1H), 3.68-3.76 (m, 3H), 3.40-3.48 (m, 2H), 2.94-2.97 (m, 3H), 2.37 (s, 3H), 2.28 (s, 3H), 1.25 (t, J = 7 Hz, 3H); [M + H]$^+$ 513 | Single isomer, absolute stereochemistry unknown; Enantiomer of Ex. 159; 100% ee; retention time: 2.535 min; column: Chiralcel OJ-3 100 × 4.6 mm ID., 3 um; mobile phase: 5-40% ethanol (0.05% DEA) in CO2 |
| 159 | 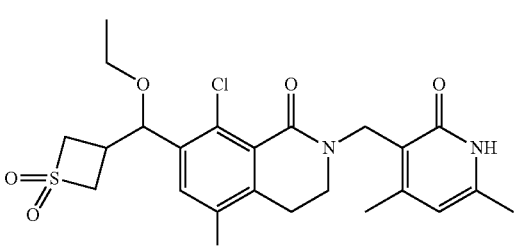<br>5,8-dichloro-2-[(4,6-dimethyl-2-oxo-1,2-dihydropyridin-3-yl)-methyl]-7-[(1,1-dioxidothietan-3-yl)(ethoxy)methyl]-3,4-dihydroisoquinolin-1(2H)-one - Isomer B | I | $^1$H NMR (400 MHz, CDCl3) δ 11.35 (brs, 1H), 7.49 (s, 1H), 5.95 (s, 1H), 5.02 (d, J = 4.8 Hz, 1H), 4.77-4.8 (m, 2H), 4.21-4.26 (m, 2H), 4.03-4.04 (m, 1H), 3.68-3.76 (m, 3H), 3.40-3.48 (m, 2H), 2.94-2.97 (m, 3H), 2.37 (s, 3H), 2.28 (s, 3H), 1.25 (t, J = 6.8 Hz, 3H); [M + H]$^+$ 513 | Single isomer, absolute stereochemistry unknown; Enantiomer of Ex. 158; 100% ee; retention time: 22.782 min; column: Chiralcel OJ-3 100 × 4.6 mm I.D., 3 um; mobile phase: 5-40% ethanol (0.05% DEA) in CO2 |

TABLE 1-continued

| Ex. No. | Structure/IUPAC name | LCMs Method | $^1$H NMR (ppm); [M + H]$^+$ | Stereochemistry Note |
|---|---|---|---|---|
| 160 | 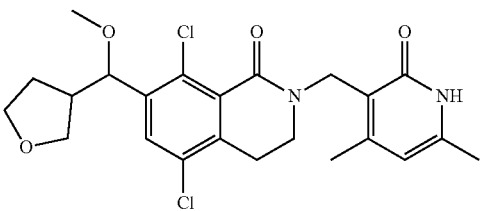<br>(−)-5,8-dichloro-2-[(4,6-dimethyl-2-oxo-1,2-dihydropyridin-3-yl)methyl]-7-[methoxy(tetrahydrofuran-3-yl)methyl]-3,4-dihydroisoquinolin-1(2H)-one - Isomer A | I | $^1$H NMR (400 MHz, CD3OD) δ 7.61 (s, 1H), 6.10 (s, 1H), 4.76 (S, 2H), 3.83-3.91 (m, 1H), 3.67-3.76 (m, 2H), 3.58 (t, J = 7.83 Hz, 1H), 3.53 (t, J = 6.24 Hz, 2H), 3.22 (s, 3H), 2.99 (t, J = 6.24 Hz, 2H), 2.64 (m, 1H), 2.30 (s, 3H), 2.25 (s, 3H), 1.93-2.05 (m, 1H), 1.78-1.89 (m, 1H) One proton obscured by solvent; [M + H]$^+$ 465 | $[α]_D$ = −48.0° (c 0.1 MeOH), >99% ee; Absolute and relative stereochemistry undetermined; Enantiomer of Ex. 161; Diastereomer of Ex. 162 and Ex. 163 |
| 161 | 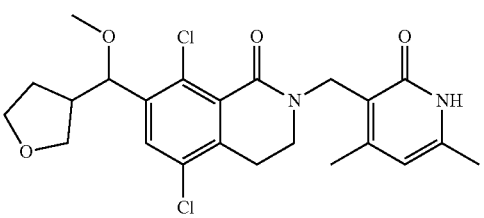<br>(+)-5,8-dichloro-2-[(4,6-dimethyl-2-oxo-1,2-dihydropyridin-3-yl)methyl]-7-[methoxy-(tetrahydrofuran-3-yl)methyl]-3,4-dihydroisoquinolin-1(2H)-one - Isomer B | I | $^1$H NMR (400 MHz, CD3OD) δ 7.61 (s, 1H), 6.10 (s, 1H), 4.76 (s, 2H), 3.83-3.92 (m, 1H), 3.67-3.76 (m, 2H), 3.58 (t, J = 7.82 Hz, 1H), 3.53 (t, J = 6.24 Hz, 2H), 3.22 (s, 3H), 2.99 (t, J = 6.11 Hz, 2H), 2.64 (m, 1H), 2.30 (s, 3H), 2.25 (s, 3H), 1.93-2.04 (m, 1H), 1.78-1.92 (m, 1H) One proton obscured by solvent; [M + H]$^+$ 465 | $[α]_D$ = +74.7° (c 0.1 MeOH), 90% ee, Absolute and relative stereochemistry undetermined; Enantiomer of Ex. 160; Diastereomer of Ex. 162 and Ex. 163 |
| 162 | 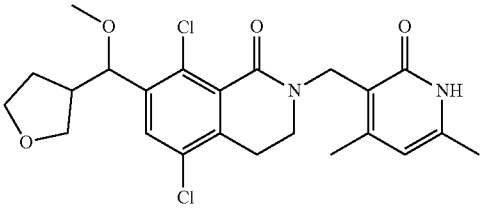<br>(−)-5,8-dichloro-2-[(4,6-dimethyl-2-oxo-1,2-dihydropyridin-3-yl)methyl]-7-[methoxy-(tetrahydrofuran-3-yl)methyl]-3,4-dihydroisoquinolin-1(2H)-one - Isomer C | I | $^1$H NMR (400 MHz, CD3OD) δ 7.61 (s, 1H), 6.11 (s, 1H), 4.76 (s, 2H), 3.76-3.90 (m, 3H), 3.70 (q, J = 7.50 Hz, 1H), 3.53 (t, J = 6.24 Hz, 2H), 3.18 (s, 3H), 2.97-3.03 (m, 2H), 2.54-2.66 (m, 1H), 2.30 (s, 3H), 2.25 (s, 3H), 1.62-181 (m, 2H) One proton obscured by solvent; [M + H]$^+$ 465 | $[α]_D$ = −68.8° (c 0.1 MeOH); >99% ee; Absolute and relative stereochemistry undetermined; Enantiomer of Ex. 163; Diastereomer Ex. 160 and Ex. 161 |
| 163 | 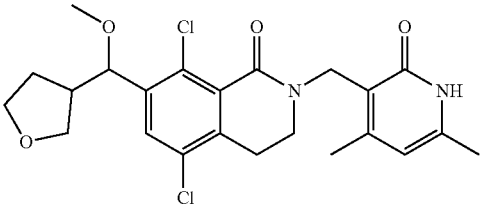<br>(+)-5,8-dichloro-2-[(4,6-dimethyl-2-oxo-1,2-dihydropyridin-3-yl)methyl]-7-[methoxy-(tetrahydrofuran-3-yl)methyl]-3,4-dihydroisoquinolin-1(2H)-one - Isomer D | I | $^1$H NMR (400 MHz, CD3OD) δ 7.61 (s, 1H), 6.11 (s, 1H), 4.76 (s, 2H), 3.76-3.91 (m, 3H), 3.70 (q, J = 7.58 Hz, 1H), 3.53 (t, J = 6.24 Hz, 2H), 3.18 (s, 3H), 2.96-3.03 (m, 2H), 2.60 (sxt, J = 7.38 Hz, 1H), 2.30 (s, 3H), 2.25 (s, 3H), 1.63-1.81 (m, 2H) One proton obscured by solvent; [M + H]$^+$ 465 | $[α]_D$ = +59.4° (c 0.1 MeOH); >99% ee; Absolute and relative stereochemistry undetermined; Enantiomer of Ex. 162; Diastereomer of Ex. 160 and Ex. 161 |

TABLE 1-continued

| Ex. No. | Structure/IUPAC name | ¹H NMR (ppm); LCMs Method [M + H]⁺ | Stereochemistry Note |
|---|---|---|---|
| 164 | (−)-5,8-dichloro-2-[(4,6-dimethyl-2-oxo-1,2-dihydropyridin-3-yl)-methyl]-7-{[1-(hydroxyacetyl)piperidin-4-yl][($^2$H$_3$)methyloxy]-methyl}-3,4-dihydroisoquinolin-1(2H)-one | I  ¹H NMR (400 MHz, CD3OD) δ 7.54 (s, 1H), 6.11 (s, 1H), 4.76 (s, 2H), 4.66 (d, J = 5.62 Hz, 1H), 4.44-4.56 (m, 1H), 4.12-4.27 (m, 2H), 3.66-3.78 (m, 1H), 3.53 (t, J = 6.24 Hz, 2H), 2.99 (t, J = 6.11 Hz, 2H), 2.85-296 (m, 1H), 2.51-2.66 (m, 1H), 2.30 (s, 3H), 2.25 (s, 3H), 1.86-2.00 (m, 1H), 1.69-1.79 (m, 1H), 1.31-1.54 (m, 3H); [M + H]⁺ 539 | [α]$_D$ = −36.9° (c 0.1 MeOH); Absolute stereochemistry undetermined; Enantiomer of Ex. 165; (−) isomer of Ex. 70 racemate |
| 165 | (+)-5,8-dichloro-2-[(4,6-dimethyl-2-oxo-1,2-dihydropyridin-3-yl)-methyl]-7-{[1-(hydroxyacetyl)piperidin-4-yl][($^2$H$_3$)methyloxy]-methyl}-3,4-dihydroisoquinolin-1(2H)-one | I  ¹H NMR (400 MHz, CD3OD) δ 7.54 (s, 1H), 6.11 (s, 1H), 4.76 (s, 2H), 4.66 (d, J = 5.62 Hz, 1H), 4.43-4.56 (m, 1H), 4.12-4.27 (m, 2H), 3.67-3.78 (m, 1H), 3.53 (t, J = 6.11 Hz, 2H), 2.99 (t, J = 6.11 Hz, 2H), 2.84-2.96 (m, 1H), 2.49-2.67 (m, 1H), 2.30 (s, 3H), 2.25 (s, 3H), 1.86-2.01 (m, 1H), 1.69-1.79 (m, 1H), 1.32-1.56 (m, 3H); [M + H]⁺ 539 | [α]$_D$ = +139.1° (c 0.1 MeOH); Absolute stereochemistry undetermined; Enantiomer of Ex. 164; (+) isomer of Ex. 70 racemate |
| 166 | (+)-5,8-dichloro-2-[(4,6-dimethyl-2-oxo-1,2-dihydro-pyridin-3-yl)methyl]-7-[methoxy(piperidin-4-yl)-methyl]-3,4-dihydroisoquinolin-1(2H)-one | I  ¹H NMR (600 MHz, DMSO-d6) δ 7.42 (s, 1H), 5.91 (s, 1H), 4.55 (s, 2H), 4.51 (d, J = 5.50 Hz, 1H), 3.43-3.45 (m, 2H), 3.10 (s, 3H), 2.87 (t, J = 5.59 Hz, 2H), 2.16 (s, 3H), 2.12 (s, 3H), 1.45-1.74 (m, 2H), 1.20-1.40 (m, 3H) Four protons obscured by solvent; [M + H]⁺ 478 | [α]$_D$ = +73.0 (c 0.1 MeOH); 97% ee; Absolute stereo-chemistry undetermined; Enantiomer of Ex. 167 |
| 167 | (−)-5,8-dichloro-2-[(4,6-dimethyl-2-oxo-1,2-dihydro-pyridin-3-yl)methyl]-7-[methoxy(piperidin-4-yl)-methyl]-3,4-dihydroisoquinolin-1(2H)-one | I  ¹H NMR (700 MHz, DMSO-d6) δ 7.43 (s, 1H), 5.89 (8, 1H), 4.54-4.58 (m, 2H), 4.52 (d, J = 5.72 Hz, 1H), 3.46 (t, J = 5.94 Hz, 2H), 3.11 (s, 3H), 2.83-300 (m, 4H), 2.17 (s, 3H), 2.12 (s, 3H), 1.62-1.72 (m, 1H), 1.51-1.62 (m, 1H), 1.29-1.42 (m, 1H), 1.19-1.28 (m, 2H). Two protons obscured by solvent; [M + H]⁺ 478 | [α]$_D$ = −59.7° (c 0.1 MeOH); 99% ee; Absolute stereochemistry undetermined; Enantiomer of Ex. 166 |

TABLE 1-continued

| Ex. No. | Structure/IUPAC name | Method | $^1$H NMR (ppm); LCMs [M + H]$^+$ | Stereochemistry Note |
|---|---|---|---|---|
| 168 | (+)-8-chloro-2-[(4,6-dimethyl-2-oxo-1,2-dihydropyridin-3-yl)methyl]-7-{[1-(hydroxyacetyl)piperidin-4-yl](methoxy)methyl}-5-methyl-3,4-dihydroisoquinolin-1(2H)-one | I | $^1$H NMR (700 MHz, DMSO-d6) δ 11.55 (br. s., 1H), 7.26 (s, 1H), 5.88 (s, 1H), 4.52-4.62 (m, 3H), 4.44 (br. s., 1H), 4.28-439 (m, 1H), 4.04-4.11 (m, 1H), 396-404 (m, 1H), 3.57-3.71 (m, 1H), 3.40 (br. s., 2H), 3.08 (s, 3H), 2.82 (t, J = 11.88 Hz, 1H), 2.72 (t, J = 5.94 Hz, 2H), 2.43-2.48 (m, 1H), 2.24 (s, 3H), 2.16 (s, 3H), 2.12 (s, 3H), 1.79-1.88 (m, 1H), 1.65-1.74 (m, 1H), 1.15-1.37 (m, 3H); [M + H]$^+$ 516 | [α]$_D$ = +60.2° (c 0.1 MeOH); 99% ee; Absolute stereochemistry undetermined; Enantiomer of Ex. 169 |
| 169 | (−)-8-chloro-2-[(4,6-dimethyl-2-oxo-1,2-dihydropyridin-3-yl)-methyl]-7-{[1-(hydroxyacetyl)piperidin-4-yl](methoxy)methyl}-5-methyl-3,4-dihydroisoquinolin-1(2H)-one | I | $^1$H NMR (700 MHz, DMSO-d6) δ 11.55 (br. s., 1H), 7.26 (s, 1H), 5.88 (s, 1H), 4.51-4.60 (m, 3H), 4.44 (br. s., 1H), 4.29-4.39 (m, 1H), 4.04-4.10 (m, 1H), 3.95-4.04 (m, 1H), 3.58-3.70 (m, 1H), 3.40 (br. s., 2H), 3.08 (s, 3H), 2.82 (t, J = 11.99 Hz, 1H), 2.72 (t, J = 5.94 Hz, 2H), 2.43-2.47 (m, 1H), 2.24 (s, 3H), 2.16 (s, 3H), 2.12 (s, 3H), 1.79-1.87 (m, 1H), 1.66-1.72 (m, 1H), 1.16-1.36 (m, 3H); [M + H]$^+$ 516 | [α]$_D$ = −31.2° (c 0.1 MeOH): −80% ee; Absolute stereochemistry undetermined; Enantiomer of Ex. 168 |
| 170 | (+)-5,8-dichloro-2-[(4,6-dimethyl-2-oxo-1,2-dihydropyridin-3-yl)methyl]-7-[{1-[(2R)-2-hydroxypropanoyl]azetidin-3-yl}(methoxy)methyl]-3,4-dihydroisoquinolin-1(2H)-one | I | $^1$H NMR (400 MHz, DMSO-d6) δ 11.54 (br. s., 1H), 7.55 (s, 1H), 5.88 (s, 1H), 5.00 (dd, J = 4.89, 5.87 Hz, 1H), 4.91 (d, J = 4.89 Hz, 1H), 4.57 (s, 2H), 4.02-4.24 (m, 3H), 3.78-3.89 (m, 1H), 3.66-3.75 (m, 1H), 3.46 (t, J = 5.99 Hz, 2H), 3.21 (s, 3H), 2.94-3.04 (m, 1H), 2.90 (t, J = 6.11 Hz, 2H), 2.17 (s, 3H), 2.12 (s, 3H), 1.15 (d, J = 6.85 Hz, 3H); [M + H]$^+$ 522 | [α]$_D$ = +123.5° (c = 0.1, MeOH); >99% de; Single diastereomer containing (R)-2-hydroxypropanamide; other chiral center undetermined; Enantiomer of Ex. 173 Diastereomer of Ex. 171 and Ex. 172 |
| 171 | (−)-5,8-dichloro-2-[(4,6-dimethyl-2-oxo-1,2-dihydropyridin-3-yl)methyl]-7-[{1-[(2R)-2-hydroxypropanoyl]azetidin-3-yl}-(methoxy)methyl]-3,4-dihydroisoquinolin-1(2H)-one | I | $^1$H NMR (400 MHz, DMSO-d6) δ 11.54 (br. s., 1H), 7.55 (s, 1H), 5.89 (s, 1H), 4.97 (dd, J = 6.05, 15.34 Hz, 1H), 4.91 (t, J = 6.42 Hz, 1H), 4.57 (s, 2H), 4.17-4.29 (m, 1H), 4.00-4.14 (m, 2H), 3.70-3.86 (m, 2H), 3.46 (t, J = 5.62 Hz, 2H), 3.21 (d, J = 1.96 Hz, 3H), 2.93-3.03 (m, 1H), | [α]$_D$ = −110.6° (c = 0.1, MeOH); >99% de; Single diastereomer containing (R)-2-hydroxypropanamide; other chiral center undetermined; Enantiomer of Ex. 172 Diastereomer of Ex. 170 and Ex. 173 |

TABLE 1-continued

| Ex. No. | Structure/IUPAC name | Method | ¹H NMR (ppm); LCMs [M + H]⁺ | Stereochemistry Note |
|---|---|---|---|---|
| | | | 2.90 (t, J = 5.99 Hz, 2H), 2.17 (s, 3H), 2.12 (s, 3H), 1.14 (dd, J = 4.34, 6.66 Hz, 3H); [M + H]⁺ 522 | |
| 172 | 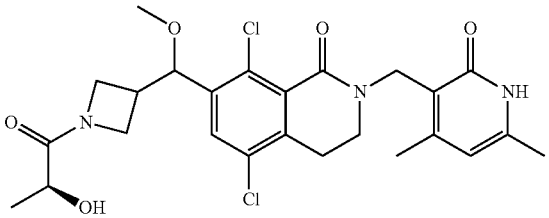<br>(+)-5,8-dichloro-2-[(4,6-dimethyl-2-oxo-1,2-dihydropyridin-3-yl)methyl]-7-[{1-[(2S)-2-hydroxypropanoyl]azetidin-3-yl}(methoxy)methyl]-3,4-dihydroisoquinolin-1(2H)-one | I | ¹H NMR (400 MHz, DMSO-d6) δ 11.53 (br. s., 1H). 7.55 (s, 1H), 5.88 (s, 1H), 4.96 (dd, J = 6.11, 15.41 Hz, 1H), 4.90 (t, J = 6.36 Hz, 1H), 4.56 (s, 2H), 4.17-4.27 (m, 1H), 4.00-4.12 (m. 2H), 3.68-3.87 (m, 2H), 3.46 (t, J = 5.87 Hz, 2H), 3.21 (d, J = 1.96 Hz, 3H), 2.93-3.02 (m, 1H), 2.89 (t, J = 6.11 Hz, 2H), 2.16 (s, 3H), 2.12 (s, 3H), 1.14 (dd, J = 4.16, 6.60 Hz, 3H); [M + H]⁺ 522 | [α]$_D$ = +69.5° (c = 0.1, MeOH); >99% de; Single diastereomer containing (S)-2-hydroxypropanamide; other chiral center undetermined; Enantiomer of Ex. 171 Diastereomer of Ex. 173 and Ex. 170 |
| 173 | 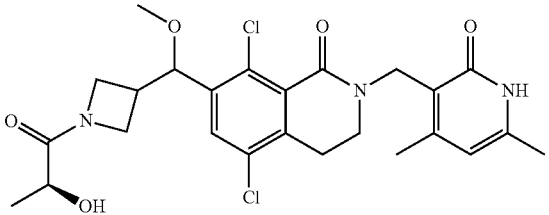<br>(−)-5,8-dichloro-2-[(4,6-dimethyl-2-oxo-1,2-dihydropyridin-3-yl)methyl]-7-[{1-[(2S)-2-hydroxypropanoyl]azetidin-3-yl}(methoxy)methyl]-3,4-dihydroisoquinolin-1(2H)-one | I | ¹H NMR (400 MHz, DMSO-d6) δ 11.54 (br. s., 1H), 7.54 (s, 1H), 5.89 (s, 1H), 5.00 (t, J = 5.26 Hz, 1H), 4.91 (d, J = 4.89 Hz, 1H), 4.57 (s, 2H), 4.01-4.26 (m, 3H), 3.77-3.90 (m, 1H), 3.66-3.74 (m, 1H), 3.46 (t, J = 5.87 Hz, 2H), 3.21 (s, 3H), 2.93-3.03 (m, 1H), 2.90 (t, J = 6.11 Hz, 2H), 2.17 (s, 3H), 2.12 (s, 3H), 1.15 (d, J = 6.36 Hz, 3H); [M + H]⁺ 522 | [α]$_D$ = −105.1° (c = 0.1, MeOH); ~88% de; Single diastereomer containing (S)-2-hydroxypropanamide; other chiral center undetermined; Enantiomer of Ex. 170 Diastereomer of Ex. 172 and Ex. 171 |
| 174 | 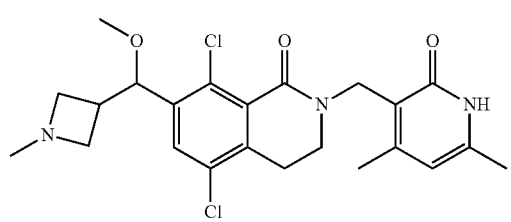<br>(+)-5,8-dichloro-2-[(4,6-dimethyl-2-oxo-1,2-dihydropyridin-3-yl)methyl]-7-[methoxy(1-methylazetidin-3-yl)methyl]-3,4-dihydroisoquinolin-1(2H)-one | I | ¹H NMR (400 MHz, DMSO-d6) δ 11.48 (br. s., 1H), 7.47 (s, 1H), 5.88 (s, 1H), 4.89 (d, J = 7.09 Hz, 1H), 4.56 (s, 2H), 3.46 (t, J = 6.11 Hz, 2H), 3.10-3.19 (m, 4H), 2.97-3.09 (m, 2H), 2.79-2.94 (m, 3H), 2.62-2.71 (m, 1H), 2.17 (s, 3H), 2.15 (s, 3H), 2.12 (s, 3H); [M + H]⁺ 464 | [α]$_D$ = +88.5° (c = 0.1, MeOH); >99% ee; Absolute stereochemistry undetermined; Enantiomer of Ex. 175 |
| 175 | 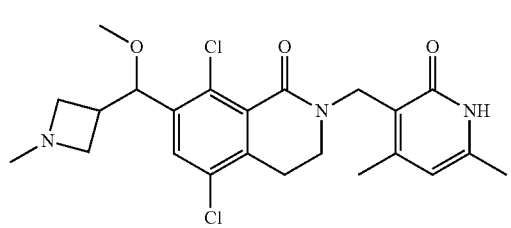<br>(−)-5,8-dichloro-2-[(4,6-dimethyl-2-oxo-1,2-dihydropyridin-3-yl)methyl]-7-[methoxy(1-methylazetidin-3-yl)methyl]-3,4-dihydroisoquinolin-1(2H)-one | I | ¹H NMR (400 MHz, DMSO-d6) δ 11.48 (br. s., 1H), 7.47 (s, 1H), 5.88 (s, 1H), 4.89 (d, J = 7.09 Hz, 1H), 4.56 (s, 2H), 3.46 (t, J = 6.11 Hz, 2H), 3.10-3.19 (m, 4H), 2.97-3.09 (m, 2H), 2.79-2.94 (m, 3H), 2.62-2.71 (m, 1H), 2.17 (s, 3H), 2.15 (s, 3H), 2.12 (s, 3H); [M + H]⁺ 464 | [α]$_D$ = −70.2° (c = 0.1, MeOH); >99% ee; Absolute stereochemistry undetermined; Enantiomer of Ex. 174 |

TABLE 1-continued

| Ex. No. | Structure/IUPAC name | Method | $^1$H NMR (ppm); LCMs [M + H]$^+$ | Stereochemistry Note |
|---|---|---|---|---|
| 176 | 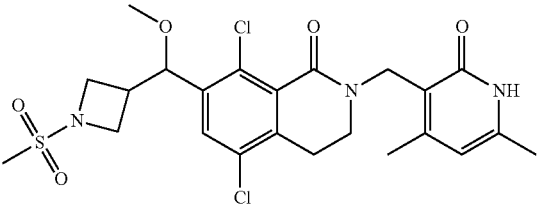<br>(+)-5,8-dichloro-2-[(4,6-dimethyl-2-oxo-1,2-dihydropyridin-3-yl)methyl]-7-{methoxy[1-(methylsulfonyl)azetidin-3-yl]-methyl}-3,4-dihydroisoquinolin-1(2H)-one | I | $^1$H NMR (400 MHz, DMSO-d6) δ 11.54 (br. s., 1H), 7.61 (s, 1H), 5.88 (s, 1H), 4.87 (d, J = 5.14 Hz, 1H), 4.57 (s, 2H), 3.97 (t, J = 7.46 Hz, 1H), 3.75-3.87 (m, 2H), 3.67 (t, J = 8.31 Hz, 1H), 3.45 (t, J = 6.24 Hz, 2H), 3.23 (s, 3H), 2.99 (s, 3H), 2.93-3.03 (m, 1H), 2.89 (t, J = 5.99 Hz, 2H), 2.17 (s, 3H), 2.12 (s, 3H); [M + H]$^+$ 528 | $[α]_D$ = +104.4° (c = 0.2, MeOH); >99% ee; Absolute stereochemistry undetermined; Enantiomer of Ex. 177 |
| 177 | 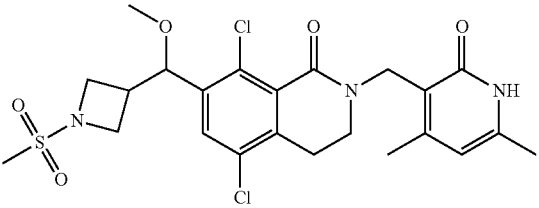<br>(−)-5,8-dichloro-2-[(4,6-dimethyl-2-oxo-1,2-dihydropyridin-3-yl)methyl]-7-{methoxy[1-(methylsulfonyl)acetidin-3-yl]-methyl}-3,4-dihydroisoquinolin-1(2H)-one | I | $^1$H NMR (400 MHz, DMSO-d6) δ 11.54 (br. s., 1H), 7.61 (s, 1H), 5.88 (s, 1H), 4.87 (d, J = 5.14 Hz, 1H), 4.57 (s, 2H), 3.97 (t, J = 7.34 Hz, 1H), 3.76-3.86 (m, 2H), 3.67 (t, J = 8.31 Hz, 1H), 3.45 (t, J = 6.11 Hz, 2H), 3.23 (s, 3H), 2.99 (s, 3H), 2.94-3.02 (m, 1H), 2.89 (t, J = 6.11 Hz, 2H), 2.17 (s, 3H), 2.12 (s, 3H); [M + H]$^+$ 528 | $[α]_D$ = −111.7° (c = 0.1, MeOH); ~97% ee; Absolute stereochemistry undetermined; Enantiomer of Ex. 176 |
| 178 | 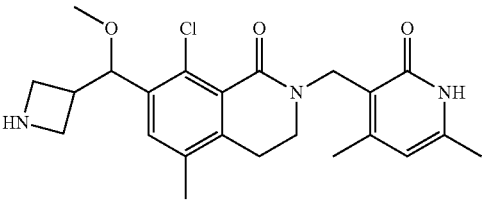<br>(±)-7-[azetidin-3-yl(methoxy)methyl]-8-chloro-2-[(4,6-dimethyl-2-oxo-1,2-dihydropyridin-3-yl)methyl]-5-methyl-3,4-dihydroisoquinolin-1(2H)-one | I | $^1$H NMR (400 MHz, CD3OD) δ 7.37 (s, 1H), 6.10 (s, 1H), 4.99 (d, J = 5.50 Hz, 1H), 4.77 (s, 2H), 3.79-3.95 (m, 2H), 3.55-3.72 (m, 2H), 3.46 (t, J = 5.99 Hz, 2H), 3.29 (s, 3H), 3.16 (dd, J = 7.76, 14.12 Hz, 1H), 2.81 (t, J = 5.93 Hz, 2H), 2.29 (s, 6H), 2.25 (s, 3H); [M + H]$^+$ 430 | racemic mixture |
| 179 | 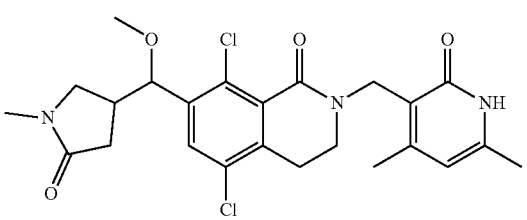<br>(+)-5,8-dichloro-2-[(4,6-dimethyl-2-oxo-1,2-dihydropyridin-3-yl)methyl]-7-[methoxy(1-methyl-5-oxopyrrolidin-3-yl)-methyl]-3,4-dihydroisoquinolin-1(2H)-one | I | $^1$H NMR (400 MHz, DMSO-d6) δ 11.54 (br. s., 1H), 7.55 (s, 1H), 5.89 (s, 1H), 4.74 (d, J = 5.87 Hz, 1H), 4.56 (s, 2H), 3.47 (t, J = 6.11 Hz, 2H), 3.16 (s, 3H), 3.09 (dd, J = 6.36, 9.54 Hz, 1H), 2.90 (t, J = 5.87 Hz, 2H), 2.70-2.78 (m, 1H), 2.67 (s, 3H), 2.26-2.35 (m, 1H), 2.17 (s, 3H), 2.07-2.16 (m, 4H) One proton under water peak; [M + H]$^+$ 492 | $[α]_D$ = +51.2° (c = 0.1, MeOH); >99% de; Absolute and relative stereochemistry undetermined; Enantiomer of Ex. 180 |

TABLE 1-continued

| Ex. No. | Structure/IUPAC name | Method | ¹H NMR (ppm); LCMs [M + H]⁺ | Stereochemistry Note |
|---|---|---|---|---|
| 180 | 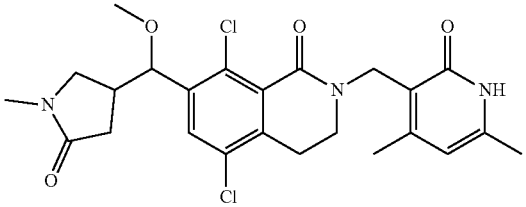<br>(−)-5,8-dichloro-2-[(4,6-dimethyl-2-oxo-1,2-dihydropyridin-3-yl)methyl]-7-[methoxy(1-methyl-5-oxopyrrolidin-3-yl)methyl]-3,4-dihydroisoquinolin-1(2H)-one | I | ¹H NMR (400 MHz, DMSO-d6) δ 11.54 (s, 1H), 7.55 (s, 1H), 5.89 (s, 1H), 4.74 (d, J = 6.11 Hz, 1H), 4.56 (s, 2H), 3.47 (t, J = 6.24 Hz, 2H), 3.16 (s, 3H), 3.09 (dd, J = 6.24, 9.66 Hz, 1H), 2.90 (t, J = 6.11 Hz, 2H), 2.69-2.77 (m, 1H), 2.67 (s, 3H), 2.26-2.34 (m, 1H), 2.18 (s, 3H), 2.08-2.16 (m, 4H) One proton under water peak; [M + H]⁺ 492 | [α]$_D$ = −69.5° (c = 0.1, MeOH); ~99% de; Absolute and relative stereochemistry undetermined; Enantiomer of Ex. 179 |
| 181 | 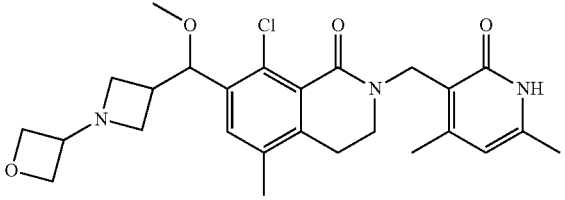<br>(+)-8-chloro-2-[(4,6-dimethyl-2-oxo-1,2-dihydropyridin-3-yl)methyl]-7-{methoxy[1-(oxetan-3-yl)azetidin-3-yl]methyl}-5-methyl-3,4-dihydroisoquinolin-1(2H)-one | I | ¹H NMR (400 MHz, DMSO-d6) δ 11.52 (br. s., 1H), 7.29 (s, 1H), 5.88 (s, 1H), 4.91 (d, J = 6.85 Hz, 1H), 4.56 (s, 2H), 4.52 (t, J = 6.48 Hz, 2H), 4.28-4.38 (m, 2H), 3.60-3.74 (m, 1H), 3.40 (t, J = 6.11 Hz, 2H), 3.16-3.25 (m, 2H), 3.06-3.15 (m, 4H), 2.97-3.06 (m, 1H), 2.68-2.79 (m, 3H), 2.22 (s, 3H), 2.17 (s, 3H), 2.12 (s, 3H); [M + H]⁺ 486 | [α]$_D$ = +110.8° (c = 0.1, MeOH); ~99% ee; Absolute stereochemistry undetermined; Enantiomer of Ex. 182 |
| 182 | 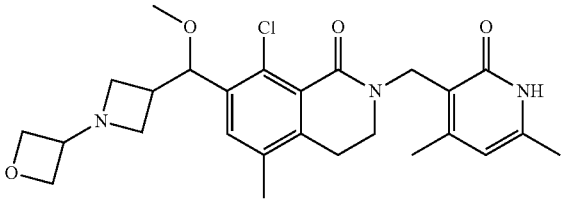<br>(−)-8-chloro-2-[(4,6-dimethyl-2-oxo-1,2-dihydropyridin-3-yl)methyl]-7-{methoxy[1-(oxetan-3-yl)azetidin-3-yl]methyl}-5-methyl-3,4-dihydroisoquinolin-1(2H)-one | I | ¹H NMR (400 MHz, DMSO-d6) δ 11.53 (br. s., 1H), 7.29 (s, 1H), 5.88 (s, 1H), 4.91 (d, J = 7.09 Hz, 1H), 4.56 (s, 2H), 4.52 (t, J = 6.48 Hz, 2H), 4.33 (td, J = 5.93, 8.19 Hz, 2H), 3.66 (quin, J = 5.93 Hz, 1H), 3.40 (t, J = 5.99 Hz, 2H), 3.15-3.23 (m, 2H), 3.13 (s, 3H), 3.09 (t, J = 7.46 Hz, 1H), 3.00 (t, J = 6.97 Hz, 1H), 2.68-2.78 (m, 3H), 2.22 (s, 3H), 2.17 (s, 3H), 2.12 (s, 3H); [M + H]⁺ 486 | [α]$_D$ = −85.3° (c = 0.1, MeOH); >99% ee; Absolute stereochemistry undetermined; Enantiomer of Ex. 181 |
| 183 | 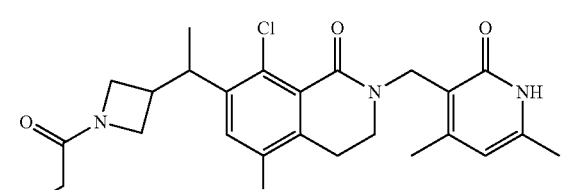<br>5,8-dichloro-2-[(4,6-dimethyl-2-oxo-1,2-dihydropyridin-3-yl)methyl]-7-{1-[1-(hydroxyacetyl)azetidin-3-yl]ethyl}-3,4-dihydroisoquinolin-1(2H)-one - Isomer A | J | ¹H NMR (400 MHz, CDCl3) δ 11.37 (brs, 1H), 7.17 (s, 1H), 5.94 (s, 1H), 4.77 (s, 2H), 4.19-4.27 (m, 1H), 3.92-4.00 (m, 4H), 3.57-3.74 (m, 4H), 3.16-3.22 (m, 1H), 3.01-2.88 (m 3H), 2.36 (s, 3H), 2.27 (s, 3H), 1.19 (d, J = 6.01 Hz, 3H); [M + H]⁺ 492 | Single isomer, absolute stereochemistry unknown; Enantiomer of Ex. 184; 96% ee; retention time: 2.459 min; column: Chiralcel OJ-3 100 × 4.6 mm I.D., 3 um; mobile phase: 5-40% methanol (0.05% DEA) in CO2 |

TABLE 1-continued

| Ex. No. | Structure/IUPAC name | Method | ¹H NMR (ppm); LCMs [M + H]⁺ | Stereochemistry Note |
|---|---|---|---|---|
| 184 | 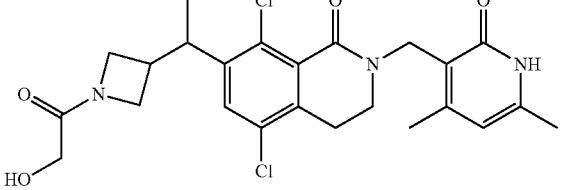<br>5,8-dichloro-2-[(4,6-dimethyl-2-oxo-1,2-dihydropyridin-3-yl)methyl]-7-{1-[1-(hydroxyacetyl)azetidin-3-yl]ethyl}-3,4-dihydroisoquinolin-1(2H)-one - Isomer B | J | ¹H NMR (400 MHz, CDCl3) δ 11.70 (brs, 1H), 7.17 (s, 1H), 5.94 (s, 1H), 4.77 (s, 2H), 4.22- 4.38 (m, 1H), 3.89-4.00 (m, 4H), 3.55-3.75 (m, 4H), 3.16-3.23 (m, 1H), 2.99-2.86 (m, 3H), 2.36 (s, 3H), 2.28 (s, 3H), 1.19 (d, J = 6.01 Hz, 3H); [M + H]⁺ 492 | Single isomer, absolute stereochemistry unknown; Enantiomer of Ex. 183; 94% ee; retention time: 2.661 min; column: Chiralcel OJ-3 100 × 4.6 mm I.D., 3 um; mobile phase: 5-40% methanol (0.05% DEA) in CO2 |
| 185 | 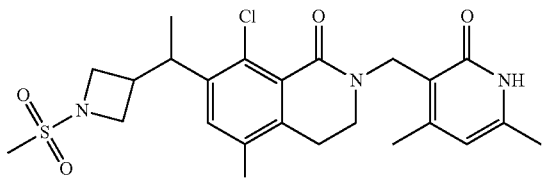<br>5,8-dichloro-2-[(4,6-dimethyl-2-oxo-1,2-dihydropyridin-3-yl)-methyl]-7-{1-[1-(methylsulfonyl)azetidin-3-yl]ethyl}-3,4-dihydroisoquinolin-1(2H)-one - Isomer A | J | ¹H NMR (400 MHz, DMSO-d6) δ 11.59 (br. s., 1H), 7.55 (s, 1H), 5.89 (br. s., 1H), 4.57 (br. s., 2H), 3.97 (br. s., 2H), 3.77 (d, J = 12.30 Hz, 2H), 3.62 (br. s., 2H), 3.44-3.47 (m, 2H), 2.98 (s, 3H), 2.85 (br. s., 2H), 2.15 (d, J = 14.05 Hz, 6H), 1.13 (d, J = 6.02 Hz, 3H); [M + Na]⁺ 534 | Single isomer, absolute stereochemistry unknown; Enantiomer of Ex. 186; 100% ee; retention time 5.299 min; column: Chiralpak AD-3 100 × 4.6 mm I.D., 3 um; mobile phase: 5-40% ethanol (0.05% DEA) in CO2 |
| 186 | 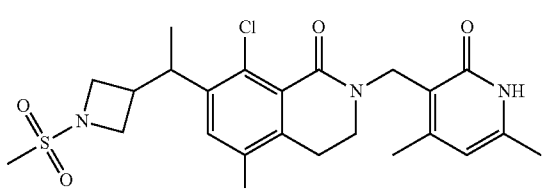<br>5,8-dichloro-2-[(4,6-dimethyl-2-oxo-1,2-dihydropyridin-3-yl)-methyl]-7-{1-[1-(methylsulfonyl)azetidin-3-yl]ethyl}-3,4-dihydroisoquinolin-1(2H)-one - Isomer B | J | ¹H NMR (400 MHz, DMSO-d6) δ 11.57 (br. s., 1H), 7.55 (s, 1H), 5.89 (s, 1H), 4.57 (s, 2H), 3.97 (t, J = 8.03 Hz, 2H), 3.74-3.83 (m, 2H), 3.62 (d, J = 9.29 Hz, 2H), 3.44 (br. s., 2H), 2.99 (s, 3H), 2.87 (d, J = 6.02 Hz, 2H), 2.15 (d, J = 16.56 Hz, 6H), 1.13 (d, J = 6.78 Hz, 3H); [M + Na]⁺ 534 | Single isomer, absolute stereochemistry unknown; Enantiomer of Ex. 185; 99% ee; retention time 5.807 min; column: Chiralpak AD-3 100 × 4.6 mm I.D., 3 um; mobile phase: 5-40% ethanol (0.05% DEA) in CO2 |
| 187 | 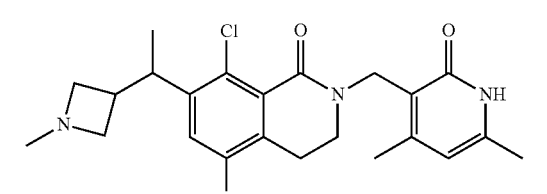<br>5,8-dichloro-2-[(4,6-dimethyl-2-oxo-1,2-dihydropyridin-3-yl)methyl]-7-[1-(1-methylazetidin-3-yl)ethyl]-3,4-dihydroisoquinolin-1(2H)-one - Isomer A | J | ¹H NMR (400 MHz, CD3OD) δ 7.50 (br. s, 1H), 6.14 (s, 1H), 4.77 (s, 2H), 4.13 (d, J = 7.53 Hz, 2H), 3.77-4.02 (m, 3H), 3.68 (d, J = 10.29 Hz, 1H), 3.53 (t, J = 6.02 Hz, 2H), 2.88-3.01 (m, 5H), 2.32 (s, 3H), 2.27 (s, 3H), 1.22 (d, J = 6.78 Hz, 3H); [M + H]⁺ 448 | Single isomer, absolute stereochemistry unknown; Enantiomer of Ex. 188; 100% ee; retention time 5.295 min; column: Chiralpak AD-3 150 × 4.6 mm I.D., 3 um; mobile phase: 5-40% methanol (0.05% DEA) in CO2 |
| 188 | 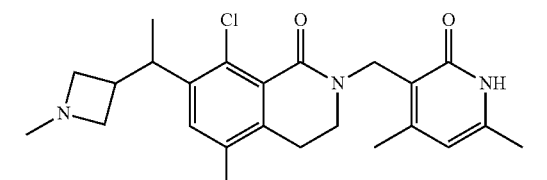<br>5,8-dichloro-2-[(4,6-dimethyl-2-oxo-1,2-dihydropyridin-3-yl)methyl]-7-[1-(1-methylzaetidin-3-yl)ethyl]-3,4-dihydroisoquinolin-1(2H)-one - Isomer B | J | ¹H NMR (400 MHz, CD3OD) δ 7.48 (s, 1H), 6.14 (s, 1H), 4.77 (s, 2H), 4.09 (t, J = 8.41 Hz, 1H), 3.73-3.89 (m, 3H), 3.53 (t, J = 6.27 Hz, 2H), 3.44 (t, J = 8.53 Hz, 1H), 3.07-3.19 (m, 1H), 2.97 (q, J = 5.77 Hz, 2H), 2.74 (s, 3H), 2.32 (s, 3H), 2.27 (s, 3H), 1.20 (d, J = 6.78 Hz, 3H); [M + H]⁺ 448 | Single isomer, absolute stereochemistry unknown; Enantiomer of Ex. 187; 100% ee; retention time 5.420 min; column: Chiralpak AD-3 150 × 4.6 mm I.D., 3 um; mobile phase: 5-40% methanol (0.05% DEA) in CO2 |

TABLE 1-continued

| Ex. No. | Structure/IUPAC name | Method | ¹H NMR (ppm); LCMs [M + H]⁺ | Stereochemistry Note |
|---|---|---|---|---|
| 189 | 7-[1-(azetidin-3-yl)ethyl]-5,8-dichloro-2-[(4,6-dimethyl-2-oxo-1,2-dihydropyridin-3-yl)methyl]-3,4-dihydroisoquinolin-1(2H)-one - Isomer A | J | ¹H NMR (400 MHz, CDCl3) δ 7.12 (s, 1H), 5.92 (s, 1H), 5.33-5.37 (m, 1H), 4.89-4.93 (m, 1H), 4.36-4.39 (m, 1H), 4.13-4.17 (m, 1H), 3.82-3.91 (m, 3H), 3.65-3.70 (m, 3H), 3.19-3.23 (m, 1H), 2.88-2.91 (m, 2H), 2.40 (s, 3H), 2.30 (s, 3H), 1.15 (d, J = 6.80 Hz, 3H); [M + Na]⁺ 456 | Single isomer, absolute stereochemistry unknown; Enantiomer of Ex. 190; 100% ee; retention time 6.673 min; column: Chiralcel OD-3 150 × 4.6 mm I.D., 3 um; mobile phase: 5-40% ethanol (0.05% DEA) in CO2 |
| 190 | 7-[1-(azetidin-3-yl)ethyl]-5,8-dichloro-2-[(4,6-dimethyl-2-oxo-1,2-dihydropyridin-3-yl)methyl]-3,4-dihydroisoquinolin-1(2H)-one - Isomer B | J | ¹H NMR (400 MHz, CDCl3) δ 7.15 (s, 1H), 5.95 (s, 1H), 5.33-5.37 (m, 1H), 4.82-4.92 (m, 1H), 4.38-4.42 (m, 1H), 4.13-4.17 (m, 1H), 3.82-3.91 (m, 3H), 3.65-3.70 (m, 3H), 3.19-3.23 (m, 1H), 2.88-2.91 (m, 2H), 2.40 (s, 3H), 2.30 (s, 3H), 1.15 (d, J = 6.80 Hz, 3H); [M + H]⁺ 434 | Single isomer, absolute stereochemistry unknown; Enantiomer Ex. 189; 97% ee; retention time 5.996 min; column: Chiralcel OD-3 150 × 4.6 mm I.D., 3 um; mobile phase: 5-40% ethanol (0.05% DEA) in CO2 |
| 191 | 8-chloro-2-[(4-methoxy-6-methyl-2-oxo-1,2-dihydropyridin-3-yl)methyl]-5-methyl-7-{1-[1-(methylsulfonyl)azetidin-3-yl]-ethyl}-3,4-dihydroisoquinolin-1(2H)-one - Isomer A | J | ¹H NMR (400 MHz, CD3OD) δ 7.23 (s, 1H), 6.27 (s, 1H), 4.69-4.78 (m, 2H), 4.10 (t, J = 8.03 Hz, 1H), 3.91 (s, 3H), 3.74-3.85 (m, 3H), 3.46 (dd, J = 6.78, 8.03 Hz, 1H), 3.34-3.38 (m, 2H), 3.02 (dd, J = 6.78, 17.32 Hz, 1H), 2.93 (s, 3H), 2.77 (t, J = 6.27 Hz, 2H), 2.33 (s, 3H), 2.28 (s, 3H), 1.20 (d, J = 6.78 Hz, 3H); [M + H]⁺ 508 | Single isomer, absolute stereochemistry unknown; Enantiomer of Ex. 192; 96% ee; retention time 4.765 min; column: Chiralpak AD-3 100 × 4.6 mm I.D., 3 um; mobile phase: 5-40% ethanol (0.05% DEA) in CO2 |
| 192 | 8-chloro-2-[(4-methoxy-6-methyl-2-oxo-1,2-dihydropyridin-3-yl)methyl]-5-methyl-7-{1-[1-(methylsulfonyl)azetidin-3-yl]-ethyl}-3,4-dihydroisoquinolin-1(2H)-one - Isomer B | J | ¹H NMR (400 MHz, CD3OD) δ 7.23 (s, 1H), 6.27 (s, 1H), 4.74 (d, J = 1.25 Hz, 2H), 4.10 (t, J = 8.16 Hz, 1H), 3.90 (s, 3H), 3.74-3.86 (m, 3H), 3.46 (dd, J = 6.65, 7.91 Hz, 1H), 3.34-3.38 (m, 2H), 3.05 (m, 1H), 2.93 (s, 3H), 2.74-2.81 (m, 2H), 2.33 (s, 3H), 2.28 (s, 3H), 1.20 (d, J = 6.78 Hz, 3H); [M + Na]⁺ 530 | Single isomer, absolute stereochemistry unknown; Enantiomer of Ex. 191; 100% ee; retention time 5.207 min; column: Chiralpak AD-3 100 × 4.6 mm I.D., 3 um; mobile phase: 5-40% ethanol (0.05% DEA) in CO2 |

TABLE 1-continued

| Ex. No. | Structure/IUPAC name | Method | $^1$H NMR (ppm); LCMs [M + H]$^+$ | Stereochemistry Note |
|---|---|---|---|---|
| 193 | 8-chloro-2-[(4,6-dimethyl-2-oxo-1,2-dihydropyridin-3-yl)methyl]-5-methyl-7-{1-[1-(methylsulfonyl)azetidin-3-yl]ethyl}-3,4-dihydroisoquinolin-1(2H)-one - Isomer A | J | $^1$H NMR (400 MHz, CDCl3) δ 11.33 (br. s., 1H), 6.96 (s, 1H), 5.93 (s, 1H), 4.72-4.87 (m, 2H), 4.10 (t, J = 8.03 Hz, 1H), 3.69-3.84 (m, 3H), 3.60 (t, J = 6.02 Hz, 2H), 3.50 (t, J = 7.28 Hz, 1H), 2.85-2.95 (m, 1H), 2.84 (s, 3H), 2.71 (t, J = 6.02 Hz, 2H), 2.36 (s, 3H), 2.27 (s, 3H), 2.21 (s, 3H), 1.17 (d, J = 6.78 Hz, 3H); [M + H]$^+$ 492 | Single isomer, absolute stereochemistry unknown; Enantiomer of Ex. 194; 100% ee; retention time 5.024 min; column: Chiralpak AD-3 100 × 4.6 mm I.D., 3 um; mobile phase: 5-40% ethanol (0.05% DEA) in CO2 |
| 194 | 8-chloro-2-[(4,6-dimethyl-2-oxo-1,2-dihydropyridin-3-yl)methyl]-5-methyl-7-{1-[1-(methylsulfonyl)azetidin-3-yl]ethyl}-3,4-dihydroisoquinolin-1(2H)-one - Isomer B | J | $^1$H NMR (400 MHz, CDCl3) δ 11.82 (br. s., 1H), 6.96 (s, 1H), 5.93 (s, 1H), 4.72-4.87 (m, 2H), 4.09 (t, J = 8.03 Hz, 1H), 3.67-3.84 (m, 3H), 3.60 (t, J = 6.02 Hz, 2H), 3.50 (t, J = 7.28 Hz, 1H), 2.89 (d, J = 9.29 Hz, 1H), 2.84 (s, 3H), 2.71 (t, J = 6.15 Hz, 2H), 2.36 (s, 3H), 2.28 (s, 3H), 2.21 (s, 3H), 1.17 (d, J = 6.78 Hz, 3H); [M + H]$^+$ 492 | Single isomer, absolute stereochemistry unknown; Enantiomer of Ex. 193; 95% ee; retention time 5.219 min; column: Chiralpak AD-3 100 × 4.6 mm I.D., 3 um; mobile phase: 5-40% ethanol (0.05% DEA) in CO2 |
| 195 | 8-chloro-2-[(4,6-dimethyl-2-oxo-1,2-dihydropyridin-3-yl)methyl]-5-methyl-7-[1-(oxetan-3-yl)ethyl]-3,4-dihydroisoquinolin-1(2H)-one - Isomer A | J | $^1$H NMR (400 MHz, CDCl3) δ 11.67 (brs, 1H), 6.91 (s, 1H), 5.94 (s, 1H). 4.86 (t, J = 6.8 Hz, 1H), 4.80 (2H, s), 4.55-4.65 (m, 2H), 4.30 (t, J = 6.0 Hz, 1H), 3.90-4.00 (m, 1H), 3.60 (t, J = 6.0 Hz, 2H), 3.25-3.40 (m, 1H), 2.70 (t, J = 6.0 Hz, 2H), 2.69 (s, 3H), 2.37 (s, 3H), 2.28 (s, 3H), 1.13 (d, J = 6.8 Hz, 3H); [M + H]$^+$ 415 | Single isomer, absolute stereochemistry unknown; Enantiomer of Ex. 196; 99% ee; retention time: 2.854 min; column: OJ-3 100 × 4.6 mm I.D., 3 um; mobile phase: 5-40% methanol (0.05% DEA) in CO2 |
| 196 | 8-chloro-2-[(4,6-dimethyl-2-oxo-1,2-dihydropyridin-3-yl)methyl]-5-methyl-7-[1-(oxetan-3-yl)ethyl]-3,4-dihydroisoquinolin-1(2H)-one - Isomer B | J | $^1$H NMR (400 MHz, CDCl3) δ 11.72 (brs, 1H), 6.91 (s, 1H), 5.94 (s, 1H), 4.86 (t, J = 6.8 Hz, 1H), 4.80 (s, 2H), 4.55-4.65 (m, 2H), 4.31 (t, J = 6.4 Hz, 1H), 3.90-4.00 (m, 1H), 3.60 (t, J = 6.0 Hz, 2H), 3.25-3.40 (m, 1H), 2.70 (t, J = 6.0 Hz, 2H), 2.69 (s, 3H), 2.37 (s, 3H), 2.28 (s, 3H), 1.13 (d, J = 6.8 Hz, 3H); [M + H]$^+$ 415 | Single isomer, absolute stereochemistry unknown; Enantiomer of Ex. 195; 99% ee; retention time: 3.078 min; column: OJ-3 100 × 4.6 mm I.D., 3 um; mobile phase: 5-40% methanol (0.05% DEA) in CO2 |

TABLE 1-continued

| Ex. No. | Structure/IUPAC name | Method | $^1$H NMR (ppm); LCMs [M + H]$^+$ | Stereochemistry Note |
|---|---|---|---|---|
| 197 | 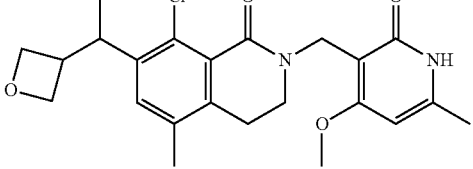<br>8-chloro-2-[(4-methoxy-6-methyl-2-oxo-1,2-dihydro-pyridin-3-yl)methyl]-5-methyl-7-[1-(oxetan-3-yl)-ethyl]-3,4-dihydroisoquinolin-1(2H)-one - Isomer A | J | $^1$H NMR (400 MHz, CDCl3) δ 12.75 (brs, 1H), 6.89 (s, 1H), 5.91 (s, 1H), 4.80-4.88 (m, 3H), 4.57-4.61 (m, 2H), 4.28 (t, J = 6.4 Hz, 1H), 3.86-3.93 (m, 4H), 3.31-3.42 (m, 3H), 2.70 (t, J = 6.0 Hz, 2H), 2.34 (s, 3H), 2.20 (s, 3H), 1.13 (d, J = 6.8 Hz, 3H); [M + H]$^+$ 431 | Single isomer, absolute stereochemistry unknown; Enantiomer of Ex. 198; 97% ee; retention time: 1.521 min; column: Chiralpak AD-3 150 × 4.6 mm I.D., 3 um; mobile phase: 40% isopropanol (0.05% DEA) in CO2 |
| 198 | 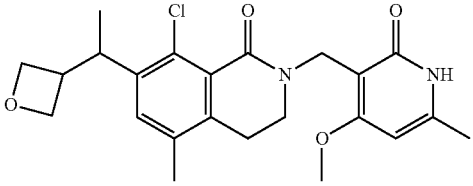<br>8-chloro-2-[(4-methoxy-6-methyl-2-oxo-1,2-dihydro-pyridin-3-yl)methyl]-5-methyl-7-[1-(oxetan-3-yl)-ethyl]-3,4-dihydroisoquinolin-1(2H)-one - Isomer B | J | $^1$H NMR (400 MHz, CDCl3) δ 12.39 (brs, 1H), 6.90 (s, 1H), 5.92 (s, 1H), 4.81-4.89 (m, 3H), 4.57-4.61 (m, 2H), 4.30 ft J = 6.0 Hz, 1H), 3.87-3.94 (m, 4H), 3.31-3.43 (m, 3H), 2.71 (t, J = 5.2 Hz, 2H), 2.34 (s, 3H), 2.22 (s, 3H), 1.13 (d, J = 6.8 Hz, 3H); [M + H]$^+$ 431 | Single isomer, absolute stereochemistry unknown; Enantiomer of Ex. 197; 94% ee; retention time: 2.081 min; column: Chiralpak AD-3 150 × 4.6 mm I.D., 3 um; mobile phase: 40% isopropanol (0.05% DEA) in CO2 |
| 199 | 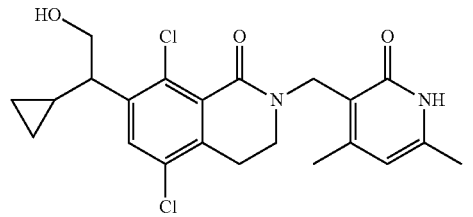<br>(±)-5,8-dichloro-7-(1-cyclopropyl-2-hydroxyethyl)-2-[(4,6-dimethyl-2-oxo-1,2-dihydropyridin-3-yl)-methyl]-3,4-dihydroisoquinolin-1(2H)-one | J | $^1$H NMR (400 MHz, CD3OD) δ 7.67 (s, 1H), 6.10 (s, 1H), 4.76 (s, 2H), 3.77-3.90 (m, 2H), 3.45-3.55 (m, 2H), 2.96 ft J = 6.24 Hz, 2H), 2.79-2.86 (m, 1H), 2.28 (s, 3H), 2.25 (s, 3H), 1.11-1.22 (m, 1H), 0.64-0.74 (m, 1H), 0.35-0.50 (m, 2H), 002-0.11 (m, 1H); [M + H]$^+$ 436 | racemic mixture |
| 200 | 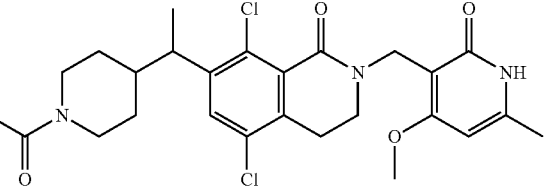<br>5,8-dichloro-7-{1-[1-(hydroxyacetyl)piperidin-4-yl]ethyl}-2-[(4-methoxy-6-methyl-2-oxo-1,2-dihydropyridin-3-yl)methyl]-3,4-dihydroisoquinolin-1(2H)-one - Isomer A | J | $^1$H NMR (400 MHz, CDCl3) δ 12.19 (s, 1H), 7.23 (d, J = 3.2 Hz, 1H), 5.91 (s, 1H), 4.82-4.73 (m, 2H), 4.70-4.50 (m, 1H), 4.15-4.11 (m, 2H), 3.87 (s, 3H), 3.70-3.66 (m, 1H), 3.54-3.40 (m, 4H), 2.92-2.86 (m, 3H), 2.64-2.58 (m, 1H), 2.34 (s, 3H), 1.84-1.62 (m, 2H), 1.50-1.40 (m, 1H), 1.26-1.19 (m, 5H); [M + H]$^+$ 536 | Single isomer, absolute stereochemistry unknown; Enantiomer of Ex. 201; 90% ee; retention time 26.03 min; column: Chiralpak AD-H 250 × 4.6 mm ID., 5u; mobile phase: 50/50 hexane (0.1% DEA)/ethanol (0.1% ethanolamine) |
| 201 | 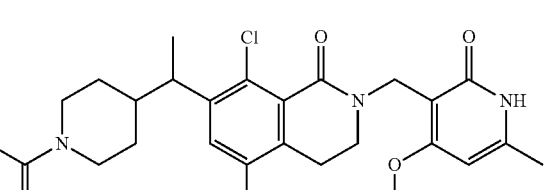<br>5,8-dichloro-7-{1-[1-(hydroxyacetyl)piperidin-4-yl]ethyl}-2-[(4-methoxy-6-methyl-2-oxo-1,2-dihydropyridin-3-yl)methyl]-3,4-dihydroisoquinolin-1(2H)-one - Isomer B | J | $^1$H NMR (400 MHz, CDCl3) δ 12.03 (s, 1H), 7.23 (d, J = 3.2 Hz, 1H), 5.92 (s, 1H), 4.82-4.73 (m, 2H), 4.70-4.50 (m, 1H), 4.14-4.11 (m, 2H), 3.87 (s, 3H), 3.70-3.66 (m, 1H), 3.47-3.40 (m, 4H), 2.92-2.86 (m, 3H), 2.64-2.61 (m, 1H), 2.34 (s, 3H), 1.84-1.62 (m, 2H), 1.50-1.40 (m, 1H), 1.26-1.19 (m, 5H); [M + H]$^+$ 536 | Single isomer, absolute stereochemistry unknown; Enantiomer Ex. 200; 97% ee; retention time: 51.00 min; column: Chiralpak AD-H 250 × 4.6 mm I.D., 5 um; mobile phase: 50/50 hexane (0.1% DEA)/ethanol(0.1% ethanolamine); |

US 10,570,121 B2

TABLE 1-continued

| Ex. No. | Structure/IUPAC name | Method | ¹H NMR (ppm); LCMs [M + H]⁺ | Stereochemistry Note |
|---|---|---|---|---|
| 202 | 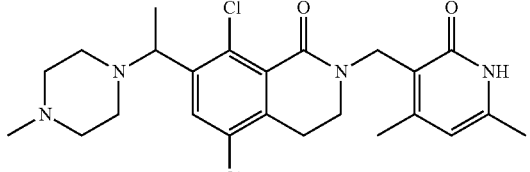<br>(±)-5,8-dichloro-2-[(4,6-dimethyl-2-oxo-1,2-dihydropyridin-3-yl)methyl]-7-[1-(4-methylpiperazin-1yl)ethyl]-3,4-dihydroisoquinolin-1(2H)-one | K | $^1$H NMR (400 MHz, CDCl3) δ 7.72 (s, 1H), 5.93 (s, 1H), 4.84-4.71 (m, 2H), 4.01 (q, J = 6.3 Hz, 1H), 3.63 (t, J = 6.1 Hz, 2H), 2.90 (d, J = 3.5 Hz, 2H), 2.42 (br. s., 6H), 2.35 (s, 3H), 2.28 (s, 6H), 1.79 (br. s., 2H), 1.24 (d, J = 6.5 Hz, 3H); [M + H]⁺ 477 | racemic mixture |
| 203 | 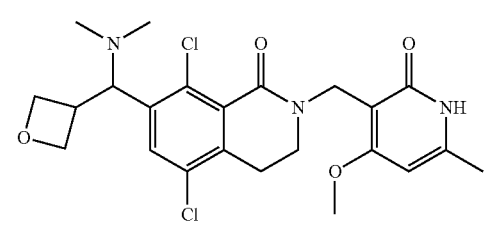<br>5,8-dichloro-7-[(dimethylamino)(oxetan-3-yl)methyl]-2-[(4-methoxy-6-methyl-2-oxo-1,2-dihydropyridin-3-yl)-methyl]-3,4-dihydroisoquinolin-1(2H)-one - Isomer A | K | $^1$H NMR (400 MHz, CDCl3) δ 12.34 (br. s., 1H), 7.43 (s, 1H), 5.95 (s, 1H), 4.61-4.88 (m, 4H), 4.48 (d, J = 10.04 Hz, 1H), 4.25-4.34 (m, 1H), 4.21 (t, J = 6.90 Hz, 1H), 3.82-3.95 (m, 3H), 3.49 (d, J = 1.76 Hz, 3H), 2.89 (t, J = 6.02 Hz, 2H), 2.35 (s, 3H), 2.13 (s, 6H); [M + H]⁺ 480 | Single isomer, absolute stereochemistry unknown; Enantiomer of Ex. 204; 88% ee; retention time 3.994 min; column: Chiralpak AD-3 100 × 4.6 mm I.D., 3 um; mobile phase: 5-40% isopropanol (0.05% DEA) in CO2 |
| 204 | 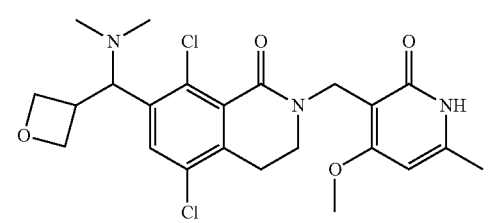<br>5,8-dichloro-7-[(dimethylamino)(oxetan-3-yl)methyl]-2-[(4-methoxy-6-methyl-2-oxo-1,2-dihydropyridin-3-yl)-methyl]-3,4-dihydroisoquinolin-1(2H)-one - Isomer B | K | $^1$H NMR (400 MHz, CDCl3) δ 12.32 (brs, 1H), 7.46 (brs, 1H), 5.96 (s, 1H), 4.57-4.88 (m, 4H), 4.50 (brs, 1H), 4.28 (t, J = 6.90 Hz, 1H), 4.19 (d, J = 6.27 Hz, 1H), 3.88 (s, 3H), 3.52 (br. s., 3H), 2.88 (brs, 2H), 2.37 (brs, 4H), 2.15 (brs, 5H); [M + H]⁺ 480 | Single isomer, absolute stereochemistry unknown; Enantiomer of Ex. 203; 97% ee; retention time 4.325 min; column: Chiralpak AD-3 100 × 4.6 mm I.D., 3 um; mobile phase: 5-40% isopropanol (0.05% DEA) in CO2 |
| 205 | 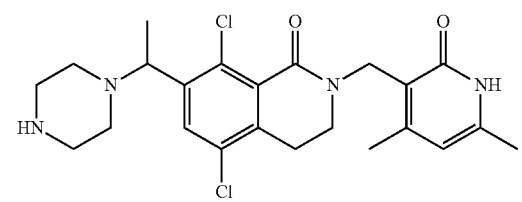<br>(±)-5,8-dichloro-2-[(4,6-dimethyl-2-oxo-1,2-dihydropyridin-3-yl)methyl]-7-[1-(piperazin-1-yl)ethyl]-3,4-dihydroisoquinolin-1(2H)-one | K | $^1$H NMR (400 MHz, CDCl3) δ 7.72 (s, 1H), 5.94 (s, 1H), 4.85-4.69 (m, 2H), 4.02 (q, J = 6.4 Hz, 2H), 3.62 (t, J = 6.4 Hz, 2H), 2.90 (br. s., 6H), 2.55 (br. s., 2H), 2.42-2.31 (m, 5H), 2.29 (s, 3H), 1.24 (d, J = 6.5 Hz, 3H); [M + H]⁺ 463 | racemic mixture |

Biological Assays and Data

Purification of WT and mutant EZH2 Y641N

WT and mutant EZH2 were purified using the same procedure. The genes for EZH2, EED, SUZ12, and RBBP4 proteins were cloned into pBacPAK9 vectors (Clontech). RBBP4 was FLAG tagged on the N-terminal end. The baculovirus expressions of these proteins were used to co-infect SF9 insect cells. Insect cell pellets were lysed in a buffer containing 25 mM Tris pH8.0, 300 mM NaCl, 0.5 mM TCEP, complete EDTA-free protease inhibitor (Roche), 0.1% NP-40. The supernatant from the lysate was incubated with FLAG® M2 antibody resin (Sigma). The resin was washed on the chromatography column and eluted with 0.2 mg/ml FLAG peptide. The elute was incubated with omnicleave nucleases (Epicentre Technologies) at 4° C. overnight, then concentrated and loaded onto a Superdex 200 (GE Healthcare) column. The Superdex 200 column was eluted with 25 mM Tris pH8.0, 150 mM NaCl, 0.5 mM TCEP. Fractions containing the PRC2 complex were pooled.

Nucleosome Assay Protocol: (the Same Protocol was Used for the WT and Mutant EZH2 Y6412N Assays)

A. Compound preparation
1. Prepare 10 mM stock solutions in 100% DMSO from solid material
2. Serial dilute 10 mM compound stocks either 2 or 3-fold in 100% DMSO to generate compounds for 11 point dose response B. Reagent preparation
1. Prepare 1× assay buffer containing 100 mM Tris pH 8.5, 4 mM DTT and 0.01% Tween-20

2. Dilute purified HeLa oligonucleosomes and recombinant histone H1 (New England Biolabs) in assay buffer to 1.67×.
3. Dilute PRC2 4 protein complex (EZH2, EED, SUZ12, RbAp48) to 3.5× in assay buffer
4. Prepare 10×$^3$H SAM solution in assay buffer using 0.94 μCi/well of radioactive SAM (Perkin Elmer) and sufficient non-labeled SAM (Sigma) for 1.5 μM final concentration.
5. Dilute TCA to 20% in DI water C. Enzyme reaction
1. Final reaction conditions are PRC2 4-protein complex at 4 nM when using WT EZH2 or 6 nM when using Y641N mutant EZH2, 1.5 μM SAM, 25 μg/mL oligonucleosomes, 50 nM rH1 in a 50 μl reaction volume.
2. Add 1 μl of diluted compound to the assay plate (96-well V-bottom polypropylene plates) or 1 μl of DMSO for control wells.
3. Add 30 μl of nucleosomes to the assay plate
4. Add 14 μl of either WT or Y641N mutant PRC2 4 protein complex to the assay plate
5. Add 5 μl of $^3$H SAM to start the reaction.
6. Stop the reaction after 60 minutes with the addition of 100 μl of 20% TCA
7. Transfer 150 μl of quenched reaction into a prepared filterplate (Millipore # MSIPN4B10)
8. Apply vacuum to the filterplate to filter the reaction mix through the membrane.
9. Wash the filterplate with 5×200 μl of PBS, blot dry and dry in an oven for 30 minutes
10. Add 50 μl of microscint-20 scintillation fluid (Perkin Elmer) to each well, wait 30 minutes and count on a liquid scintillation counter.
11. Some compounds were tested under high SAM conditions. In this case, the assay is as described above except that the reaction contains 15 uM SAM. SAM is added to the assay as a 3.3× stock with a total of 14.5 uCi/well.

D. Data analysis
1. $IC_{50}$ values were determined by fitting the data to a 4-parameter $IC_{50}$ equation using proprietary curve fitting software.
2. For compounds tested under high SAM conditions, $K_i^{app}$ values were obtained by fitting the dose response curve to a model for competitive inhibition using proprietary curve fitting software.

Preparation of HeLa Oligonucleosomes:
Reagents
  Cell Pellet: 15 L HeLa S3 (Accelgen)+6 L HeLa S3 (in house)
  Mnase (Worthington Biochemicals)
Equipment
  SW-28 Rotor
  Dounce Homogenizer/B Pestle
Buffers
  Lysis: 20 mM Hepes pH 7.5, 0.25M Sucrose, 3 mM $MgCl_2$, 0.5% Nonidet P-40, 0.5 mM TCEP, 1 Roche Protease Tablet
  B: 20 mM Hepes pH7.5, 3 mM $MgCl_2$, 0.5 mM EDTA, 0.5 mM TCEP, 1 Roche Protease Tablet
  MSB: 20 mM Hepes pH7.5, 0.4 M NaCl, 1 mM EDTA, 5% v/v Glycerol, 0.5 mM TCEP, 0.2 mM PMSF
  LSB: 20 mM Hepes pH7.5, 0.1M NaCl, 1 mM EDTA, 0.5 mM TCEP, 0.2 mM PMSF
  NG: 20 mM Hepes pH7.5, 1 mM EDTA, 0.4 m NaCl, 0.2 mM PMSF, 0.5 mM TCEP
  Storage: 20 mM Hepes pH7.5, 1 mM EDTA, 10% Glycerol, 0.2 mM PMSF, 0.5 mM TCEP Protocol
A. Nuclei
1. Resuspend ~10 L pellet in 2×40 mL lysis using dounce homogenizer
2. Spin 3000×g 15'
3. Repeat 2 more times
4. Resuspend pellet in 2×40 mL B
5. Spin 3000×g 15'

B. Nuclei Resuspension
1. Resuspend pellet in 2×40 mL MSB. Spin 5000×g 20'
2. Resuspend pellet in 2×15 mL HSB
3. Pool and Homogenize 40 Strokes to shear DNA
4. Pellet 10000×g 20'
5. Dialyze O/N 4° C. in LSB except for Batch A which was Dialyzed LSB at 50 nM NaCl for 3 hr C. Mnase Digestion
Test Mnase digestion (200 ul)
  1. Warm to 37° C. for 5'
  2. Add $CaCl_2$ to 3 mM and add 10 U of Mnase
  3. 37° C. 30' taking 25 μL sample every 5'
  4. Process reaction with 1 μL 0.5M EDTA, 40 μL $H_2O$, 15 μL 10% SDS, 10 μL 5M NaCl, and 100 μL phenol-chloroform vortexing after each addition
  5. Spin 5' 13 k
  6. Run 5 μL of Aqueous phase on 1% agarose gel
  7. Take time that yields ~2 kb fragments
  8. Selected 15' for A & B and 20' for C & D for scale up
Added NaCl to 0.6M D. Sucrose Gradient 1
1. Poured 6×34 mL gradient from 5 to 35% sucrose in NG using AKTA purifier in 38.5 mL pollyallomer tubes
2. Lead ~4.0 mL on top of MN1 digest
3. Spin 26 k 16 hr 4° C.
4. Take 2 mL fractions from top
5. Run on Page Gel
6. Dialyze Fractions 7-14 O/N 4° C. in 4 L LSB except Batch D which had 2×2 hr
7. Repeat 3×

E. Final
1. Pool all and concentrate in Amicon (somewhat cloudy)
2. Added 10% Glycerol
3. Spun 5K 15'
4. 1.8 mg/mL at 80 mL for 144 mg Total Biological Activity
Biological activity of selected examples in the EZH2 nucleosome assay are provided in Tables 3. Data are presented as WT and Mutant Y641N EZH2 $IC_{50}$ value (μM) or $K_i^{app}$ (μM) as indicated.

TABLE 2

| Ex. No. | WT EZH2 Nucleosome assay $IC_{50}$ (μM) | WT EZH2 Nucleosome assay (10X SAM) Ki (μM) | EZH2 Mutant Y641N Nucleosome assay $IC_{50}$ (μM) |
| --- | --- | --- | --- |
| 1 | 0.001 | | 0.003 |
| 2 | 0.002 | | 0.004 |
| 3 | 0.066 | | 0.302 |
| 4 | 0.316 | | 1.954 |
| 5 | | 0.033 | 0.189 |
| 6 | | 0.019 | 0.136 |
| 7 | | 0.171 | 1.617 |
| 8 | | 0.652 | 5.016 |
| 9 | | 0.005 | 0.035 |

TABLE 2-continued

| Ex. No. | WT EZH2 Nucleosome assay IC$_{50}$ (μM) | WT EZH2 Nucleosome assay (10X SAM) Ki (μM) | EZH2 Mutant Y641N Nucleosome assay IC$_{50}$ (μM) |
|---|---|---|---|
| 10 | 0.326 | | 1.980 |
| 11 | 0.038 | | 0.174 |
| 12 | | 0.004 | 0.016 |
| 13 | | 0.003 | 0.018 |
| 14 | 0.008 | | 0.040 |
| 15 | | 0.003 | 0.019 |
| 16 | | 0.004 | 0.040 |
| 17 | 0.035 | | 0.125 |
| 18 | 0.126 | 0.115 | 0.995 |
| 19 | 0.013 | 0.010 | 0.132 |
| 20 | 0.011 | | 0.053 |
| 21 | 0.015 | | 0.109 |
| 22 | 7.817 | | 95.165 |
| 23 | 0.009 | | 0.067 |
| 24 | 0.004 | | 0.008 |
| 25 | 0.084 | | 0.693 |
| 26 | 0.027 | | 0.057 |
| 27 | 0.037 | | 0.300 |
| 28 | 0.126 | | 1.894 |
| 29 | 0.017 | | 0.107 |
| 30 | 0.004 | | 0.020 |
| 31 | 0.004 | | 0.006 |
| 32 | 0.093 | | 1.133 |
| 33 | 0.012 | | 0.070 |
| 35 | 0.002 | 0.000 | 0.002 |
| 36 | 0.105 | 0.136 | 0.443 |
| 37 | 0.001 | | 0.002 |
| 38 | 0.378 | | 0.740 |
| 39 | 0.040 | | 0.242 |
| 40 | 0.006 | | 0.024 |
| 41 | 0.012 | | 0.082 |
| 42 | 0.012 | | 0.102 |
| 43 | | 0.039 | 0.348 |
| 44 | | 0.022 | 0.144 |
| 45 | | 0.103 | 0.345 |
| 46 | | 0.121 | 0.423 |
| 47 | | 0.138 | 0.847 |
| 48 | | 0.008 | 0.050 |
| 49 | | 0.215 | 0.996 |
| 50 | | 0.077 | 0.129 |
| 51 | | 0.000 | 0.002 |
| 52 | | 0.298 | 1.038 |
| 53 | | 0.001 | 0.017 |
| 54 | | 0.004 | 0.012 |
| 55 | | 0.162 | 0.843 |
| 56 | | 0.000 | 0.004 |
| 57 | | 0.406 | 1.352 |
| 58 | | 0.057 | 0.513 |
| 59 | | 0.025 | 0.155 |
| 60 | | 0.031 | 0.180 |
| 61 | | 0.031 | 0.127 |
| 62 | | 0.035 | 0.262 |
| 63 | | 0.528 | 4.104 |
| 64 | | 0.007 | 0.043 |
| 65 | | 0.006 | 0.047 |
| 66 | | 0.009 | 0.081 |
| 67 | | 1.599 | 19.543 |
| 68 | | 0.007 | 0.074 |
| 69 | | 0.417 | 4.308 |
| 70 | | 0.000 | 0.006 |
| 71 | | 0.000 | 0.003 |
| 72 | | 0.041 | 0.128 |
| 73 | | 0.000 | 0.002 |
| 74 | | 0.005 | 0.051 |
| 75 | | 0.002 | 0.020 |
| 76 | | 0.005 | 0.043 |
| 77 | | 0.022 | 0.132 |
| 78 | | 0.004 | 0.040 |
| 79 | | 0.017 | 0.133 |
| 80 | | 0.001 | 0.007 |
| 81 | | 0.0002 | 0.003 |
| 82 | | 0.006 | 0.131 |
| 83 | | 0.0004 | 0.004 |
| 84 | | 0.0002 | 0.002 |
| 85 | | 0.052 | 0.238 |
| 86 | | 0.061 | 0.637 |
| 87 | | 0.00001 | 0.002 |
| 88 | | 0.028 | 0.122 |
| 89 | | 0.008 | 0.088 |
| 90 | | 0.459 | 5.634 |
| 91 | | 0.001 | 0.023 |
| 92 | | 0.001 | 0.009 |
| 93 | | 0.159 | 1.332 |
| 94 | | 0.323 | 4.870 |
| 95 | | 0.001 | 0.012 |
| 96 | | 0.204 | 2.99 |
| 97 | | 0.003 | 0.027 |
| 98 | | 1.22 | 8.72 |
| 99 | | 0.003 | 0.017 |
| 100 | | 0.309 | 3.73 |
| 101 | | 0.0003 | 0.007 |
| 102 | | 0.018 | 0.178 |
| 103 | | 0.052 | 0.320 |
| 104 | | 0.673 | 7.77 |
| 105 | | 0.0008 | 0.013 |
| 106 | | 0.0006 | 0.008 |
| 107 | | 0.0019 | 0.018 |
| 108 | | 0.0017 | 0.016 |
| 109 | | 0.086 | 0.911 |
| 110 | | 0.00004 | 0.002 |
| 111 | | 0.00002 | 0.001 |
| 112 | | 0.021 | 0.125 |
| 113 | | 0.0008 | 0.005 |
| 114 | | 0.016 | 0.152 |
| 115 | | 0.0003 | 0.005 |
| 116 | | 0.071 | 0.340 |
| 117 | | 0.0004 | 0.005 |
| 118 | | 0.0001 | 0.003 |
| 119 | | 0.015 | 0.100 |
| 120 | | 0.002 | 0.014 |
| 121 | | 0.029 | 0.255 |
| 122 | | 0.073 | 0.236 |
| 123 | | 0.0002 | 0.005 |
| 124 | | 0.058 | 0.892 |
| 125 | | 0.0009 | 0.008 |
| 126 | | 0.056 | 0.165 |
| 127 | | 0.0002 | 0.0022 |
| 128 | | 0.184 | 1.167 |
| 129 | | 0.0008 | 0.008 |
| 130 | | 0.220 | 1.99 |
| 131 | | 0.0007 | 0.005 |
| 132 | | 0.001 | 0.013 |
| 133 | | 0.837 | 8.635 |
| 134 | | 0.131 | 1.926 |
| 135 | | 0.002 | 0.014 |
| 136 | | 0.0001 | 0.003 |
| 137 | | 0.133 | 1.166 |
| 138 | | 0.046 | 0.249 |
| 139 | | 0.0005 | 0.0085 |
| 140 | | 0.103 | 1.17 |
| 141 | | 0.002 | 0.016 |
| 142 | | 0.008 | 0.109 |
| 143 | | 0.276 | 1.77 |
| 144 | | 0.0002 | 0.005 |
| 145 | | 0.070 | 0.272 |
| 146 | | 0.0001 | 0.0035 |
| 147 | | 0.128 | 0.543 |
| 148 | | 0.056 | 0.439 |
| 149 | | 0.539 | 2.267 |
| 150 | | 0.0001 | 0.003 |
| 151 | | 0.0008 | 0.009 |
| 152 | | 0.0003 | 0.004 |
| 153 | | 0.416 | 3.10 |
| 154 | | 0.0446 | 0.553 |
| 155 | | 0.0013 | 0.027 |
| 156 | | 0.375 | 1.711 |
| 157 | | 0.0006 | 0.009 |
| 158 | | 0.578 | 5.13 |

TABLE 2-continued

| Ex. No. | WT EZH2 Nucleosome assay IC$_{50}$ (μM) | WT EZH2 Nucleosome assay (10X SAM) Ki (μM) | EZH2 Mutant Y641N Nucleosome assay IC$_{50}$ (μM) |
|---|---|---|---|
| 159 | | 0.0016 | 0.017 |
| 160 | | 0.021 | 0.086 |
| 161 | | 0.0004 | 0.004 |
| 162 | | 0.148 | 2.971 |
| 163 | | 0.0004 | 0.004 |
| 164 | | 0.200 | 1.971 |
| 165 | | 0.0003 | 0.005 |
| 166 | | 0.0002 | 0.002 |
| 167 | | 0.062 | 0.850 |
| 168 | | 0.0007 | 0.008 |
| 169 | | 0.0151 | 0.070 |
| 170 | | 0.0008 | 0.014 |
| 171 | | 0.328 | 2.63 |
| 172 | | 0.0008 | 0.012 |
| 173 | | 0.016 | 0.206 |
| 174 | | 0.0006 | 0.013 |
| 175 | | 0.085 | 1.00 |
| 176 | | 0.0003 | 0.005 |
| 177 | | 0.049 | 0.282 |
| 178 | | 0.003 | 0.020 |
| 179 | | 0.001 | 0.009 |
| 180 | | 0.390 | 2.16 |
| 181 | | 0.001 | 0.041 |
| 182 | | 2.23 | 9.15 |
| 183 | | 0.056 | 0.517 |
| 184 | | 0.0006 | 0.005 |
| 185 | | 0.001 | 0.012 |
| 186 | | 0.014 | 0.240 |
| 187 | | 0.001 | 0.010 |
| 188 | | 0.014 | 0.151 |
| 189 | | 0.0007 | 0.006 |
| 190 | | 0.016 | 0.100 |
| 191 | | 0.0003 | 0.005 |
| 192 | | 0.117 | 0.605 |
| 193 | | 0.001 | 0.010 |
| 194 | | 0.044 | 0.309 |
| 195 | | 0.046 | 0.216 |
| 196 | | 0.0002 | 0.003 |
| 197 | | 0.033 | 0.062 |
| 198 | | 0.00001 | 0.001 |
| 199 | | 0.003 | 0.037 |
| 200 | | 0.0001 | 0.002 |
| 201 | | 0.007 | 0.037 |
| 202 | | 0.016 | 0.207 |
| 203 | | 0.055 | 0.204 |
| 204 | | 0.002 | 0.062 |
| 205 | | 0.0007 | 0.008 |

All publications and patent applications cited in the specification are herein incorporated by reference in their entirety. Although the foregoing invention has been described in some detail by way of illustration and example, it will be readily apparent to those of ordinary skill in the art in light of the teachings of this invention that certain changes and modifications may be made thereto without departing from the spirit or scope of the appended claims.

We claim:
1. A compound of Formula (I-A):

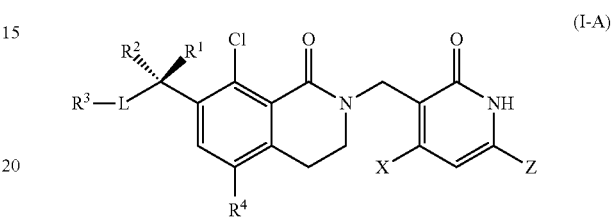

or a pharmaceutically acceptable salt thereof, wherein:
R$^1$ is OCH$_3$;
R$^2$ is H;
L is a bond;
R$^3$ is 3-12 membered heterocyclyl, optionally substituted by one or more R$^7$;
R$^4$ is Cl;
each R$^7$ is independently C$_1$-C$_4$ alkyl, OH, or F;
X is CH$_3$, OCH$_3$, or OCHF$_2$; and
Z is CH$_3$.

2. The compound or salt of claim 1, wherein R$^3$ is 3-12 membered heterocyclyl selected from the group consisting of oxetanyl, tetrahydrofuranyl and tetrahydropyranyl, each optionally substituted by one or more R$^7$.

3. A pharmaceutical composition comprising a compound of claim 1, or a pharmaceutically acceptable salt thereof, and a pharmaceutically acceptable carrier or excipient.

4. A method for the treatment of abnormal cell growth in a subject, comprising administering to the subject a therapeutically effective amount of a compound of claim 1, or a pharmaceutically acceptable salt thereof.

* * * * *